「 
US009322041B2

(12) United States Patent
Brockmann et al.

(10) Patent No.: US 9,322,041 B2
(45) Date of Patent: Apr. 26, 2016

(54) GENETICALLY MODIFIED MICROORGANISMS CAPABLE OF PRODUCING BETA-GLUCANS AND METHODS FOR PRODUCING BETA-GLUCANS

(71) Applicants: BASF SE, Ludwigshafen (DE); Wintershall Holding GmbH, Kassel (DE)

(72) Inventors: Beata Brockmann, Mannheim (DE); Andrea Herold, Weinheim (DE); Oskar Zelder, Speyer (DE); Stefan Haefner, Speyer (DE); Christian Fleck, Leimen (DE); Hartwig Schröder, Nußloch (DE); Mari Granström, Mannheim (DE); Julia Kristiane Schmidt, Heidelberg (DE)

(73) Assignees: BASF SE, Ludwigshafen (DE); Wintershall Holding GmbH, Kassel (DE)

( * ) Notice: Subject to any disclaimer, the term of this patent is extended or adjusted under 35 U.S.C. 154(b) by 56 days.

(21) Appl. No.: 13/935,043

(22) Filed: Jul. 3, 2013

(65) Prior Publication Data
US 2014/0011243 A1    Jan. 9, 2014

Related U.S. Application Data

(60) Provisional application No. 61/667,961, filed on Jul. 4, 2012.

(51) Int. Cl.
*C12P 19/04*      (2006.01)
*C12N 15/80*      (2006.01)
*C12N 9/10*       (2006.01)
*C08B 37/00*      (2006.01)
*C08L 5/00*       (2006.01)

(52) U.S. Cl.
CPC .............. *C12P 19/04* (2013.01); *C08B 37/0024* (2013.01); *C08L 5/00* (2013.01); *C12N 9/1051* (2013.01); *C12N 15/80* (2013.01); *Y02P 20/52* (2015.11)

(58) Field of Classification Search
None
See application file for complete search history.

(56) References Cited

PUBLICATIONS

Ishihara et al. (Eukaryotic Cell, Feb. 2007, p. 143-156).*
Nett, J. E., et al., "Genetic Basis of *Candida* Biofilm Resistance Due to Drug-Sequestering Matrix Glucan", The Journal of Infectious Diseases, 2010, vol. 202, No. 1, pp. 171-175.
Nett, J. E., et al., "Interface of Candida albicans Biofilm Matrix-Associated Drug Resistance and Cell Wall Intes rity Regulation", Eukaryotic Cell, 2011, vol. 10, No. 12, pp. 1660-1669.
"SubName: Full=Glycosyltransferase Family 48 Protein", Database UniProt Accession No. D8PVE6, Oct. 5, 2010.
SubName: Full=Glycosyltransferase Family 48 Protein, Database UniProt Accession No. D8Q7W6, Oct. 5, 2010.
Schuren, F. H. J., et al., "Highly-Efficient Transformation of the Homobasidiomycete *Schizophyllum commune* to Phleomycin Resistance", Current Genetics, 1994, vol. 26, No. 2, pp. 179-183.
Schmid, J., et al., "Scleroglucan: Biosynthesis, Production and Application of a Versatile Hydrocolloid", Applied Microbiology and Biotechnology, 2011, vol. 91, No. 4, pp. 937-947.
International Search Report and Written Opinion of The International Searching Authority for PCT/EP2013/064024 mailed Sep. 25, 2013.

* cited by examiner

*Primary Examiner* — Suzanne M Noakes
*Assistant Examiner* — Jae W Lee
(74) *Attorney, Agent, or Firm* — Drinker Biddle & Reath LLP

(57) ABSTRACT

The present invention relates to genetically modified microorganisms capable of producing beta-glucans, characterized in that the genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain. The present invention also relates to the use of a polynucleotide encoding a polypeptide having 1,3-β-D-glucan synthase-activity or the use of such a polypeptide for producing β-glucans. Furthermore, the present invention relates to methods for producing β-glucans comprising the introduction of a promoter upstream of a polynucleotide encoding a polypeptide having 1,3-β-D-glucan synthase-activity thereby increasing the expression of the polynucleotide, or a polynucleotide encoding a polypeptide having 1,3-β-D-glucan synthase-activity into a microorganism being able to synthesize β-glucans.

20 Claims, 4 Drawing Sheets

Figure 1:
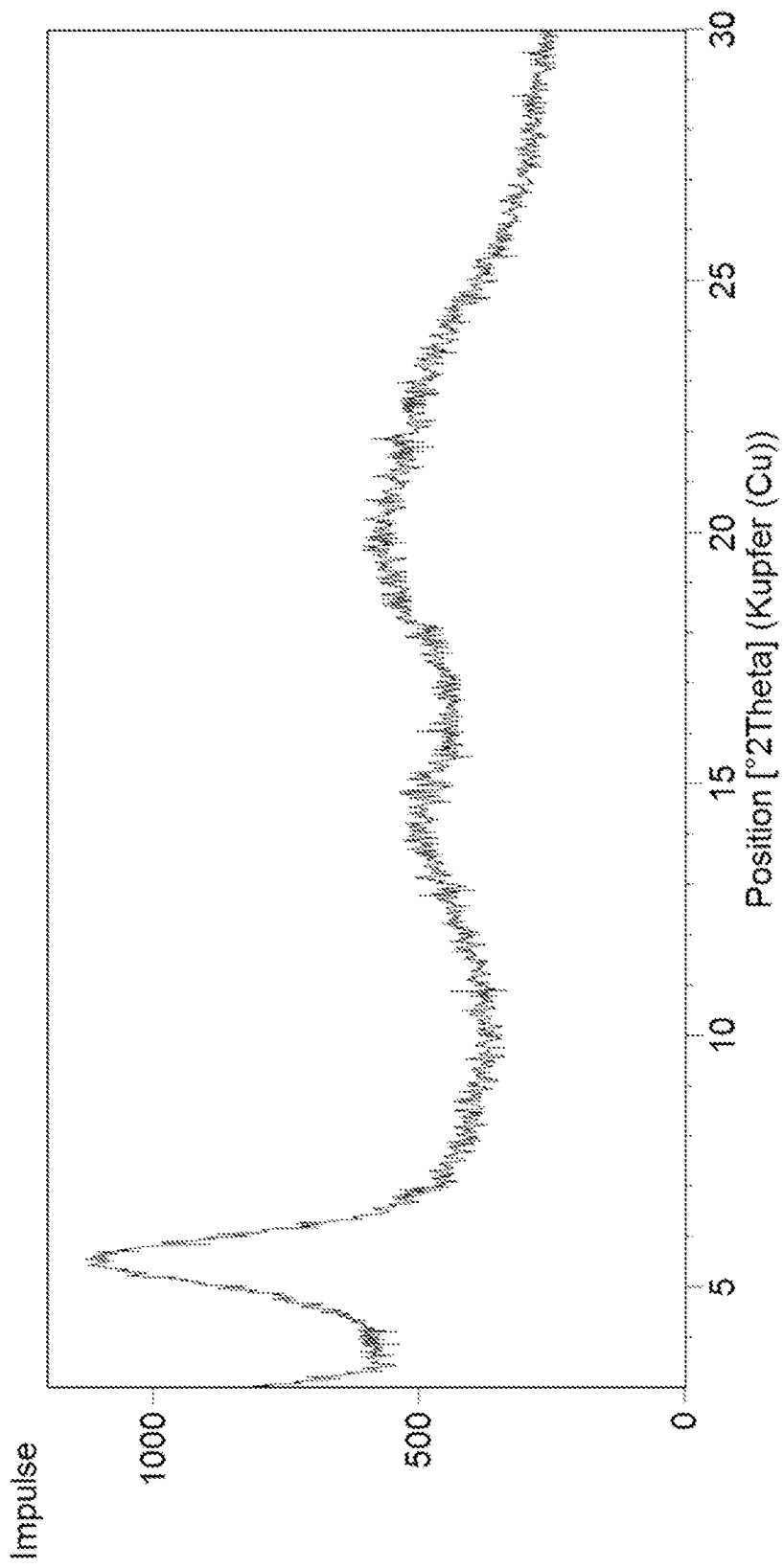

GENETICALLY MODIFIED MICROORGANISMS CAPABLE OF PRODUCING BETA-GLUCANS AND METHODS FOR PRODUCING BETA-GLUCANS

CROSS-REFERENCE TO RELATED APPLICATIONS

This application claims benefit (under 35 USC 119(e)) of U.S. Provisional Application No. 61/667,961, filed Jul. 4, 2012, which is incorporated by reference.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_12810_01544. The size of the text file is 185 KB, and the text file was created on Aug. 8, 2013.

The present invention relates to genetically modified microorganisms capable of producing beta-glucans (herein also referred to as β-glucans), characterized said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain. D-glucan synthase-activity compared to a corresponding non-modified control microorganism of the same strain. The present invention also relates to the use of a polynucleotide encoding a polypeptide having 1,3-β-D-glucan synthase-activity or the use of such a polypeptide for producing β-glucans. Furthermore, the present invention relates to methods for producing β-glucans comprising the introduction of a polynucleotide encoding a polypeptide having 1,3-β-D-glucan synthase-activity into a microorganism being able to synthesize β-glucans. In context of the present invention, the term "β-glucans" may particularly comprise polymers consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3.

β-glucans are known well-conserved components of cell walls in several microorganisms, particularly in fungi and yeast (Novak, Endocrine, Metabol & Immune Disorders—Drug Targets (2009), 9: 67-75). Biochemically, β-glucans comprise non-cellulosic polymers of β-glucose linked via glycosidic β(1-3) bonds exhibiting a certain branching pattern with β(1-6) bound glucose molecules (Novak, loc cit). A large number of closely related β-glucans exhibit a similar branching pattern such as schizophyllan, scleroglucan, pendulan, cinerian, laminarin, lentinan and pleuran, all of which exhibit a linear main chain of β-D-(1-3)-glucopyranosyl units with a single β-D-glucopyranosyl unit (1-6) linked to a β-D-glucopyranosyl unit of the linear main chain with an average branching degree of about 0.3 (Novak, loc cit, EP-B1 463540; Stahmann, Appl Environ Microbiol (1992), 58: 3347-3354; Kim, Biotechnol Letters (2006), 28: 439-446; Nikitina, Food Technol Biotechnol (2007), 45: 230-237). Although these β-glucans are structurally closely related, their respective microbial producers are not. Examples of microorganisms producing these structurally closely related β-glucans are *Schizophyllum commune* (for schizophyllan; Martin, Biomacromolecules (2000), 1: 49-60; Rau, Methods in Biotechnol (1999), 10: 43-55, DOI: 10.1007/978-1-59259-261-6_4); *Sclerotium rolfsii*, *Sclerotium glucanicum*, and *Sclerotium delphinii* (for scleroglucan; Survase, Food Technol Biotechnol (2007), 107-118); *Porodisculus pendulus* (for pendulan; EP-B1 463540); *Botrytis cinerea* (for cinerian; Stahmann, loc cit) *Laminaria* sp. (for laminarin; Kim, loc cit); and *Lentinula edoles* (for lentinan; Nikitina, loc cit). At least two of said β-glucans—schizophyllan and scleroglucan—even share an identical structure and differ only slightly in their molecular mass, i.e. in their chain length (Survase, loc cit).

Such β-glucans are widely used as thickeners and find application in several applications such as food industry and particularly oil industry (enhanced oil recovery, EOR) (Survase, loc cit). Also, such β-glucans are used in the pharmaceutical industry in tablet formulations and excipients as well as in immunotherapy as antiviral agents (Survase, loc cit).

Industrial production of β-glucans is mostly performed by fermentation processes using their natural microbial producers. Classical ways to improve β-glucan synthesis, e.g., of schizophyllan is based on manipulation of the development of *S. commune* (Rau, Habilitation, Braunschweig 1997). The most common approach is to convert dicaryotic cells via protoplast generation into monocaryotic cells (Rau, Habilitation, Braunschweig 1997). Another approach is to cross different monocaryotic cells to form a new dicaryotic cell (Rau, Habilitation, Braunschweig 1997). Further possible approaches comprise, e.g., a classical random based mutagenesis using UV radiation, transposon mutagenesis or using suitable chemicals (e.g., nitrosoguanidin (NTG or N-methyl-N'-nitro-N-nitrosoguanidin), 2-aminofluorene (2-AF), 4-nitro-o-phenylenediamine (NPD), 2-methoxy-6-chloro-9-(3-(2-chloroethyl)aminopropylamino)acridine× 2HCl (ICR-191), 4-nitroquinolone-N-oxide (NQNO), benzo [α]pyrene (B[alpha]p), or sodium azide (SA)) (Czyz, J Appl Genet (2002), 43(3): 377-389). Due to the rearrangement of genetic material within the crossing event it is possible to select strains exhibiting higher β-glucan (schizophyllan) productivity.

Yet, all of these approaches are undirected and do not allow targeted modification of the β-glucan producing microorganisms. In fact, results and efficiency of such approaches are not predictable and identification and selection of improved strains is labored and costly.

This technical problem has been solved by the means and methods described herein below and as defined in the claims.

In particular, as has been surprisingly found in context with the present invention, overexpression of 1,3-β-D-glucan synthase in a β-glucan producing microorganism such as, e.g., *S. commune* or *S. rolfsii* leads to significant higher yields of the respective β-glucan. This finding was indeed unexpected given the fact that the biosynthetic pathway of β-glucan synthesis was only poorly understood and moreover, for most β-glucan producing microorganisms (such as *Schizophyllum commune*), there was no proposed β-glucan biosynthesis pathway available at all. Moreover, in context of those microorganisms whose β-glucan biosynthesis pathway was at least investigated (such as *Pediococcus parvulus*), enzymes such as α-phosphoglucomutase (α-PGM) and particularly UDP-glucose pyrophosphorylase (UGP) were assumed to represent a bottle-neck in β-glucan synthesis (Velasco, Int J Food Microbiol (2007), 115: 325-354). Accordingly, overexpression of these enzymes was assumed to increase the yields of β-glucan synthesis (Velasco, loc cit). Yet, as has been found in context with the present invention, overexpression of UGP in *S. commune* did not result in an increased yield of the β-glucan schizophyllan. In sharp contrast, as further described herein below and in the Examples, it has been found in context of the present invention that *S. commune* possesses two copies of 1,3-β-D-glucan synthase (genome sequence known from Ohm, Nature Biotech (2010), 28: 957-963) and, surprisingly, that overexpressing either of the two copies of 1,3-β-D-glucan synthase in *S. commune* leads to significant higher yields in the production of schizophyllan. Given that schizophyllan has a structure which is closely related to other β-glucans such as scleroglucan, pendulan, cinerian, laminarin, lentinan and pleuran (all of which are polymers consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3), it appears to be likely that overexpression of polypeptides having 1,3-β-D-glucan synthase activity in corresponding microorganisms as also described herein may therefore result in higher yields of those β-glucans.

Accordingly, the present invention relates to a genetically modified microorganism capable of producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain. Said polynucleotide may be endogenous or exogenous. For example, in context with the present invention, the overexpression of said polynucleotide may result from the introduction of a strong (e.g., constitutive or inducible) promoter upstream of said polynucleotide thereby increasing the expression level of said polynucleotide, or, preferably, from the introduction of at least one copy of a polynucleotide encoding a polypeptide having 1,3-β-D-glucan synthase-activity. In one embodiment, the present invention relates to a genetically modified microorganism capable of producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, characterized in that said genetically modified microorganism contains at least one copy more of a polynucleotide encoding a polypeptide having 1,3-β-D-glucan synthase-activity compared to a corresponding non-modified control microorganism of the same strain. Said genetically modified microorganism is preferably capable of stably maintaining and expressing the additional polynucleotide encoding a polypeptide having 1,3-β-D-glucan synthase-activity. Said genetically modified microorganism may originate from a corresponding non-modified microorganism which preferably per se, i.e. naturally, contains a polynucleotide encoding a polypeptide having 1,3-β-D-glucan synthase-activity. Also, said genetically modified microorganism is preferably per se, i.e. before modification, able to produce a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3 as described herein. Into said genetically modified microorganism, a strong promoter or at least one polynucleotide encoding a polypeptide having 1,3-β-D-glucan synthase-activity may have been introduced. Non-limiting examples of means and methods for the introduction of a promoter sequence into a microorganism may comprise inter alia homologous recombination as known in the art (Ohm, World J Microbiol Biotechnol (2010), 26: 1919-1923). Also, in context with the present invention, the microorganism may have been modified such that more polypeptide having 1,3-β-D-glucan synthase-activity is expressed, e.g., by inserting a strong promoter as described herein, by adding introns into a polynucleotide encoding a polypeptide having 1,3-β-D-glucan synthase-activity, by adapting the codon usage, by improving the ribosomal binding site for better translational initiation, by is introducing elements in the mRNA that stabilize it, or by inserting a polynucleotide with a higher transcription level having 1,3-β-D-glucan synthase-activity into the microorganism (cf. Ohm, loc cit).

In context with the present invention, the promoter may be introduced into said microorganism upstream of a polynucleotide encoding a polypeptide having 1,3-β-D-glucan synthase-activity and in a manner that said promoter increases or enhances the expression of said polynucleotide. Non-limiting examples of means and methods for the introduction of a polynucleotide into a microorganism may comprise transformation, transduction and transfection as commonly known in the art and as also exemplified herein (Sambrook and Russell (2001), Molecular Cloning: A Laboratory Manual, CSH Press, Cold Spring Harbor, N.Y., USA; Current Protocols in Molecular Biology, Update May 9, 2012, Print ISSN: 1934-3639, Online ISSN: 1934-3647; Methods in Yeast Genetics, A Laboratory Course Manual, Cold Spring Harbor Laboratory Press, 1990; van Peer, Applied Environ Microbiol (2009), 75: 1243-1247; Schmid, "Genetics of Scleroglucan Production by *Sclerotium rolfsii*", dissertation Technische Universität Berlin, D83 (2008)). Non-limiting examples of means and methods for the introduction of a promoter sequence into a microorganism may comprise inter alia homologous recombination as known in the art (Ohm, World J Microbiol Biotechnol (2010), 26: 1919-1923). Strong promoters to be introduced upstream of a polynucleotide encoding a polypeptide having 1,3-β-D-glucan synthase-activity in context with the present invention may comprise, inter alia, constitutive promoters such as, e.g., tef1 promoter (translation and elongation factor 1a, *S. commune, A. niger*), gpdA promoter (glyceraldehyde-3-phosphate dehydrogenase, *S. commune, A. niger*, Schuren, Cur Genet (1998), 33: 151-156), trpC promoter (tryptophan biosynthesis, *Aspergillus nidulans*) or inducible promoters such as, e.g., glaA promoter (glucoamylase, *A. niger*), alcA (alcohol dehydrogenase, *A. nidulans*) cbhI (cellobiohydrolase I, *Trichoderma reesei*; Knabe, Dissertation "Untersuchung von Signalkomponenten der sexuellen Entwicklung bei dem Basidiomyceten *Schizophyllum commune*" (2008)) thiA (thiamine biosynthesis, *Aspergillus oryzae*) (Moore, Biotechnology, Vol. III, Genetic Engineering of Fungal Cells, Enceclopedia of Life Support Systems (2007)). In context with the present invention, preferred promoters comprise tef1 and gdpA.

Generally, in context with the present invention, the polynucleotide encoding a polypeptide having 1,3-β-D-glucan synthase-activity may be introduced into the microorganism in any suitable form, e.g., comprised in a vector, a plasmid, or as naked nucleic acid as further described and exemplified herein. The polynucleotide introduced into the microorganism may then be exogenous, on a vector/plasmid within the microorganism (i.e. outside of the microbial chromosome(s)), or it may be incorporated into the microbial chromosome(s) by, e.g., random (ectopic) or homologous recombination or any other suitable method as known in the art. In context with the present invention, the polynucleotide encoding a polypeptide having 1,3-β-D-glucan synthase-activity which has been introduced into the microorganism (i.e. the additional copy to the natural endogenous polynucleotide encoding a polypeptide having 1,3-β-D-glucan synthase-activity of a corresponding unmodified strain) does not necessarily have to have the same nucleotide sequence as the natural endogenous polynucleotide encoding a polypeptide having 1,3-β-D-glucan synthase-activity of a corresponding unmodified strain, as long as it has 1,3-β-D-glucan synthase-activity as described herein.

In one embodiment of the present invention, the genetically modified microorganism is able to produce at least 1.5 times, more preferably at least 1.8 times more, more preferably at least 2.0 times more, and most preferably at least 2.2 times more β-glucan polymer compared to the corresponding non-modified control microorganism. In this context, production of, e.g., 1.5 times "more" β-glucan polymer may mean that a genetically modified microorganism produces an amount of β-glucan polymer which is 1.5 times higher compared to the amount of β-glucan polymer produced in the same time under the same conditions by a corresponding non-modified control microorganism. Alternatively, production of, e.g., 1.5 times "more" β-glucan polymer may mean that a genetically modified microorganism produces the same amount of β-glucan polymer as a corresponding non-modified control organism under the same conditions, however, 1.5 times faster. The amount of produced β-glucan polymer may be measured by methods known in the art and as also described herein.

Furthermore, the present invention relates to the use of a polynucleotide encoding a polypeptide having 1,3-β-D-glucan synthase-activity, or a polypeptide having 1,3-β-D-glucan synthase-activity, or of a genetically modified microorganism according to claim 1 for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3.

Furthermore, the present invention relates to a method of producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, said method comprising the steps of:
(a) introducing (i) a strong (e.g., constitutive or inducible) promoter upstream of a polynucleotide encoding a polypeptide having 1,3-β-D-glucan synthase-activity thereby increasing the expression of said polynucleotide, or, preferably, (ii) a polynucleotide encoding a polypeptide having 1,3-β-D-glucan synthase-activity into a microorganism being able to synthesize said polymer;
(b) culturing said microorganism of (a) in a medium, thereby allowing said microorganism to produce said polymer; and
(c) optionally recovering said polymer from the medium.

As regards step (c) of the method described and provided herein, it is noted that in some cases (e.g., when β-glucans such as schizophyllan is used for oil drilling purposes), the culture broth may also be used directly (e.g., pumped into the drill hole), without previous recovery of the pure β-glucan. As such, the recovery step (c) is optional. Strong promoters to be introduced upstream of a polynucleotide encoding a polypeptide having 1,3-β-D-glucan synthase-activity in context with the present invention may comprise, inter alia, constitutive promoters such as, e.g., tef1 promoter (translation and elongation factor 1a, *S. commune, A. niger*), gpdA promoter (glyceraldehyde-3-phosphate, *S. commune, A. niger*), trpC promoter (tryptophan biosynthesis, *Aspergilus nidulans*) or inducible promoters such as, e.g., glaA promoter (glucoamylase, *A. niger*), alcA (alcohol dehydrogenase, *A. nidulans*) cbhI (cellobiohydrolase I, *Trichoderma reesei*) thiA (thiamine biosynthesis, *Aspergillus oryzae*), tef1 and gdpA being preferred promoters. In context with the present invention, the promoter is preferably introduced into said microorganism upstream of a polynucleotide encoding a polypeptide having 1,3-β-D-glucan synthase-activity and in a manner that said promoter increases or enhances the expression of said polynucleotide. Said promoter or said polynucleotide encoding a polypeptide having 1,3-β-D-glucan synthase-activity may be introduced in said microorganism by any means and methods known in the art, preferably in a manner that after introduction the promoter can increase the expression of said polynucleotide or that said polynucleotide can be stably maintained and expressed by the microorganism, respectively. Non-limiting examples of means and methods for the introduction of a promoter sequence into a microorganism may comprise, inter alia, recombinant homology as known in the art (Ohm, loc cit). Non-limiting examples of such methods for the introduction of a polynucleotide into a microorganism may comprise transformation, transduction and transfection as commonly known in the art and as also exemplified herein (Sambrook and Russell (2001), Molecular Cloning: A Laboratory Manual, CSH Press, Cold Spring Harbor, N.Y., USA; Current Protocols in Molecular Biology, Update May 9, 2012, Print ISSN: 1934-3639, Online ISSN: 1934-3647; Methods in Yeast Genetics. A Laboratory Course Manual, Cold Spring Harbor Laboratory Press, 1990; van Peer, Applied Environ Microbiol (2009), 75: 1243-1247; Schmid, "Genetics of Scleroglucan Production by *Sclerotium rolfsii*", dissertation Technische Universität Berlin, D83 (2008)).

In context with the present invention, the strong promoter introduced into a microorganism upstream of a polynucleotide encoding a polypeptide having 1,3-β-D-glucan synthase-activity preferably increases the expression level of said polynucleotide at least 1.5-fold, more preferably at least 1.8-fold, more preferably at least 2.0-fold, and most preferably at least 2.2-fold. In this context, the expression level of a polynucleotide can be easily assessed by the skilled person by methods known in the art, e.g., by quantitative RT-PCR, Northern Blot (for assessing the amount of expressed mRNA levels), Dot Blot, Microarray or the like.

Generally, the term "overexpression" as used herein comprises both, overexpression is of polynucleotides (e.g., on the transcriptional level) and overexpression of polypeptides (e.g., on the translation level). Accordingly, the present invention relates to a genetically modified microorganism capable of producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain. In context with the present invention, a genetically modified microorganism is to be considered as "overexpressing" a polynucleotide encoding a polypeptide having 1,3-β-D-glucan synthase-activity if it expresses at least 1.5-fold, more preferably at least 1.8-fold, more preferably at least 2.0-fold, and most preferably at least 2.2-fold of said polynucleotide compared to a non-modified control microorganism of the same strain. In this context, the expression level of a polynucleotide can be easily assessed by the skilled person by methods known in the art, e.g., by quantitative RT-PCR (qRT-PCR), Northern Blot (for assessing the amount of expressed mRNA levels), Dot Blot, Microarray or the like (see, e.g., Sambrook, loc cit; Current Protocols in Molecular Biology, Update May 9, 2012, Print ISSN: 1934-3639, Online ISSN: 1934-3647). Preferably, the amount of expressed polynucleotide is measured by qRT-PCR. Furthermore, in context with the present invention, a genetically modified microorganism is to be considered as "overexpressing" a polypeptide having 1,3-β-D-glucan synthase-activity if it expresses at least 1.5-fold, more preferably at least 1.8-fold, more preferably at least 2.0-fold, and most preferably at least 2.2-fold of said polypeptide compared to a non-modified control microorganism of the same strain. In this context, the expression level of a polypeptide can be easily assessed by the skilled person by methods known in the art, e.g., by Western Blot, ELISA, EIA, RIA, or the like (see, e.g., Sambrook, loc cit; Current Protocols in Molecular Biology, Update May 9, 2012, Print ISSN: 1934-3639, Online ISSN: 1934-3647). Preferably, the amount of expressed polypeptide is measured by Western Blot.

Generally, in context with the present invention, the polynucleotide encoding a polypeptide having 1,3-β-D-glucan synthase-activity may be introduced into the microorganism in any suitable form, e.g., comprised in a vector, a plasmid or as naked nucleic acid. The polynucleotide introduced into the microorganism may then be exogenous (e.g., on a vector or a plasmid) within the microorganism (i.e. outside of the microbial chromosome(s)), or it may be incorporated into the microbial chromosome(s) by, e.g., random (ectopic) or homologous recombination or any other suitable method as known in the art. In context with the present invention, the polynucleotide encoding a polypeptide having 1,3-β-D-glucan synthase-activity which has been introduced into the microorganism (i.e. the additional copy to the natural endogenous polynucleotide encoding a polypeptide having 1,3-β-D-glucan synthase-activity of a corresponding unmodified strain) does not necessarily have to have the same nucleotide sequence as the natural endogenous polynucleotide encoding a polypeptide having 1,3-β-D-glucan synthase-activity of a corresponding unmodified strain, as long as it has 1,3-β-D-glucan synthase-activity as described herein.

Methods for culturing microorganisms such as fermentation processes are known in the art and also described and exemplified herein (Kumari, Bioresource Technol (2008), 99: 1036-1043; Reyes, J Natural Studies (2009), 7(2), January-June). In context with the present invention, such methods allow the respective microorganism to grow and to produce the desired β-glucan as described and exemplified herein. Suitable media may comprise, e.g., coconut water as described in Reyes, loc cit. Furthermore, as known in the art, there are several media particularly suitable for particular microorganisms. For example, also in context with the present invention, suitable media for culturing S. commune comprise CYM medium (25 g agar (Difco), 20 g glucose (Sigma), 2 g trypticase peptone (Roth), 2 g yeast extract (Difco), 0.5 g MgSO$_4$×7H$_2$O (Roth), 0.5 g KH$_2$PO$_4$ and 1 g K$_2$HPO$_4$ (both from Riedel-de Haën) per liter H$_2$O) (particularly useful for cultivation on solid support) or a medium comprising 30 g glucose (Sigma), 3 g yeast extract (Difco), 1 g KH$_2$PO$_4$ (Riedel-de Haën), 0.5 g MgSO$_4$×7H$_2$O (Roth) per liter H$_2$O (particularly useful for liquid cultures) as also described and exemplified herein. Further suitable media for culturing S. rolfsii are known in the art (Survase, Bioresource Technol (2006), 97: 989-993). The β-glucan produced in accordance to the present invention can be recovered by various methods known in the art and described herein (see also "Recommended Practices for Evaluation of Polymers Used in Enhanced Oil Recovery Operations, API Recommended Practice 63 (RP 63), 1$^{st}$ Ed, American Petoleum Institute, Washington D.C., Jun. 1, 1990; Kumari, Bioresource Technol (2008), 99: 1036-1043).

In context with the present invention, the term "average branching degree about 0.3" may mean that in average about 3 of 10 β-D-(1-3)-glucopyranosyl units are (1-6) linked to a single β-D-glucopyranosyl unit. In this context, the term "about" may mean that the average branching degree may be within the range from 0.1 to 0.5, preferably from 0.2 to 0.4, more preferably from 0.25 to 0.35, more preferably from 0.25 to 0.33, more preferably from 0.27 to 0.33, and most preferably from 0.3 to 0.33. It may also be 0.3 or 0.33. Schizophyllan, scleroglucan, pendulan, cinerian, laminarin, lentinan and pleuran all have an average branching degree between 0.25 and 0.33; for example, scleroglucan and schizophyllan have an average branching degree of 0.3 to 0.33 (Survase, loc cit; Novak, loc cit). The average branching degree of a β-glucan can be determined by methods known in the art, e.g., by periodic oxidation analysis, methylated sugar analysis and NMR (Brigand, Industrial Gums, Academic Press, New York/USA (1993), 461-472).

In one embodiment of the present invention, the polymer to be produced is selected from the group consisting of schizophyllan, scleroglucan, pendulan, cinerian, laminarin, lentinan and pleuran. For example, the polymer may be schizophyllan or scleroglucan, particularly schizophyllan.

The microorganism of the present invention and as referred to and as employed in context with the present invention (hereinafter also referred to as "microorganism in context of the present invention") may generally be a microorganism which is per se (i.e. naturally, in a non-modified state in context with the present invention) capable of synthesizing β-glucan polymers, particularly those polymers consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3. That is, such microorganisms preferably possess per se (i.e. naturally, in a non-modified state in context with the present invention) a is polynucleotide encoding a polypeptide having 1,3-β-D-glucan synthase-activity. Non-limiting examples of microorganisms in context of the present invention are *Schizophyllum commune, Sclerotium rolfsii, Sclerotium glucanicum, Sclerotium, delphinii, Porodisculus pendulus, Botrytis cinerea, Laminaria* sp., *Lentinula edoles*, and *Monilinia fructigena*. For example, the microorganism in context with the present invention may be *S. commune* or *S. rolfsii*, particularly *S. commune*.

The polynucleotide encoding a polypeptide having 1,3-β-D-glucan synthase-activity as referred to and to be employed in context with the present invention (hereinafter also referred to as the "polynucleotide in context of the present invention") may be a 1,3-β-D-glucan synthase gene. For example, the polynucleotide in context of the present invention may comprise or may consist of a nucleic acid sequence which is at least 70%, preferably at least 75%, more preferably at least 80%, more preferably at least 85%, more preferably at least 90%, more preferably at least 95%, more preferably at least 96%, more preferably at least 97%, more preferably at least 98%, more preferably at least 99%, more preferably at least 99.5%, and most preferably 100% identical to SEQ ID NO: 1, 3, 5, 7, 9, 11, 13 or 15, provided that the polypeptide encoded by said polynucleotide has 1,3-β-D-glucan synthase-activity as further described and exemplified herein below. SEQ ID NO: 1 represents the nucleotide sequence of the gene of glucan synthase I of *S. commune* strain Lu15531 (obtained from Jena University (Germany) strain collection, Germany, Prof. E. Kothe; Jena University internal strain name: W22). SEQ ID NO: 3 represents the nucleotide sequence of the gene of glucan synthase II of *S. commune* strain Lu15531. SEQ ID NO: 5 represents the cDNA sequence of glucan synthase I of S. commune strain Lu15531. SEQ ID NO: 7 represents the cDNA sequence of glucan synthase II of S. commune strain Lu15531. SEQ ID NO: 9 represents the nucleotide sequence of the gene of glucan synthase I of S. commune strain Lu15634 (strain collection, BASF SE; monocaryotic strain originating from dicaryotic S. commune strain from strain collection at the Technical University of Braunschweig (Germany), Prof. Rau; generated by spore isolation). SEQ ID NO: 11 represents the nucleotide sequence of the gene of glucan synthase II of S. commune strain Lu15634. SEQ ID NO: 13 represents the cDNA sequence of glucan synthase I of S. commune strain Lu 15634. SEQ ID NO: 15 represents the cDNA sequence of glucan synthase II of S. commune strain Lu15634.

The polypeptide as referred to and to be used in context with the present invention and the polypeptide encoded by the polynucleotide in context of the present invention (said polypeptides hereinafter also referred to as the "polypeptide in context of the present invention") has 1,3-β-D-glucan synthase-activity. In one embodiment, it is a 1,3-β-D-glucan synthase. For example, the polypeptide in context of the present invention may comprise or consist of an amino acid sequence which at least 70%, preferably at least 75%, more preferably at least 80%, more preferably at least 85%, more preferably at least 90%, more preferably at least 95%, more preferably at least 96%, more preferably at least 97%, more preferably at least 98%, more preferably at least 99%, more preferably at least 99.5%, and most preferably 100% identical to SEQ ID NO: 6, 8, 14 or 16, provided that the polypeptide has 1,3-β-D-glucan synthase-activity. SEQ ID NO: 6 represents the amino acid sequence of glucan synthase I of S. commune strain Lu15531. SEQ ID NO: 8 represents the amino acid sequence of glucan synthase II of S. commune strain Lu15531. SEQ ID NO: 14 represents the amino acid sequence of glucan synthase I of S. commune strain Lu15634. SEQ ID NO: 16 represents the amino acid sequence of glucan synthase II of S. commune strain Lu15634.

In context with the present invention, the term "1,3-β-D-glucan synthase-activity" means that the respective polypeptide is capable of catalyzing the elongation of the 1,3-β-D-glucan chain (chain can be linear or branched) using UDP-glucose as substrate (see Inoue, Eur J Biochem (1995), 231: 845-854). For example, in context with the present invention, a polynucleotide may be considered to encode a polypeptide having 1,3-β-D-glucan synthase-activity if an S. commune cell which is transformed with said polynucleotide and which expresses said polynucleotide constitutively is able to produce at least 50%, more preferably at least 75%, more preferably at least 100%, more preferably at least 120%, more preferably at least 150%, more preferably at least 200%, and most preferably at least 220% more schizophyllan compared to an S. commune cell not being transformed with said polynucleotide, wherein the following conditions may be applied. The respective S. commune cultures with transformed and non-transformed cells, respectively, may be cultivated as follows. For the liquid cultures, the following medium may be used (hereinafter referred to as "Standard Medium"): 30 g glucose (Sigma), 3 g yeast extract (Difco), 1 g $KH_2PO_4$ (Riedel-de Haën), 0.5 g $MgSO_4 \times 7H_2O$ (Roth) per liter $H_2O$. For both, pre-cultures and for main culture, 250 ml shaking flasks filled with 30 ml Standard Medium may be used. The cultivation may be carried out at 27° C. and 225 rpm. Before each inoculation, the biomass may be homogenized for 1 minute at 13500 rpm using T 25 digital ULTRA-TURRAX® (IKA). The first pre-culture may be inoculated with 50 mg of wet biomass. The cultures may then be incubated for 72 hours. After 72 hours, the second pre-culture may be started. The concentration of the homogenized wet biomass from the first pre-culture used for inoculation may be 250 mg. Cultivation time may be 45 hours. After 45 hours, the main culture may be inoculated with 500 mg of homogenized wet biomass from the second pre-culture and cultivated for another 45 hours. Subsequently, the cultures may be treated as follows. 10 ml of the culture, 20 ml $H_2O$ and 90 µl Acticide BW20 may be mixed. The sample may then be digested for 24 h at 40° C. with β-glucanase (0.3 ml) (Erbslöh). After the incubation, the sample may be centrifuged (e.g., 30 minutes at 3400 g) and the supernatant may be analyzed for glucose content using HPLC cation exchanger (Aminex HPX-87-H, BIO-RAD) with 0.5 M $H_2SO_4$ (Roth) as eluent and 0.5 ml/min flow rate at 30° C. The typical schizophyllan structure as described herein may be confirmed by further analytical approaches as described in the Example herein below (e.g., by NMR and XRD). The same evaluation may be performed mutatis mutandis for assessing whether a given polypeptide has 1,3-β-D-glucan synthase-activity in context of the present invention. In this case, a corresponding polynucleotide encoding said polypeptide to be assessed is evaluated mutatis mutandis as described above. If the expression of such a polynucleotide encoding said polypeptide to be assessed is considered to encode a polypeptide having 1,3-β-D-glucan synthase-activity as described above, the polypeptide itself is considered to have 1,3-β-D-glucan synthase-activity.

The level of identity between two or more sequences (e.g., nucleic acid sequences or amino acid sequences) can be easily determined by methods known in the art, e.g., by BLAST analysis. Generally, in context with the present invention, if two sequences (e.g., polynucleotide sequences or amino acid sequences) to be compared by, e.g., sequence comparisons differ in identity, then the term "identity" may refer to the shorter sequence and that part of the longer sequence that matches said shorter sequence. Therefore, when the sequences which are compared do not have the same length, the degree of identity may preferably either refer to the percentage of nucleotide residues in the shorter sequence which are identical to nucleotide residues in the longer sequence or to the percentage of nucleotides in the longer sequence which are identical to nucleotide sequence in the shorter sequence. In this context, the skilled person is readily in the position to determine that part of a longer sequence that matches the shorter sequence. Furthermore, as used herein, identity levels of nucleic acid sequences or amino acid sequences may refer to the entire length of the respective sequence and is preferably assessed pair-wise, wherein each gap is to be counted as one mismatch. These definitions for sequence comparisons (e.g., establishment of "identity" values) are to be applied for all sequences described and disclosed herein.

Moreover, the term "identity" as used herein means that there is a functional and/or structural equivalence between the corresponding sequences. Nucleic acid/amino acid sequences having the given identity levels to the herein-described particular nucleic acid/amino acid sequences may represent derivatives/variants of these sequences which, preferably, have the same biological function. They may be either naturally occurring variations, for instance sequences from other varieties, species, etc., or mutations, and said mutations may have formed naturally or may have been produced by deliberate mutagenesis. Furthermore, the variations may be synthetically produced sequences. The variants may be naturally occurring variants or synthetically produced variants or variants produced by recombinant DNA techniques. Deviations from the above-described nucleic acid sequences may have been produced, e.g., by deletion, substitution, addition, insertion and/or recombination. The term "addition" refers to adding at least one nucleic acid to residue/amino acid to the end of the given sequence, whereas "insertion" refers to inserting at least one nucleic acid residue/amino acid within a given sequence. The term "deletion" refers to deleting or removal of at least one nucleic acid residue or amino acid residue in a given sequence. The term "substitution" refers to the replacement of at least one nucleic acid residue/amino acid residue in a given sequence. Again, these definitions as used here apply, mutatis mutandis, for all sequences provided and described herein.

Generally, as used herein, the terms "polynucleotide" and "nucleic acid" or "nucleic acid molecule" are to be construed synonymously. Generally, nucleic acid molecules may comprise inter alia DNA molecules, RNA molecules, oligonucleotide thiophosphates, substituted ribo-oligonucleotides or PNA molecules. Furthermore, the term "nucleic acid molecule" may refer to DNA or RNA or hybrids thereof or any modification thereof that is known in the art (see, e.g., U.S. Pat. Nos. 5,525,711, 4,711,955, 5,792,608 or EP 302175 for examples of modifications). The polynucleotide sequence may be single- or double-stranded, linear or circular, natural or synthetic, and without any size limitation. For instance, the polynucleotide sequence may be genomic DNA, cDNA, mitochondrial DNA, mRNA, antisense RNA, ribozymal RNA or a DNA encoding such RNAs or chimeroplasts (Gamper, Nucleic Acids Research, 2000, 28, 4332-4339). Said polynucleotide sequence may be in the form of a vector, plasmid or of viral DNA or RNA. Also described herein are nucleic acid molecules which are complementary to the nucleic acid molecules described above and nucleic acid molecules which are able to hybridize to nucleic acid molecules described herein. A nucleic acid molecule described herein may also be a fragment of the nucleic acid molecules in context of the present invention. Particularly, such a fragment is a functional fragment. Examples for such functional fragments are nucleic acid molecules which can serve as primers.

The term "hybridization" or "hybridizes" as used herein in context of nucleic acid molecules/DNA sequences may relate to hybridizations under stringent or non-stringent conditions. If not further specified, the conditions are preferably non-stringent. Said hybridization conditions may be established according to conventional protocols described, for example, in Sambrook, Russell "Molecular Cloning, A Laboratory Manual", Cold Spring Harbor Laboratory, N.Y. (2001); Current Protocols in Molecular Biology, Update May 9, 2012, Print ISSN: 1934-3639, Online ISSN: 1934-3647; Ausubel, "Current Protocols in Molecular Biology", Green Publishing Associates and Wiley Interscience, N.Y. (1989), or Higgins and Hames (Eds.) "Nucleic acid hybridization, a practical approach" IRL Press Oxford, Washington D.C., (1985). The setting of conditions is well within the skill of the artisan and can be determined according to protocols described in the art. Thus, the detection of only specifically hybridizing sequences will usually require stringent hybridization and washing conditions such as 0.1×SSC, 0.1% SDS at 65° C. Non-stringent hybridization conditions for the detection of homologous or not exactly complementary sequences may be set at 6×SSC, 1% SDS at 65° C. As is well known, the length of the probe and the composition of the nucleic acid to be determined constitute further parameters of the hybridization conditions. Variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility. In accordance to the invention described herein, low stringent hybridization conditions for the detection of homologous or not exactly complementary sequences may, for example, be set at 6×SSC, 1% SDS at 65° C. As is well known, the length of the probe and the composition of the nucleic acid to be determined constitute further parameters of the hybridization conditions.

Hybridizing nucleic acid molecules also comprise fragments of the above described molecules. Such fragments may represent nucleic acid molecules which code for a functional 1,3-β-D-glucan synthase as described herein or a functional fragment thereof which can serve as a primer. Furthermore, nucleic acid molecules which hybridize with any of the aforementioned nucleic acid molecules also include complementary fragments, derivatives and variants of these molecules. Additionally, a hybridization complex refers to a complex between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which, e.g., cells have been fixed). The terms complementary or complementarity refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between single-stranded molecules. The degree of complementarity between nucleic acid strands has significant effects on the efficiency and strength of hybridization between nucleic acid strands. This is of particular importance in amplification reactions, which depend upon binding between nucleic acids strands. The term "hybridizing sequences" preferably refers to sequences which display a sequence identity of at least 45%, more preferably at least 50%, more preferably at least 55%, more preferably at least 60%, more preferably at least 65%, more preferably at least 70%, more preferably at least 75%, more preferably at least 80%. more preferably at least 85%, more preferably at least 90%, more preferably at least 95%, more preferably at least 96%, more preferably at least 97%, more preferably at least 98% more preferably at least 99%, more preferably at least 99.5%, and most preferably 100% identity with a nucleic acid sequence as described herein encoding a 1,3-β-D-glucan synthase.

Also described herein are vectors containing a polynucleotide in context of the present invention. The present invention relates also to a vector comprising the polynucleotide in context of the present invention. The term "vector" as used herein particularly refers to plasmids, cosmids, viruses, bacteriophages and other vectors commonly used in genetic engineering. In a preferred embodiment, the vectors are suitable for the transformation, transduction and/or transfection of microorganisms as described herein, e.g., fungal cells, prokaryotic ells (e.g., bacteria), yeast, and the like. Specific examples of microorganisms in context with the present invention are *Schizophyllum commune, Sclerotium rolfsii, Sclerotium glucanicum, Sclerotium delphinii, Porodisculus pendulus, Botrytis cinerea, Laminaria* sp., *Lentinula edoles,* and *Monilinia fructigena*. In a particularly preferred embodiment, said vectors are suitable for stable transformation of the microorganism, for example to express the polypeptide having 1,3-β-D-glucan synthase activity as described herein.

Accordingly, in one aspect of the invention, the vector as provided is an expression vector. Generally, expression vectors have been widely described in the literature. As a rule, they may not only contain a selection marker gene and a replication-origin ensuring replication in the host selected, but also a promoter, and in most cases a termination signal for transcription. Between the promoter and the termination signal there is preferably at least one restriction site or a polylinker which enables the insertion of a nucleic acid sequence/molecule desired to be expressed.

It is to be understood that when the vector provided herein is generated by taking advantage of an expression vector known in the prior art that already comprises a promoter suitable to be employed in context of this invention, for example expression of a polypeptide having 1,3-β-D-glucan synthase activity as described herein. The nucleic acid construct is preferably inserted into that vector in a manner the resulting vector comprises only one promoter suitable to be employed in context of this invention. The skilled person knows how such insertion can be put into practice. For example, the promoter can be excised either from the nucleic acid construct or from the expression vector prior to ligation. A non-limiting example of the vector of the present invention is pBluescript II comprising the polynucleotide in context of the present invention. Further examples of vectors suitable to comprise the polynucleotide in context of the present invention to form the described herein are known in the art and comprise, for example pDrive, pTOPO, pUC19 and pUC21.

Generally, the present invention relates to all the embodiments described herein as well as to all permutations and combinations thereof. The following particular aspects of the present invention must not be construed as limiting the scope of the present invention on such aspects.

In one aspect, the present invention relates to a genetically modified microorganism capable of producing schizophyllan, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain.

In one aspect, the present invention relates to a genetically modified microorganism capable of producing schizophyllan, characterized in that said genetically modified microorganism contains at least one copy more of a polynucleotide encoding a polypeptide having 1,3-β-D-glucan synthase-activity compared to a corresponding non-modified control microorganism of the same strain.

In another aspect, the present invention relates to a genetically modified microorganism of the species *Schizoyphyllum commune*, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain.

In another aspect, the present invention relates to a genetically modified microorganism of the species *Schizoyphyllum commune*, characterized in that said genetically modified microorganism contains at least one copy more of a polynucleotide encoding a polypeptide having 1,3-β-D-glucan synthase-activity compared to a corresponding non-modified control microorganism of the same strain.

In one aspect, the present invention relates to a genetically modified microorganism capable of producing scleroglucan, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain.

In another aspect, the present invention relates to a genetically modified microorganism capable of producing scleroglucan, characterized in that said genetically modified microorganism contains at least one copy more of a polynucleotide encoding a polypeptide having 1,3-β-D-glucan synthase-activity compared to a corresponding non-modified control microorganism of the same strain.

In another aspect, the present invention relates to a genetically modified microorganism of the species *Sclerotium rolfsii*, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain.

In another aspect, the present invention relates to a genetically modified microorganism of the species *Sclerotium rolfsii*, characterized in that said genetically modified microorganism contains at least one copy more of a polynucleotide encoding a polypeptide having 1,3-β-D-glucan synthase-activity compared to a corresponding non-modified control microorganism of the same strain.

In another aspect, the present invention relates to a genetically modified microorganism capable of producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15.

In another aspect, the present invention relates to a genetically modified microorganism capable of producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, characterized in that said genetically modified microorganism contains at least one copy more of a polynucleotide encoding a polypeptide having 1,3-β-D-glucan synthase-activity compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15.

In another aspect, the present invention relates to a genetically modified microorganism capable of producing schizophyllan, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polynucleotide is at least 70%, 75%, 80%, 85%, 90%, 95%, 98%, 97%, 98%, 99%, 99.5%, or 100% identical to SEQ ID NO: 1, 3, 5, 7, 9, 11, 13 or 15.

In another aspect, the present invention relates to a genetically modified microorganism capable of producing schizophyllan, characterized in that said genetically modified microorganism contains at least one copy more of a polynucleotide encoding a polypeptide having 1,3-β-D-glucan synthase-activity compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15.

In another aspect, the present invention relates to a genetically modified microorganism of the species Schizoyphyllum commune, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15.

In another aspect, the present invention relates to a genetically modified microorganism of the species Schizoyphyllum commune, characterized in that said genetically modified microorganism contains at least one copy more of a polynucleotide encoding a polypeptide having 1,3-β-D-glucan synthase-activity compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15.

In another aspect, the present invention relates to a genetically modified microorganism capable of producing scleroglucan, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15.

In another aspect, the present invention relates to a genetically modified microorganism capable of producing scleroglucan, characterized in that said genetically modified microorganism contains at least one copy more of a polynucleotide encoding a polypeptide having 1,3-β-D-glucan synthase-activity compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15.

In another aspect, the present invention relates to a genetically modified microorganism of the species Sclerotium rolfsii, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15.

In another aspect, the present invention relates to a genetically modified microorganism of the species Sclerotium rolfsii, characterized in that said genetically modified microorganism contains at least one copy more of a polynucleotide encoding a polypeptide having 1,3-β-D-glucan synthase-activity compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15.

In another aspect, the present invention relates to a genetically modified microorganism capable of producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16.

In another aspect, the present invention relates to a genetically modified microorganism capable of producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, characterized in that said genetically modified microorganism contains at least one copy more of a polynucleotide encoding a polypeptide having 1,3-β-D-glucan synthase-activity compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16.

In another aspect, the present invention relates to a genetically modified microorganism capable of producing schizophyllan, characterized in that said to genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16.

In another aspect, the present invention relates to a genetically modified microorganism capable of producing schizophyllan, characterized in that said genetically modified microorganism contains at least one copy more of a polynucleotide encoding a polypeptide having 1,3-β-D-glucan synthase-activity compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16.

In another aspect, the present invention relates to a genetically modified microorganism of the species Schizoyphyllum commune, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16.

In another aspect, the present invention relates to a genetically modified microorganism of the species *Schizoyphyllum commune*, characterized in that said genetically modified microorganism contains at least one copy more of a polynucleotide encoding a polypeptide having 1,3-β-D-glucan synthase-activity compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16.

In another aspect, the present invention relates to a genetically modified to microorganism capable of producing scleroglucan, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16.

In another aspect, the present invention relates to a genetically modified microorganism capable of producing scleroglucan, characterized in that said genetically modified microorganism contains at least one copy more of a polynucleotide encoding a polypeptide having 1,3-β-D-glucan synthase-activity compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16.

In another aspect, the present invention relates to a genetically modified microorganism of the species *Sclerotium rolfsii*, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16.

In another aspect, the present invention relates to a genetically modified microorganism of the species *Sclerotium rolfsii*, characterized in that said genetically modified microorganism contains at least one copy more of a polynucleotide encoding a polypeptide having 1,3-β-D-glucan synthase-activity compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16.

In another aspect, the present invention relates to the use of a polynucleotide encoding a polypeptide having 1,3-β-D-glucan synthase-activity for producing schizophyllan.

In another aspect, the present invention relates to the use of a polynucleotide encoding a polypeptide having 1,3-β-D-glucan synthase-activity for producing scleroglucan.

In another aspect, the present invention relates to the use of a polynucleotide encoding a polypeptide having 1,3-β-D-glucan synthase-activity for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15.

In another aspect, the present invention relates to the use of a polynucleotide encoding a polypeptide having 1,3-β-D-glucan synthase-activity for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, wherein said polypeptide is at least 70%, 75%, 80%, 85%, 90%, 95%, 96%, 97%, 98%, 99%, 99.5%, or 100% identical to SEQ ID NO: 6, 8, 14 or 16.

In another aspect, the present invention relates to the use of a polynucleotide encoding a polypeptide having 1,3-β-D-glucan synthase-activity for producing schizophyllan, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15.

In another aspect, the present invention relates to the use of a polynucleotide encoding a polypeptide having 1,3-β-D-glucan synthase-activity for producing schizophyllan, wherein said polypeptide is at least 70%, 75%, 80%, 85%, 90%, 95%, 96%, 97%, 98%, 99%, 99.5%, or 100% identical to SEQ ID NO: 6, 8, 14 or 16.

In another aspect, the present invention relates to the use of a polynucleotide encoding a polypeptide having 1,3-β-D-glucan synthase-activity for producing scleroglucan, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15.

In another aspect, the present invention relates to the use of a polynucleotide encoding a polypeptide having 1,3-β-D-glucan synthase-activity for producing scleroglucan, wherein said polypeptide is at least 70%, 75%, 80%, 85%, 90%, 95%, 96%, 97%, 98%, 99%, 99.5%, or 100% identical to SEQ ID NO: 6, 8, 14 or 16.

In another aspect, the present invention relates to the use of a polypeptide having 1,3-β-D-glucan synthase-activity for producing schizophyllan.

In another aspect, the present invention relates to the use of a polypeptide having 1,3-β-D-glucan synthase-activity for producing scleroglucan.

In another aspect, the present invention relates to the use of polypeptide having 1,3-β-D-glucan synthase-activity for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, wherein said polypeptide is at least 70%, 75%, 80%, 85%, 90%, 95%, 96%, 97%, 98%, 99%, 99.5%, or 100% identical to SEQ ID NO: 6, 8, 14 or 16.

In another aspect, the present invention relates to the use of a polypeptide having 1,3-β-D-glucan synthase-activity for producing schizophyllan, wherein said polypeptide is at least 70%, 75%, 80%, 85%, 90%, 95%, 96%, 97%, 98%, 99%, 99.5%, or 100% identical to SEQ ID NO: 6, 8, 14 or 16.

In another aspect, the present invention relates to the use of polypeptide having 1,3-β-D-glucan synthase-activity for producing scleroglucan, wherein said polypeptide is at least 70%, 75%, 80%, 85%, 90%, 95%, 96%, 97%, 98%, 99%, 99.5%, or 100% identical to SEQ ID NO: 6, 8, 14 or 16.

In another aspect, the present invention relates to the use of a genetically modified microorganism capable of producing schizophyllan, wherein said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3.

In another aspect, the present invention relates to the use of a genetically modified microorganism capable of producing schizophyllan, wherein said genetically modified microorganism contains at least one copy more of a polynucleotide encoding a polypeptide having 1,3-β-D-glucan synthase-activity compared to a corresponding non-modified control microorganism of the same strain, for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3.

In another aspect, the present invention relates to the use of a genetically modified microorganism capable of producing schizophyllan, wherein said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, for producing schizophyllan.

In another aspect, the present invention relates to the use of a genetically modified microorganism capable of producing schizophyllan, wherein said genetically modified microorganism contains at least one copy more of a polynucleotide encoding a polypeptide having 1,3-β-D-glucan synthase-activity compared to a corresponding non-modified control microorganism of the same strain, for producing schizophyllan.

In another aspect, the present invention relates to the use of a genetically modified microorganism capable of producing schizophyllan, wherein said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, for producing scleroglucan.

In another aspect, the present invention relates to the use of a genetically modified microorganism capable of producing schizophyllan, wherein said genetically modified microorganism contains at least one copy more of a polynucleotide encoding a polypeptide having 1,3-β-D-glucan synthase-activity compared to a corresponding non-modified control microorganism of the same strain, for producing scleroglucan.

In another aspect, the present invention relates to the use of a genetically modified microorganism of the species *Schizoyphyllum commune*, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3.

In another aspect, the present invention relates to the use of a genetically modified microorganism of the species *Schizoyphyllum commune*, characterized in that said genetically modified microorganism contains at least one copy more of a polynucleotide encoding a polypeptide having 1,3-β-D-glucan synthase-activity compared to a corresponding non-modified control microorganism of the same strain, for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3.

In another aspect, the present invention relates to the use of a genetically modified microorganism of the species *Schizoyphyllum commune*, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, for producing schizophyllan.

In another aspect, the present invention relates to the use of a genetically modified microorganism of the species *Schizoyphyllum commune*, characterized in that said genetically modified microorganism contains at least one copy more of a polynucleotide encoding a polypeptide having 1,3-β-D-glucan synthase-activity compared to a corresponding non-modified control microorganism of the same strain, for producing schizophyllan.

In another aspect, the present invention relates to the use of a genetically modified microorganism of the species *Schizoyphyllum commune*, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, for producing scleroglucan.

In another aspect, the present invention relates to the use of a genetically modified microorganism of the species *Schizoyphyllum commune*, characterized in that said genetically modified microorganism contains at least one copy more of a polynucleotide encoding a polypeptide having 1,3-β-D-glucan synthase-activity compared to a corresponding non-modified control microorganism of the same strain, for producing scleroglucan.

In another aspect, the present invention relates to the use of a genetically modified microorganism capable of producing scleroglucan, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3.

In another aspect, the present invention relates to the use of a genetically modified microorganism capable of producing scleroglucan, characterized in that said genetically modified microorganism contains at least one copy more of a polynucleotide encoding a polypeptide having 1,3-β-D-glucan synthase-activity compared to a corresponding non-modified control microorganism of the same strain, for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3.

In another aspect, the present invention relates to the use of a genetically modified microorganism capable of producing scleroglucan, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, for producing schizophyllan.

In another aspect, the present invention relates to the use of a genetically modified microorganism capable of producing scleroglucan, characterized in that said genetically modified microorganism contains at least one copy more of a polynucleotide encoding a polypeptide having 1,3-β-D-glucan synthase-activity compared to a corresponding non-modified control microorganism of the same strain, for producing schizophyllan.

In another aspect, the present invention relates to the use of a genetically modified microorganism capable of producing scleroglucan, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, for producing scleroglucan.

In another aspect, the present invention relates to the use of a genetically modified microorganism capable of producing scleroglucan, characterized in that said genetically modified microorganism contains at least one copy more of a polynucleotide encoding a polypeptide having 1,3-β-D-glucan synthase-activity compared to a corresponding non-modified control microorganism of the same strain, for producing scleroglucan.

In another aspect, the present invention relates to the use of a genetically modified microorganism of the species *Sclerotium rolfsii*, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3.

In another aspect, the present invention relates to the use of a genetically modified microorganism of the species *Sclerotium rolfsii*, characterized in that said genetically modified microorganism contains at least one copy more of a polynucleotide encoding a polypeptide having 1,3-β-D-glucan synthase-activity compared to a corresponding non-modified control microorganism of the same strain, for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3.

In another aspect, the present invention relates to the use of a genetically modified microorganism of the species *Sclerotium rolfsii*, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, for schizophyllan.

In another aspect, the present invention relates to the use of a genetically modified microorganism of the species *Sclerotium rolfsii*, characterized in that said genetically modified microorganism contains at least one copy more of a polynucleotide encoding a polypeptide having 1,3-β-D-glucan synthase-activity compared to a corresponding non-modified control microorganism of the same strain, for schizophyllan.

In another aspect, the present invention relates to the use of a genetically modified microorganism of the species *Sclerotium rolfsii*, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, for scleroglucan.

In another aspect, the present invention relates to the use of a genetically modified microorganism of the species *Sclerotium rolfsii*, characterized in that said genetically modified microorganism contains at least one copy more of a polynucleotide encoding a polypeptide having 1,3-β-D-glucan synthase-activity compared to a corresponding non-modified control microorganism of the same strain, for scleroglucan.

In another aspect, the present invention relates to the use of a genetically modified microorganism capable of producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, characterized in that said genetically modified microorganism overexpresses (i) a polynucleotide encoding a polypeptide having 1,3-β-glucan synthase-activity, and/or (ii) a polypeptide having 1,3-β-D-glucan synthase-activity, compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3.

In another aspect, the present invention relates to the use of a genetically modified microorganism capable of producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, characterized in that said genetically modified microorganism contains at least one copy more of a polynucleotide encoding a polypeptide having 1,3-β-D-glucan synthase-activity compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3.

In another aspect, the present invention relates to the use of a genetically modified microorganism capable of producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing schizophyllan.

In another aspect, the present invention relates to the use of a genetically modified microorganism capable of producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, characterized in that said genetically modified microorganism contains at least one copy more of a polynucleotide encoding a polypeptide having 1,3-β-D-glucan synthase-activity compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing schizophyllan.

In another aspect, the present invention relates to the use of a genetically modified microorganism capable of producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing scleroglucan.

In another aspect, the present invention relates to the use of a genetically modified microorganism capable of producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, characterized in that said genetically modified microorganism contains at least one copy more of a polynucleotide encoding a polypeptide having 1,3-β-D-glucan synthase-activity compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing scleroglucan.

In another aspect, the present invention relates to the use of a genetically modified microorganism capable of producing schizophyllan, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3.

In another aspect, the present invention relates to the use of a genetically modified microorganism capable of producing schizophyllan, characterized in that said genetically modified microorganism contains at least one copy more of a polynucleotide encoding a polypeptide having 1,3-β-D-glucan synthase-activity compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3.

In another aspect, the present invention relates to the use of a genetically modified microorganism capable of producing schizophyllan, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing schizophyllan.

In another aspect, the present invention relates to the use of a genetically modified microorganism capable of producing schizophyllan, characterized in that said genetically modified microorganism contains at least one copy more of a polynucleotide encoding a polypeptide having 1,3-β-D-glucan synthase-activity compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing schizophyllan.

In another aspect, the present invention relates to the use of a genetically modified microorganism capable of producing schizophyllan, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing scleroglucan.

In another aspect, the present invention relates to the use of a genetically modified microorganism capable of producing schizophyllan, characterized in that said genetically modified microorganism contains at least one copy more of a polynucleotide encoding a polypeptide having 1,3-β-D-glucan synthase-activity compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing scleroglucan.

In another aspect, the present invention relates to the use of a genetically modified microorganism of the species *Schizoyphyllum commune*, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3.

In another aspect, the present invention relates to the use of a genetically modified microorganism of the species *Schizoyphyllum commune*, characterized in that said genetically modified microorganism contains at least one copy more of a polynucleotide encoding a polypeptide having 1,3-β-glucan synthase-activity compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3.

In another aspect, the present invention relates to the use of a genetically modified microorganism of the species *Schizophyllum commune*, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing schizophyllan.

In another aspect, the present invention relates to the use of a genetically modified microorganism of the species *Schizophyllum commune*, characterized in that said genetically modified microorganism contains at least one copy more of a polynucleotide encoding a polypeptide having 1,3-β-D-glucan synthase-activity compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing schizophyllan.

In another aspect, the present invention relates to the use of a genetically modified microorganism of the species *Schizophyllum commune*, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing scleroglucan.

In another aspect, the present invention relates to the use of a genetically modified microorganism of the species *Schizophyllum commune*, characterized in that said genetically modified microorganism contains at least one copy more of a polynucleotide encoding a polypeptide having 1,3-β-D-glucan synthase-activity compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing scleroglucan.

In another aspect, the present invention relates to the use of a genetically modified microorganism capable of producing scleroglucan, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3.

In another aspect, the present invention relates to the use of a genetically modified microorganism capable of producing scleroglucan, characterized in that said genetically modified microorganism contains at least one copy more of a polynucleotide encoding a polypeptide having 1,3-β-D-glucan synthase-activity compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3.

In another aspect, the present invention relates to a genetically modified microorganism capable of producing scleroglucan, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing schizophyllan.

In another aspect, the present invention relates to a genetically modified microorganism capable of producing scleroglucan, characterized in that said genetically modified microorganism contains at least one copy more of a polynucleotide encoding a polypeptide having 1,3-β-D-glucan synthase-activity compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing schizophyllan.

In another aspect, the present invention relates to the use of a genetically modified microorganism capable of producing scleroglucan, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing scleroglucan.

In another aspect, the present invention relates to the use of a genetically modified microorganism capable of producing scleroglucan, characterized in that said genetically modified microorganism contains at least one copy more of a polynucleotide encoding a polypeptide having 1,3-β-D-glucan synthase-activity compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing scleroglucan.

In another aspect, the present invention relates to the use of a genetically modified microorganism of the species *Sclerotium rolfsii*, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3.

In another aspect, the present invention relates to the use of a genetically modified microorganism of the species *Sclerotium rolfsii*, characterized in that said genetically modified microorganism contains at least one copy more of a polynucleotide encoding a polypeptide having 1,3-β-D-glucan synthase-activity compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing a polymer consisting of a linear main chain of β-D-(1-3)-glucopyranosyl units having a single β-D-glucopyranosyl unit (1-6) linked to a β-D-glucopyranosyl unit of the linear to main chain with an average branching degree of about 0.3.

In another aspect, the present invention relates to the use of a genetically modified microorganism of the species *Sclerotium rolfsii*, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing schizophyllan.

In another aspect, the present invention relates to the use of a genetically modified microorganism of the species *Sclerotium rolfsii*, characterized in that said genetically modified microorganism contains at least one copy more of a polynucleotide encoding a polypeptide having 1,3-β-D-glucan synthase-activity compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing schizophyllan.

In another aspect, the present invention relates to the use of a genetically modified microorganism of the species *Sclerotium rolfsii*, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing scleroglucan.

In another aspect, the present invention relates to the use of a genetically modified microorganism of the species *Sclerotium rolfsii*, characterized in that said genetically modified microorganism contains at least one copy more of a polynucleotide encoding a polypeptide having 1,3-β-D-glucan synthase-activity compared to a corresponding non-modified control microorganism of the same strain, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15, for producing scleroglucan.

In another aspect, the present invention relates to the use of a genetically modified microorganism capable of producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3.

In another aspect, the present invention relates to the use of a genetically modified microorganism capable of producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, characterized in that said genetically modified microorganism contains at least one copy more of a polynucleotide encoding a polypeptide having 1,3-β-D-glucan synthase-activity compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3.

In another aspect, the present invention relates to the use of a genetically modified microorganism capable of producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing schizophyllan.

In another aspect, the present invention relates to the use of a genetically modified microorganism capable of producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, characterized in that said genetically modified microorganism contains at least one copy more of a polynucleotide encoding a polypeptide having 1,3-β-D-glucan synthase-activity compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing schizophyllan.

In another aspect, the present invention relates to the use of a genetically modified microorganism capable of producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing scleroglucan.

In another aspect, the present invention relates to the use of a genetically modified microorganism capable of producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, characterized in that said genetically modified microorganism contains at least one copy more of a polynucleotide encoding a polypeptide having 1,3-β-D-glucan synthase-activity compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing scleroglucan.

In another aspect, the present invention relates to the use of a genetically modified microorganism capable of producing schizophyllan, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3.

In another aspect, the present invention relates to the use of a genetically modified microorganism capable of producing schizophyllan, characterized in that said genetically modified microorganism contains at least one copy more of a polynucleotide encoding a polypeptide having 1,3-β-D-glucan synthase-activity compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3.

In another aspect, the present invention relates to the use of a genetically modified microorganism capable of producing schizophyllan, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing schizophyllan.

In another aspect, the present invention relates to the use of a genetically modified microorganism capable of producing schizophyllan, characterized in that said genetically modified microorganism contains at least one copy more of a polynucleotide encoding a polypeptide having 1,3-β-D-glucan synthase-activity compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing schizophyllan.

In another aspect, the present invention relates to the use of a genetically modified microorganism capable of producing schizophyllan, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing scleroglucan.

In another aspect, the present invention relates to the use of a genetically modified microorganism capable of producing schizophyllan, characterized in that said genetically modified microorganism contains at least one copy more of a polynucleotide encoding a polypeptide having 1,3-β-D-glucan synthase-activity compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing scleroglucan.

In another aspect, the present invention relates to the use of a genetically modified microorganism of the species *Schizoyphyllum commune*, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3.

In another aspect, the present invention relates to the use of a genetically modified microorganism of the species *Schizoyphyllum commune*, characterized in that said genetically modified microorganism contains at least one copy more of a polynucleotide encoding a polypeptide having 1,3-β-D-glucan synthase-activity compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3.

In another aspect, the present invention relates to the use of a genetically modified microorganism of the species *Schizoyphyllum commune*, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing schizophyllan.

In another aspect, the present invention relates to the use of a genetically modified microorganism of the species *Schizoyphyllum commune*, characterized in that said genetically modified microorganism contains at least one copy more of a polynucleotide encoding a polypeptide having 1,3-β-D-glucan synthase-activity compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing schizophyllan.

In another aspect, the present invention relates to the use of a genetically modified microorganism of the species *Schizophyllum commune*, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing scleroglucan.

In another aspect, the present invention relates to the use of a genetically modified microorganism of the species *Schizophyllum commune*, characterized in that said genetically modified microorganism contains at least one copy more of a polynucleotide encoding a polypeptide having 1,3-β-D-glucan synthase-activity compared to a corresponding non-modified control microorganism of the same strain, wherein said polypeptide is at least 70%, 75%, 80%, 85%, 90%, 95%, 96%, 97%, to 98%, 99%, 99.5%, or 100% identical to SEQ ID NO: 6, 8, 14 or 16, for producing scleroglucan.

In another aspect, the present invention relates to the use of a genetically modified microorganism capable of producing scleroglucan, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing a polymer consisting of a linear main chain of β-D-(1-3)-glucopyranosyl units having a single β-D-glucopyranosyl unit (1-6) linked to a 1-D-glucopyranosyl unit of the linear main chain with an average branching degree of about 0.3.

In another aspect, the present invention relates to the use of a genetically modified microorganism capable of producing scleroglucan, characterized in that said genetically modified microorganism contains at least one copy more of a polynucleotide encoding a polypeptide having 1,3-β-D-glucan synthase-activity compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3.

In another aspect, the present invention relates to the use of a genetically modified microorganism capable of producing scleroglucan, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing schizophyllan.

In another aspect, the present invention relates to the use of a genetically modified microorganism capable of producing scleroglucan, characterized in that said genetically modified microorganism contains at least one copy more of a polynucleotide encoding a polypeptide having 1,3-β-D-glucan synthase-activity compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing schizophyllan.

In another aspect, the present invention relates to the use of a genetically modified microorganism capable of producing scleroglucan, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing scleroglucan.

In another aspect, the present invention relates to the use of a genetically modified microorganism capable of producing scleroglucan, characterized in that said genetically modified microorganism contains at least one copy more of a polynucleotide encoding a polypeptide having 1,3-β-D-glucan synthase-activity compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing scleroglucan.

In another aspect, the present invention relates to the use of a genetically modified microorganism of the species *Sclerotium rolfsii*, characterized in that said genetically modified microorganism overexpresses (i) a polynucleotide encoding a polypeptide to having 1,3-β-D-glucan synthase-activity, and/or (ii) a polypeptide having 1,3-β-D-glucan synthase-activity, compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3.

In another aspect, the present invention relates to the use of a genetically modified microorganism of the species *Sclerotium rolfsii*, characterized in that said genetically modified microorganism contains at least one copy more of a polynucleotide encoding a polypeptide having 1,3-β-D-glucan synthase-activity compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3.

In another aspect, the present invention relates to the use of a genetically modified microorganism of the species *Sclerotium rolfsii*, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing schizophyllan.

In another aspect, the present invention relates to the use of a genetically modified microorganism of the species *Sclerotium rolfsii*, characterized in that said genetically modified microorganism contains at least one copy more of a polynucleotide encoding a polypeptide having 1,3-β-D-glucan synthase-activity compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing schizophyllan.

In another aspect, the present invention relates to the use of a genetically modified microorganism of the species *Sclerotium rolfsii*, characterized in that said genetically modified microorganism overexpresses (i) a polynucleotide encoding a polypeptide having 1,3-β-D-glucan synthase-activity, and/or (ii) a polypeptide having 1,3-β-D-glucan synthase-activity, compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing scleroglucan.

In another aspect, the present invention relates to the use of a genetically modified microorganism of the species *Sclerotium rolfsii*, characterized in that said genetically modified microorganism contains at least one copy more of a polynucleotide encoding a polypeptide having 1,3-β-D-glucan synthase-activity compared to a corresponding non-modified control microorganism of the same strain, wherein said polypeptide is at least 70%, 75%, 80%, 85%, 90%, 95%, 96%, 97%, 98%, 99%, 99.5%, or 100% identical to SEQ ID NO: 6, 8, 14 or 16, for producing scleroglucan.

In another aspect, the present invention relates to a method of producing schizophyllan, said method comprising the steps of:
(a) introducing a strong (e.g., constitutive or inducible) promoter upstream of a polynucleotide encoding a polypeptide having 1,3-β-D-glucan synthase-activity thereby increasing the expression of said polynucleotide, or a polynucleotide encoding a polypeptide having 1,3-β-D-glucan synthase-activity into a microorganism being able to synthesize schizophyllan;
(b) culturing said microorganism of (a) in a medium, thereby allowing said microorganism to produce schizophyllan; and
(c) optionally recovering schizophyllan from the medium.

In another aspect, the present invention relates to a method of producing scleroglucan, said method comprising the steps of:
(a) introducing a strong (e.g., constitutive or inducible) promoter upstream of a polynucleotide encoding a polypeptide having 1,3-β-D-glucan synthase-activity thereby increasing the expression of said polynucleotide, or a polynucleotide encoding a polypeptide having 1,3-β-D-glucan synthase-activity into a microorganism being able to synthesize scleroglucan;
(b) culturing said microorganism of (a) in a medium, thereby allowing said microorganism to produce scleroglucan; and
(c) optionally recovering scleroglucan from the medium.

In another aspect, the present invention relates to a method of producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, said method comprising the steps of:
(a) introducing a strong (e.g., constitutive or inducible) promoter upstream of a polynucleotide encoding a polypeptide having 1,3-β-D-glucan synthase-activity thereby increasing the expression of said polynucleotide, or a polynucleotide encoding a polypeptide having 1,3-β-D-glucan synthase-activity into a microorganism of the species *Schizophyllum commune* being able to synthesize said polymer;
(b) culturing said microorganism of (a) in a medium, thereby allowing said microorganism to produce said polymer; and
(c) optionally recovering said polymer from the medium.

In another aspect, the present invention relates to a method of producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, said method comprising the steps of:
(a) introducing a strong (e.g., constitutive or inducible) promoter upstream of a polynucleotide encoding a polypeptide having 1,3-β-D-glucan synthase-activity thereby increasing the expression of said polynucleotide, or a polynucleotide encoding a polypeptide having 1,3-β-D-glucan synthase-activity into a microorganism of the species *Sclerotium rolfsii* being able to synthesize said polymer;
(b) culturing said microorganism of (a) in a medium, thereby allowing said is microorganism to produce said polymer; and
(c) optionally recovering said polymer from the medium.

In another aspect, the present invention relates to a method of producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, said method comprising the steps of:
(a) introducing a polynucleotide encoding a polypeptide having 1,3-β-D-glucan synthase-activity into a microorganism being able to synthesize said polymer, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15;
(b) culturing said microorganism of (a) in a medium, thereby allowing said microorganism to produce said polymer; and
(c) optionally recovering said polymer from the medium.

In another aspect, the present invention relates to a method of producing a polymer consisting of a linear main chain of β-D-(1-3)-glucopyranosyl units having a single β-D-glucopyranosyl unit (1-6) linked to a (1-D-glucopyranosyl unit of the linear main chain with an average branching degree of about 0.3, said method comprising the steps of:
(a) introducing a polynucleotide encoding a polypeptide having 1,3-β-D-glucan synthase-activity into a microorganism being able to synthesize said polymer, wherein said polypeptide is at least 70%, 75%, 80%, 85%, 90%, 95%, 96%, 97%, 98%, 99%, 99.5%, or 100% identical to SEQ ID NO: 6, 8, 14 or 16;
(b) culturing said microorganism of (a) in a medium, thereby allowing said microorganism to produce said polymer; and
(c) optionally recovering said polymer from the medium.

In another aspect, the present invention relates to a method of producing schizophyllan, said method comprising the steps of:
(a) introducing a polynucleotide encoding a polypeptide having 1,3-β-D-glucan synthase-activity into a microorganism being able to synthesize schizophyllan, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15;
(b) culturing said microorganism of (a) in a medium, thereby allowing said microorganism to produce schizophyllan; and
(c) optionally recovering schizophyllan from the medium.

In another aspect, the present invention relates to a method of producing scleroglucan, said method comprising the steps of:
(a) introducing a polynucleotide encoding a polypeptide having 1,3-β-D-glucan synthase-activity into a microorganism being able to synthesize scleroglucan, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15;
(b) culturing said microorganism of (a) in a medium, thereby allowing said microorganism to produce scleroglucan; and
(c) optionally recovering scleroglucan from the medium.

In another aspect, the present invention relates to a method of producing schizophyllan, said method comprising the steps of:
(a) introducing a polynucleotide encoding a polypeptide having 1,3-β-D-glucan synthase-activity into a microorganism being able to synthesize schizophyllan, wherein said polypeptide is at least 70%, 75%, 80%, 85%, 90%, 95%, 96%, 97%, 98%, 99%, 99.5%, or 100% identical to SEQ ID NO: 6, 8, 14 or 16;
(b) culturing said microorganism of (a) in a medium, thereby allowing said microorganism to produce schizophyllan; and
(c) optionally recovering schizophyllan from the medium.

In another aspect, the present invention relates to a method of producing scleroglucan, said method comprising the steps of:
(a) introducing a polynucleotide encoding a polypeptide having 1,3-β-D-glucan synthase-activity into a microorganism being able to synthesize scleroglucan, is wherein said polypeptide is at least 70%, 75%, 80%, 85%, 90%, 95%, 96%, 97%, 98%, 99%, 99.5%, or 100% identical to SEQ ID NO: 6, 8, 14 or 16;
(b) culturing said microorganism of (a) in a medium, thereby allowing said microorganism to produce scleroglucan; and
(c) optionally recovering scleroglucan from the medium.

In another aspect, the present invention relates to a method of producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, said method comprising the steps of:
(a) introducing a polynucleotide encoding a polypeptide having 1,3-β-D-glucan synthase-activity into a microorganism of the species *Schizophyllum commune* being able to synthesize said polymer, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15;
(b) culturing said microorganism of (a) in a medium, thereby allowing said microorganism to produce said polymer; and
(c) optionally recovering said polymer from the medium.

In another aspect, the present invention relates to a method of producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, said method comprising the steps of:
(a) introducing a polynucleotide encoding a polypeptide having 1,3-β-D-glucan synthase-activity into a microorganism of the species *Sclerotium rolfsii* being able to synthesize said polymer, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15;
(b) culturing said microorganism of (a) in a medium, thereby allowing said microorganism to produce said polymer; and
(c) optionally recovering said polymer from the medium.

In another aspect, the present invention relates to a method of producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, said method comprising the steps of:
(a) introducing a polynucleotide encoding a polypeptide having 1,3-β-D-glucan synthase-activity into a microorganism of the species *Schizophyllum commune* being able to synthesize said polymer, wherein said polypeptide is at least 70%, 75%, 80%, 85%, 90%, 95%, 96%, 97%, 98%, 99%, 99.5%, or 100% identical to SEQ ID NO: 6, 8, 14 or 16;
(b) culturing said microorganism of (a) in a medium, thereby allowing said microorganism to produce said polymer; and
(c) optionally recovering said polymer from the medium.

In another aspect, the present invention relates to a method of producing a polymer consisting of a linear main chain of β-D-(1-3)-glucopyranosyl units having a single β-D-glucopyranosyl unit (1-6) linked to a f-D-glucopyranosyl unit of the linear main chain with an average branching degree of about 0.3, said method comprising the steps of:
(a) introducing a polynucleotide encoding a polypeptide having 1,3-β-D-glucan synthase-activity into a microorganism of the species *Sclerotium rolfsii* being able to synthesize said polymer, wherein said polypeptide is at least 70%, 75%, 80%, 85%, 90%, 95%, 96%, 97%, 98%, 99%, 99.5%, or 100% identical to SEQ ID NO: 6, 8, 14 or 16;
(b) culturing said microorganism of (a) in a medium, thereby allowing said microorganism to produce said polymer; and
(c) optionally recovering said polymer from the medium.

In another aspect, the present invention relates to a method of producing schizophyllan, said method comprising the steps of:
(a) introducing a polynucleotide encoding a polypeptide having 1,3-β-D-glucan synthase-activity into a microorganism of the species *Schizophyllum commune* being able to synthesize said polymer, wherein said polynucleotide is at least is 70%, 75%, 80%, 85%, 90%, 95%, 96%, 97%, 98%, 99%, 99.5%, or 100% identical to SEQ ID NO: 1, 3, 5, 7, 9, 11, 13 or 15;
(b) culturing said microorganism of (a) in a medium, thereby allowing said microorganism to produce said polymer; and
(c) optionally recovering said polymer from the medium.

In another aspect, the present invention relates to a method of producing scleroglucan, said method comprising the steps of:
(a) introducing a polynucleotide encoding a polypeptide having 1,3-β-D-glucan synthase-activity into a microorganism of the species *Sclerotium rolfsii* being able to synthesize said polymer, wherein said polynucleotide is at least 70%, 75%, 80%, 85%, 90%, 95%, 96%, 97%, 98%, 99%, 99.5%, or 100% identical to SEQ ID NO: 1, 3, 5, 7, 9, 11, 13 or 15;
(b) culturing said microorganism of (a) in a medium, thereby allowing said microorganism to produce said polymer; and
(c) optionally recovering said polymer from the medium.

In another aspect, the present invention relates to a method of producing schizophyllan, said method comprising the steps of:
(a) introducing a polynucleotide encoding a polypeptide having 1,3-β-D-glucan synthase-activity into a microorganism of the species *Schizophyllum commune* being able to synthesize said polymer, wherein said polypeptide is at least 70%, 75%, 80%, 85%, 90%, 95%, 96%, 97%, 98%, 99%, 99.5%, or 100% identical to SEQ ID NO: 6, 8, 14 or 16;
(b) culturing said microorganism of (a) in a medium, thereby allowing said microorganism to produce said polymer; and
(c) optionally recovering said polymer from the medium.

In another aspect, the present invention relates to a method of producing scleroglucan, said method comprising the steps of:
(a) introducing a polynucleotide encoding a polypeptide having 1,3-β-D-glucan synthase-activity into a microorganism of the species *Sclerotium rolfsii* being able to synthesize said polymer, wherein said polypeptide is at least 70%, 75%, 80%, 85%, 90%, 95%, 96%, 97%, 98%, 99%, 99.5%, or 100% identical to SEQ ID NO: 6, 8, 14 or 16;
(b) culturing said microorganism of (a) in a medium, thereby allowing said microorganism to produce said polymer; and
(c) optionally recovering said polymer from the medium.

The Figures show:

FIG. 1 XRD Spectrum of Schizophyllan sample. The triple helix could be seen as an intensive diffraction at 5° 2θ and the amorphous region of the material gives broad diffraction in the range of 20-25° 2θ

Figure 2:
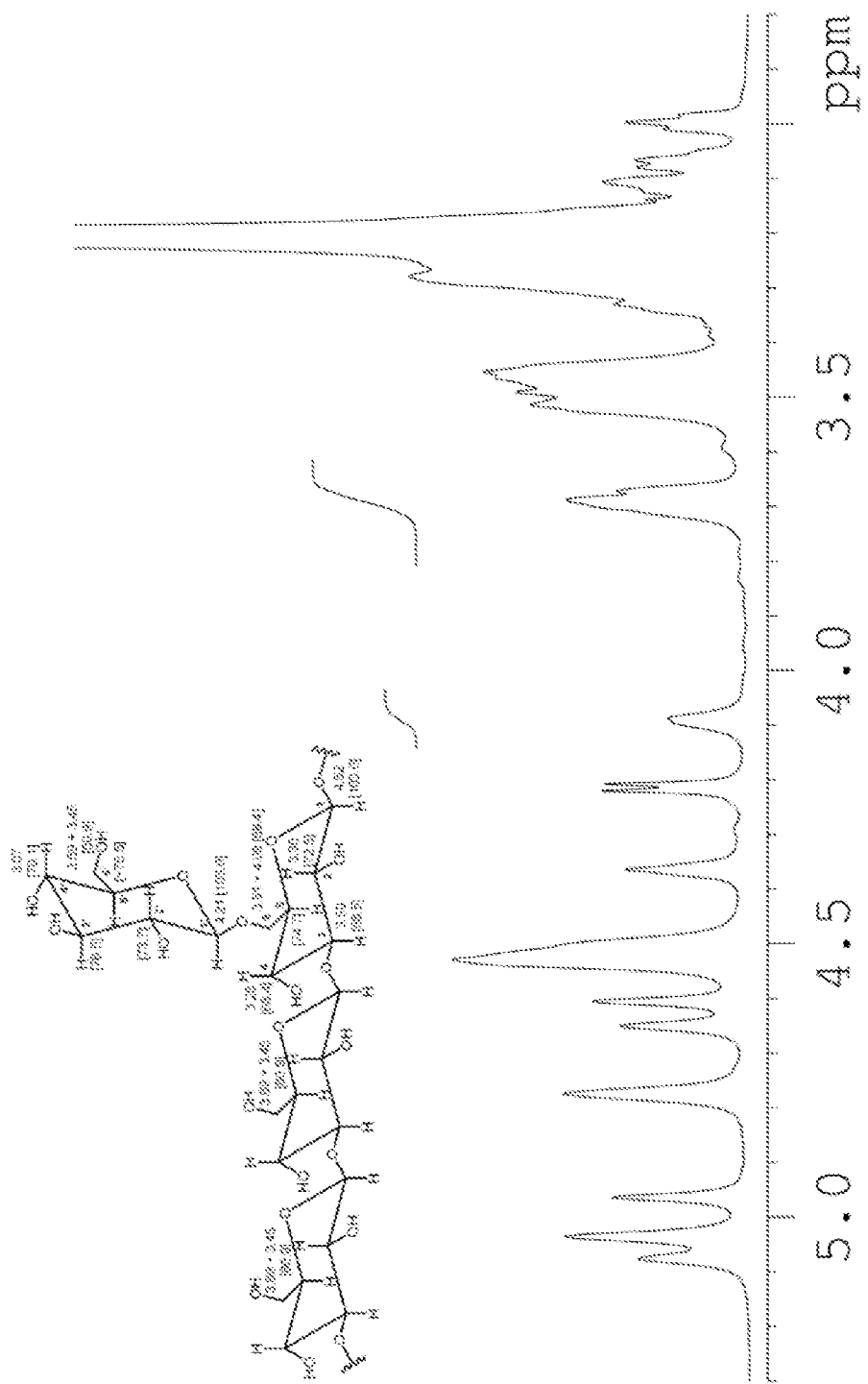

FIG. 2 $^1$H-NMR of schizophyllan (50 mg of gel) in [$D_6$]-DMSO measured at 50° C. (16 scans, 600 MHz). The substitution pattern of schizophyllan can be assigned from the integrations of the $CH_2OH$ at 3.7 ppm and $CH_2O$ (ether) at 4.1 ppm signals, the ratio was determined to be 3.3:1 indicating the correct repeating unit.

Figure 3:
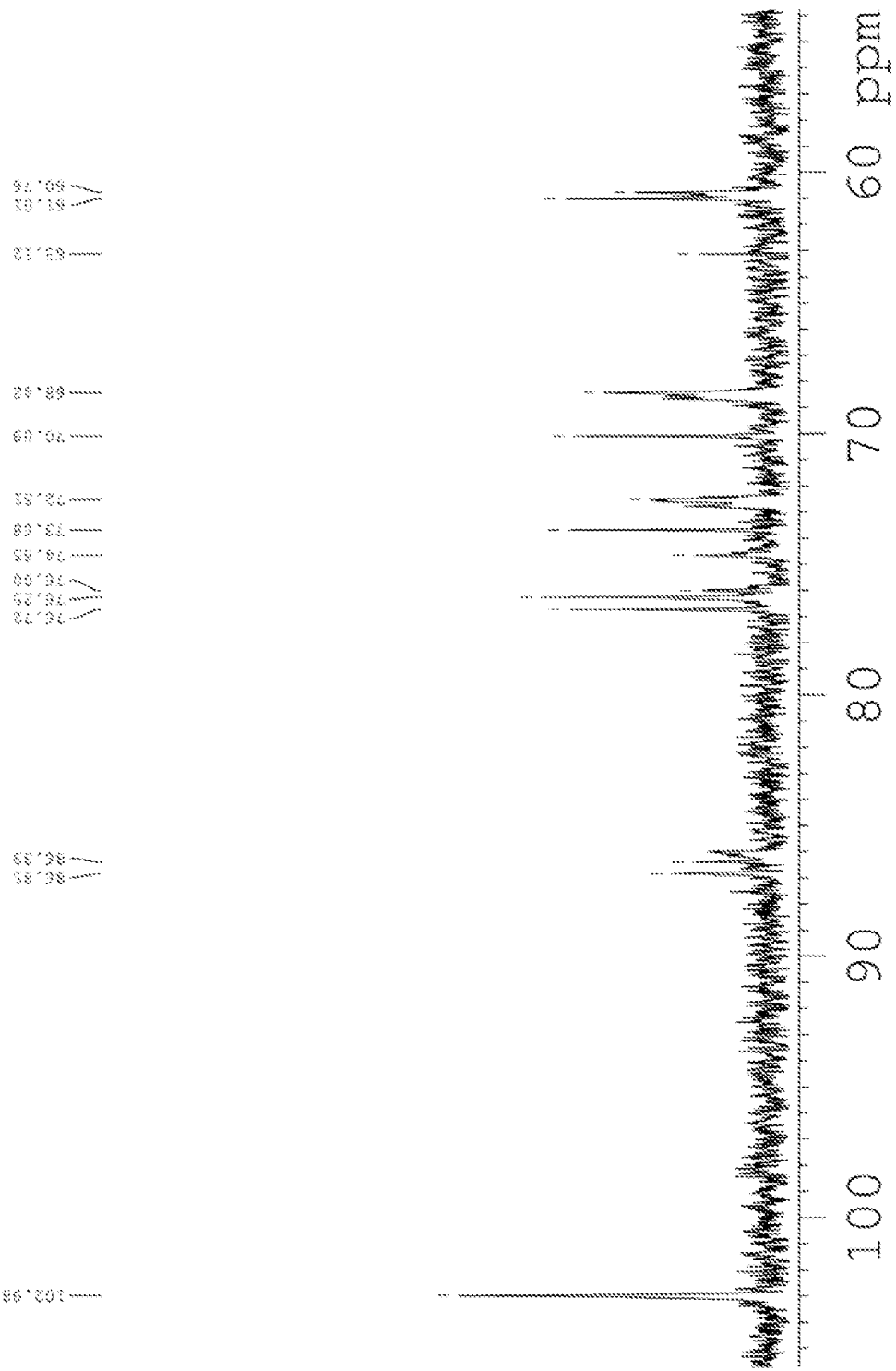

FIG. 3 13C-NMR of schizophyllan (50 mg of gel) in [D6]-DMSO measured at 50° C. (10.000 scans, 600 MHz). Assignment of the signals, δ (ppm): 60 and 61 (C-6), 68 (C6-C β(1-6)), 68 (C4-OH side glucose), 70 (C-2 backbone), 72 (C-2), 76 (C-5), 76.7 (C-3 side glucose), 86 (c-§backbone), 103 (C-1).

Figure 4:
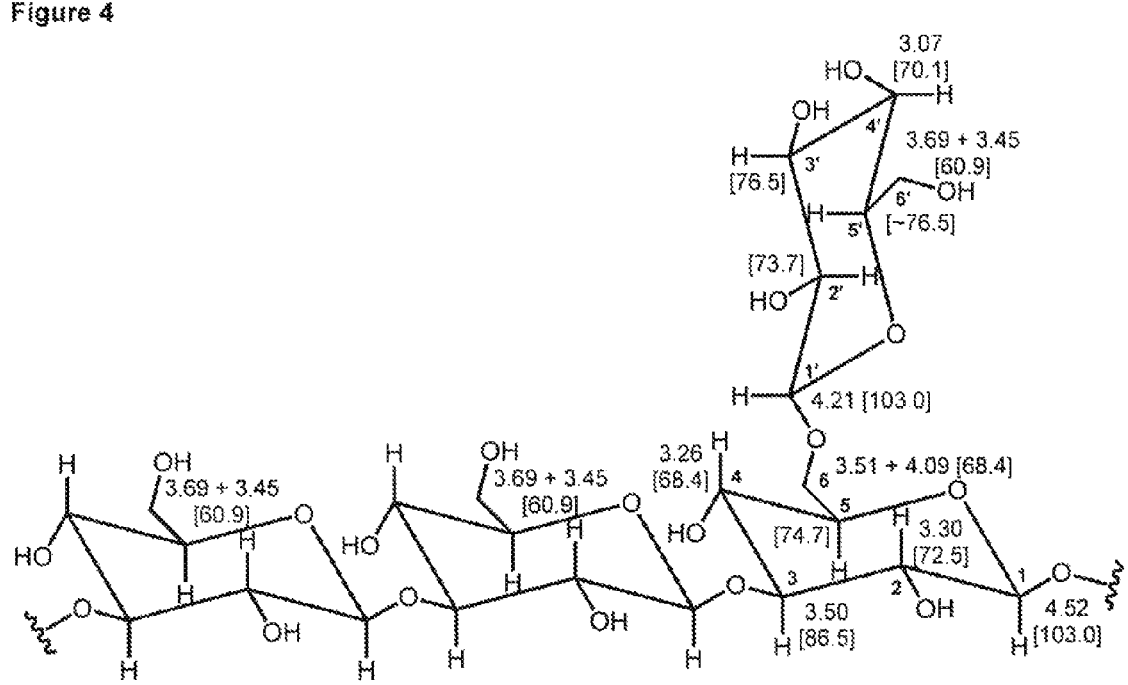

FIG. 4 Schematic picture of the repeating unit of schizophyllan.

The following Examples illustrate the present invention. Yet, the present invention must not be construed as being limited by the following Examples.

EXAMPLES

Example 1

Cloning of the β-1,3-Glucan Synthase Expression Plasmid (pGS_1) and Transformation into *S. commune*

In the genome of *Schizophyllum commune*, two genes encoding for β-1,3-glucan synthase were identified by using BLAST analysis (query genes: 1,3-β-glucan synthase sequence from *Mycosphaerella graminicola, Saccharomyces cerevisiae, Cryptococcus neoformans, Schizosaccharomyces pombe*); cf. Ullman, Biochem J (1997), 326: 929-942. In context of the present invention, it was proven that the overexpression of either of these β-1,3-glucan syntheses in *S. commune* results in increased yields of schizophyllan production.

Two expression plasmids (pGS_1)] and (pGS_2) (having pBluescript II as backbone) were generated carrying selection marker cassette ($amp^R$, ura1), strong constitutive promoter (Tef1 promoter), the synthase gene sequence (genomic sequence) and terminator sequence (Tef1 terminator).

All polynucleotide sequences described herein originate from *Schizopyllum commune*. The polynucleotides represented by SEQ ID NO: 1 and 3 (genes β-1,3-glucan synthases I and II of Lu15531, respectively) were synthesized by Eurofins MWG GmbH/Germany (eurofinsdna.com/de) according to the original sequence data sourced from JGI data base (jgi.doe.gov/Scommune; gene position: scaffold 2, 1194740-1200474 and gene position: scaffold 6, 1391067-1396555). The sequences were delivered on pMK plasmids (pMK_GS_1) and (pMK_GS_2) (Eurofins plasmids containing $kan^R$, ColE1 origin and genomic sequence of respective β-1,3-glucan synthases). The polynucleotides were further used for the cloning of the complete expression plasmid. Plasmid (pMK_GS_1) contained a polynucleotide represented by SEQ ID NO: 1 flanked by 5' SpeI and 3' SalI restriction sites. Plasmid (pMK_GS_2) contained a polynucleotide represented by SEQ ID NO: 3 flanked by 5' SpeI and 3' EcoRV restriction sites, respectively.

The individual elements (SEQ ID NO: 17, 18 and 33 (Tef1 promoter, Tef1 terminator and ura1) were isolated from the genomic DNA of *Schizophyllum commune* using PCR technology prepared by established microbiologic protocols (Sambrook, Current Protocols in Molecular Biology, Update May 9, 2012, Print ISSN: 1934-3639, Online ISSN: 1934-3647).

All plasmid isolations were conducted according to manufacturer's instructions using HiSpeed Maxi Kit (Quiagen/Germany). For this purpose, *Escherichia coli* XL10 cells (Stratagene) containing the final expression plasmid or one of the interim plasmids were cultivated in Luria-Bertoni (LB) medium (Sigma-Aldrich) containing 50 mg/ml Ampicillin (Sigma-Aldrich).

For isolation of tef1 promoter sequence (SEQ ID NO: 17), 50 μl PCR reaction contained 1.25 U PfuUltra Hotstart Mastermix (Stratagene) and 1.25 U Taq PCR Mastermix (Quiagen), 22 μl $H_2O$, 22.1 pmol of forward primer TefP_forw (XbaI) (SEQ ID NO: 21) and 100 pmol of reverse primer TefP_rev (SpeI) (SEQ ID NO: 22), and 100 ng of template (genomic DNA of *Schizophyllum commune*). The reaction was carried out in Gene Amp® PCR System 9700 Thermal Cycler from PE Applied Biosystems. The following program was used for the amplification: initial heating step up to 95° C. for 4 minutes was followed by 30 cycles of 30 seconds denaturing at 95° C., 30 seconds of annealing step at 55° C., 1 minute elongation step at 72° C., followed by one cycle at 72° C. for 10 minutes.

For amplification of the synthetic β-1,3-glucan synthase gene (SEQ ID NO: 1), 50 μl PCR reaction contained 1.25 U PfuUltra Hotstart Mastermix (Stratagene) and 1.25 U Taq PCR Mastermix (Quiagen), 22 μl $H_2O$, 100 pmol of forward primer GS1_forw (SpeI) (SEQ ID NO: 27) and 22 pmol of reverse primer GS1_rev (SalI) (SEQ ID NO: 28), 100 ng template (pMK_GS_1). The reaction was carried out in Gene Amp® PCR System 9700 Thermal Cycler from PE Applied Biosystems. The following program was used for the amplification: an initial heating step up to 95° C. for 4 minutes was followed by 30 cycles of 30 seconds denaturing at 95° C., 30 seconds of annealing step at 55° C., 8 minutes elongation step at 72° C., followed by one cycle at 72° C. for 10 minutes.

In the next PCR reaction step, fusion of the first two PCR products (tef1 promoter to (SEQ ID NO: 17) with β-1,3-glucan synthase gene (SEQ ID NO: 1) was carried out. 50 μl PCR reaction contained 1.25 U of Pwo Hotstart Mastermix (Roche) and 1.25 U Taq PCR Mastermix (Quiagen), 22 μl of $H_2O$, 22.1 pmol of each primer: Fusion TefP_GS1_forw (XbaI) (SEQ ID NO: 29) and Fusion TefP_GS1_rev (SalI) (SEQ ID NO: 30) and 100 ng of both templates. The reaction was carried out in Gene Amp® PCR System 9700 Thermal Cycler from PE Applied Biosystems. The following program was used for the fusion of both sequences: an initial heating step up to 95° C. for 4 minutes was followed by 30 cycles of 30 seconds denaturing at 95° C., 30 seconds of annealing step at 55° C., 8 minutes elongation step at 72° C., followed by one cycle at 72° C. for 10 minutes.

The product of the fusion PCR was treated with SalI and XbaI restriction enzymes (Roche) according to manufacturer's instructions and the vector (pBluescript 2KSP, Stratagene Cloning Systems) was linearized using the same restriction enzymes and subsequently treated with alkaline phosphatase (Roche) according to manufacturer's instructions. Both, the digested PCR product and the linearized pBluescript 2KSP vector, were ligated using T4 DNA Ligase (New England Biolabs, Inc., Beverly, Mass./USA) and transformed into *Escherichia coli* XL10 cells (Stratagene) according to manufacturer's instructions.

For isolation of tef1 terminator sequence (SEQ ID NO: 18) following PCR reaction was carried out: 50 µl PCR reaction contained 1.25 U of Pwo Hotstart Mastermix (Roche) and 1.25 U Taq PCR Mastermix (Quiagen), 22 µl of $H_2O$, 24 pmol of forward primer TefT_forw (SalI) (SEQ ID NO: 23) and 21 pmol of reverse primer TefT_rev (SalI) (SEQ ID NO: 24), and 100 ng of template (genomic DNA of *Schizophyllum commune*). The reaction was carried out in Gene Amp® PCR System 9700 Thermal Cycler from PE Applied Biosystems. The following program was used: an initial heating step up to 95° C. for 4 minutes was followed by 30 cycles of 30 seconds denaturing at 95° C., 30 seconds of annealing step at 60° C., 1 minute elongation step at 72° C., followed by one cycle at 72° C. for 10 minutes. The PCR product was treated with SalI restriction enzyme (Roche) and ligated with the plasmid containing tef1 promoter and β-1,3-glucan synthase, which was before linearized with SalI restriction enzyme (Roche) and treated with alkaline phosphatase (Roche) according to manufacturer's instructions. After ligation, the DNA construct was transformed into *Escherichia coli* XL10 cells (Stratagene) according to manufacturer's instructions.

To enable screening of *Schizophyllum commune* strains after transformation with the β-1,3-glucan synthase expression, a plasmid selection marker (ura1; SEQ ID NO: 33) was introduced into the plasmid. For that purpose, ura1 gene was isolated from the genomic DNA of *Schizophyllum commune*. The PCR reaction contained 2.5 U of Pwo Hotstart Mastermix (Roche), 22 µl of $H_2O$, 21 pmol of forward primer Ura_forw (NotI) (SEQ ID NO: 19),38 pmol of reverse primer Ura_rev (XbaI) (SEQ ID NO: 20) and 100 ng of the template (genomic DNA of *Schizophyllum commune*). The reaction was carried out in Gene Amp® PCR System 9700 Thermal Cycler from PE Applied Biosystems. The following program was used: an initial heating step up to 95° C. for 4 minutes was followed by 30 cycles of 30 seconds denaturing at 95° C., 30 seconds of annealing step at 60° C., 2 minutes elongation step at 72° C., followed by one cycle at 72° C. for 10 minutes. The PCR Product was digested with XbaI and NotI restriction enzymes (Roche) and ligated into the XbaI/NotI site of the β-1,3-glucan synthase expression plasmid (pGS_1) using T4 DNA Ligase (New England Biolabs, Inc., Beverly, Mass./ USA). The resulting plasmid encoding β-1,3-glucan synthase with tef1 promoter and terminator, and containing ura1 selection marker was transformed into *Escherichia coli* XL10 cells (Stratagene) according to manufacturer's instructions.

For the transformation of *Schizophyllum commune* with the β-1,3-glucan synthase expression plasmid (pGS_1), plasmid preparation was carried out as follows. *Escherichia coli* XL10 cells containing the 1-1,3-glucan synthase expression plasmid were cultivated in Luria-Bertoni (LB) medium (Sigma-Aldrich) containing 50 mg/ml Ampicillin (Sigma-Aldrich) and the plasmid isolation was conducted according to manufacturer's instructions using HiSpeed Maxi Kit (Quiagen).

*Schizophyllum commune* (Lu15527; obtained from strain collection of University of Jena (Germany), Prof. E. Kothe, Jena University internal strain name: 12-43) was transformed based on the method described by van Peer et al. (van Peer, loc cit) as basis. The method was modified according to the description below.

For preparation of *S. commune* protoplasts, fresh culture was inoculated on a plate containing complex medium (CYM). For incubation at 26° C. for 2-3 days, plates were sealed with parafilm.

For inoculation of liquid preculture (50 ml working volume), the biomass from the plate was macerated for 1 minute at 13500 rpm using T 25 digital ULTRA-TURRAX®(IKA), inoculated in shaking flask containing liquid CYM medium and incubated at 30° C., 220 rpm for further 3 days. Main culture was inoculated with 15 ml of the preculture in 200 ml CYM medium and incubated further 3 days at 30° C. at 220 rpm. After finishing the culture growth, the main culture was divided in four 50 ml samples and centrifuged (4000 rpm, 15 min). Obtained pellet was washed twice with 1 M $MgSO_4$ (50 ml) (Roth). After washing, four samples were united and dissolved 50 ml 1M $MgSO_4$.

To enable cell wall lysis, 100 mg Caylase (Cayla, Toulouse, France) were dissolved in 1 mL 1 M $MgSO_4$ and added to the pellet suspension. The sample was incubated over night at 30° C. under slight shaking (70 rpm). Subsequently distilled water was added to the sample (in 1:1 ratio), which was then incubated under slight shaking (70 rpm) for further 5 min. After this step, cells were incubated without shaking for 10 min and subsequently centrifuged (1100 rpm, 20 min, 4° C.). After the supernatant was filtrated using Miracloth-Membrane, one volume of cold 1 M sorbitol was added and the sample was allowed to equilibrate for 10 min. Subsequently, the sample was centrifuged (2000 rpm, 20 min, 2° C.). Pellet was washed by re-suspending carefully in 1 M sorbitol and centrifugation step was repeated. Finally the protoplasts were re-suspended in 1 M sorbitol and 50 mM $CaCl_2$ at a concentration of $10^8$ protoplasts per ml.

DNA used for transformation was a circular plasmid (pGS_1) and the integration in the genome of *S. commune* was ectopic. To transform the protoplasts with the DNA, 100 µl protoplasts and 10 µl DNA (5-10 µg) were gently mixed and incubated for 60 min on ice. Subsequently, one volume of PEG 4000 (40%) was added and the sample was incubated for 5 to 10 min on ice. After adding 2.5 ml regeneration medium (complete medium containing 0.1 µg/ml Phleomycin and 0.5 M $MgSO_4$), the sample was incubated at 30° C., 70 rpm overnight.

After PEG mediated transformation, regenerated protoplasts were spread on petri dishes containing 40 ml solidified minimal medium: 2 g aspartic acid (Roth), 20 g glucose (Sigma), 0.5 g $MgSO_4$ (Roth), 0.5 g $KH_2PO_4$, 1 g $K_2HPO_4$ (both from Riedel-de Haën), 120 µg thiaminhydrochlorid (Roth) per liter, pH 6.3 containing 1% low melting agarose (Sigma). Selection plates were incubated 5 days at 30° C.

Example 2

Cloning of the β-1,3-Glucan Synthase Expression Plasmid [pGS_2] and Transformation into *S. commune*

The expression plasmid for the second β-1,3-glucan synthase (SEQ ID NO: 3) (pGS_2) was prepared analogously to the preparation of (pGS_1) as described above in Example 1.

As a source of the promoter sequence tef1 (SEQ ID NO: 17); the same PCR product as in Example 1 was used.

Polynucleotide represented by SEQ ID NO: 3 was amplified from the (pMK_GS_2) plasmid following PCR reaction: 50 μl PCR reaction contained 1.25 U PfuUltra Hotstart Mastermix (Stratagene) and 1.25 U Taq PCR Mastermix (Quiagen), 22 μl H$_2$O, 23 pmol of each primer: GS2_forw (SpeI)/ SEQ ID NO: 31) and GS2_rev (EcoRV) (SEQ ID NO: 32), 100 ng of template (pMK_GS_2). The reaction was carried out in Gene Amp® PCR System 9700 Thermal Cycler from PE Applied Biosystems. The following program was used for the amplification: an initial heating step up to 95° C. for 4 minutes was followed by 30 cycles of 30 seconds denaturing at 95° C., 30 seconds of annealing step at 53° C., 8 minutes elongation step at 72° C., followed by one cycle at 72° C. for 10 minutes.

For isolation of tef1 terminator sequence (SEQ ID NO: 18) and introduction of the EcoRV (5') and ApaI (3') sites, the following PCR reaction was carried out: 50 μl PCR reaction contained 1.25 U of Pwo Hotstart Mastermix (Roche) and 1.25 U Taq PCR Mastermix (Quiagen), 22 μl of H$_2$O, 37 pmol of forward primer TefT_forw (EcoRV) (SEQ ID NO: 25) and 25 pmol of reverse primer TefT_rev (ApaI) (SEQ ID NO: 26), and 100 ng of template (genomic DNA of *Schizophyllum commune*). The reaction was carried out in Gene Amp® PCR System 9700 Thermal Cycler from PE Applied Biosystems. The following program was used: an initial heating step up to 95° C. for 4 minutes was followed by 30 cycles of 30 seconds denaturing at 95° C., 30 seconds of annealing step at 58° C., 1 minute elongation step at 72° C., followed by one cycle at 72° C. for 10 minutes. The PCR product was treated with EcoRV and ApaI restriction enzyme (Roche) and ligated with the vector (pBluescript 2KSP, Stratagene Cloning Systems), which was before digested the same restriction enzymes. After ligation, the DNA construct was transformed into *Escherichia coli* XL10 cells (Stratagene), according to manufacturer's instructions.

Subsequently, tef1 promoter was cloned into the plasmid. For this purpose, the PCR product was digested with XbaI and SpeI (Roche) and ligated with the plasmid described above according to manufacturer's instructions, containing tef1 terminator which was linearized using XbaI and SpeI. The ligation was carried out as described in Example 1 herein. After ligation, the DNA construct was transformed into *Escherichia coli* XL10 cells (Stratagene) according to manufacturer's instructions.

Subsequently, ura1 was cloned into the plasmid. The same PCR product as in Example 1 was used. After digestion of the PCR product with NotI and XbaI, the fragment was cloned into the plasmid carrying the polynucleotide represented by SEQ ID NO: 7, tef1 promoter and terminator sequences. Before ligation, the plasmid was linearized by NotI and XbaI. Transformation was carried out as described above in Example 1.

Finally, β-1,3-glucan synthase (SEQ ID NO: 3) was ligated into the plasmid. For this purpose, the PCR product was treated with SpeI and EcoRV and ligated into the target expression plasmid as described above. Transformation was carried out as described above in Example 1.

Transformation of *Schizophyllum commune* with (pGS_2) followed as described in Example 1.

Example 3

Verification of the Functionality of the Engineered *S. commune* Strains

Genetically modified *S. commune* strains generated as described above were tested in shaking flasks for increased schizophyllan production. To assure the reproducibility of the results, a three-step cultivation was applied, consisting of two pre-cultures and one main culture as further described herein below.

For the cultivation of the genetically modified *Schizophyllum commune* strains, two different media were used. For cultivation on solid media, CYM medium (25 g agar (Difco), 20 g glucose (Sigma), 2 g trypticase peptone (Roth), 2 g yeast extract (Difco), 0.5 g MgSO$_4$×7H$_2$O (Roth), 0.5 g KH$_2$PO$_4$ and 1 g K$_2$HPO$_4$ (both from Riedel-de Haën) per liter H$_2$O) was used. Strains were inoculated on agar plates containing CYM medium covered with cellophane (to avoid mycelium growth into the agar) and incubated for three to four days at 26° C.

For the liquid cultures, the following medium was used (hereinafter referred to as "Standard Medium"): 30 g glucose (Sigma), 3 g yeast extract (Difco), 1 g KH$_2$PO$_4$ (Riedel-de Haën), 0.5 g MgSO$_4$×7H$_2$O (Roth) per liter H$_2$O.

For both pre-cultures and for main culture, 250 ml shaking flasks filled with 30 ml Standard Medium were used. The cultivation was carried out at 27° C. and 225 rpm. Before each inoculation, the biomass was homogenized for 1 minute at 13500 rpm using T 25 digital ULTRA-TURRAX® (IKA).

The first pre-culture was inoculated with 50 mg of wet biomass. The cultures were incubated for 72 hours. After 72 hours, the second pre-culture was started. The concentration of the homogenized wet biomass from the first pre-culture used for inoculation was 250 mg. Cultivation time was 45 hours. After 45 hours, the main culture was inoculated with 500 mg of homogenized wet biomass from the second pre-culture and cultivated for another 45 hours.

After the cultivation was finished, standard analytical methods as described herein below were applied to define the biomass concentration, schizophyllan concentration, ethanol concentration and residual glucose in medium. 50 ml aliquots of the cultures were stabilized with 3 g/l Acticide BW20 (Thor).

Ethanol and glucose concentration was estimated using HPLC method. For this purpose 14 ml of the culture were centrifuged (30 min, 8500 rpm). The supernatant was sterile-filtrated and 1 ml of the filtrate was injected for the HPLC analysis (HPLC cation exchanger: Aminex HPX-87-H, BIO-RAD with 0.5 M H$_2$SO$_4$, Roth, as eluent and 0.5 ml/min flow rate at 30° C.).

Due to the fact that schizophyllan consists only of glucose molecules, the quantification of this polymer can be done using standard analytical methods for glucose. 10 ml of the culture, 20 ml H$_2$O and 90 μl Acticide BW20 were mixed. The sample was digested for 24 h at 40° C. with β-glucanase (0.3 ml) (Erbslöh). After the incubation, the sample was centrifuged (30 minutes at 3400 g) and the supernatant was analyzed for glucose and ethanol content using HPLC cation exchanger (Aminex HPX-87-H, BIO-RAD) with 0.5 M H$_2$SO$_4$ (Roth) as eluent and 0.5 ml/min flow rate at 30° C.

For the biomass determination, the remaining biomass in form of pellet (after β-glucanase digestion sample was centrifuged) was washed twice with 50 ml H$_2$O, filtrated using Whatman-Filter (with determination of filter's weight before filtration), washed twice with H$_2$O and dried in HB43S drying scale from Mettler Toledo. Drying of the filter was carried out for 5 to 10 minutes at 180° C. Subsequently, weight of the dry filter was determined.

The evaluation of the results obtained in shaking flasks showed clear effect of the overexpression of both β-1,3-glucan synthases on the schizophyllan production. Because of the fact that in the expression plasmid was ectopically integrated into genome and the integration locus has an explicit effect on the expression of the target gene, 40 clones carrying the plasmid (pGS_1) and 40 clones carrying the to plasmid (pGS_2) were tested in shaking flask experiments. The increase of schizophyllan production in the genetically modified strains is shown in Table 1 in comparison to the non-modified *Schizophyllum commune* control strain. The results shown in the Table 1 refer to the best strain of each 40 strains tested. For classification of the strains, the amount of schizophyllan in the sample was decisive. 10 ml of the culture, 20 ml $H_2O$ and 90 μl Acticide BW20 were mixed. The sample was digested for 24 h at 40° C. with 0.3 ml β-glucanase (Erbslöh). After the incubation, the sample was centrifuged (30 minutes at 3400 g) and the supernatant was analyzed for glucose and ethanol content using HPLC cation exchanger (Aminex HPX-87-H, BIO-RAD) with 0.5 M $H_2SO_4$ (Roth) as eluent and 0.5 mil/min flow rate at 30° C.

In addition to increased yields of schizophyllan production in the genetically modified *S. commune* strains, a clear decrease in the synthesis of the by-product ethanol was observed. This can be an indication that the excess rate of glucose by up-regulated β-1,3-glucan synthase activity is metabolized more directly in the schizophyllan pathway instead of partly being used for ethanol synthesis.

TABLE 1

Comparison of *Schizophyllum commune* control strain with two genetically modified *S. commune* strains carrying glucan synthase expression plasmid (pGS_1) or (pGS_2).

| Strain | Schizophyllan [%] | EtOH [%] |
| --- | --- | --- |
| *S. commune* control strain | 100 | 100 |
| *S. commune* (pGS_1) | 220 | 9 |
| *S. commune* (pGS_2) | 215 | 3.6 |

Structure and Conformation Analysis of the Product

To assure that the polymer synthesized through genetically modified *S. commune* strains is schizophyllan, XRD and NMR methods were applied to confirm the structure of the molecule as follows.

Powder X-ray diffraction (XRD) allows rapid, non-destructive analysis of materials consisting of multiple components. Moreover, the sample preparation is straightforward. The data from the measurement is presented as a diffractogram in which the diffracted intensity (I) is shown as a function of scattering angle 2θ. The crystallinity of the given material can be determined by this measurement. In general, crystalline materials have reflection patterns of a series of sharp peaks whereas amorphous materials give a broad signals. Many polymers exhibit semicrystalline behaviour which can also be detected by XRD (Hammond, The basics of chrystallography and diffraction, $3^{rd}$ Ed., Oxford University Press 2009).

Sample Preparation from Aqueous Solution

Aqueous solution containing schizophyllan was poured in ethanol to precipitate schizophyllan. The precipitation was filtered and dried either in a vacuum oven. The dried sample was measured by XRD.

Sample Measurement and Results by XRD

Schizophyllan exhibits a triple helical structure. This was evident from the diffractogram of the precipitated and dried schizophyllan sample (FIG. 2). The triple helix could be seen as an intensive diffraction at 5° 2θ and the amorphous region of the material gives broad diffraction in the range of 20-25° 2θ (Hisamatsu, Carbohydr Res (1997), 298: 117).

Sample Measurement and Results by NMR

The NMR spectra were recorded on a Varian VNMRS 600 MHz system equipped with a $^{13}$C-enhanced cryo probe (inverse configuration) at ambient temperatures or at 50° C. using standard pulse sequences for $^1H$ and $^{13}C$.

It is known that schizophyllan has a triple helical structure formed by three β(1-3)-D-glucan chains held together by hydrogen bonds in water. This structure is shielded in the magnetic field due to the rigid, ordered conformation. This means that in NMR spectrum, chemical shifts for schizophyllan are not obtained (Rinaudo, Carbohydr Polym (1982), 2: 135; Vlachou, Carbohydr Polym (2001), 46: 349) (2D NMR). In order to investigate the molecular structure of schizophyllan and not the macromolecular structure consisting of triple helices and further to record the successful NMR spectra with a good signal-to-noise ratio, the conformation of the triple helix has to be changed. It is also known that the triple helix of schizophyllan can be altered to form a random coil structure by addition of DMSO. When the DMSO concentration exceeds a certain threshold values (i.e. 87%), the conformation change takes place; therefore deuterated $[D_6]$-DMSO was used as a solvent for the measurements. This conformation matter is important to take into consideration when conducting NMR experiments for schizophyllan. Hence, the sample was measured in $[D_6]$-DMSO, the well-resolved spectra can be obtained (FIGS. 2 and 3).

SUMMARY

The chemical structures of the materials from *S. commune* (GS_1) and *S. commune* (GS_2) strain was identified to be the correct for that of schizophyllan. In addition, the materials exhibit the triple helix conformations.

Sequences Referred to in the Present Application

TABLE 2

Assignment of SEQ ID NOs.

| SEQ ID NO: | type of sequence | description |
| --- | --- | --- |
| 1 | nucleotide sequence | Gene sequence* 1,3-β-D-glucan synthase I of *S. commune* strain Lu15531 |
| 2 | amino acid sequence | translation of SEQ ID NO: 5 |
| 3 | nucleotide sequence | Gene sequence* 1,3-β-D-glucan synthase II of *S. commune* strain Lu15531 |
| 4 | amino acid sequence | translation of SEQ ID NO: 7 |

TABLE 2-continued

Assignment of SEQ ID NOs.

| | | |
|---|---|---|
| 5 | nucleotide sequence | cDNA 1,3-β-D-glucan synthase I of *S. commune* strain Lu15531 |
| 6 | amino acid sequence | polypeptide sequence 1,3-β-D-glucan synthase I of *S. commune* strain Lu15531 |
| 7 | nucleotide sequence | cDNA 1,3-β-D-glucan synthase II of *S. commune* strain Lu15531 |
| 8 | amino acid sequence | polypeptide sequence 1,3-β-D-glucan synthase II of *S. commune* strain Lu15531 |
| 9 | nucleotide sequence | Gene sequence* 1,3-β-D-glucan synthase I of *S. commune* strain Lu15634 |
| 10 | amino acid sequence | translation of SEQ ID NO: 13 |
| 11 | nucleotide sequence | Gene sequence* 1,3-β-D-glucan synthase II of *S. commune* strain Lu15634 |
| 12 | amino acid sequence | translation of SEQ ID NO: 15 |
| 13 | nucleotide sequence | cDNA 1,3-β-D-glucan synthase I of *S. commune* strain Lu15634 |
| 14 | amino acid sequence | polypeptide sequence 1,3-β-D-glucan synthase I of *S. commune* strain Lu15634 |
| 15 | nucleotide sequence | cDNA 1,3-β-D-glucan synthase II of *S. commune* strain Lu15634 |
| 16 | amino acid sequence | polypeptide sequence 1,3-β-D-glucan synthase II of *S. commune* strain Lu15634 |
| 17 | nucleotide sequence | tef1 promoter from *S. commune* |
| 18 | nucleotide sequence | tef1 terminator from *S. commune* |
| 19 | nucleotide sequence | Ura_forw (NotI) primer |
| 20 | nucleotide sequence | Ura_rev (XbaI) primer |
| 21 | nucleotide sequence | TefP_forw (XbaI) primer |
| 22 | nucleotide sequence | TefP_rev (SpeI) primer |
| 23 | nucleotide sequence | TefT_forw (SalI) primer |
| 24 | nucleotide sequence | TefT_rev (SalI) primer |
| 25 | nucleotide sequence | TefT_forw (EcoRV) primer |
| 26 | nucleotide sequence | TefT_rev (ApaI) primer |
| 27 | nucleotide sequence | GS1_forw (SpeI) primer |
| 28 | nucleotide sequence | GS1_rev (SalI) primer |
| 29 | nucleotide sequence | Fusion TefP_GS1_forw (XbaI) primer |
| 30 | nucleotide sequence | Fusion TefP_GS1_rev (SalI) primer |
| 31 | nucleotide sequence | GS2_forw (SpeI) primer |
| 32 | nucleotide sequence | GS2_rev (EcoRV) primer |

TABLE 2-continued

Assignment of SEQ ID NOs.

| | | |
|---|---|---|
| | 33 | nucleotide sequence ura gene (*S. commune*) |
| | 34 | amino acid sequence Ura protein |

*Gene sequence includes introns and flanking regions. In the gene sequences below (for SEQ ID NOs. 1, 3, 9 and 11), predicted exons are shown in capital letters, introns are shown in lower case letters.

Gene sequence 1,3-β-D-glucan synthase I of *S. commune* strain Lu15531
DNA
*S. commune*

SEQ ID NO: 1

CCCGTCCCTCAAGGCCGTTCTTTCGCTGGCGACCGACCCGGTGTTCGCGAGAA

CCTGTTGTTTCTGACGATCATCAGCCCTTTCTTCTCGTCGCTCTTTAGCTCTCCC

TAGACCGTCTTTTACTCTACTCTTCGACGCACGCCATGTCCGGCCCAGGATATG

GCAGGAATCCATTCGACAATCCCCCGCCCAACAGAGGTCCCTATGGCCAGCAG

CCAGGTTTCCCGGGGCCCGGCCCTCGGCCTTACGACTCGGACGCGGACATGA

GCCAGACCTATGGCAGCACAACCAGGCTCGCCGGCAGTGCCGGTTACAGCGA

CAGAAACGgtgcgcacgtcgctaccgtacttcctcgatcgtcgattcacataccatgcagGCAGCTTCGAC

GGCGACCGCTCCTACGCGCCCTCAATTGACTCGCGCGCCAGCGTGCCCAGCAT

ATCGCCCTTCGCAGACCCGGGTATCGGGTCTAATGAGCCGTATCCCGCTTGGT

CGGTCGAACGCCAGATTCCCATGTCCACGGAGGAGATTGAGGACATCTTCCTC

GACCTCACCCAAAAGTTTGGCTTCCAGCGCGACTCCATGCGGAATACGgtgcgtga ataagcagcccactcgaccgcgggaacagcacaattgacctgtcacccagTTCGACTTCATGATGCAC

CTCCTCGATTCCCGTGCCTCGCGCATGACGCCCAACCAAGCTCTGCTCACGCTT

CACGCCGACTACATTGGTGGCCAGCATGCCAATTACCGGAAGTGGTATTTCGCC

GCACAGCTCAACCTCGATGACGCGGTCGGGCAAACCAATAACCCCGGTATCCA

GCGCTTGAAGACCATCAAGGGCGCTACGAAGACCAAGTCGCTCGACAGCGCAC

TCAACCGCTGGCGCAACGCGATGAACAACATGAGCCAGTACGATCGCCTCCGG

CAAATTGCGCTCTACCTCCTCTGCTGGGGTGAAGCAGGCAACATCCGTCTGGC

GCCCGAGTGCTTGTGCTTCATCTTCAAGTGCGCGGACGACTACTACAGAAGTCC

CGAGTGTCAGAACCGGATGGACCCCGTGCCGGAAGGGCTGTACCTGCAGACG

GTCATCAAGCCGCTCTATCGCTTCCTACGTGATCAGGCGTACGAAGTCGTTGAT

GGGAAGCAAGTGAAGCGCGAGAAGGACCACGACCAGATTATCGGTTATGACGA

CGTCAACCAGTTATTCTGGTATCCGGAAGGTTTGGCTAAGATCGTCATGTCGGA

CAACgtgcgtatgatcttatcggttaaaattcgtccgctcacatctttccagACACGACTTGTAGATGTAC

CTCCGGCGCAGCGGTTCATGAAGTTCGCCAAGATCGAGTGGAACCGCGTCTTC

TTCAAGACGTACTTTGAGAAGCGCTCTACTGCCCATCTCCTGGTCAACTTCAAC

CGTATATGGATCCTCCACGTCTCGATGTACTTCTTCTACACGGCATTCAACTCTC

CACGAGTCTACGCGCCGCACGGCAAACTCGACCCCTCCCCTGAGATGACCTGG

TCCGCGACTGCCCTTGGAGGCGCTGTGTCCACCATGATCATGATCCTTGCCACT

ATCGCGGAGTACACCTACATCCCCACGACATGGAACAATGCGTCGCACCTCAC

CACGCGGCTCATTTTCCTCCTGGTCATCCTCGCGCTCACTGCTGGCCCAACATT

CTATATCGCCATGATAGACGGACGCACGGACATCGGCCAAGTACCACTCATCGT

GGCCATAGTGCAGTTCTTCATCTCCGTCGTCGCCACCCTCGCTTTCGCTACCAT

TABLE 2-continued

Assignment of SEQ ID NOs.

```
CCCTTCTGGTCGCATGTTCGGCGACCGTGTGGCTGGCAAGTCAAGAAAGCACA

TGGCATCGCAGACGTTCACAGCGTCGTACCCGTCCATGAAGCGGTCATCTCGC

GTAGCGAGTATCATGCTGTGGCTTTTGGTCTTTGGCTGCAAATACGTCGAGTCT

TACTTCTTCTTGACGTCCTCCTTCTCCAGCCCGATCGCGGTCATGGCGCGTACG

AAGGTACAGGGCTGCAACGACCGTATCTTCGGCAGCCAGCTGTGCACGAATCA

GGTCCCGTTCGCGCTGGCAATCATGTACGTGATGGACCTGGTACTGTTCTTCCT

GGACACGTACCTGTGGTAGATCATCTGGCTGGTGATCTTCTCGATGGTGCGCG

CGTTCAAGCTTGGTATCTCGATCTGGACGCCCTGGAGCGAGATCTTCACCCGCA

TGCCGAAGCGTATTTACGCAAAGCTGCTGGCGACGGCCGAGATGGAGGTCAAG

TATAAGCCCAAGgtatgctgaattcaatctggtcaggtgaattcaccctcatattgtggtacagGTGCTCGT

CTCACAAATCTGGAACGCGGTCATCATCTCCATGTACCGGGAGCATCTCTTGTC

CATCGAGCACGTCCAGCGCTTGCTTTACCACCAGGTTGATGGTCCCGATGGCC

GCCGCACCCTCAGGGCACCGCCGTTCTTCACCAGCCAGCGAACTGCGAAGCCA

GGCCTGTTCTTCCCTCCTGGTGGCGAGGCTGAGCGCCGCATCTCGTTCTTTGC

CTCATCGCTGACGACCGCGCTCCCGGAGCCTCTGCCGATCGACGCCATGCCCA

CCTTCACCGTGCTCGTTCCCCATTACTCCGAGAAGATTCTGCTCAGTCTGCGCG

AGATTATCCGCGAGGAGGACCAGAACACCCGCGTTACCTTACTGGAGTACCTCA

AGCAGCTCCACCCTGTCGAATGGGACAATTTCGTCAAGGACACCAAGATCTTGG

CGGAAGAGTCGGGAGACGTCCAGGACGAGAAGCGCGCGCGCACGGACGACTT

GCCGTTCTATTGCATCGGGTTCAAGACCTCGTCACCAGAGTACACCCTGCGTAC

GCGTATCTGGGCCTCACTGCGCGCACAGACGCTGTACCGCACGGTCTCCGGTA

TGATGAACTACTCCAAGGCGATTAAGCTCCTCTATCGCGTCGAGAACCCGGATG

TCGTTCATGCCTTCGGTGGGAACACGGAACGTCTTGAACGCGAGCTTGAGCGC

ATGTCTCGCCGCAAGTTCAAGTTCGTCATCTCGATGCAGCGGTACTCCAAGTTC

AACAAGGAGGAGCAGGAGAACGCCGAGTTCCTTCTGCGCGCGTACGCGGATTT

GCAGATCGCGTACCTCGATGAAGAGCCCGGTCCCAGCAAGAGCGACGAGGTTC

GGTTGTTTTCGACACTCATCGACGGACACTCCGAGGTGGACGAGAAGACGGGC

CGCCGCAAGCCGAAGTTCCGCATCGAGCTGCCCGGTAACCCCATCCTCGGTGA

CGGGAAGTCGGATAACCAGAACCACGCCATCGTCTTCTACCGCGGCGAGTACA

TTCAGGTCATTGACGCTAACCAGGACAATTACCTGGAAGAGTGTCTCAAGATCC

GTAATGTCCTGGGCGAGTTTGAGGAATACTCCGTGTCGAGCCAGAGCCCGTAC

GCGCAGTGGGGCCACAAGGAGTTCAACAAGTGCCCCGTCGCTATCCTGGGTTC

CCGCGAGTACATCTTCTCGGAGAACATCGGTATCCTCGGTGACATCGCTGCCG

GCAAGGAACAGACGTTCGGTACCATTACGGCGCGTGCGCTTGCGTGGATCGGC

GGCAAGCTGCATTACGGTCACCCGGATTTCCTCAATGCGACGTTCATGACGACG

CGTGGTGGCGTGTCAAAAGCGCAGAAGGGCTTGCATCTTAACGAGGATATCTTC

GCTGGTATGACCGCCGTGTCGCGCGGAGGGCGCATCAAGCACATGGAGTACTA

CCAGTGCGGCAAAGGTCGTGATCTCGGATTCGGCACGATCTTGAACTTCCAGA

CCAAGATCGGTACTGGTATGGGCGAGCAGCTGCTCTCGCGCGAGTACTACTAT
```

TABLE 2-continued

Assignment of SEQ ID NOs.

CTGGGCACGCAATTGCCTATCGACCGGTTCTTGACGTTCTACTACGCGCACGCT

GGTTTCCATGTCAACAACATCCTGGTCATCTACTCCATCCAGGTCTTCATGGTCA

CCCgtaagtgcaggccctcatgaccgccgagcaagcagtctaacggatgtcagTGCTGTACCTGGGC

ACATTGAACAAGCAGCTGTTCATCTGCAAGGTCAACTCCAATGGCCAGGTTCTT

AGTGGACAAGCTGGGTGCTACAACCTCATCCCGGTCTTCGAGTGGATTCGCCG

GAGTATCATCTCCATCTTCTTGGTGTTCTTCATCGCCTTCTTGCCGTTGTTCTTG

CAAGgtatgttcacttctcatgtgccatttgtcaatcgctcactcgtacgacagAGCTTTGCGAACGCGGA

ACAGGAAAGGCGTTGCTGCGTCTCGGGAAGCACTTCCTGTCACTGTCGCCCAT

CTTCGAAGTGTTCTCCACCCAAATCTACTCGCAGGCGCTCTTGAACAACATGAG

TTTCGGTGGTGCGCGCTACATCGCTACAGGACGCGGTTTCGCGACGAGTCGGA

TACCCTTCAACATCCTCTACTCGCGTTTCGCGCCGCCGAGCATCTACATGGGCA

TGCGTAATCTGCTGCTCTTGCTGTACGCGACGATGGCCATTTGGATCCCACACC

TGATCTACTTCTGGTTCTCCGTCCTCTCCCTCTGCATCGCGCCATTCATGTTCAA

TCCGCATCAATTCTCGTACGCTGACTTCATCATCGACTACCGGGAGTTCTTGCG

CTGGATGTCGCGCGGTAACTCGCGGACGAAGGCGAGTAGCTGGTACGGATATT

GCCGTCTGTCGCGTACCGCGATTACTGGGTACAAGAACGAAGAAACTGGGACAC

CCGTCGGAGAAGCTGTCGGGCGATGTGCCGCGTGCGCCGTGGAGGAACGTCA

TCTTCTCGGAGATCCTTTGGCCCATCGGCGCGTGCATCATCTTCATCGTCGCGT

ACATGTTCGTCAAATCGTTCCCTGACGAGCAGGGCAACGCGCCGCCGAGCCCG

CTGGTCCGCATTCTGCTCATCGCGGTTGGCCCTACTGTGTGGAACGCGGCGGT

GCTCATCACGCTGTTCTTCCTGTCGCTCTTCCTGGGCCCGATGATGGATGGCTG

GGTCAAGTTCGGCTCAGTCATGGCGGCACTTGCGCATGGTCTAGCGCTCATAG

GCATGCTCACGTTCTTCGAGTTCTTCgtacgtccttcgcgttgttgtggtcgagtgctttgctaacaccg ccttcagTGGTTCCTCGAGCTCTGGGATGCCTCGCACGCCGTGCTCGGCGTCATC

GCCATTATTGCCGTTCAGCGCGGGATCCAGAAGATCCTCATTGCCGTCTTCCTG

ACGCGTGAGTACAAGCACGACGAGACGAACCGCGCGTGGTGGACAGGTAAATG

GTATGGACGCGGGCTGGGTACCTCGGCCATGTCCCAGCCGGCGCGCGAGTTC

ATCGTGAAGATCGTGGAGATGTCGCTGTGGACGTCGGACTTCCTGCTTGCGCA

CCTGTTGCTCATCATCTTGACGGTGCCGCTACTGCTGCCGTTCTTCAACTCGAT

CCATTCGACGATGCTTTgtgagtgatttgtagtcgttggtcacggatgattgctgactcgcgtgcagTCTG

GTTGCGCCCTTCGAAGCAGATTAGGCAACCTCTGTTCTCCACTAAGCAGAAGCG

GCAACGGCGATGGATTgtaagttcctttgattgctctggctaccgaccttcgctcacctgtctcagGTCATG

AAGTATACCGTGGTATATCTCGTGGTGGTGGCTTTCCTCGTTGCGCTCATCGCT

CTGCgtacgttttctgtcgcgctcaccctctattttcactaacgtttcctccagCCGCGCTCTTCCGCGAGA

GCATCCACTTCAACTGCGAGATCTGCCAGAGTATATAGTCATATAACGACGTCTA

TCGTATCGCCGGACGAGAGCCCCGTCGCCTACACACTGACATGGAATTGCTGT

GTATACAATCGATCTTCTGACCGCGTCGGGGGCGTTGCCGTCTTTCTACTATCA

TABLE 2-continued

Assignment of SEQ ID NOs.

ACTTGCTTGTGTATCAACATTTCTTCTCTCCAAGCCTACATTGACATAGAGTAATA

GCCCATGTTCATACAACAATCGCATAGCATTGCATATACCAT

Translation of SEQ ID NO: 5
amino acid
S. commune

SEQ ID NO: 2

MSGPGYGRNPFDNPPPNRGPYGQQPGFPGPGPRPYDSDADMSQTYGSTTRLAG

SAGYSDRNGSFDGDRSYAPSIDSRASVPSISPFADPGIGSNEPYPAWSVERQIPMS

TEEIEDIFLDLTQKFGFQRDSMRNTFDFMMHLLDSRASRMTPNQALLTLHADYIGGQ

HANYRKWYFAAQLNLDDAVGQTNNPGIQRLKTIKGATKTIKSLDSALNRWRNAMNN

MSQYDRLRQIALYLLCWGEAGNIRLAPECLCFIFKCADDYYRSPECQNRMDPVPEG

LYLQTVIKPLYRFLRDQAYEVVDGKQVKREKDHDQIIGYDDVNQLFWYPEGLAKIVM

SDNTRLVDVPPAQRFMKFAKIEWNRVFFKTYFEKRSTAHLLVNFNRIWILHVSMYFF

YTAFNSPRVYAPHGKLDPSPEMTWSATALGGAVSTMIMILATIAEYTYIPTTWNNAS

HLTTRLIFLLVILALTAGPTFYIAMIDGRTDIGQVPLIVAIVQFFISVVATLAFATIPSGRM

FGDRVAGKSRKHMASQTFTASYPSMKRSSRVASIMLAAILLVFGCKYVESYFFLTSSF

SSPIAVMARTKVQGCNDRIFGSQLCTNQVPFALAIMYVMDLVLFFLDTYLWYIIWLVI

FSWVRAFKLGISIWTPWSEIFTRMPKRIYAKLLATAEMEVKYKPKVLVSQIWNAVIISM

YREFILLSIEFIVQRLLYHQVDGPDGRRTLRAPPFFTSQRTAKPGISFPPGGEAERRIS

FFASSLTTALPEPLPIDAMPTFTVLVPHYSEKILLSLREIIREEDQNTRVTLLEYLKQLH

PVEWDNFVKDTKILAEESGDVQDEKRARTDDLPFYCIGFKISSPEYTLRTRIWASLR

AQTLYRTVSGMMNYSKAIKLLYRVENPDVVHAFGGNTERLERELERMSRRKFKFVI

SMQRYSKFNKEEQENAEFLLRAYPDLQIAYLDEEPGPSKSDEVRLFSTLIDGHSEVD

EKTGRRKPKFRIELPGNPILGDGKSDNQNHAIWYRGEYIQVIDANQDNYLEECLKIR

NVLGEFEEYSVSSQSPYAQWGHKEFNKCPVAILGSREYIFSENIGILGDIAAGKEQTF

GTITARALAWIGGKLHYGHPDFLNATFMTTRGGVSKAQKGLHLNEDIFAGMTAVSR

GGRIKHMEYYQCGKGRDLGFGTILNFQTKIGTGMGEDLLSREYYYLGTQLPIDRFLT

FYYAHAGFHVNNILVIYSIQVFMVTLLYLGTLNKQLFICKVNSNGQVLSGQAGCYNLI

PVFEWIRRSIISIFLVFFIAFLPLFLQELCERGTGKALLRLGKHFLSLSPIFEVFSTQIYS

QALLNNMSFGGARYIATGRGFATSRIPFNILYSRFAPPSIYMGMRNLLLLLYATMAIW

IPHLIYFWFSVLSLCIAPFMFNPHQFSYADFIIDYREFLRWMSRGNSRTKASSWYGY

CRLSRTAITGYKKKKLGHPSEKLSGDVPRAPWRNVIFSEILWPIGACIIFIVAYMFVKS

FPDEQGNAPPSPLVRILLIAVGPTVWNAAVLITLFFLSLFLGPMMDGWVKFGSVMAA

LAHGLALIGMLTFFEFFWFLELWDASHAVLGVIAIIAVQRGIQKILIAVFLTREYKHDET

NRAWWTGKWYGRGLGTSAMSQPAREFIVKIVEMSLWTSDFLLAHLLLIILTVPLLLP

FFNSIHSTMLFWLRPSKQIRQPLFSTKQKRQRRWIVMKYTVVYLVWAFLVALIALPA

LFRESIHFNCEICQSI

Gene sequence 1,3-β-D-glucan synthase II of S. commune strain Lu15531
DNA
S. commune

SEQ ID NO: 3

CTGTCCAAAGAAGAGATCGAGGACATCTTCCTCGATCTGACGCAGAAGTTTGGC

TTTCAGCGGGATTCCATGCGGAACATGgtacgtggcgtatgcccatgtgcggcgttctgaggcctaa

TABLE 2-continued

Assignment of SEQ ID NOs.

acgttttccgccagTTCGACTTCACCATGCAGCTGCTTGACAGCCGAGCGTCTCGTATG

ACCCCCAACCAGGCGCTCCTCACCCTCCACGCCGACTACATTGGTGGCCAGCA

TGCGAACTACCGGAAGTGGTACTTCGCGGCGCAGCTCGACCTTGACGACGCCG

TGGGACAAACTCAGAATCCGGGTCTCAACCGCCTCAAGTCCACTCGCGGATCG

GGCAAGCGACCACGCCATGAAAAGTCGCTGAACACGGCATTGGAGCGCTGGC

GGCAAGCCATGAACAACATGTCGCAGTATGACCGCTTACGCCAGATCGCGCTC

TACCTGCTCTGCTGGGGCGAAGCGGCGCAAGTGCGATTCATGCCCGAGTGCTT

GTGCTTCATCTTCAAGTGCGCCGACGACTATTATCGTTCGCCGGAGTGCCAGAA

CAGGATGGAGCCGGTACCGGAGGGTCTCTACCTGAGGACGGTCGTAAAGCCG

CTCTACAGATTTGTCCGGGATCAAGGCTATGAGGTGGTGGAGGGAAAATTCGTA

CGGCGGGAACGGGATCACGACCAAATCATTGGTTACGATGACGTGAATCAGCT

GTTCTGGTACCCGGAGGGCATTGCCCGTATCGTCCTGTCGGACAAGgtaagcacctc tgtgcatcttctgtgacatacagggctaattgtcgagcagAGTCGTCTGGTCGACCTCCCTCCAGCA

CAGCGCTTCATGAAGTTCGACCGTATCGAGTGGAATCGCGTCTTCTTCAAGACG

TTCTACGAGACTCGATCCTTTACGCATCTTTTGGTCGACTTCAACCGTATCTGGG

TCGTGCACATCGCTCTCTACTTCTTCTACACCGCATACAACTCCCCCACGATCTA

CGCCATCAACGGCAACACTCCGACGTCTCTGGCTTGGAGCGCGACTGCGCTCG

GCGGTGCGGTAGCGACAGGTATCATGATCCTCGCCACGATCGCCGAGTTCTCG

CACATCCCCACGACATGGAACAACACCTCGCATCTGACTCGCCGCCTCGCCTTC

CTCCTCGTCACGCTCGGCCTCACATGTGGTCCGACGTTCTACGTCGCGATTGCA

GAGAGCAACGGGAGCGGCGGCTCTTTGGCCTTGATTCTCGGCATCGTCCAGTT

CTTCATCTCCGTCGTAGCGACTGCGCTCTTCACTATCATGCCTTCTGGTCGTAT

GTTCGGCGACCGCGTCGCAGGCAAGAGTCGCAAGTATCTCGCCAGCCAGACGT

TCACGGCCAGCTACCCGTCGTTGCCCAAGCACCAGCGGTTCGCATCACTCCTG

ATGTGGTTCCTCATCTTCGGGTGCAAGTTGACGGAGAGTTACTTCTTCCTGACG

TTGTCCTTCCGCGACCCTATTCGCGTCATGGTCGGCATGAAGATCCAGAACTGC

GAGGACAAGATTTTCGGCAGCGGCCTTTGCAGGAATCACGCAGCATTCACCCT

CACGATCATGTACATCATGGACCTCGTCTTGTTCTTCCTCGACACCTTCCTTTGG

TATGTCATCTGGAACTCGGTTTTCAGTATCGCACGCTCTTTCGTACTCGGCCTTT

CGATCTGGACACCATGGAGGGACATCTTCCAGCGTCTGCCGAAGCGTATCTAC

GCGAAGCTTCTAGCGACCGGCGACATGGAGGTCAAGTACAAGCCCAAGgtgtgtga atagctcgctgtaaggttcttgattctgactcattcgcagGTCTTGGTTTCGCAAATCTGGAACGCCA

TCATCATCTCCATGTACCGCGAGCACTTGCTCTCTATCGAGCACGTTCAAAAGC

TCCTGTACCATCAAGTGGACACTGGCGAAGCCGGCAAGCGGAGTCTTCGCGCG

CCTCCGTTCTTCGTCGCGCAGGGCAGCAGCGGTGGCTCGGGCGAGTTCTTCCC

GCCTGGTAGCGAGGCTGAGCGTCGTATCTCTTTCTTCGCGCAGTCTCTATCTAC

GGAGATTCCTCAGCCCATCCCGGTTGACGCCATGCCGACGTTCACAGTGCTTA

CGCCTCACTACAGCGAGAAGgtgcgcttttttcctgggcgcattcaacattagctgactgtcgtgcacagA

TCCTTCTTTCGCTCCGTGAGATTATCCGCGAGGAGGACCAGAACACCCGCGTG

TABLE 2-continued

Assignment of SEQ ID NOs.

ACATTGCTTGAGTATCTCAAGCAGCTTCACCCGGTCGAGTGGGAGAACTTCGTC

AAGGACACCAAGATTTTGGCCGAGGAGTCCGCTATGTTCAACGGTCCAAGTCCT

TTCGGCAACGATGAGAAGGGTCAGTCCAAGATGGACGATCTTCCTTTCTACTGC

ATCGGTTTCAAGAGCGCCGCGCCCGAGTACACCCTCCGCACCCGTATCTGGGC

GTCCTTGCGCGCGCAGACCCTCTACCGCACGGTCTCCGGCATGATGAACTATG

CGAAGGCGATTAAGCTGCTCTACCGCGTCGAGAACCCCGAGGTCGTGCAGCAG

TTCGGCGGTAACACGGACAAGCTCGAGCGCGAGTTGGAGCGGATGGCCCGGC

GGAAGTTCAAGTTCCTGGTGTCCATGCAGCGCTACTCGAAGTTCAACAAGGAGG

AGCACGAGAACGCCGAGTTCTTGCTCCGCGCGTACCCGGACCTGCAGATCGCG

TACCTGGAGGAAGAGCCTCCTCGCAAGGAGGGTGGCGATCCACGCATCTTCTC

TGCCCTCGTCGACGGCCACAGCGACATCATCCCGGAGACCGGCAAGCGGCGC

CCCAAGTTCCGCATCGAGCTGCCCGGCAACCCCATTCTCGGTGACGGCAAGTC

GGACAACCAGAACCACGCCATCGTCTTCTACCGCGGCGAGTACCTCCAGCTTAT

CGACGCCAACCAGGACAACTACCTCGAGGAGTGCTTGAAGATCCGTAACGTAC

TCGCCGAGTTCGAGGAGTACGACGTCTCTAGCCAGAGTCCGTACGCGCAGTGG

AGTGTCAAGGAGTTCAAGCGCTCCCCGGTCGCCATCGTCGGTGCACGCGAGTA

TATCTTCTCGGAGCACATCGGTATTCTCGGTGATTTGGCGGCTGGCAAGGAACA

GACGTTCGGTACGCTCACGGCACGCAACAACGCCTTCCTTGGCGGCAAGCTGC

ACTACGGTCACCCGGATTTCCTCAACGCCCTCTACATGAACACGCGCGGTGGT

GTCTCCAAGGCGCAGAAGGGTCTCCATCTCAACGAGGATATTTACGCCGGTATG

AACGCGGTCGGTCGCGGTGGACGCATCAAGCATAGCGAATACTACCAGTGCGG

CAAGGGTCGTGACCTCGGTTTTGGCACCATCTTGAACTTCCAGACCAAGATCGG

TACGGGTATGGGCGAGCAGATCCTCTCGCGCGAGTACTACTACCTCGGAACCC

AATTGCCCATCGATCGCTTCCTCACGTTCTACTACGCGCACCCAGGTTTCCAGA

TCAACAACATGCTGGTTATCCTATCCGTGCAGGTCTTCATCGTTACCAgtacgttgatt gcatatcgttagcctgacagcgtctgacgaattcccagTGGTCTTCCTCGGTACCTTGAAGTCTTC

GGTCACGATCTGCAAGTACACGTCCAGCGGTCAGTACATCGGTGGTCAATCCG

GTTGCTACAACCTCGTCCCGGTCTTCCAGTGGATCGAGCGCTGCATCATCAGCA

TCTTCTTGGTGTTCATGATCGCTTTCATGCCGCTCTTCCTGCAAGgtaagagctcgtca acctgctcaagggccttgcgctgatcatcatctcagAACTCGTCGAGCGCGGTACCTGGAGTGCC

ATCTGGCGTCTGCTCAAGCAGTTTATGTCGCTGTCGCCTGTCTTCGAGGTGTTC

TCCACCCAGATTCAGACACACTCCGTGTTGAGCAACTTGACGTTCGGTGGTGCG

CGTTACATCGCTACCGGTCGTGGGTTCGCCACCAGTCGTATCAGCTTCAGCATC

TTGTTCTCGCGTTTCGCAGGCCCGAGTATCTACCTCGGCATGCGCACGCTCATT

ATGCTGCTCTACGTGACGTTGACGATCTGGACGCCATGGGTCATTTACTTCTGG

GTTTCCATTCTCTCGCTCTGCATCGCGCCGTTCTTGTTCAATCCGCATCAATTCG

TCTTCTCGGATTTCCTCATCGACTACAGgtacgtcggacgagcgctgttccgcgacgtaagctgac cggttatacagGGAATACCTCCGGTGGATGTCGCGTGGTAACTCGCGCTCGCACAAC

AACTCCTGGATTGGGTACTGCCGGTTGTCCCGCACGATGATCACTGGATACAA

TABLE 2-continued

Assignment of SEQ ID NOs.

GAAGAAGAAGCTGGGCCACCCGTCGGAGAAGCTTTCCGGCGACGTTCCTCGTG

CAGGCTGGCGCGCCGTCTTATTCTCGGAGATCATCTTCCCGGCATGCATGGCC

ATCCTCTTCATCATCGCGTACATGTTCGTCAAGTCGTTCCCTCTCGACGGCAAG

CAGCCTCCCTCCGGCCTCGTTCGCATCGCCGTCGTGTCTATCGGCCCCATCGT

GTGGAACGCCGCCATCCTGTTGACGCTCTTCCTTGTGTCGTTGTTCCTCGGCCC

CATGCTCGACCCGGTCTTCCCCCTCTTCGGTCCGTTATGGCCTTCATCGCGCA

TTTCCTCGGCACAATCGGAATGATTGGGTTCTTCGAGTTCCTGgtatgtgcccatacctttt cattcgtcttcaactatctaacagattcatagTGGTTCCTCGAGTCCTGGGAGGCGTCGCATGCC

GTGCTGGGTCTCATCGCCGTCATCTCCATCCAGCGCGCCATTCACAAAATTCTT

ATCGCCGTTTTCCTCAGTCGCGAGTTCAAGCACGACGAGACGAACAGGGCTTG

GTGGACTGGTCGCTGGTATGGCCGTGGCCTCGGCACGCACGCCATGTCGCAG

CCGGCGCGTGAGTTCGTCGTCAAGATCATCGAGTTGTCGCTCTGGAGCTCGGA

TCTCATACTCGGCCACATCCTGCTGTTCATGCTTACTCCGGCTGTCCTCATCCC

GTACTTCGACCGTCTGCACGCCATGATGCTCTgtacgtcgtgtctcattgtttgtgttggtcatactct taccctctcttagTCTGGCTGCGCCCCTCAAAGCAAATCCGCGCCTCTGTACTCAAT CAAGCAGAAGAGGCAAAGACGCTGGATTgtcagtgttcagtgccttattctatcagctcttactgacgt cttcatagATCATGAAGTACGGTACTGTATACGTTACCGTCATCGCGATCTTCGTCG CGCTCATCGCGCTTCgtgagtacccttgctatctttcgtacctgagcgtcgctgacccctttcccagCCCTC

GTCTTCCGACACACTCTAAAGGTCGAGTGCTCCCTTTGCGACAGCTTGTAATAT

CGGACTCGTATATATCTAGACTTCTCCGCACCATGTGTAGCTGACGCTTGGGTA

TACTTCGCGGTGCCGAGCTAATTGTCGACGGACATTCTCCATCGTTGAGTGCAG

CGACATCGGGTGGTTTACGACACGGACACTTTTCATTGTACCCTCTACGAATGC

AAGAACTCTCTTACGACCAGTACCTATGTGCTAAGCCGTCGCCTGTTCAGGATC

ATACATACATACGTTTCTAGATACCTTACAGTTAGGCCTATTCAGGGAGAGTCTG

CATAAAA

Translation of SEQ ID NO: 7
amino acid
S. commune

SEQ ID NO: 4

MRNMFDFTMQLLDSRASRMTPNQALLTLHADYIGGQHANYRKWYFAAQLDLDDAV

GDTQNPGLNRLKSTRGSGKRPRHEKSLNTALERWRQAMNNMSQYDRLRQIALYLL

CWGEAAQVRFMPECLCFIFKCADDYYRSPECQNRMEPVPEGLYLRTVVKPLYRFV

RDQGYEVVEGKFVRRERDHDQIIGYDDVNQLFWYPEGIARIVLSDKSRLVDLPPAQ

RFMKFDRIEWNRVFFKTFYETRSFTHLLVDFNRIWVVHIALYFFYTAYNSPTIYAING

NTPTSLAWSATALGGAVATGIMILATIAEFSHIPTTWNNTSHLTRRLAFLLVTLGLTCG

PTFYVAIAESNGSGGSLALILGIVQFFISVVATALFTIMPSGRMFGDRVAGKSRKYLA

SQTFTASYPSLPKHQRFASLLMWFLIFGCKLTESYFFLTLSFRDPIRVMVGMKIQNC

EDKIFGSGLCRNHAAFTLTIMYIMDLVLFFLDTFLWYVIWNSVFSIARSFVLGLSIWTP

WRDIFQRLPKRIYAKLLATGDMEVKYKPKVLVSQIWNAIIISMYREHLLSIEHVQKLLY

HQVDTGEAGKRSLRAPPFFVAQGSSGGSGEFFPPGSEAERRISFFAQSLSTEIPQPI

PVDAMPTFTVLTPHYSEKILLSLREIIREEDQNTRVTLLEYLKQLHPVEWENFVKDTKI

TABLE 2-continued

Assignment of SEQ ID NOs.

LAEESAMFNGPSPFGNDEKGQSKMDDLPFYCIGFKSAAPEYTLRTRIWASLRAQTL

YRTVSGMMNYAKAIKLLYRVENPEVVQQFGGNTDKLERELERMARRKFKFLVSMQ

RYSKFNKEEHENAEFLLRAYPDLQIAYLEEEPPRKEGGDPRIFSALVDGHSDIIPETG

KRRPKFRIELPGNPILGDGKSDNQNHAIVFYRGEYLQLIDANQDNYLEECLKIRNVLA

EFEEYDVSSQSPYAQWSVKEFKRSPVAIVGAREYIFSEHIGILGDLAAGKEQTFGTL

TARNNAFLGGKLHYGHPDFLNALYMNTRGGVSKAQKGLHLNEDIYAGMNAVGRGG

RIKHSEYYQCGKGRDLGFGTILNFQTKIGTGMGEQILSREYYYLGTQLPIDRFLTFYY

AHPGFQINNMLVILSVQVFIVTMVFLGTLKSSVTICKYTSSGQYIGGQSGCYNLVPVF

QWIERCIISIFLVFMIAFMPLFLQELVERGTWSAIWRLLKQFMSLSPVFEVFSTQIQTH

SVLSNLTFGGARYIATGRGFATSRISFSILFSRFAGPSIYLGMRTLIMLLYVTLTIWTP

WVIYFWVSILSLCIAPFLFNPHQFVFSDFLIDYREYLRWMSRGNSRSHNNSWIGYCR

LSRTMITGYKKKKLGHPSEKLSGDVPRAGWRAVLFSEIIFPACMAILFIIAYMFVKSFP

LDGKQPPSGLVRIAVVSIGPIVWNAAILLTLFLVSLFLGPMLDPVFPLFGSVMAFIAHF

LGTIGMIGFFEFLWFLESWEASHAVLGLIAVISIQRAIHKILIAVFLSREFKHDETNRAW

WTGRWYGRGLGTHAMSQPAREFVVKIIELSLWSSDLILGHILLFMLTPAVLIPYFDRL

HAMMLFWLRPSKQIRAPLYSIKQKRQRRWIIMKYGTVYVTVIAIFVALIALPLVFRHTL

KVECSLCDSL cDNA 1,3-β-D-glucan synthase I of *S. commune* strain Lu15531
DNA
*S. commune*

SEQ ID NO: 5

ATGTCCGGCCCAGGATATGGCAGGAATCCATTCGACAATCCCCCGCCCAACAG

AGGTCCCTATGGCCAGCAGCCAGGTTTCCCGGGGCCCGGCCCTCGGCCTTAC

GACTCGGACGCGGACATGAGCCAGACCTATGGCAGCACAACCAGGCTCGCCG

GCAGTGCCGGTTACAGCGACAGAAACGGCAGCTTCGACGGCGACCGCTCCTAC

GCGCCCTCAATTGACTCGCGCGCCAGCGTGCCCAGCATATCGCCCTTCGCAGA

CCCGGGTATCGGCTCTAATGAGCCGTATCCCGCTTGGTCGGTCGAACGCCAGA

TTCCCATGTCCACGGAGGAGATTGAGGACATCTTCCTCGACCTCACCCAAAAGT

TTGGCTTCCAGCGCGACTCCATGCGGAATACGTTCGACTTCATGATGCACCTCC

TCGATTCCCGTGCCTCGCGCATGACGCCCAACCAAGCTCTGCTCACGCTTCAC

GCCGACTACATTGGTGGCCAGCATGCCAATTACCGGAAGTGGTATTTCGCCGC

ACAGCTCAACCTCGATGACGCGGTCGGGCAAACCAATAACCCCGGTATCCAGC

GCTTGAAGACCATCAAGGGCGCTACGAAGACCAAGTCGCTCGACAGCGCACTC

AACCGCTGGCGCAACGCGATGAACAACATGAGCCAGTACGATCGCCTCCGGCA

AATTGCGCTCTACCTCCTCTGCTGGGGTGAAGCAGGCAACATCCGTCTGGCGC

CCGAGTGCTTGTGCTTCATCTTCAAGTGCGCGGACGACTACTACAGAAGTCCCG

AGTGTCAGAACCGGATGGACCCCGTGCCGGAAGGGCTGTACCTGCAGACGGT

CATCAAGCCGCTCTATCGCTTCCTACGTGATCAGGCGTACGAAGTCGTTGATGG

GAAGCAAGTGAAGCGCGAGAAGGACCACGACCAGATTATCGGTTATGACGACG

TCAACCAGTTATTCTGGTATCCGGAAGGTTTGGCTAAGATCGTCATGTCGGACA

ACACACGACTTGTAGATGTACCTCCGGCGCAGCGGTTCATGAAGTTCGCCAAGA

TABLE 2-continued

Assignment of SEQ ID NOs.

```
TCGAGTGGAACCGCGTCTTCTTCAAGACGTACTTTGAGAAGCGCTCTACTGCCC

ATCTCCTGGTCAACTTCAACCGTATATGGATCCTCCACGTCTCGATGTACTTCTT

CTACACGGCATTCAACTCTCCACGAGTCTACGCGCCGCACGGCAAACTCGACC

CCTCCCCTGAGATGACCTGGTCCGCGACTGCCCTTGGAGGCGCTGTGTCCACC

ATGATCATGATCCTTGCCACTATCGCGGAGTACACCTACATCCCCACGACATGG

AACAATGCGTCGCACCTCACCACGCGGCTCATTTTCCTCCTGGTCATCCTCGCG

CTCACTGCTGGCCCAACATTCTATATCGCCATGATAGACGGACGCACGGACATC

GGCCAAGTACCACTCATCGTGGCCATAGTGCAGTTCTTCATCTCCGTCGTCGCC

ACCCTCGCTTTCGCTACCATCCCTTCTGGTCGCATGTTCGGCGACCGTGTGGCT

GGCAAGTCAAGAAAGCACATGGCATCGCAGACGTTCACAGCGTCGTACCCGTC

CATGAAGCGGTCATCTCGCGTAGCGAGTATCATGCTGTGGCTTTTGGTCTTTGG

CTGCAAATACGTCGAGTCTTACTTCTTCTTGACGTCCTCCTTCTCCAGCCCGATC

GCGGTCATGGCGCGTACGAAGGTACAGGGCTGCAACGACCGTATCTTCGGCAG

CCAGCTGTGCACGAATCAGGTCCCGTTCGCGCTGGCAATCATGTACGTGATGG

ACCTGGTACTGTTCTTCCTGGACACGTACCTGTGGTACATCATCTGGCTGGTGA

TCTTCTCGATGGTGCGCGCGTTCAAGCTTGGTATCTCGATCTGGACGCCCTGGA

GCGAGATCTTCACCCGCATGCCGAAGCGTATTTACGCAAAGCTGCTGGCGACG

GCCGAGATGGAGGTCAAGTATAAGCCCAAGGTGCTCGTCTCACAAATCTGGAA

CGCGGTCATCATCTCCATGTACCGGGAGCATCTCTTGTCCATCGAGCACGTCCA

GCGCTTGCTTTACCACCAGGTTGATGGTCCCGATGGCCGCCGCACCCTCAGGG

CACCGCCGTTCTTCACCAGCCAGCGAACTGCGAAGCCAGGCCTGTTCTTCCCT

CCTGGTGGCGAGGCTGAGCGCCGCATCTCGTTCTTTGCCTCATCGCTGACGAC

CGCGCTCCCGGAGCCTCTGCCGATCGACGCCATGCCCACCTTCACCGTGCTCG

TTCCCCATTACTCCGAGAAGATTCTGCTCAGTCTGCGCGAGATTATCCGCGAGG

AGGACCAGAACACCCGCGTTACCTTACTGGAGTACCTCAAGCAGCTCCACCCT

GTCGAATGGGACAATTTCGTCAAGGACACCAAGATCTTGGCGGAAGAGTCGGG

AGACGTCCAGGACGAGAAGCGCGCGCACGGACGACTTGCCGTTCTATTGCA

TCGGGTTCAAGACCTCGTCACCAGAGTACACCCTGCGTACGCGTATCTGGGCC

TCACTGCGCGCACAGACGCTGTACCGCACGGTCTCCGGTATGATGAACTACTC

CAAGGCGATTAAGCTCCTCTATCGCGTCGAGAACCCGGATGTCGTTCATGCAAT

CGGTGGGAACACGGAACGTCTTGAACGCGAGCTTGAGCGCATGTCTCGCCGCA

AGTTCAAGTTCGTCATCTCGATGCAGCGGTACTCCAAGTTCAACAAGGAGGAGC

AGGAGAACGCCGAGTTCCTTCTGCGCGCGTACCCGGATTTGCAGATCGCGTAC

CTCGATGAAGAGCCCGGTCCCAGCAAGAGCGACGAGGTTCGGTTGTTTTCGAC

ACTCATCGACGGACACTCCGAGGTGGACGAGAAGACGGGCCGCCGCAAGCCC

AAGTTCCGCATCGAGCTGCCCGGTAACCCCATCCTCGGTGACGGGAAGTCGGA

TAACCAGAACCACGCCATCGTCTTCTACCGCGGCGAGTACATTCAGGTCATTGA

CGCTAACCAGGACAATTACCTGGAAGAGTGTCTCAAGATCCGTAATGTCCTGGG

CGAGTTTGAGGAATACTCCGTGTCGAGCCAGAGCCCGTACGCGCAGTGGGGCC
```

TABLE 2-continued

Assignment of SEQ ID NOs.

```
ACAAGGAGTTCAACAAGTGCCCCGTCGCTATCCTGGGTTCCCGCGAGTACATCT
TCTCGGAGAACATCGGTATCCTCGGTGACATCGCTGCCGGCAAGGAACAGACG
TTCGGTACCATTACGGCGCGTGCGCTTGCGTGGATCGGCGGCAAGCTGCATTA
CGGTCACCCGGATTTCCTCAATGCGACGTTCATGACGACGCGTGGTGGCGTGT
CAAAAGCGCAGAAGGGCTTGCATCTTAACGAGGATATCTTCGCTGGTATGACCG
CCGTGTCCCGCGGAGGGCGCATCAAGCACATGGAGTACTACCAGTGCGGCAAA
GGTCGTGATCTCGGATTCGGCACGATCTTGAACTTCCAGACCAAGATCGGTACT
GGTATGGGCGAGCAGCTGCTGTCGCGCGAGTACTACTATCTGGGCACGCAATT
GCCTATCGACCGGTTCTTGACGTTCTACTACGCGCACGCTGGTTTCCATGTCAA
CAACATCCTGGTCATCTACTCCATCCAGGTCTTCATGGTCACCCTGCTGTACCT
GGGCACATTGAACAAGCAGCTGATCATCTGCAAGGTCAACTCCAATGGCCAGGT
TCTTAGTGGACAAGCTGGGTGCTACAACCTCATCCCGGTCTTCGAGTGGATTCG
CCGGAGTATCATCTCCATCTTCTTGGTGTTCTTCATCGCCTTCTTGCCGTTGTTC
TTGCAAGAGCTTTGCGAACGCGGAACAGGAAAGGCGTTGCTGCGTCTCGGGAA
GCACTTCCTGTCACTGTCGCCCATCTTCGAAGTGTTCTCCACCCAAATCTACTC
GCAGGCGCTCTTGAACAACATGAGTTTCGGTGGTGCGCGCTACATCGCTACAG
GACGCGGTTTCGCGACGAGTCGGATACCCTTCAACATCCTCTACTCGCGTTTCG
CGCCGCCGAGCATCTACATGGGCATGCGTAATCTGCTGCTCTTGCTGTACGCG
ACGATGGCCATTTGGATCCCACACCTGATCTACTTCTGGTTCTCCGTCCTCTCC
CTCTGCATCGCGCCATTCATGTTCAATCCGCATCAATTCTCGTACGCTGACTTCA
TCATCGACTACCGGGAGTTCTTGCGCTGGATGTCGCGCGGTAACTCGCGGACG
AAGGCGAGTAGCTGGTACGGATATTGCCGTCTGTCGCGTACCGCGATTACTGG
GTACAAGAAGAAGAAACTGGGACACCCGTCGGAGAAGCTGTCGGGCGATGTGC
CGCGTGCGCCGTGGAGGAACGTCATCTTCTCGGAGATCCTTTGGCCCATCGGC
GCGTGCATCATCTTCATCGTCGCGTACATGTTCGTCAAATCGTTCCCTGACGAG
CAGGGCAACGCGCCGCCGAGCCCGCTGGTCCGCATTCTGCTCATCGCGGTTG
GCCCTACTGTGTGGAACGCGGCGGTGCTCATCACGCTGTTCTTCCTGTCGCTCT
TCCTGGGCCCGATGATGGATGGCTGGGTCAAGTTCGGCTCAGTCATGGCGGCA
CTTGCGCATGGTCTAGCGCTCATAGGCATGCTCACGTTCTTCGAGTTCTTCTGG
TTCCTCGAGCTCTGGGATGCCTCGCACGCCGTGCTCGGCGTCATCGCCATTATT
GCCGTTCAGCGCGGGATCCAGAAGATCCTCATTGCCGTCTTCCTGACGCGTGA
GTACAAGCACGACGAGACGAACCGCGCGTGGTGGACAGGTAAATGGTATGGAC
GCGGGCTGGGTACCTCGGCCATGTCCCAGCCGGCGCGCGAGTTCATCGTGAA
GATCGTGGAGATGTCGCTGTGGACGTCGGACTTCCTGCTTGCGCACCTGTTGC
TCATCATCTTGACGGTGCCGCTACTGCTGCCGTTCTTCAACTCGATCCATTCGA
CGATGCTTTTCTGGTTGCGCCCTTCGAAGCAGATTAGGCAACCTCTGTTCTCCA
CTAAGCAGAAGCGGCAACGGCGATGGATTGTCATGAAGTATACCGTGGTATATC
```

TABLE 2-continued

Assignment of SEQ ID NOs.

TCGTGGTGGTGGCTTTCCTCGTTGCGCTCATCGCTCTGCCCGCGCTCTTCCGC

GAGAGCATCCACTTCAACTGCGAGATCTGCCAGAGTATATAG polypeptide sequence 1,3-β-D-glucan synthase I of *S. commune* strain Lu15531
amino acid
*S. commune*

SEQ ID NO: 6

MSGPGYGRNPFDNPPPNRGPYGQQPGFPGPGPRPYDSDADMSQTYGSTTRLAG

SAGYSDRNGSFDGDRSYAPSIDSRASVPSISPFADPGIGSNEPYPAWSVERQIPMS

TEEIEDIFLDLTQKFGFQRDSMRNTFDFMMHLLDSRASRMTPNQALLTLHADYIGGQ

HANYRKWYFAAQLNLDDAVGQTNNPGIQRLKTIKGATKTKSLDSALNRWRNAMNN

MSQYDRLRQIALYLLCWGEAGNIRLAPECLCFIFKCADDYYRSPECQNRMDPVPEG

LYLQTVIKPLYRFLRDQAYEVVDGKQVKREKDHDQIIGYDDVNQLFWYPEGLAKIVM

SDNTRLVDVPPAQRFMKFAKIEWNRVFFKTYFEKRSTAHLLVNFNRIWILHVSMYFF

YTAFNSPRVYAPHGKLDPSPEMTWSATALGGAVSTMIMILATIAEYTYIPTTWNNAS

HLTTRLIFLLVILALTAGPTFYIAMIDGRTDIGQVPLIVAIVQFFISVVATLAFATIPSGRM

FGDRVAGKSRKHMASQTFTASYPSMKRSSRVASIMLWLLVFGCKYVESYFFLTSSF

SSPIAVMARTKVQGCNDRIFGSQLCTNQVPFALAIMYVMDLVLFFLDTYLWYIIWLVI

FSMVRAFKLGISIWTPWSEIFTRMPKRIYAKLLATAEMEVKYKPKVLVSQIWNAVIISM

YREHLLSIEHVQRLLYHQVDGPDGRRTLRAPPFFTSQRTAKPGLFFPPGGEAERRIS

FFASSLTTALPEPLPIDAMPTFTVLVPHYSEKILLSLREIIREEDQNTRVTLLEYLKQLH

PVEWDNFVKDTKILAEESGDVQDEKRARTDDLPFYCIGFKTSSPEYTLRTRIWASLR

AQTLYRTVSGMMNYSKAIKLLYRVENPDVVHAFGGNTERLERELERMSRRKFKFVI

SMQRYSKFNKEEQENAEFLLRAYPDLQIAYLDEEPGPSKSDEVRLFSTLIDGHSEVD

EKTGRRKPKFRIELPGNPILGDGKSDNQNHAIVFYRGEYIQVIDANQDNYLEECLKIR

NVLGEFEEYSVSSQSPYAQWGHKEFNKCPVAILGSREYIFSENIGILGDIAAGKEQTF

GTITARALAWIGGKLHYGHPDFLNATFMTTRGGVSKAQKGLHLNEDIFAGMTAVSR

GGRIKHMEYYQCGKGRDLGFGTILNFQTKIGTGMGEQLLSREYYYLGTQLPIDRFLT

FYYAHAGFHVNNILVIYSIQVFMVTLLYLGTLNKQLFICKVNSNGQVLSGQAGCYNLI

PVFEWIRRSIISIFLVFFIAFLPLFLQELCERGTGKALLRLGKHFLSLSPIFEVFSTQIYS

QALLNNMSFGGARYIATGRGFATSRIPFNILYSRFAPPSIYMGMRNLLLLLYATMAIW

IPHLIYFWFSVLSLCIAPFMFNPHQFSYADFIIDYREFLRWMSRGNSRTKASSWYGY

CRLSRTAITGYKKKKLGHPSEKLSGDVPRAPWRNVIFSEILWPIGACIIFIVAYMFVKS

FPDEQGNAPPSPLVRILLIAVGPTVWVNAAVLITLFFLSLFLGPMMDGWVKFGSVMAA

LAHGLALIGMLTFFEFFWFLELWDASHAVLGVIAIIAVQRGIQKILIAVFLTREYKHDET

NRAWWTGKWYGRGLGTSAMSQPAREFIVKIVEMSLWTSDFLLAHLLLIILTVPLLLP

FFNSIHSTMLFWLRPSKQIRQPLFSTKQKRQRRWIVMKYTVVYLVVVAFLVALIALPA

LFRESIHFNCEICQSI cDNA 1,3-β-D-glucan syntase II of *S. commune* strain Lu15531
DNA
*S. commune*

SEQ ID NO: 7

ATGCGGAACATGTTCGACTTCACCATGCAGCTGCTTGACAGCCGAGCGTCTCGT

ATGACCCCCAACCAGGCGCTCCTCACCCTCCACGCCGACTACATTGGTGGCCA

TABLE 2-continued

Assignment of SEQ ID NOs.

```
GCATGCGAACTACCGGAAGTGGTACTTCGCGGCGCAGCTCGACCTTGACGACG

CCGTGGGACAAACTCAGAATCCGGGTCTCAACCGCCTCAAGTCCACTCGCCGGA

TCGGGCAAGCGACCACGCCATGAAAAGTCGCTGAACACGGCATTGGAGCGCTG

GCGGCAAGCCATGAACAACATGTCGCAGTATGACCGCTTACGCCAGATCGCGC

TCTACCTGCTCTGCTGGGGCGAAGCGGCGCAAGTGCGATTCATGCCCGAGTGC

TTGTGCTTCATCTTCAAGTGCGCCGACGACTATTATCGTTCGCCGGAGTGCCAG

AACAGGATGGAGCCGGTACCGGAGGGTCTCTACCTGAGGACGGTCGTAAAGCC

GCTCTACAGATTTGTCCGGGATCAAGGCTATGAGGTGGTGGAGGGAAAATTCGT

ACGGCGGGAACGGGATCACGACCAAATCATTGGTTACGATGACGTGAATCAGC

TGTTCTGGTACCCGGAGGGCATTGCCCGTATCGTCCTGTCGGACAAGAGTCGT

CTGGTCGACCTCCCTCCAGCACAGCGCTTCATGAAGTTCGACCGTATCGAGTG

GAATCGCGTCTTCTTCAAGACGTTCTACGAGACTCGATCCTTTACGCATCTTTTG

GTCGACTTCAACCGTATCTGGGTCGTGCACATCGCTCTCTACTTCTTCTACACC

GCATACAACTCCCCCACGATCTACGCCATCAACGGCAACACTCCGACGTCTCTG

GCTTGGAGCGCGACTGCGCTCGGCGGTGCGGTAGCGACAGGTATCATGATCCT

CGCCACGATCGCCGAGTTCTCGCACATCCCCACGACATGGAACAACACCTCGC

ATCTGACTCGCCGCCTCGCCTTCCTCCTCGTCACGCTCGGCCTCACATGTGGTC

CGACGTTCTACGTCGCGATTGCAGAGAGCAACGGGAGCGGCGGCTCTTTGGCC

TTGATTCTCGGCATCGTCCAGTTCTTCATCTCCGTCGTAGCGACTGCGCTCTTC

ACTATCATGCCTTCTGGTCGTATGTTCGGCGACCGCGTCGCAGGCAAGAGTCG

CAAGTATCTCGCCAGCCAGACGTTCACGGCCAGCTACCCGTCGTTGCCCAAGC

ACCAGCGGTTCGCATCACTCCTGATGTGGTTCCTCATCTTCGGGTGCAAGTTGA

CGGAGAGTTACTTCTTCCTGACGTTGTCCTTCCGCGACCCTATTCGCGTCATGG

TCGGCATGAAGATCCAGAACTGCGAGGACAAGATTTTCGGCAGCGGCCTTTGC

AGGAATCACGCAGCATTCACCCTCACGATCATGTACATCATGGACCTCGTCTTG

TTCTTCCTCGACACCTTCCTTTGGTATGTCATCTGGAACTCGGTTTTCAGTATCG

CACGCTCTTTCGTACTCGGCCTTTCGATCTGGACACCATGGAGGGACATCTTCC

AGCGTCTGCCGAAGCGTATCTACGCGAAGCTTCTAGCGACCGGCGACATGGAG

GTCAAGTACAAGCCCAAGGTCTTGGTTTCGCAAATCTGGAACGCCATCATCATC

TCCATGTACCGCGAGCACTTGCTCTCTATCGAGCACGTTCAAAAGCTCCTGTAC

CATCAAGTGGACACTGGCGAAGCCGGCAAGCGGAGTCTTCGCGCGCCTCCGTT

CTTCGTCGCGCAGGGCAGCAGCGGTGGCTCGGGCGAGTTCTTCCCGCCTGGT

AGCGAGGCTGAGCGTCGTATCTCTTTCTTCGCGCAGTCTCTATCTACGGAGATT

CCTCAGCCCATCCCGGTTGACGCCATGCCGACGTTCACAGTGCTTACGCCTCA

CTACAGCGAGAAGATCCTTCTTTCGCTCCGTGAGATTATCCGCGAGGAGGACCA

GAACACCCGCGTGACATTGCTTGAGTATCTCAAGCAGCTTCACCCGGTCGAGTG

GGAGAACTTCGTCAAGGACACCAAGATAAGGCCGAGGAGTCCGCTATGTTCAA

CGGTCCAAGTCCTTTCGGCAACGATGAGAAGGGTCAGTCCAAGATGGACGATC

TTCCTTTCTACTGCATCGGTTTCAAGAGCGCCGCGCCCGAGTACACCCTCCGCA
```

TABLE 2-continued

Assignment of SEQ ID NOs.

CCCGTATCTGGGCGTCCTTGCGCGCGCAGACCCTCTACCGCACGGTCTCCGGC

ATGATGAACTATGCGAAGGCGATTAAGCTGCTCTACCGCGTCGAGAACCCCGA

GGTCGTGCAGCAGTTCGGCGGTAACACGGACAAGCTCGAGCGCGAGTTGGAG

CGGATGGCCCGGCGGAAGTTGAAGTTCCTGGTGTCCATGCAGCGCTACTCGAA

GTTCAACAAGGAGGAGCACGAGAACGCCGAGTTCTTGCTCCGCGCGTACCCGG

ACCTGCAGATCGCGTACCTGGAGGAAGAGCCTCCTCGCAAGGAGGGTGGCGAT

CCACGCATCTTCTCTGCCCTCGTCGACGGCCACAGCGACATCATCCCGGAGAC

CGGCAAGCGGCGCCCCAAGTTCCGCATCGAGCTGCCCGGCAACCCCATTCTCG

GTGACGGCAAGTCGCGACAACCAGAACCACGCCATCGTCTTCTACCGCGGCGAG

TACCTCCAGCTTATCGACGCCAACCAGGACAACTACCTCGAGGAGTGCTTGAAG

ATCCGTAACGTACTCGCCGAGTTCGAGGAGTACGACGTCTCTAGCCAGAGTCC

GTACGCGCAGTGGAGTGTCAAGGAGTTCAAGCGCTCCCCGGTCGCCATCGTCG

GTGCACGCGAGTATATCTTCTCGGAGCACATCGGTATTCTCGGTGATTTGGCGG

CTGGCAAGGAACAGACGTTCGGTACGCTCACGGCACGCAACAACGCCTTCCTT

GGCGGCAAGCTGCACTACGGTCACCCGGATTTCCTCAACGCCCTCTACATGAA

CACGCGCGGTGGTGTCTCCAAGGCGCAGAAGGGTCTCCATCTCAACGAGGATA

TTTACGCCGGTATGAACGCGGTCGGTCGCGGTGGACGCATCAAGCATAGCGAA

TACTACCAGTGCGGCAAGGGTCGTGACCTCGGTTTTGGCACCATCTTGAACTTC

CAGACCAAGATCGGTACCGGGTATGGGCGAGCAGATCCTCTCGCGCGAGTACTA

CTACCTCGGAACCCAATTGCCCATCGATCGCTTCCTCACGTTCTACTACGCGCA

CCCAGGTTTCCAGATCAACAACATGCTGGTTATCCTATCCGTGCAGGTCTTCAT

CGTTACCATGGTCTTCCTCGGTACCTTGAAGTCTTCGGTCACGATCTGCAAGTA

CACGTCCAGCGGTCAGTACATCGGTGGTCAATCCGGTTGCTACAACCTCGTCC

CGGTCTTCCAGTGGATCGAGCGCTGCATCATCAGCATCTTCTTGGTGTTCATGA

TCGCTTTCATGCCGCTCTTCCTGCAAGAACTCGTCGAGCGCGGTACCTGGAGT

GCCATCTGGCGTCTGCTCAAGCAGTTTATGTCGCTGTCGCCTGTCTTCGAGGTG

TTCTCCACCCAGATTCAGACACACTCCGTGTTGAGCAACTTGACGTTCGGTGGT

GCGCGTTACATCGCTACCGGTCGTGGGTTCGCCACCAGTCGTATCAGCTTCAG

CATCTTGTTCTCGCGTTTCGCAGGCCCGAGTATCTACCTCGGCATGCGCACGCT

CATTATGCTGCTCTACGTGACGTTGACGATCTGGACGCCATGGGTCATTTACTT

CTGGGTTTCCATTCTCTCGCTCTGCATCGCGCCGTTCTTGTTCAATCCGCATCAA

TTCGTCTTCTCGGATTTCCTCATCGACTACAGGGAATACCTCCGGTGGATGTCG

CGTGGTAACTCGCGCTCGCACAACAACTCCTGGATTGGGTACTGCCGGTTGTC

CCGCACGATGATCACTGGGTACAAGAAGAAGAAGCTGGGCCACCCGTCGGAGA

AGCTTTCCGGGGACGTTCCTCGTGCAGGCTGGCGCGCCGTCTTATTCTCGGAG

ATCATCTTCCCGGCATGCATGGCCATCCTCTTCATCATCGCGTACATGTTCGTCA

AGTCGTTCCCTCTCGACGGCAAGCAGCCTCCCTCCGGCCTCGTTCGCATCGCC

GTCGTGTCTATCGGCCCCATCGTGTGGAACGCCGCCATCCTGTTGACGCTCTTC

CTTGTGTCGTTGTTCCTCGGCCCCATGCTCGACCCGGTCTTCCCCCTCTTCGGT

TABLE 2-continued

Assignment of SEQ ID NOs.

TCCGTTATGGCCTTCATCGCGCATTTCCTCGGCACAATCGGAATGATTGGGTTC

TTCGAGTTCCTGTGGTTCCTCGAGTCCTGGGAGGCGTCGCATGCCGTGCTGGG

TCTCATCGCCGTCATCTCCATCCAGCGCGCCATTCACAAAATTCTTATCGCCGTT

TTCCTCAGTCGCGAGTTCAAGCACGACGAGACGAACAGGGCTTGGTGGACTGG

TCGCTGGTATGGCCGTGGCCTCGGCACGCACGCCATGTCGCAGCCGGCGCGT

GAGTTCGTCGTCAAGATCATCGAGTTGTCGCTCTGGAGCTCGGATCTCATACTC

GGCCACATCCTGCTGTTCATGCTTACTCCGGCTGTCCTCATCCCGTACTTCGAC

CGTCTGCACGCCATGATGCTCTTCTGGCTGCGCCCCTCAAAGCAAATCCGCGC

GCCTCTGTACTCAATCAAGCAGAAGAGGCAAAGACGCTGGATTATCATGAAGTA

CGGTACTGTATACGTTACCGTCATCGCGATCTTCGTCGCGCTCATCGCGCTTCC

CCTCGTCTTCCGACACACTCTAAAGGTCGAGTGCTCCCTTTGCGACAGCTTGTAA polypeptide sequence 1,3-β-D-glucan synthase II of S. commune strain Lu15531
amino acid
S. commune

SEQ ID NO: 8

MRNMFDFTMQLLDSRASRMTPNQALLTLHADYIGGQHANYRKWYFAAQLDLDDAV

GQTQNPGLNRLKSTRGSGKRPRHEKSLNTALERWRQAMNNMSQYDRLRQIALYLL

CWGEAAQVRFMPECLCFIFKCADDYYRSPECQNRMEPVPEGLYLRTVVKPLYRFV

RDQGYEVVEGKFVRRERDHDQIIGYDDVNQLFWYPEGIARIVLSDKSRLVDLPPAQ

RFMKFDRIEWNRVFFKTFYETRSFTHLLVDFNRIWVVHIALYFFYTAYNSPTIYAING

NTPTSLAWSATALGGAVATGIMILATIAEFSHIPTTWNNTSHLTRRLAFLLVTLGLTCG

PTFYVAIAESNGSGGSLALILGIVQFFISVVATALFTIMPSGRMFGDRVAGKSRKYLA

SQTFTASYPSLPKHQRFASLLMWFLIFGCKLTESYFFLTLSFRDPIRVMVGMKIQNC

EDKIFGSGLCRNHAAFTLTIMYIMDLVLFFLDTFLWYVIWNSVFSIARSFVLGLSIWTP

WRDIFQRLPKRIYAKLLATGDMEVKYKPKVLVSQIWNAIIISMYREHLLSIEHVQKLLY

HQVDTGEAGKRSLRAPPFFVAQGSSGGSGEFFPPGSEAERRISFFAQSLSTEIPQPI

PVDAMPTFTVLTPHYSEKILLSLREIIREEDQNTRVTLLEYLKQLHPVEWENFVKDTKI

LAEESAMFNGPSPFGNDEKGQSKMDDLPFYCIGFKSAAPEYTLRTRIWASLRAQTL

YRTVSGMMNYAKAIKLLYRVENPEVVQQFGGNTDKLERELERMARRKFKFLVSMQ

RYSKFNKEEHENAEFLLRAYPDLQIAYLEEEPPRKEGGDPRIFSALVDGHSDIIPETG

KRRPKFRIELPGNPILGDGKSDNQNHAIVFYRGEYLQLIDANQDNYLEECLKIRNVLA

EFEEYDVSSQSPYAQWSVKEFKRSPVAIVGAREYIFSEHIGILGDLAAGKEQTFGTL

TARNNAFLGGKLHYGHPDFLNALYMNTRGGVSKAQKGLHLNEDIYAGMNAVGRGG

RIKHSEYYQCGKGRDLGFGTILNFQTKIGTGMGEQILSREYYYLGTQLPIDRFLTFYY

AHPGFQINNMLVILSVQVFIVTMVFLGTLKSSVTICKYTSSGQYIGGQSGCYNLVPVF

QWIERCIISIFLVFMIAFMPLFLQELVERGTWSAIWRLLKQFMSLSPVFEVFSTQIQTH

SVLSNLTFGGARYIATGRGFATSRISFSILFSRFAGPSIYLGMRTLIMLLYVTLTIWTP

WVIYFWVSILSLCIAPFLFNPHQFVFSDFLIDYREYLRWMSRGNSRSHNNSWIGYCR

LSRTMITGYKKKKLGHPSEKLSGDVPRAGWRAVLFSEIIFPACMAILFIIAYMFVKSFP

LDGKQPPSGLVRIAVVSIGPIVWNAAILLTLFLVSLFLGPMLDPVFPLFGSVMAFIAHF

LGTIGMIGFFEFLWFLESWEASHAVLGLIAVISIQRAIHKILIAVFLSREFKHDETNRAW

TABLE 2-continued

Assignment of SEQ ID NOs.

WTGRWYGRGLGTHAMSQPAREFVVKIIELSLWSSDLILGHILLFMLTPAVLIPYFDRL

HAMMLFWLRPSKQIRAPLYSIKQKRQRRWIIMKYGTVYVTVIAIFVALIALPLVFRHTL

KVECSLCDSL

Gene sequence 1,3-β-D-glucan synthase I of *S. commune* strain Lu15634
DNA
*S. commune*

SEQ ID NO: 9

CCCGTCCCTCAAGGCCGTTCTTTCGCTGGCGACCGACCCGGTGTTCGCGAGAA

CCTGTTGTTTCTGACGATCATCAACCCTTTCTTCTCGTCGCTCTTTAGCTCTCCC

TAGACCGTCTTTTACTCTACTCTTCGACGCACGCCATGTCCGGTCCAGGATATG

GCAGGAATCCATTCGACAATCCCCCGCCCAACAGAGGTCCCTATGGCCAGCAG

CCAGGTTTCCCGGGGCCCGGCCCTCGGCCTTACGACTCGGACGCGGACATGA

GCCAGACCTATGGCAGCACAACCAGGCTCGCCGGCAGTGCCGGTTACAGCGA

CAGAAACGgtgcgaacgtcgctaccgtacttcctcgatcgtcgactcacatatcacgcagGCAGCTTCGA

CGGCGACCGCTCCTACGCGCCCTCAATTGACTCGCGCGCCAGCGTGCCCAGC

ATATCGCCCTTCGCAGACCCGGGTATCGGCTCTAATGAGCCGTATCCCGCTTG

GTCGGTCGAACGCCAGATCCCCATGTCCACGGAGGAGATTGAGGATATCTTCC

TCGACCTCACCCAAAAGTTTGGCTTCCAGCGCGACTCCATGCGGAATACGgtgcgt gaataagcagcccactcgaccgcgggaacagctcaattgacctgtcacccagTTCGACTTCATGATGCA

CCTCCTTGATTCCCGTGCCTCGCGCATGACGCCCAACCAAGCTCTGCTCACGCT

TCACGCCGACTACATTGGTGGCCAGCACGCCAACTATAGGAAGTGGTATTTCGC

CGCTCAGCTCAACCTCGATGACGCGGTCGGGCAAACCAATAACCCCGGTATCC

AGCGCTTGAAGACCATCAAGGGCGCTACGAAGACCAAGTCGCTCGACAGCGCA

CTCAACCGCTGGCGCAATGCGATGAACAACATGAGCCAGTACGATCGCCTCCG

GCAAATTGCGCTCTATCTCCTCTGCTGGGGAGAAGCAGGCAACATCCGTCTGG

CGCCCGAGTGCTTGTGCTTCATCTTCAAGTGCGCGGACGACTACTACAGAAGTC

CCGAGTGTCAGAACCGGATGGACCCCGTGCCGGAAGGGCTGTACCTCCAGAC

GGTCATCAAGCCGCTCTATCGCTTCCTACGTGATCAGGCGTACGAAGTCGTTGA

TGGGAAGCAAGTGAAGCGCGAGAAGGACCACGACCAGATTATCGGTTATGACG

ACGTCAACCAGTTATTCTGGTATCCGGAAGGTTTGGCTAAGATCGTCATGTCGG

ACAACgtgcgtatgatcttatcggttacaattcgtccgctcacatctttccagACACGACTTGTAGATGTAC

CTCCGGCGCAGCGGTTCATGAAGTTCGCCAAGATCGAGTGGAACCGCGTCTTC

TTCAAGACGTACTTTGAGAAGCGCTCTACTGCCCATCTCCTGGTCAACTTCAAC

CGTATATGGATCCTCCACGTCTCGATGTACTTCTTCTACACGGCATTCAACTCTC

CACGAGTCTACGCGCCGCACGGCAAACTCGACCCCTCCCCTGAGATGACCTGG

TCCGCGACTGCCCTTGGAGGCGCTGTGTCCACCATGATCATGATCCTTGCCACT

ATCGCGGAGTACACCTACATCCCCACGACATGGAACAATGCGTCGCACCTCAC

CACGCGGCTCATTTTCCTCCTGGTCATCCTCGCGCTCACTGCTGGACCAACATT

CTATATCGCCATGATAGACGGACGCACGGACATCGGCCAAGTACCACTCATCGT

GGCCATAGTGCAGTTCTTCATCTCCGTCGTCGCCACCCTCGCTTTCGCTACCAT

CCCTTCTGGTCGCATGTTCGGCGACCGTGTGGCTGGCAAGTCAAGAAAGCACA

TABLE 2-continued

Assignment of SEQ ID NOs.

TGGCATCGCAGACGTTCACAGCGTCGTACCCGTCCATGAAGCGGTCATCTCGC

GTAGCGAGTATCATGCTGTGGCTTTTGGTCTTTGGCTGCAAATACGTCGAGTCT

TACTTCTTCTTGACGTCCTCCTTCTCCAGCCCGATCGCGGTCATGGCGCGTACG

AAGGTACAGGGCTGCAACGACCGTATCTTCGGCAGCCAGCTGTGCACGAATCA

GGTCCCGTTCGCGCTGGCAATCATGTACGTGATGGACCTGGTACTGTTCTTCCT

GGACACGTACCTGTGGTACATCATCTGGCTGGTGATCTTCTCGATGGTGCGCG

CGTTCAAGCTTGGTATCTCGATCTGGACGCCCTGGAGCGAGATCTTCACCCGCA

TGCCGAAGCGTATCTACGCGAAGCTGCTGGCGACGGCCGAGATGGAGGTCAA

GTATAAGCCCAAGgtatgctgaatgcaatctggtcaggtgaattcaccctcatattgttgtgcagGTGCTCG

TCTCGCAAATCTGGAACGCGGTCATCATCTCCATGTACCGGGAGCATCTCTTGT

CCATCGAGCACGTCCAGCGCCTGCTATACCACCAGGTTGATGGTCCAGACGGT

CGCCGCACCCTCAGGGCACCGCCGTTCTTCACCAGCCAGCGAACTGCGAAGCC

AGGCCTGTTCTTCCCTCCTGGTGGCGAGGCTGAGCGCCGTATCTCGTTCTTTGC

CTCATCGCTGACGACCGCGCTCCCTGAGCCTCTGCCGATCGACGCCATGCCCA

CCTTCACCGTGCTCGTTCCCCATTACTCGGAGAAGATTCTGCTCAGTCTGCGCG

AGATTATTCGCGAGGAGGACCAGAACACCCGCGTCACCTTGCTGGAGTACCTC

AAGCAGCTCCACCCTGTCGAATGGGACAACTTCGTCAAGGACACCAAGATCTTG

GCGGAAGAGTCGGGCGACGTCCAGGACGAGAAGCGCGCGCGCACGGACGACT

TGCCGTTCTACTGCATCGGGTTCAAGACCTCGTCACCAGAGTACACCCTGCGTA

CGCGTATCTGGGCTTCACTGCGCGCACAGACGCTGTACCGCACGGTCTCCGGT

ATGATGAACTACTCCAAGGCGATCAAGCTCCTCTATCGCGTCGAGAACCCGGAT

GTCGTTCATGCCTTCGGTGGGAACACGGAACGTCTTGAACGCGAGCTTGAGCG

CATGTCTCGCCGCAAGTTCAAGTTCGTCATCTCGATGCAGCGGTACTCTAAGTT

CAACAAGGAGGAGCAAGAGAACGCCGAATTCCTTCTGCGCGCGTACCCGGATT

TGCAGATCGCGTACCTCGATGAAGAGCCCGGTCCCAGCAAGAGCGACGAGGTT

CGGTTGTTTTCGACACTCATCGATGGACACTCCGAGGTGGATGAGAAGACCGG

CCGCCGCAAGCCCAAGTTCCGCATTGAGCTGCCCGGTAACCCCATCCTCGGTG

ACGGGAAGTCGGATAACCAGAACCACGCCATTGTCTTCTACCGCGGCGAGTAC

ATCCAGGTCATCGACGCTAACCAGGACAATTACCTGGAAGAGTGTCTCAAGATC

CGTAACGTCCTGGGCGAGTTTGAGGAATACTCCGTGTCGAGCCAGAGCCCGTA

CGCACAGTGGGGCCACAAGGAGTTCAACAAGTGCCCCGTCGCTATCCTGGGTT

CTCGCGAGTACATCTTCTCGGAGAACATCGGTATCCTCGGTGACATCGCCGCC

GGCAAGGAACAGACGTTCGGTACCATTACGGCGCGTGCGCTTGCGTGGATCGG

CGGCAAGCTGCATTACGGTCACCCGGATTTCCTCAATGCGACGTTCATGACGAC

GCGTGGTGGCGTGTCAAAAGCGCAGAAGGGCTTGCATCTCAACGAGGATATCT

TCGCTGGTATGACCGCCGTGTCCCGCGGAGGGCGCATCAAGCACATGGAGTAC

TACCAGTGCGGCAAAGGTCGTGATCTCGGTTTCGGCACGATCTTGAACTTCCAG

ACGAAGATCGGTACTGGTATGGGCGAGCAGCTCCTCTCGCGCGAGTACTACTA

CCTGGGCACGCAATTGCCTATCGACCGGTTCTTGACGTTCTACTACGCGCACGC

TABLE 2-continued

Assignment of SEQ ID NOs.

TGGTTTCCACGTCAACAACATCCTGGTCATCTACTCCATCCAGGTCTTCATGGTC

ACCTgtaagtgcaggcgctcatgaccgccgagaacgtagtctgacggatgtgcagTGCTGTACCTGGG

CACATTGAACAAGCAGCTGTTCATCTGCAAGGTCAACTCCAATGGCCAGGTTCT

TAGTGGACAAGCTGGGTGCTACAACCTCATCCCGGTCTTCGAGTGGATTCGCC

GGAGTATCATCTCCATCTTCTTGGTGTTCTTCATCGCCTTCTTGCCTCTATTCTT

GCAAGgtatgttcactttccatgtgtcatccgttagccgctcaccatacgacagAGCTGTGCGAGCGCGG

AACGGGAAAGGCGTTGCTGCGTCTCGGGAAGCACTTCTTGTCACTGTCGCCCA

TTTTCGAAGTGTTCTCCACCCAGATTTACTCGCAGGCGCTCTTGAACAACATGA

GCTTCGGTGGTGCGCGCTACATCGCCACAGGTCGTGGTTTCGCGACTAGTCGC

ATACCCTTCAACATCCTCTACTCGCGTTTCGCGCCGCCAAGCATCTACATGGGC

ATGCGTAACCTGCTGCTCCTGCTGTACGCGACGATGGCCATTTGGATCCCGCA

CCTGATCTACTTCTGGTTCTCCGTCCTCTCCCTCTGCATCGCGCCATTCATGTTC

AATCCGCATCAATTCTCGTACGCCGACTTCATCATCGACTACCGGGAGTTCTTG

CGCTGGATGTCGCGCGGTAACTCGCGAACGAAGGCGAGCAGCTGGTACGGAT

ACTGCCGTCTGTCGCGTACCGCGATTACTGGGTACAAGAAGAAGAAGCTGGGA

CACCCGTCGGAGAAGCTGTCGGGCGACGTACCGCGTGCGCCGTGGAGGAACG

TTATCTTCTCGGAGATCCTGTGGCCCATCGGCGCGTGCATCATCTTCATCGTCG

CGTACATGTTCGTCAAGTCGTTCCCCGACGAGCAGGGCAACGCGCCGCCGAGC

CCGCTGGTCCGGATTCTGCTCATCGCGGTTGGCCCTACTGTGTGGAACGCGGC

GGTGCTCATAACGCTGTTCTTCCTGTCGCTCTTCCTGGGCCCGATGATGGATGG

CTGGGTCAAGTTCGGCTCGGTCATGGCGGCCCTTGCGCATGGCCTGGCGCTTA

TAGGCATGCTCACGTTCTTTGAGTTCTTCgtacgtccttcgcgttgtgtcgtcaagtgctctgctaacg ccgtcttcagTGGTTCCTTGAGCTCTGGGATGCCTCGCACGCCGTGCTCGGCGTCAT

CGCTATCATTGCCGTTCAGCGCGGGATCCAGAAGATCCTCATTGCCGTCTTCCT

GACGCGTGAGTACAAGCACGACGAGACGAACCGCGCGTGGTGGACAGGTAAAT

GGTATGGACGCGGGCTGGGTACCTCGGCCATGTCCCAGCCGGCGCGCGAGTT

CATCGTGAAGATCGTGGAGATGTCGTTGTGGACGTCGGACTTCCTGCTTGCGC

ACCTGTTGCTCATCATCTTGACGGTGCCGCTACTGCTGCCGTTCTTCAACTCAAT

TCATTCGACGATGCTTTgtgagtggtttgtagtcgttggtcatggatgatttctgactcgcgtgcagTCTGG

TTGCGCCCTTCGAAGCAGATTAGGCAACCTCTGTTCTCCACCAAGCAGAAGCGG

CAACGGCGATGGATTgtgagttcctttgattgctctgggtaccgaccttcgctcacctttcttagGTCATGAA

GTATACCGTGGTATATCTCGTGGTGGTGGCTTTCCTCGTCGCGCTCATCGCTCT

GCgtacgttttccctcgcgctcaccctgtatttttcactaacgtttcctccagCCGCCCTCTTCCGCGAGAGC

ATCCACTTCAACTGCGAGATCTGCCAGAGTATATAGTCATATAACGACGTCTATC

GTATCGCCGGACGAGAGCCCCGTCGCCTACACACTGACATGGAATCGCTGTGT

ATACAATCGATCTTCTGACCGCGTCGGGGGCGTTGCCGTCTTTCTACTATCAAT

TABLE 2-continued

Assignment of SEQ ID NOs.

TTGCTTGTGTATCAACATTTCTTCTCTCCAAGCCTACATTGACATAGAGTAATAG

CCCATGTTCATACAACAATCGCATAGCATTGCATATACCAT translation of SEQ ID NO: 13
amino acid
S. commune

SEQ ID NO: 10

MSGPGYGRNPFDNPPPNRGPYGQQPGFPGPGPRPYDSDADMSQTYGSTTRLAG

SAGYSDRNGSFDGDRSYAPSIDSRASVPSISPFADPGIGSNEPYPAWSVERQIPMS

TEEIEDIFLDLTQKFGFQRDSMRNTFDFMMHLLDSRASRMTPNQALLTLHADYIGGQ

HANYRKWYFAAQLNLDDAVGQTNNPGIQRLKTIKGATKTKSLDSALNRWRNAMNN

MSQYDRLRQIALYLLCWGEAGNIRLAPECLCFIFKCADDYYRSPECQNRMDPVPEG

LYLQTVIKPLYRFLRDQAYEVVDGKQVKREKDHDQIIGYDDVNQLFWYPEGLAKIVM

SDNTRLVDVPPAQRFMKFAKIEWNRVFFKTYFEKRSTAHLLVNFNRIWILHVSMYFF

YTAFNSPRVYAPHGKLDPSPEMTWSATALGGAVSTMIMILATIAEYTYIPTTWNNAS

HLTTRLIFLLVILALTAGPTFYIAMIDGRTDIGQVPLIVAIVQFFISVVATLAFATIPSGRM

FGDRVAGKSRKHMASQTFTASYPSMKRSSRVASIMLWLLVFGCKYVESYFFLTSSF

SSPIAVMARTKVQGCNDRIFGSQLCTNQVPFALAIMYVMDLVLFFLDTYLWYIIWLVI

FSMVRAFKLGISIWTPWSEIFTRMPKRIYAKLLATAEMEVKYKPKVLVSQIWNAVIISM

YREHLLSIEHVQRLLYHQVDGPDGRRTLRAPPFFTSQRTAKPGLFFPPGGEAERRIS

FFASSLTTALPEPLPIDAMPTFTVLVPHYSEKILLSLREIIREEDQNTRVTLLEYLKQLH

PVEWDNFVKDTKILAEESGDVQDEKRARTDDLPFYCIGFKTSSPEYTLRTRIWASLR

AQTLYRTVSGMMNYSKAIKLLYRVENPDVVHAFGGNTERLERELERMSRRKFKFVI

SMQRYSKFNKEEQENAEFLLRAYPDLQIAYLDEEPGPSKSDEVRLFSTLIDGHSEVD

EKTGRRKPKFRIELPGNPILGDGKSDNQNHAIVFYRGEYIQVIDANQDNYLEECLKIR

NVLGEFEEYSVSSQSPYAQWGHKEFNKCPVAILGSREYIFSENIGILGDIAAGKEQTF

GTITARALAWIGGKLHYGHPDFLNATFMTTRGGVSKAQKGLHLNEDIFAGMTAVSR

GGRIKHMEYYQCGKGRDLGFGTILNFQTKIGTGMGEQLLSREYYYLGTQLPIDRFLT

FYYAHAGFHVNNILVIYSIQVFMVTLLYLGTLNKQLFICKVNSNGQVLSGQAGCYNLI

PVFEWIRRSIISIFLVFFIAFLPLFLQELCERGTGKALLRLGKHFLSLSPIFEVFSTQIVS

QALLNNMSFGGARYIATGRGFATSRIPFNILYSRFAPPSIYMGMRNLLLLLYATMAIW

IPHLIYFWFSVLSLCIAPFMFNPHQFSYADFIIDYREFLRWMSRGNSRTKASSWYGY

CRLSRTAITGYKKKKLGHPSEKLSGDVPRAPWRNVIFSEILWPIGACIIFIVAYMFVKS

FPDEQGNAPPSPLVRILLIAVGPTVWNAAVLITLFFLSLFLGPMMDGWVKFGSVMAA

LAHGLALIGMLTFFEFFWFLELWDASHAVLGVIAIIAVQRGIQKILIAVFLTRKWYGRG

LGTSAMSQPAREFIVKIVEMSLWTSDFLLAHLLLIILTVPLLLPFFNSIHSTMLFWLRPS

KQIRQPLFSTKQKRQRRWIVMKYTVVYLVVVAFLVALIALPALFRESIHFNCEICQSI

Gene sequence 1,3-β-D-glucan synthase II of S. commune strain Lu15634
DNA
S. commune

SEQ ID NO: 11

CTGTCCAAGGAGGAGATCGAGGACATCTTCCTCGATTTGACGCAGAAGTTTGGC

TTTCAGCGGGATTCCATGCGGAATATGgtacgtggcgtgtgcccatgtgcggcgttctgaggcctaa cgttttccgccagTTCGACTTCACCATGCAGCTGCTTGACAGCCGAGCGTCTCGTATG TABLE 2-continued Assignment of SEQ ID NOs.

ACCCCCAACCAGGCGCTCCTCACCCTCCACGCCGACTACATTGGTGGCCAGCA

TGCGAACTACCGGAAGTGGTACTTCGCGGCGCAGCTCGACCTTGACGACGCCG

TGGGACAAACTCAGAATCCGGGTCTCAACCGCCTCAAGTCCACTCGCGGATCG

GGCAAGCGACCACGCCATGAAAAGTCGCTGAACACGGCATTGGAGCGCTGGC

GGCAAGCCATGAACAACATGTCGCAGTATGACCGCTTACGCCAGATCGCGCTC

TACCTGCTCTGCTGGGGCGAAGCGGCGCAAGTGCGATTCATGCCCGAGTGCTT

GTGCTTCATCTTCAAGTGCGCCGACGACTACTATCGTTCGCCGGAGTGCCAGAA

CAGGATGGAGCCGGTACCGGAGGGTCTCTACCTGAGGACGGTCGTAAAGCCG

CTCTACAGATTTGTCCGGGATCAAGGCTATGAGGTGGTGGAGGGAAAATTCGTA

CGGCGGGAACGGGATCACGACCAAATCATTGGTTACGATGACGTGAATCAGCT

GTTCTGGTACCCGGAGGGAATTGCCCGTATCGTCCTGTCGGACAAGgtaagcacctc tgtgcatcttctgtgacatacagggctaattgtcgagcagAGTCGTCTAGTCGACCTCCCCCCAGCA

CAGCGCTTCATGAAGTTCGACCGTATCGAGTGGAATCGCGTCTTCTTCAAGACG

TTTTACGAGACTCGATCCTTCACGCATCTTTTGGTCGACTTCAACCGTATCTGGG

TCGTGCACATCGCTCTCTACTTCTTCTACACTGCATACAACTCCCCCACGATCTA

CGCCATCAACGGCAACACACCGACGTCTCTGGCTTGGAGCGCGACTGCGCTCG

GCGGTGCGGTAGCGACAGGTATCATGATCCTCGCCACGATCGCCGAGTTCTCG

CACATCCCCACGACATGGAACAACACCTCGCATCTGACTCGCCGCCTCGCCTTC

CTCCTCGTCACGCTCGGCCTCACATGTGGTCCGACGTTCTACGTCGCGATTGCA

GAGAGCAACGGGAGCGGCGGCTCTTTGGCCTTGATTCTCGGTATCGTCCAGTT

CTTCATCTCCGTCGTGGCAACTGCGCTCTTCACTATCATGCCTTCTGGTCGTAT

GTTCGGCGACCGTGTCGCAGGCAAGAGTCGCAAGTATCTCGCCAGCCAGACGT

TCACGGCCAGCTACCCGTCGTTGCCCAAGCACCAGCGGTTCGCCTCACTCCTG

ATGTGGTTCCTCATCTTCGGGTGCAAGTTGACGGAGAGTTACTTCTTTCTGACG

CTGTCCTTCCGCGACCCTATCCGCGTCATGGTCGGCATGAAGATCCAGAACTG

CGAGGACAAGATTTTCGGCAGCGGCCTTTGCAGGAATCACGCAGCATTCACCC

TCACGATCATGTACATCATGGACCTCGTCTTGTTCTTCCTCGACACCTTCCTTTG

GTATGTCATCTGGAACTCGGTTTTCAGTATCGCACGCTCTTTCGTACTCGGCCTT

TCGATCTGGACACCGTGGAGAGACATCTTCCAGCGTCTGCCGAAGCGGATCTA

CGCGAAGCTTCTGGCGACTGGCGACATGGAGGTCAAGTACAAGCCCAAGgtatgc gttgagctcgccgtaaatccacttaaggctaacacgttcgcagGTCTTGGTCTCGCAAATCTGGAAC

GCCATCATCATCTCCATGTACCGCGAGCACTTGCTCTCTATTGAGCACGTCCAG

AAGCTCCTGTACCACCAAGTGGACACTGGCGAAGCCGGCAAGCGGAGTCTTCG

CGCGCCTCCGTTCTTCGTCGCGCAGGGCAGCAGCGGTGGCTCGGGCGAGTTC

TTCCCGCCTGGCAGCGAGGCCGAGCGTCGTATCTCTTTCTTCGCGCAGTCGCT

TTCTACGGAGATTCCTCAGCCCATCCCGGTCGACGCCATGCCGACGTTCACGG

TGCTTACGCCTCACTACAGCGAGAAGgtccatgctccccttgtagccatatgacatcagctgactgtc gtgcacagATCCTTCTCTCTCCGTGAAATTATCCGCGAGGAGGACCAGAACACT

CGCGTTACGTTGCTCGAGTACCTGAAGCAGCTGCATCCGGTCGAGTGGGAGAA

TABLE 2-continued

Assignment of SEQ ID NOs.

TTTCGTCAAGGACACTAAAATTTTGGCCGAGGAGTCCGCTATGTTTAACGGTCC

GAGTCCTTTCGGCAACGACGAGAAGGGTCAGTCCAAGATGGACGATCTACCGT

TCTACTGCATCGGTTTCAAGAGCGCCGCGCCCGAGTACACCCTCCGCACCCGT

ATCTGGGCGTCCCTGCGCGCGCAGACGCTGTACCGCACGGTCTCCGGCATGAT

GAACTATGCGAAGGCGATCAAGCTGCTCTACCGCGTTGAGAACCCGGAGGTCG

TACAACAGTTCGGCGGCAACACGGACAAGCTCGAGCGCGAGTTGGAGCGGATG

GCGCGACGGAAGTTCAAGTTCCTCGTGTCCATGCAGCGCTACTCGAAGTTCAAC

AAGGAGGAGCACGAGAACGCCGAGTTCTTGCTCCGCGCGTACCCGGACTTGCA

GATCGCGTACCTCGAGGAAGAGCCCCCTCGCAAGGAGGGCGGCGATCCACGC

ATCTTCTCTGCCCTCGTCGACGGCCACAGCGACATCATCCCGGAGACCGGCAA

GCGGCGCCCCAAGTTCCGTATCGAGCTGCCCGGTAACCCCATTCTCGGTGACG

GTAAATCCGACAATCAGAACCACGCTATCGTCTTCTACCGCGGCGAGTACCTCC

AGCTTATCGACGCCAACCAGGACAACTACCTCGAGGAGTGCTTGAAGATCCGTA

ACGTGCTCGCCGAGTTTGAGGAGTACGACGTCTCCAGCCAGAGCCCGTACGCG

CAGTGGAGTGTCAAGGAGTTCAAGCGCTCTCCGGTCGCCATCGTCGGTGCACG

CGAGTACATCTTCTCAGAGCACATCGGTATCCTCGGTGATCTGGCGGCTGGCAA

GGAACAGACGTTCGGTACGCTCACGGCACGCAACAACGCCTTCCTTGGCGGCA

AGCTGCACTACGGTCACCCCGATTTCCTCAACGCCCTCTACATGAACACGCGCG

GTGGTGTCTCCAAGGCGCAGAAGGGTCTCCATCTCAACGAGGATATCTACGCC

GGTATGAACGCGGTCGGTCGCGGTGGACGCATTAAGCACAGCGAGTACTATCA

GTGCGGCAAGGGTCGTGACCTCGGTTTCGGCACCATCTTGAACTTCCAGACCA

AGATCGGTACGGGTATGGGCGAGCAGATCCTCTCGCGCGAGTACTACTATCTC

GGAACACAACTGCCCATCGATCGCTTCCTCACGTTCTACTACGCGCACCCGGGT

TTCCAGATCAACAACATGCTGGTCATCCTCTCCGTGCAGGTCTTCATCGTTACCA gtacgttcaatgcatattgttagcctgacaacgtctgacgaatttccagTGGTCTTCCTCGGTACCTTGAA

GTCTTCGGTCACGATCTGCAAGTACACGTCCAGCGGTCAGTACATCGGTGGTCA

ATCCGGTTGCTACAACCTCGTCCCGGTCTTCCAGTGGATCGAGCGCTGCATCAT

CAGCATCTTCTTGGTGTTCATGATCGCTTTCATGCCGCTCTTCCTGCAAGgtaaga gcttgtcaacctgctcaaggggcttgcgctgatcatcatctcagAACTCGTCGAGCGCGGTACCTGGA

GTGCCATCTGGCGTCTGCTCAAGCAGTTTATGTCGCTGTCGCCTGTCTTCGAGG

TGTTCTCCACCCAGATTCAGACGCACTCCGTGTTGAGCAACTTGACGTTCGGTG

GTGCGCGTTACATCGCTACCGGTCGTGGGTTCGCCACCAGTCGTATCAGCTTC

AGCATCTTGTTCTCGCGTTTCGCAGGCCCGAGTATCTACCTCGGCATGCGCACG

CTCATTATGCTGCTCTACGTGACGTTGACGATCTGGACGCCATGGGTCATTTAC

TTCTGGGTTTCCATTCTCTCGCTCTGCATCGCGCCGTTCTTGTTCAACCCGCATC

AATTCGTATTCTCGGACTTCCTCATCGACTACAGgtacgtcggacgagcgctgttccgcgacgt aagctgaccggttatacagGGAATACCTGCGGTGGATGTCGCGTGGCAACTCGCGCTCG

CACAACAACTCCTGGATTGGGTACTGCCGGTTGTCCCGCACGATGATCACTGG

GTACAAGAAGAAGAAGCTGGGCCACCCGTCGGAGAAGCTTTCCGGCGACGTTC

TABLE 2-continued

Assignment of SEQ ID NOs.

CTCGTGCAGGCTGGCGCGCCGTCTTGTTCTCGGAGATCATCTTCCCGGCGTGC

ATGGCCATCCTCTTCATCATCGCGTACATGTTCGTCAAGTCGTTCCCTCTCGAC

GGCAAGCAGCCTCCCTCCGGCCTCGTTCGCATCGCCGTCGTGTCTATCGGCCC

CATCGTGTGGAACGCCGCCATCCTGTTGACGCTCTTCCTTGTGTCGTTGTTCCT

CGGCCCCATGCTCGACCCGGTCTTCCCCCTCTTCGGTTCCGTTATGGCCTTCAT

CGCGCATTTCCTTGGCACAATCGGAATGATTGGGTTCTTCGAGTTCCTGgtatgtgc ccataccttccattcgacttcaactatctaacagattcatagTGGTTCCTCGAGTCCTGGGAGGCGTC

GCATGCCGTGCTGGGTCTCATCGCCGTCATCTCCATCCAGCGCGCCATTCACA

AGATCCTTATCGCCGTTTTCCTCAGTCGCGAGTTCAAGCACGACGAGACGAACA

GGGCCTGGTGGACTGGTCGCTGGTATGGCCGTGGCCTCGGCACGACGCCAT

GTCGCAGCCGGCGCGTGAGTTCGTCGTCAAGATCATCGAGTTGTCGCTTTGGA

GCTCGGATCTCATACTCGGCCACATCCTGCTGTTCATGCTTACTCCGGCCGTCC

TCATCCCGTACTTCGACCGTTTGCACGCCATGATGCTCTgtacgtcgtgtctcattgtctgtgtt ggtcatactcttaccctctcttagTCTGGCTGCGTCCCTCGAAGCAAATCCGCGCGCCTCTG TACTCGATCAAGCAGAAGAGGCAAAGACGCTGGATTgtcagtgttcagtgccttattctatcag ctcttactaacgtcttcatagATCATGAAGTACGGTACTGTATACGTTACCGTCATCGCGAT CTTCGTCGCGCTCATCGCGCTTCgtgagtttccttgctattttcgtacctgagcgtcgctgaccccttccc agCCCTCGTATTCCGACACACTCTAAAGGTCGAGTGCTCCCTTTGCGACAGCTT

GTAATATCGGACTCGTATATATCTAGACTTCTCCGCACCATGTGTAGCTGACGCT

TGGGTATACTTCGCGGTGCCGAGCTAATTGTCGACGGACATTCTCCATCGTTGA

GTGCAGCGACGTCGGGTGGTTTACGACACGGACACTTTTCATTGTACCCTCTAC

GAATGCAAGAACTCTCTTACGACCAGTACCTATGTGCTAAGCCGTCGCCTGTTC

AGGATCATACATACATACGTTTCTAGATACCTTACAGTTAGGCCTATTCAGGGAG

AGTCTGCATAAAA

```
translation of SEQ ID NO: 15
amino acid
S. commune
                                                                SEQ ID NO: 12
MPRPGGTSAEGGYASSPSMETTPSDPFGTANGAPRRYYDNDSEEYGPGRRDTYA

SDSSNQGLTDPGYYDQNGAYDPYPTGDTDSDGDVYGQRYGPSAESLGTHKFGHS

DSSTPTFVDYSASSGGRDSYPAWTAERNIPLSKEEIEDIFLDLTQKFGFQRDSMRN

MFDFTMQLLDSRASRMTPNQALLTLHADYIGGQHANYRKWYFAAQLDLDDAVGQT

QNPGLNRLKSTRGSGKRPRHEKSLNTALERWRQAMNNMSQYDRLRQIALYLLCW

GEAAQVRFMPECLCFIPKCADDYYRSPECQNRMEPVPEGLYLRTVVKPLYRFVRD

QGYEVVEGKFVRRERDHDQIIGYDDVNQLFWYPEGIARIVLSDKSRLVDLPPAQRF

MKFDRIEWNRVFFKTFYETRSFTHLLVDFNRIWVVHIALYFFYTAYNSPTIYAINGNT

PTSLAWSATALGGAVATGIMILATIAEFSHIPTTWNNTSHLTRRLAFLLVTLGLTCGPT

FYVAIAESNGSGGSLALILGIVQFFISVVATALFTIMPSGRMFGDRVAGKSRKYLASQ

TFTASYPSLPKHQRFASLLMWFLIFGCKLTESYFFLTLSFRDPIRVMVGMKIQNCED

KIFGSGLCRNHAAFTLTIMYIMDLVLFFLDTFLWYVIWNSVFSIARSFVLGLSIWTPWR

DIFQRLPKRIYAKLLATGDMEVKYKPKVLVSQIWNAIIISMYREHLLSIEHVQKLLYHQ
```

TABLE 2-continued

Assignment of SEQ ID NOs.

VDTGEAGKRSLRAPPFFVAQGSSGGSGEFFPPGSEAERRISFFAQSLSTEIPQPIPV

DAMPTFTVLTPHYSEKILLSLREIIREEDQNTRVTLLEYLKQLHPVEWENFVKDTKILA

EESAMFNGPSPFGNDEKGQSKMDDLPFYCIGFKSAAPEYTLRTRIWASLRAQTLYR

TVSGMMNYAKAIKLLYRVENPEVVQQFGGNTDKLERELERMARRKFKFLVSMQRY

SKFNKEEHENAEFLLRAYPDLQIAYLEEEPPRKEGGDPRIFSALVDGHSDIIPETGKR

RPKFRIELPGNPILGDGKSDNQNHAIVFYRGEYLQLIDANQDNYLEECLKIRNVLAEF

EEYDVSSQSPYAQWSVKEFKRSPVAIVGAREYIFSEHIGILGDLAAGKEQTFGTLTA

RNNAFLGGKLHYGHPDFLNALYMNTRGGVSKAQKGLHLNEDIYAGMNAVGRGGRI

KHSEYYQCGKGRDLGFGTILNFQTKIGTGMGEQILSREYYYLGTQLPIDRFLTFYYA

HPGFQINNMLVILSVQVFIVTMVFLGTLKSSVTICKYTSSGQYIGGQSGCYNLVPVFQ

WIERCIISIFLVFMIAFMPLFLQELVERGTWSAIWRLLKQFMSLSPVFEVFSTQIQTHS

VLSNLTFGGARYIATGRGFATSRISFSILFSRFAGPSIYLGMRTLIMLLYVTLTIWTPW

VIYFWVSILSLCIAPFLFNPHQFVFSDFLIDYREYLRWMSRGNSRSHNNSWIGYCRL

SRTMITGYKKKKLGHPSEKLSGDVPRAGWRAVLFSEIIFPACMAILFIIAYMFVKSFPL

DGKQPPSGLVRIAVVSIGPIVWNAAILLTLFLVSLFLGPMLDPVFPLFGSVMAFIAHFL

GTIGMIGFFEFLWFLESWEASHAVLGLIAVISIQRAIHKILIAVFLSREFKHDETNRAW

WTGRWYGRLGTHAMSQPAREFVVKIIELSLWSSDLILGHILLFMLTPAVLIPYFDRL

HAMMLFWLRPSKQIRAPLYSIKQKRQRRWIIMKYGTVYVTVIAIFVALIALPLVFRHTL

KVECSLCDSL cDNA 1,3-β-D-glucan synthase I of *S. commune* strain Lu15634  
DNA  
*S. commune*

SEQ ID NO: 13

ATGTCCGGTCCAGGATATGGCAGGAATCCATTCGACAATCCCCCGCCCAACAG

AGGTCCCTATGGCCAGCAGCCAGGTTTCCCGGGGCCCGGCCCTCGGCCTTAC

GACTCGGACGCGGACATGAGCCAGACCTATGGCAGCACAACCAGGCTCGCCG

GCAGTGCCGGTTACAGCGACAGAAACGGCAGCTTCGACGGCGACCGCTCCTAC

GCGCCCTCAATTGACTCGCGCGCCAGCGTGCCCAGCATATCGCCCTTCGCAGA

CCCGGGTATCGGCTCTAATGAGCCGTATCCCGCTTGGTCGGTCGAACGCCAGA

TCCCCATGTCCACGGAGGAGATTGAGGATATCTTCCTCGACCTCACCCAAAAGT

TTGGCTTCCAGCGCGACTCCATGCGGAATACGTTCGACTTCATGATGCACCTCC

TTGATTCCCGTGCCTCGCGCATGACGCCCAACCAAGCTCTGCTCACGCTTCACG

CCGACTACATTGGTGGCCAGCACGCCAACTATAGGAAGTGGTATTTCGCCGCTC

AGCTCAACCTCGATGACGCGGTCGGGCAAACCAATAACCCCGGTATCCAGCGC

TTGAAGACCATCAAGGGCGCTACGAAGACCAAGTCGCTCGACAGCGCACTCAA

CCGCTGGCGCAATGCGATGAACAACATGAGCCAGTACGATCGCCTCCGGCAAA

TTGCGCTCTATCTCCTCTGCTGGGGAGAAGCAGGCAACATCCGTCTGGCGCCC

GAGTGCTTGTGCTTCATCTTCAAGTGCGCGGACGACTACTACAGAAGTCCCGAG

TGTCAGAACCGGATGGACCCCGTGCCGGAAGGGCTGTACCTCCAGACGGTCAT

CAAGCCGCTCTATCGCTTCCTACGTGATCAGGCGTACGAAGTCGTTGATGGGAA

GCAAGTGAAGCGCGAGAAGGACCACGACCAGATTATCGGTTATGACGACGTCA

TABLE 2-continued

Assignment of SEQ ID NOs.

ACCAGTTATTCTGGTATCCGGAAGGTTTGGCTAAGATCGTCATGTCGGACAACA

CACGACTTGTAGATGTACCTCCGGCGCAGCGGTTCATGAAGTTCGCCAAGATC

GAGTGGAACCGCGTCTTCTTCAAGACGTACTTTGAGAAGCGCTCTACTGCCCAT

CTCCTGGTCAACTTCAACCGTATATGGATCCTCCACGTCTCGATGTACTTCTTCT

ACACGGCATTCAACTCTCCACGAGTCTACGCGCCGCACGGCAAACTCGACCCC

TCCCCTGAGATGACCTGGTCCGCGACTGCCCTTGGAGGCGCTGTGTCCACCAT

GATCATGATCCTTGCCACTATCGCGGAGTACACCTACATCCCCACGACATGGAA

CAATGCGTCGCACCTCACCACGCGGCTCATTTCCTCCTGGTCATCCTCGCGCT

CACTGCTGGACCAACATTCTATATCGCCATGATAGACGGACGCACGGACATCGG

CCAAGTACCACTCATCGTGGCCATAGTGCAGTTCTTCATCTCCGTCGTCGCCAC

CCTCGCTTTCGCTACCATCCCTTCTGGTCGCATGTTCGGCGACCGTGTGGCTG

GCAAGTCAAGAAAGCACATGGCATCGCAGACGTTCACAGCGTCGTACCCGTCC

ATGAAGCGGTCATCTCGCGTAGCGAGTATCATGCTGTGGCTTTTGGTCTTTGGC

TGCAAATACGTCGAGTCTTACTTCTTCTTGACGTCCTCCTTCTCCAGCCCGATCG

CGGTCATGGCGCGTACGAAGGTACAGGGCTGCAACGACCGTATCTTCGGCAGC

CAGCTGTGCACGAATCAGGTCCCGTTCGCGCTGGCAATCATGTACGTGATGGA

CCTGGTACTGTTCTTCCTGGACACGTACCTGTGGTACATCATCTGGCTGGTGAT

CTTCTCGATGGTGCGCGCGTTCAAGCTTGGTATCTCGATCTGGACGCCCTGGA

GCGAGATCTTCACCCGCATGCCGAAGCGTATCTACGCGAAGCTGCTGGCGACG

GCCGAGATGGAGGTCAAGTATAAGCCCAAGGTGCTCGTCTCGCAAATCTGGAA

CGCGGTCATCATCTCCATGTACCGGGAGCATCTCTTGTCCATCGAGCACGTCCA

GCGCCTGCTATACCACCAGGTTGATGGTCCAGACGGTCGCCGCACCCTCAGGG

CACCGCCGTTCTTCACCAGCCAGCGAACTGCGAAGCCAGGCCTGTTCTTCCCT

CCTGGTGGCGAGGCTGAGCGCCGTATCTCGTTCTTTGCCTCATCGCTGACGAC

CGCGCTCCCTGAGCCTCTGCCGATCGACGCCATGCCCACCTTCACCGTGCTCG

TTCCCCATTACTCGGAGAAGATTCTGCTCAGTCTGCGCGAGATTATTCGCGAGG

AGGACCAGAACACCCGCGTCACCTTGCTGGAGTACCTCAAGCAGCTCCACCCT

GTCGAATGGGACAACTTCGTCAAGGACACCAAGATCTTGGCGGAAGAGTCGGG

CGACGTCCAGGACGAGAAGCGCGCGCACGGACGACTTGCCGTTCTACTGC

ATCGGGTTCAAGACCTCGTCACCAGAGTACACCCTGCGTACGCGTATCTGGGC

TTCACTGCGCGCACAGACGCTGTACCGCACGGTCTCCGGTATGATGAACTACTC

CAAGGCGATCAAGCTCCTCTATCGCGTCGAGAACCCGGATGTCGTTCATGCCTT

CGGTGGGAACACGGAACGTCTTGAACGCGAGCTTGAGCGCATGTCTCGCCGCA

AGTTCAAGTTCGTCATCTCGATGCAGCGGTACTCTAAGTTCAACAAGGAGGAGC

AAGAGAACGCCGAATTCCTTCTGCGCGCGTACCCGGATTTGCAGATCGCGTAC

CTCGATGAAGAGCCCGGTCCCAGCAAGAGCGACGAGGTTCGGTTGTTTTCGAC

ACTCATCGATGGACACTCCGAGGTGGATGAGAAGACCGGCCGCCGCAAGCCCA

AGTTCCGCATTGAGCTGCCCGGTAACCCCATCCTCGGTGACGGGAAGTCGGAT

AACCAGAACCACGCCATTGTCTTCTACCGCGGCGAGTACATCCAGGTCATCGAC

TABLE 2-continued

Assignment of SEQ ID NOs.

GCTAACCAGGACAATTACCTGGAAGAGTGTCTCAAGATCCGTAACGTCCTGGGC

GAGTTTGAGGAATACTCCGTGTCGAGCCAGAGCCCGTACGCACAGTGGGGCCA

CAAGGAGTTCAACAAGTGCCCCGTCGCTATCCTGGGTTCTCGCGAGTACATCTT

CTCGGAGAACATCGGTATCCTCGGTGACATCGCCGCCGGCAAGGAACAGACGT

TCGGTACCATTACGGCGCGTGCGCTTGCGTGGATCGGCGGCAAGCTGCATTAC

GGTCACCCGGATTTCCTCAATGCGACGTTCATGACGACGCGTGGTGGCGTGTC

AAAAGCGCAGAAGGGCTTGCATCTCAACGAGGATATCTTCGCTGGTATGACCGC

CGTGTCCCGCGGAGGGCGCATCAAGCACATGGAGTACTACCAGTGCGGCAAAG

GTCGTGATCTCGGTTTCGGCACGATCTTGAACTTCCAGACGAAGATCGGTACTG

GTATGGGCGAGCAGCTCCTCTCGCGCGAGTACTACTACCTGGGCACGCAATTG

CCTATCGACCGGTTCTTGACGTTCTACTACGCGCACGCTGGTTTCCACGTCAAC

AACATCCTGGTCATCTACTCCATCCAGGTCTTCATGGTCACCTTGCTGTACCTG

GGCACATTGAACAAGCAGCTGTTCATCTGCAAGGTCAACTCCAATGGCCAGGTT

CTTAGTGGACAAGCTGGGTGCTACAACCTCATCCCGGTCTTCGAGTGGATTCGC

CGGAGTATCATCTCCATCTTCTTGGTGTTCTTCATCGCCTTCTTGCCTCTATTCTT

GCAAGAGCTGTGCGAGCGCGGAACGGGAAAGGCGTTGCTGCGTCTCGGGAAG

CACTTCTTGTCACTGTCGCCCATTTTCGAAGTGTTCTCCACCCAGATTTACTCGC

AGGCGCTCTTGAACAACATGAGCTTCGGTGGTGCGCGCTACATCGCCACAGGT

CGTGGTTTCGCGACTAGTCGCATACCCTTCAACATCCTCTACTCGCGTTTCGCG

CCGCCAAGCATCTACATGGGCATGCGTAACCTGCTGCTCCTGCTGTACGCGAC

GATGGCCATTTGGATCCCGCACCTGATCTACTTCTGGTTCTCCGTCCTCTCCCT

CTGCATCGCGCCATTCATGTTCAATCCGCATCAATTCTCGTACGCCGACTTCATC

ATCGACTACCGGGAGTTCTTGCGCTGGATGTCGCGCGGTAACTCGCGAACGAA

GGCGAGCAGCTGGTACGGATACTGCCGTCTGTCGCGTACCGCGATTACTGGGT

ACAAGAAGAAGAAGCTGGGACACCCGTCGGAGAAGCTGTCGGGCGACGTACC

GCGTGCGCCGTGGAGGAACGTTATCTTCTCGGAGATCCTGTGGCCCATCGGCG

CGTGCATCATCTTCATCGTCGCGTACATGTTCGTCAAGTCGTTCCCCGACGAGC

AGGGCAACGCGCCGCCGAGCCCGCTGGTCCGGATTCTGCTCATCGCGGTTGG

CCCTACTGTGTGGAACGCGGCGGTGCTCATAACGCTGTTCTTCCTGTCGCTCTT

CCTGGGCCCGATGATGGATGCTGGGTCAAGTTCGGCTCGGTCATGGCGGCC

CTTGCGCATGGCCTGGCGCTTATAGGCATGCTCACGTTCTTTGAGTTCTTCTGG

TTCCTTGAGCTCTGGGATGCCTCGCACGCCGTGCTCGGCGTCATCGCTATCATT

GCCGTTCAGCGCGGGATCCAGAAGATCCTCATTGCCGTCTTCCTGACGCGTGA

GTACAAGCACGACGAGACGAACCGCGCGTGGTGGACAGGTAAATGGTATGGAC

GCGGGCTGGGTACCTCGGCCATGTCCCAGCCGGCGCGCGAGTTCATCGTGAA

GATCGTGGAGATGTCGTTGTGGACGTCGGACTTCCTGCTTGCGCACCTGTTGCT

CATCATCTTGACGGTGCCGCTACTGCTGCCGTTCTTCAACTCAATTCATTCGAC

GATGCTTTTCTGGTTGCGCCCCTTCGAAGCAGATTAGGCAACCTCTGTTCTCCAC

CAAGCAGAAGCGGCAACGGCGATGGATTGTCATGAAGTATACCGTGGTATATCT

TABLE 2-continued

Assignment of SEQ ID NOs.

CGTGGTGGTGGCTTTCCTCGTCGCGCTCATCGCTCTGCCCGCCCTCTTCCGCG

AGAGCATCCACTTCAACTGCGAGATCTGCCAGAGTATATAG polypeptide sequence 1,3-β-D-glucan synthase I of *S. commune* strain Lu15634
amino acid
*S. commune*

SEQ ID NO: 14

MSGPGYGRNPFDNPPPNRGPYGQQPGFPGPGPRPYDSDADMSQTYGSTTRLAG

SAGYSDRNGSFDGDRSYAPSIDSRASVPSISPFADPGIGSNEPYPAWSVERQIPMS

TEEIEDIFLDLTQKFGFQRDSMRNTFDFMMHLLDSRASRMTPNQALLTLHADYIGGQ

HANYRKWYFAAQLNLDDAVGQTNNPGIQRLKTIKGATKTKSLDSALNRWRNAMNN

MSQYDRLRQIALYLLCWGEAGNIRLAPECLCFIFKCADDYYRSPECQNRMDPVPEG

LYLQTVIKPLYRFLRDQAYEVVDGKQVKREKDHDQIIGYDDVNQLFWYPEGLAKIVM

SDNTRLVDVPPAQRFMKFAKIEWNRVFFKTYFEKRSTAHLLVNFNRIWILHVSMYFF

YTAFNSPRVYAPHGKLDPSPEMTWSATALGGAVSTMIMILATIAEYTYIPTTWNNAS

HLTTRLIFLLVILALTAGPTFYIAMIDGRTDIGQVPLIVAIVQFFISVVATLAFATIPSGRM

FGDRVAGKSRKHMASQTFTASYPSMKRSSRVASIMLWLLVFGCKYVESYFFLTSSF

SSPIAVMARTKVQGCNDRIFGSQLCTNQVPFALAIMYVMDLVLFFLDTYLWYIIWLVI

FSMVRAFKLGISIWTPWSEIFTRMPKRIYAKLLATAEMEVKYKPKVLVSQIWNAVIISM

YREHLLSIEHVQRLLYHQVDGPDGRRTLRAPPFFTSQRTAKPGLFFPPGGEAERRIS

FFASSLTTALPEPLPIDAMPTFTVLVPHYSEKILLSLREIIREEDQNTRVTLLEYLKQLH

PVEWDNFVKDTKILAEESGDVQDEKRARTDDLPFYCIGFKTSSPEYTLRTRIWASLR

AQTLYRTVSGMMNYSKAIKLLYRVENPDVVHAFGGNTERLERELERMSRRKFKFVI

SMQRYSKFNKEEQENAEFLLRAYPDLQIAYLDEEPGPSKSDEVRLFSTLIDGHSEVD

EKTGRRKPKFRIELPGNPILGDGKSDNQNHAIVFYRGEYIQVIDANQDNYLEECLKIR

NVLGEFEEYSVSSQSPYAQWGHKEFNKCPVAILGSREYIFSENIGILGDIAAGKEQTF

GTITARALAWIGGKLHYGHPDFLNATFMTTRGGVSKAQKGLHLNEDIFAGMTAVSR

GGRIKHMEYYQCGKGRDLGFGTILNFQTKIGTGMGEQLLSREYYYLGTQLPIDRFLT

FYYAHAGFHVNNILVIYSIQVFMVTLLYLGTLNKQLFICKVNSNGQVLSGQAGCYNLI

PVFEWIRRSIISIFLVFFIAFLPLFLQELCERGTGKALLRLGKHFLSLSPIFEVFSTQIYS

QALLNNMSFGGARYIATGRGFATSRIPFNILYSRFAPPSIYMGMRNLLLLLYATMAIW

IPHLIYFWFSVLSLCIAPFMFNPHQFSYADFIIDYREFLRWMSRGNSRTKASSWYGY

CRLSRTAITGYKKKKLGHPSEKLSGDVPRAPWRNVIFSEILWPIGACIIFIVAYMFVKS

FPDEQGNAPPSPLVRILLIAVGPTVWNAAVLITLFFLSLFLGPMMDGWVKFGSVMAA

LAHGLALIGMLTFFEFPWFLELWDASHAVLGVIAIIAVQRGIQKILIAVFLTREYKHDET

NRAWWTGKWYGRGLGTSAMSQPAREFIVKIVEMSLWTSDFLLAHLLLIILTVPLLLP

FFNSIHSTMLFWLRPSKQIRQPLFSTKQKRQRRWIVMKYTVVYLVVVAFLVALIALPA

LFRESIHFNCEICQSI cDNA 1,3-β-D-gucan synthase II of *S. commune* strain Lu15634
DNA
*S. commune*

SEQ ID NO: 15

ATGCCGAGGCCGGGCGGCACCAGCGCAGAAGGCGGCTACGCATCATCGCCGT

CGATGGAGACGACCCCCAGCGATCCCTTCGGAACCGCGAACGGCGCGCCCCG

TABLE 2-continued

Assignment of SEQ ID NOs.

CCGCTACTACGACAATGATTCTGAGGAGTACGGACCTGGCCGTAGAGACACCT

ACGCGTCCGACAGCAGTAATCAGGGCCTCACGGACCCGGGCTACTACGACCAG

AATGGCGCCTATGATCCCTATCCGACCGGGGACACCGATTCCGACGGCGACGT

CTACGGCCAGCGATATGGACCCTCAGCAGAGTCGCTTGGCACCCACAAGTTCG

GCCATTCCGATTCATCCACGCCGACTTTTGTCGACTACAGCGCATCCTCCGGCG

GGAGGGATTCGTACCCTGCATGGACTGCCGAACGCAACATCCCGCTGTCCAAG

GAGGAGATCGAGGACATCTTCCTCGATTTGACGCAGAAGTTTGGCTTTCAGCGG

GATTCCATGCGGAATATGTTCGACTTCACCATGCAGCTGCTTGACAGCCGAGCG

TCTCGTATGACCCCCAACCAGGCGCTCCTCACCCTCCACGCCGACTACATTGGT

GGCCAGCATGCGAACTACCGGAAGTGGTACTTCGCGGCGCAGCTCGACCTTGA

CGACGCCGTGGGACAAACTCAGAATCCGGGTCTCAACCGCCTCAAGTCCACTC

GCGGATCGGGCAAGCGACCACGCCATGAAAAGTCGCTGAACACGGCATTGGAG

CGCTGGCGGCAAGCCATGAACAACATGTCGCAGTATGACCGCTTACGCCAGAT

CGCGCTCTACCTGCTCTGCTGGGGCGAAGCGGCGCAAGTGCGATTCATGCCCG

AGTGCTTGTGCTTCATCTTCAAGTGCGCCGACGACTACTATCGTTCGCCGGAGT

GCCAGAACAGGATGGAGCCGGTACCGGAGGGTCTCTACCTGAGGACGGTCGT

AAAGCCGCTCTACAGATTTGTCCGGGATCAAGGCTATGAGGTGGTGGAGGGAA

AATTCGTACGGCGGGAACGGGATCACGACCAAATCATTGGTTACGATGACGTGA

ATCAGCTGTTCTGGTACCCGGAGGGAATTGCCCGTATCGTCCTGTCGGACAAG

AGTCGTCTAGTCGACCTCCCCCCAGCACAGCGCTTCATGAAGTTCGACCGTATC

GAGTGGAATCGCGTCTTCTTCAAGACGTTTTACGAGACTCGATCCTTCACGCAT

CTTTTGGTCGACTTCAACCGTATCTGGGTCGTGCACATCGCTCTCTACTTCTTCT

ACACTGCATACAACTCCCCCACGATCTACGCCATCAACGGCAACACACCGACGT

CTCTGGCTTGGAGCGCGACTGCGCTCGGCGGTGCGGTAGCGACAGGTATCAT

GATCCTCGCCACGATCGCCGAGTTCTCGCACATCCCCACGACATGGAACAACA

CCTCGCATCTGACTCGCCGCCTCGCCTTCCTCCTCGTCACGCTCGGCCTCACAT

GTGGTCCGACGTTCTACGTCGCGATTGCAGAGAGCAACGGGAGCGGCGGCTCT

TTGGCCTTGATTCTCGGTATCGTCCAGTTCTTCATCTCCGTCGTGGCAACTGCG

CTCTTCACTATCATGCCTTCTGGTCGTATGTTCGGCGACCGTGTCGCAGGCAAG

AGTCGCAAGTATCTCGCCAGCCAGACGTTCACGGCCAGCTACCCGTCGTTGCC

CAAGGACCAGCGGTTCGCCTCACTCCTGATGTGGTTCCTCATCTTCGGGTGCAA

GTTGACGGAGAGTTACTTCTTTCTGACGCTGTCCTTCCGCGACCCTATCCGCGT

CATGGTCGGCATGAAGATCCAGAACTGCGAGGACAAGATTTTCGGCAGCGGCC

TTTGCAGGAATCACGCAGCATTCACCCTCACGATCATGTACATCATGGACCTCG

TCTTGTTCTTCCTCGACACCTTCCTTTGGTATGTCATCTGGAACTCGGTTTTCAG

TATCGCACGCTCTTTCGTACTCGGCCTTTCGATCTGGACACCGTGGAGAGACAT

CTTCCAGCGTCTGCCGAAGCGGATCTACGCGAAGCTTCTGGCGACTGGCGACA

TGGAGGTCAAGTACAAGCCCAAGGTCTTGGTCTCGCAAATCTGGAACGCCATCA

TCATCTCCATGTACCGCGAGCACTTGCTCTCTATTGAGCACGTCCAGAAGCTCC

TABLE 2-continued

Assignment of SEQ ID NOs.

TGTACCACCAAGTGGACACTGGCGAAGCCGGCAAGCGGAGTCTTCGCGCGCCT

CCGTTCTTCGTCGCGCAGGGCAGCAGCGGTGGCTCGGGCGAGTTCTTCCCGC

CTGGCAGCGAGGCCGAGCGTCGTATCTCTTTCTTCGCGCAGTCGCTTTCTACG

GAGATTCCTCAGCCCATCCCGGTCGACGCCATGCCGACGTTCACGGTGCTTAC

GCCTCACTACAGCGAGAAGATCCTTAATTCTCTCCGTGAAATTATCCGCGAGGA

GGACCAGAACACTCGCGTTACGTTGCTCGAGTACCTGAAGCAGCTGCATCCGG

TCGAGTGGGAGAATTTCGTCAAGGACACTAAAATTTTGGCCGAGGAGTCCGCTA

TGTTTAACGGTCCGAGTCCTTTCGGCAACGACGAGAAGGGTCAGTCCAAGATG

GACGATCTACCGTTCTACTGCATCGGTTTCAAGAGCGCCGCGCCCGAGTACAC

CCTCCGCACCCGTATCTGGGCGTCCCTGCGCGCGCAGACGCTGTACCGCACG

GTCTCCGGCATGATGAACTATGCGAAGGCGATCAAGCTGCTCTACCGCGTTGA

GAACCCGGAGGTCGTACAACAGTTCGGCGGCAACACGGACAAGCTCGAGCGC

GAGTTGGAGCGGATGGCGCGACGGAAGTTCAAGTTCCTCGTGTCCATGCAGCG

CTACTCGAAGTTCAACAAGGAGGAGCACGAGAACGCCGAGTTCTTGCTCCGCG

CGTACCCGGACTTGCAGATCGCGTACCTCGAGGAAGAGCCCCCTCGCAAGGAG

GGCGGCGATCCACGCATCTTCTCTGCCCTCGTCGACGGCCACAGCGACATCAT

CCCGGAGACCGGCAAGCGGCGCCCCAAGTTCCGTATCGAGCTGCCCGGTAAC

CCCATTCTCGGTGACGGTAAATCCGACAATCAGAACCACGCTATCGTCTTCTAC

CGCGGCGAGTACCTCCAGCTTATCGACGCCAACCAGGACAACTACCTCGAGGA

GTGCTTGAAGATCCGTAACGTGCTCGCCGAGTTTGAGGAGTACGACGTCTCCA

GCCAGAGCCCGTACGCGCAGTGGAGTGTCAAGGAGTTCAAGCGCTCTCCGGTC

GCCATCGTCGGTGCACGCGAGTACATCTTCTCAGAGCACATCGGTATCCTCGGT

GATCTGGCGGCTGGCAAGGAACAGACGTTCGGTACGCTCACGGCACGCAACAA

CGCCTTCCTTGGCGGCAAGCTGCACTACGGTCACCCCGATTTCCTCAACGCCC

TCTACATGAACACGCGCGGTGGTGTCTCCAAGGCGCAGAAGGGTCTCCATCTC

AACGAGGATATCTACGCCGGTATGAACGCGGTCGGTCGCGGTGGACGCATTAA

GCACAGCGAGTACTATCAGTGCGGCAAGGGTCGTGACCTCGGTTTCGGCACCA

TCTTGAACTTCCAGACCAAGATCGGTACGGGTATGGGCGAGCAGATCCTCTCG

CGCGAGTACTACTATCTCGGAACACAACTGCCCATCGATCGCTTCCTCACGTTC

TACTACGCGCACCCGGGTTTCCAGATCAACAACATGCTGGTCATCCTCTCCGTG

CAGGTCTTCATCGTTACCATGGTCTTCCTCGGTACCTTGAAGTCTTCGGTCACG

ATCTGCAAGTACACGTCCAGCGGTCAGTACATCGGTGGTCAATCCGGTTGCTAC

AACCTCGTCCCGGTCTTCCAGTGGATCGAGCGCTGCATCATCAGCATCTTCTTG

GTGTTCATGATCGCTTTCATGCCGCTCTTCCTGCAAGAACTCGTCGAGCGCGGT

ACCTGGAGTGCCATCTGGCGTCTGCTCAAGCAGTTTATGTCGCTGTCGCCTGTC

TTCGAGGTGTTCTCCACCCAGATTCAGACGCACTCCGTGTTGAGCAACTTGACG

TTCGGTGGTGCGCGTTACATCGCTACCGGTCGTGGGTTCGCCACCAGTCGTAT

CAGCTTCAGCATCTTGTTCTCGCGTTTCGCAGGCCCGAGTATCTACCTCGGCAT

GCGCACGCTCATTATGCTGCTCTACGTGACGTTGACGATCTGGACGCCATGGG

TABLE 2-continued

Assignment of SEQ ID NOs.

```
TCATTTACTTCTGGGTTTCCATTCTCTCGCTCTGCATCGCGCCGTTCTTGTTCAA

CCCGCATCAATTCGTATTCTCGGACTTCCTCATCGACTACAGGGAATACCTGCG

GTGGATGTCGCGTGGCAACTCGCGCTCGCACAACAACTCCTGGATTGGGTACT

GCCGGTTGTCCCGCACGATGATCACTGGGTACAAGAAGAAGAAGCTGGGCCAC

CCGTCGGAGAAGCTTTCCGGCGACGTTCCTCGTGCAGGCTGGCGCGCCGTCTT

GTTCTCGGAGATCATCTTCCCGGCGTGCATGGCCATCCTCTTCATCATCGCGTA

CATGTTCGTCAAGTCGTTCCCTCTCGACGGCAAGCAGCCTCCCTCCGGCCTCG

TTCGCATCGCCGTCGTGTCTATCGGCCCCATCGTGTGGAACGCCGCCATCCTG

TTGACGCTCTTCCTTGTGTCGTTGTTCCTCGGCCCCATGCTCGACCCGGTCTTC

CCCCTCTTCGGTTCCGTTATGGCCTTCATCGCGCATTTCCTTGGCAGAATCGGA

ATGATTGGGTTCTTCGAGTTCCTGTGGTTCCTCGAGTCCTGGGAGGCGTCGCAT

GCCGTGCTGGGTCTCATCGCCGTCATCTCCATCCAGCGCGCCATTCACAAGAT

CCTTATCGCCGTTTTCCTCAGTCGCGAGTTCAAGCACGACGAGACGAACAGGG

CCTGGTGGACTGGTCGCTGGTATGGCCGTGGCCTCGGCACGCACGCCATGTC

GCAGCCGGCGCGTGAGTTCGTCGTCAAGATCATCGAGTTGTCGCTTTGGAGCT

CGGATCTCATACTCGGCCACATCCTGCTGTTCATGCTTACTCCGGCCGTCCTCA

TCCCGTACTTCGACCGTTTGCACGCCATGATGCTCTTCTGGCTGCGTCCCTCGA

AGCAAATCCGCGCGCCTCTGTACTCGATCAAGCAGAAGAGGCAAAGACGCTGG

ATTATCATGAAGTACGGTACTGTATACGTTACCGTCATCGCGATCTTCGTCGCG

CTCATCGCGCTTCCCCTCGTATTCCGACACACTCTAAAGGTCGAGTGCTCCCTT

TGCGACAGCTTGTAA
``` polypeptide sequence 1,3-β-D-glucan synthase II of *S. commune* strain Lu15634
amino acid
*S. commune*

SEQ ID NO: 16

```
MPRPGGTSAEGGYASSPSMETTPSDPFGTANGAPRRYYDNDSEEYGPGRRDTYA

SDSSNQGLTDPGYYDQNGAYDPYPTGDTDSDGDVYGQRYGPSAESLGTHKFGHS

DSSTPTFVDYSASSGGRDSYPAWTAERNIPLSKEEIEDIFLDLTQKFGFQRDSMRN

MFDFTMQLLDSRASRMTPNQALLTLHADYIGGQHANYRKWYFAAQLDLDDAVGQT

QNPGLNRLKSTRGSGKRPRHEKSLNTALERWRQAMNNMSQYDRLRQIALYLLCW

GEAAQVRFMPECLCFIFKCADDYYRSPECQNRMEPVPEGLYLRTVVKPLYRFVRD

QGYEVVEGKFVRRERDHDQIIGYDDVNQLFWYPEGIARIVLSDKSRLVDLPPAQRF

MKFDRIEWNRVFFKTFYETRSFTHLLVDFNRIWVVHIALYFFYTAYNSPTIYAINGNT

PTSLAWSATALGGAVATGIMILATIAEFSHIPTTWNNTSHLTRRLAFLLVTLGLTCGPT

FYVAIAESNGSGGSLALILGIVQFFISVVATALFTIMPSGRMFGDRVAGKSRKYLASQ

TFTASYPSLPKHQRFASLLMWFLIFGCKLTESYFFLTLSFRDPIRVMVGMKIQNCED

KIFGSGLCRNHAAFTLTIMYIMDLVLFFLDTFLWYVIWNSVFSIARSFVLGLSIWTPWR

DIFQRLPKRIYAKLLATGDMEVKYKPKVLVSQIWNAIIISMYREHLLSIEHVQKLLYHQ

VDTGEAGKRSLRAPPFFVAQGSSGGSGEFFPPGSEAERRISFFAQSLSTEIPQPIPV

DAMPTFTVLTPHYSEKILLSLREIIREEDQNTRVTLLEYLKQLHPVEWENFVKDTKILA

EESAMFNGPSPFGNDEKGQSKMDDLPFYCIGFKSAAPEYTLRTRIWASLRAQTLYR
```

TABLE 2-continued

Assignment of SEQ ID NOs.

TVSGMMNYAKAIKLLYRVENPEVVQQFGGNTDKLERELERMARRKFKFLVSMQRY

SKFNKEEHENAEFLLRAYPDLQIAYLEEEPPRKEGGDPRIFSALVDGHSDIIPETGKR

RPKFRIELPGNPILGDGKSDNQNHAIVFYRGEYLQLIDANQDNYLEECLKIRNVLAEF

EEYDVSSQSPYAQWSVKEFKRSPVAIVGAREYIFSEHIGILGDLAAGKEQTFGTLTA

RNNAFLGGKLHYGHPDFLNALYMNTRGGVSKAQKGLHLNEDIYAGMNAVGRGGRI

KHSEYYQCGKGRDLGFGTILNFQTKIGTGMGEQILSREYYYLGTQLPIDRFLTFYYA

HPGFQINNMLVILSVQVFIVTMVFLGTLKSSVTICKYTSSGQYIGGQSGCYNLVPVFQ

WIERCIISIFLVFMIAFMPLFLQELVERGTWSAIWRLLKQFMSLSPVFEVFSTQIQTHS

VLSNLTFGGARYIATGRGFATSRISFSILFSRFAGPSIYLGMRTLIMLLYVTLTIWTPW

VIYFWVSILSLCIAPFLFNPHQFVFSDFLIDYREYLRWMSRGNSRSHNNSWIGYCRL

SRTMITGYKKKKLGHPSEKLSGDVPRAGWRAVLFSEIIFPACMAILFIIAYMFVKSFPL

DGKQPPSGLVRIAVVSIGPIVWNAAILLTLFLVSLFLGPMLDPVFPLFGSVMAFIAHFL

GTIGMIGFFEFLWFLESWEASHAVLGLIAVISIQRAIHKILIAVFLSREFKHDETNRAW

WTGRWYGRGLGTHAMSQPAREFVVKIIELSLWSSDLILGHILLFMLTPAVLIPYFDRL

HAMMLFWLRPSKQIRAPLYSIKQKRQRRWIIMKYGTVYVTVIAIFVALIALPLVFRHTL

KVECSLCDSL tef1 promoter
DNA
S. commune

SEQ ID NO: 17

ATCGCCATTGTAAGCCGCAGACGGGCACGCTTCCAACCCCCATCGATGGGCGC

TCGATGTCCATCTCATCGGCGACTCATCATTGTATCTCGCGCAGTCCCATCCCT

CGCCGCTCGCCTGTAGTTTATGCTATTTATCTTTGCACCAGTCGTTGTATTACTC

CCTCGTCGTGTAGAAAGTACCAGATAAAATGCATGTAATCCTAATGAAATTTGCA

CGACACGAAGATCCGGCAGGGTTGTGGGCAAGGGGCAGCGGGAACGAATGGA

TGGCGGGGTACAGCGAGTACCCGGCAGTGCCACAGTCAGTGTCACACACGTGA

CTGATTGTCCATTAGCGTGACCGATAACATCGATCAAAAATTTTATTTCAGAGGA

CGATAAATAAGGGCCGACGGTGCGCGTCCGTCTTTCTCTCAACCCTCATCTTCC

TCTCGTCTCTCACTCTTTCCCCCCTCCACCACTACCAAGTAAGTTCAAACTTCCTC

TCATCGCCTTTGCACACATCGCCTACGCCCCATCTCTCTCCATCTGCCTCGCGA

ACGGCGCCCCCATCGTCGCTTTCCCGCGCGAGATCTTGTGCGATCTAGTTTACT

GACAATCTCACCTAGAAAACATCAAA tef1 terminator
DNA
S. commune

SEQ ID NO: 18

ATCCAAGTCCGGTGGCAAGGTCACCAAGTCCGCCGAGAAGGCCGCCAAGAAGA

AGTAAATGTAGATGTACATATGTATTTTCTCATTCCGTTTCCTTCCTCTTGTTGTT

GTTTCACTGGTCCTCTCGTGCTCGCTCGCATCGCATACAGCCATTGTTGTCACC

ACTATAACTTCACGCATTCTGTATTTCATGCCAGGCGACGGGGTGTTCCTGCCA

GGCCTGTCGCTTGTTGTAACGCTAATGAAAAGTCACGAGTAGTGGACGAACGAC

GATGTATTTCTATGTGCTGTAGCGATTATCCATTTCGAGTTCGCCATCGAGCTCT

CTTCAAACCTAGGTGCGACGTTGTGAATGCAGTAGCAAGTGCAGAGTATTGCAG

TABLE 2-continued

Assignment of SEQ ID NOs.

```
ACTCGTCCATTGATGATAACTTCAAGCTACGTCAGAGCCAGATGCTACTGAACC

CGGGCC

Ura_forw (NotI) primer
DNA
artificial
                                                            SEQ ID NO: 19
ATAAGAATGCGGCCGCTCCAGCTCGACCTTGCGCCG Ura_rev (XbaI) primer
DNA
artificial
                                                            SEQ ID NO: 20
CTAGTCTAGAGGATCCGACGTGGAGGAGCC TefP_forw (XbaI) primer
DNA
artificial
                                                            SEQ ID NO. 21
CTAGTCTAGAATCGCCATTGTAAGCCGCAG TefP_rev (SpeI) primer
DNA
artificial
                                                            SEQ ID NO: 22
CTAGACTAGTTTTGATGTTTTCTAGGTGAG TefT_forw (SalI) primer
DNA
artificial
                                                            SEQ ID NO: 23
ACGCGTCGACCAAGTCCGGTGGCAAGGTCA TefT_rev (SalI) primer
DNA
artificial
                                                            SEQ ID NO: 24
CCGACGTCGACGGGTTCAGTAGCATCTGGCT TefT_forw (EcoRV) primer
DNA
artificial
                                                            SEQ ID NO: 25
CATGGTGATATCCAAGTCCGGTGGCAAGGTCA TefT_rev (ApaI) primer
DNA
artificial
                                                            SEQ ID NO: 26
CCGTATGGGCCCGGGTTCAGTAGCATCTGGCT GS1_forw (SpeI) primer
DNA
artificial
                                                            SEQ ID NO: 27
CTAGACTAGTCCCGTCCCTCAAGGCCGTTC GS1_rev (SalI) primer
DNA
artificial
                                                            SEQ ID NO: 28
AATGGCCGACGTCGACATGGTATATGCAATGCTATG Fusion TefP_GS1_forw (XbaI) primer
DNA
artificial
                                                            SEQ ID NO: 29
CTAGTCTAGAATCGCCATTGTAAGCCGCAG Fusion TefP_GS1_rev (SalI) primer
DNA
artificial
                                                            SEQ ID NO: 30
AATGGCCGACGTCGACATGGTATATGCAATGCTATG
```

TABLE 2-continued

Assignment of SEQ ID NOs.

GS2_forw (SpeI) primer
DNA
artificial

SEQ ID NO: 31

CTAGACTAGTCTGTCCAAAGAAGAGATCGA

GS2_rev (EcoRV) primer
DNA
artificial

SEQ ID NO: 32

TACATGCGATATCTTTTATGCAGACTCTCCCTG urn gene
DNA
S. commune

SEQ ID NO: 33

TCCAGCTCGACCTTGCGCCGCTTGGAGTAACGTTCAGCGTCTTCGTCGTCCTCG

TCGCGCTCGTGTACGATGATGGGCTCAGCCATGGCAGGTATACAAGCTCAGAG

TCAATGGGGACGAGGTCTCAAGCCGTGAAAGTCGTCGTCGAACAACGTCAAG

TTCGAGACGGACCAGAGTTGGATTTCGTGATTAGATCTACGCTCGATCACAGAA

TGATCAAAGAACAAAGCTTGCCAAAAGGGGATCTCCCATCAACTTCAACTTGCC

CCAAACCATCATGACCGCCGCTCATAAGCTCACATACGGTCAGCGCGCTGCAA

GGTTCACCAATCCCGCGGCGAAAGCCCTGCTGGAAACCATGGAGCGCAAGAAG

AGCAATCTATCCGTCAGCGTCGACGTCGTAAAATCCGCCGATCTGCTCGCTATT

GTCGATACCGTCGGGCCCTATATCTGTCTGATAAAGGCATTGCACTGTCGCTTG

CGGTCTTGGGATGCTGCTTATACTCTATGAAGACCCATGTGGATGTTGTCGAAG

ACTTCGACTCGTCGCTCGTCACCAAGCTTCAGGCTCTGGCCGAGAAGCATGATT

TCCTCATCTTTGAGGACAGAAAATTCGCCGACATAGGTCTGTCCGTCGAATCTC

TATCGATGTCAACTCTGATGACTTGCACAGGCAACACCGTCGCTCTGCAGTACT

CTAGTGGCGTGCACAAAATTGCCAGCTGGTCGCACATCACGAACGCACACCCT

GTTCCAGGACCGTCAATCATCAGTGGCCTCGCATCGGTAGGACAACCCCTCGG

TCGCGGACTCCTCCTGCTCGCAGAGATGAGCACGAAGGGCTCACTTGCGACAG

GCGCGTACACTGAAGCCGCCGTCCAGATGGCAAGGGAGAACCGCGGCTTCGT

CATCGGGTTCATCGCCCAACGGCGGATGGATGGTATTGGCGCGCCTCCAGGG

GTGAATGTCGAGGACGAGGATTTTCTTGTCTTGACACCAGGTGTCGGACTCGAT

GTGAAGGGCGATGGGATGGGGCAGCAATACAGGACGCCGAAGCAAGTGGTAC

AGGAAGATGGGTGCGATGTAATCATCGTGGGTCGCGGGATTTATGGCAAGGAC

CCATCGAAGGTGGAAGAGATACGGAGGCAGGCAGAGCGTTACCAGGCTGCAG

GATGGGCGGCGTACATTGAGAGGGTCAACGCCTTGGTATAGCTAATCTGATCG

GTGTTGTCTTGTTAAGCGTCAGGCTCAATGGAACGCTTTGGACGAGCGGAGAGT

AACTTGAATTAGCAGTGTATACTTCGGGCAAATCAATCGTGATAAATACAAGAGC

ACGCTCACGCACGTCCAATCTCCCTCAAAATCTCCATCTTTCTCGCCTCATTCAC

CTTCCTGAACCCAGCCGGCGACATCTCGAACAGACCATGCCCACCCGACAGCG

CACGCAGCCTATTCGAGTAGTCCAGCATCCGGCTGAGCGGCGCCACCGCCTGC

ACCGCGCGCTTCATCTTCACGCCCGCCGCCTCCCTCGCCGCAGTGCCGCCAGA

TABLE 2-continued

Assignment of SEQ ID NOs.

GGGCGACACCCACTCCGGGGGCACGTACACGCCGTCCGCAGGGTACGGCTCC

TCCACGTCGGATCC

Ura protein
amino acid
*S. commune*

SEQ ID NO: 34

MTAAHKLTYGQRAARFTNPAAKALLETMERKKSNLSVSVDVVKSADLLAIVDTVGPY

ICLIKTHVDVVEDFDSSLVTKLQALAEKHDFLIFEDRKFADIGNTVALQYSSGVHKIAS

WSHITNAHPVPGPSIISGLASVGQPLGRGLLLLAEMSTKGSLATGAYTEAAVQMARE

NRGFVIGFIAQRRMDGIGAPPGVNVEDEDFLVLTPGVGLDVKGDGMGQQYRTPKQ

VVQEDGCDVIIVGRGIYGKDPSKVEEIRRQAERYQAAGWAAYIERVNALV

The invention claimed is:

1. A genetically modified microorganism capable of producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, characterized in that said genetically modified microorganism overexpresses (i) a polynucleotide encoding a polypeptide having 1,3-β-D-glucan synthase-activity, wherein said polynucleotide comprises a nucleotide sequence having at least 70% sequence identity to the nucleotide sequence of SEQ ID NO: 1, SEQ ID NO: 5, SEQ ID NO: 9, or SEQ ID NO: 13, and/or (ii) a polypeptide having 1,3-β-D-glucan synthase-activity, wherein said polypeptide comprises an amino acid sequence having at least 70% sequence identity to the amino acid sequence of SEQ ID NO: 6 or SEQ ID NO: 14, compared to a corresponding non-modified control microorganism of the same strain.

2. A method of producing a polymer consisting of a linear main chain of β-D-(1-3)-glucopyranosyl units having a single β-D-glucopyranosyl unit (1-6) linked to a β-D-glucopyranosyl unit of the linear main chain with an average branching degree of about 0.3, said method comprising the steps of:
(a) introducing a polynucleotide encoding a polypeptide having 1,3-β-D-glucan synthase-activity into a microorganism being able to synthesize said polymer, wherein said polynucleotide comprises:
(i) a nucleotide sequence having at least 70% sequence identity to the nucleotide sequence of SEQ ID NO: 1, SEQ ID NO: 5, SEQ ID NO: 9, or SEQ ID NO: 13; or
(ii) a nucleotide sequence encoding a polypeptide having at least 70% sequence identity to the amino acid sequence of SEQ ID NO: 6 or SEQ ID NO: 14,
and wherein said polynucleotide is optionally downstream of a strong promoter thereby increasing the expression of said polynucleotide;
(b) culturing said microorganism of (a) in a medium, thereby allowing said microorganism to produce said polymer; and
(c) optionally recovering said polymer from the medium.

3. The genetically modified microorganism of claim 1, wherein said polymer is selected from the group consisting of schizophyllan, scleroglucan, pendulan, cinerian, laminarin, lentinan and pleuran.

4. The genetically modified microorganism of claim 1, wherein said polynucleotide is a 1,3-β-D-glucan synthase gene.

5. The genetically modified microorganism of claim 1, wherein said polynucleotide comprises a nucleotide sequence having at least 80% sequence identity to the nucleotide sequence of SEQ ID NO: 1, SEQ ID NO: 5, SEQ ID NO: 9, or SEQ ID NO: 13.

6. The genetically modified microorganism of claim 1, wherein said polypeptide is a 1,3-β-D-glucan synthase.

7. The genetically modified microorganism of claim 1, wherein said polypeptide comprises an amino acid sequence having at least 80% sequence identity to the amino acid sequence of SEQ ID NO: 6 or SEQ ID NO: 14.

8. The genetically modified microorganism of claim 1, wherein said microorganism is selected from the group consisting of *Schizophyllum commune, Sclerotium rolfsii, Sclerotium glucanicum, Sclerotium delphinii, Porodisculus pendulus, Botrytis cinerea, Laminaria* sp., *Lentinula edoles*, and *Monilinia fructigena*.

9. The genetically modified microorganism of claim 1, wherein said modified microorganism is able to produce at least 1.5 times more of said polymer compared to said non-modified control microorganism.

10. The method of claim 2, wherein said polymer is selected from the group consisting of schizophyllan, scleroglucan, pendulan, cinerian, laminarin, lentinan and pleuran.

11. The method of claim 2, wherein said polynucleotide is a 1,3-β-D-glucan synthase gene.

12. The method of claim 2, wherein said polynucleotide comprises a nucleotide sequence having at least 80% sequence identity to the nucleotide sequence of SEQ ID NO: 1, SEQ ID NO: 5, SEQ ID NO: 9, or SEQ ID NO: 13.

13. The method of claim 2, wherein said polynucleotide encodes a 1,3-β-D-glucan synthase.

14. The method of claim 2, wherein said polynucleotide encodes a polypeptide having at least 80% sequence identity to the amino acid sequence of SEQ ID NO: 6, or SEQ ID NO: 14.

15. The method of claim 2, wherein said microorganism is selected from the group consisting of *Schizophyllum commune, Sclerotium rolfsii, Sclerotium glucanicum, Sclerotium delphinii, Porodisculus pendulus, Botrytis cinerea, Laminaria* sp., *Lentinula edoles*, and *Monilinia fructigena*.

16. The genetically modified microorganism of claim 1, wherein said polynucleotide comprises a nucleotide sequence having at least 90% sequence identity to the nucleotide sequence of SEQ ID NO: 1, SEQ ID NO: 5, SEQ ID NO: 9, or SEQ ID NO: 13.

17. The genetically modified microorganism of claim 1, wherein said polypeptide comprises an amino acid sequence having at least 90% sequence identity to the amino acid sequence of SEQ ID NO: 6 or SEQ ID NO: 14.

18. The genetically modified microorganism of claim 1, wherein said polynucleotide comprises the nucleotide sequence of SEQ ID NO: 1, SEQ ID NO: 5, SEQ ID NO: 9, or SEQ ID NO: 13, or wherein said polynucleotide encodes a polypeptide comprising the amino acid sequence of SEQ ID NO: 2, SEQ ID NO: 6, SEQ ID NO: 10, or SEQ ID NO: 14.

19. The method of claim 2, wherein said polynucleotide comprises:
(a) a nucleotide sequence having at least 90% sequence identity to the nucleotide sequence of SEQ ID NO: 1, SEQ ID NO: 5, SEQ ID NO: 9, or SEQ ID NO: 13; or
(b) a nucleotide sequence encoding a polypeptide having at least 90% sequence identity to the amino acid sequence of SEQ ID NO: 6 or SEQ ID NO: 14.

20. The method of claim 2, wherein said polynucleotide comprises the nucleotide sequence of SEQ ID NO: 1, SEQ ID NO: 5, SEQ ID NO: 9, or SEQ ID NO: 13, or wherein said polynucleotide encodes a polypeptide comprising the amino acid sequence of SEQ ID NO: 2, SEQ ID NO: 6, SEQ ID NO: 10, or SEQ ID NO: 14.

* * * * *

SEQUENCE LISTING

<160> NUMBER OF SEQ ID NOS: 34

<210> SEQ ID NO 1
<211> LENGTH: 6100
<212> TYPE: DNA
<213> ORGANISM: Schizophyllum commune

<400> SEQUENCE: 1

| | | | | | |
|---|---|---|---|---|---|
| cccgtccctc | aaggccgttc | tttcgctggc | gaccgacccg | gtgttcgcga | gaacctgttg | 60 |
| tttctgacga | tcatcagccc | tttcttctcg | tcgctcttta | gctctcccta | gaccgtcttt | 120 |
| tactctactc | ttcgacgcac | gccatgtccg | gcccaggata | tggcaggaat | ccattcgaca | 180 |
| atccccgcc | caacagaggt | ccctatggcc | agcagccagg | tttcccgggg | cccggccctc | 240 |
| ggccttacga | ctcggacgcg | gacatgagcc | agacctatgg | cagcacaacc | aggctcgccg | 300 |
| gcagtgccgg | ttacagcgac | agaaacggtg | cgcacgtcgc | taccgtactt | cctcgatcgt | 360 |
| cgattcacat | accatgcagg | cagcttcgac | ggcgaccgct | cctacgcgcc | ctcaattgac | 420 |
| tcgcgcgcca | gcgtgcccag | catatcgccc | ttcgcagacc | cgggtatcgg | ctctaatgag | 480 |
| ccgtatcccg | cttggtcggt | cgaacgccag | attcccatgt | ccacggagga | gattgaggac | 540 |
| atcttcctcg | acctcaccca | aaagtttggc | ttccagcgcg | actccatgcg | gaatacggtg | 600 |
| cgtgaataag | cagcccactc | gaccgcggga | acagcacaat | tgacctgtca | cccagttcga | 660 |
| cttcatgatg | cacctcctcg | attcccgtgc | ctcgcgcatg | acgcccaacc | aagctctgct | 720 |
| cacgcttcac | gccgactaca | ttggtggcca | gcatgccaat | taccggaagt | ggtatttcgc | 780 |
| cgcacagctc | aacctcgatg | acgcggtcgg | gcaaaccaat | aaccccggta | tccagcgctt | 840 |
| gaagaccatc | aagggcgcta | cgaagaccaa | gtcgctcgac | agcgcactca | accgctggcg | 900 |
| caacgcgatg | aacaacatga | gccagtacga | tcgcctccgg | caaattgcgc | tctacctcct | 960 |
| ctgctggggt | gaagcaggca | acatccgtct | ggcgcccgag | tgcttgtgct | tcatcttcaa | 1020 |
| gtgcgcggac | gactactaca | gaagtcccga | gtgtcagaac | cggatggacc | ccgtgccgga | 1080 |
| agggctgtac | ctgcagacgg | tcatcaagcc | gctctatcgc | ttcctacgtg | atcaggcgta | 1140 |
| cgaagtcgtt | gatgggaagc | aagtgaagcg | cgagaaggac | cacgaccaga | ttatcggtta | 1200 |
| tgacgacgtc | aaccagttat | tctggtatcc | ggaaggtttg | gctaagatcg | tcatgtcgga | 1260 |
| caacgtgcgt | atgatcttat | cggttaaaat | tcgtccgctc | acatctttcc | agacacgact | 1320 |

```
tgtagatgta cctccggcgc agcggttcat gaagttcgcc aagatcgagt ggaaccgcgt    1380
cttcttcaag acgtactttg agaagcgctc tactgcccat ctcctggtca acttcaaccg    1440
tatatggatc ctccacgtct cgatgtactt cttctacacg gcattcaact ctccacgagt    1500
ctacgcgccg cacggcaaac tcgacccctc ccctgagatg acctggtccg cgactgccct    1560
tggaggcgct gtgtccacca tgatcatgat ccttgccact atcgcggagt acacctacat    1620
ccccacgaca tggaacaatg cgtcgcacct caccacgcgg ctcattttcc tcctggtcat    1680
cctcgcgctc actgctggcc aacattcta tatcgccatg atagacggac gcacggacat     1740
cggccaagta ccactcatcg tggccatagt gcagttcttc atctccgtcg tcgccaccct    1800
cgctttcgct accatccctt ctggtcgcat gttcggcgac cgtgtggctg gcaagtcaag    1860
aaagcacatg gcatcgcaga cgttcacagc gtcgtacccg tccatgaagc ggtcatctcg    1920
cgtagcgagt atcatgctgt ggcttttggt ctttggctgc aaatacgtcg agtcttactt    1980
cttcttgacg tcctccttct ccagcccgat cgcggtcatg gcgcgtacga aggtacaggg    2040
ctgcaacgac cgtatcttcg gcagccagct gtgcacgaat caggtcccgt tcgcgctggc    2100
aatcatgtac gtgatggacc tggtactgtt cttcctggac acgtacctgt ggtacatcat    2160
ctggctggtg atcttctcga tggtgcgcgc gttcaagctt ggtatctcga tctggacgcc    2220
ctggagcgag atcttcaccc gcatgccgaa gcgtatttac gcaaagctgc tggcgacggc    2280
cgagatggag gtcaagtata agcccaaggt atgctgaatt caatctggtc aggtgaattc    2340
accctcatat tgtggtacag gtgctcgtct cacaaatctg gaacgcggtc atcatctcca    2400
tgtaccggga gcatctcttg tccatcgagc acgtccagcg cttgctttac caccaggttg    2460
atggtcccga tggccgccgc accctcaggg caccgccgtt cttcaccagc cagcgaactg    2520
cgaagccagg cctgttcttc cctcctggtg gcgaggctga gcgccgcatc tcgttctttg    2580
cctcatcgct gacgaccgcg ctcccggagc ctctgccgat cgacgccatg cccaccttca    2640
ccgtgctcgt tccccattac tccgagaaga ttctgctcag tctgcgcgag attatccgcg    2700
aggaggacca gaacacccgc gttaccttac tggagtacct caagcagctc caccctgtcg    2760
aatgggacaa tttcgtcaag gacaccaaga tcttggcgga agagtcggga gacgtccagg    2820
acgagaagcg cgcgcgcacg gacgacttgc cgttctattg catcgggttc aagacctcgt    2880
caccagagta caccctgcgt acgcgtatct gggcctcact gcgcgcacag acgctgtacc    2940
gcacggtctc cggtatgatg aactactcca aggcgattaa gctcctctat cgcgtcgaga    3000
acccggatgt cgttcatgcc ttcggtggga acacggaacg tcttgaacgc gagccttgagc   3060
gcatgtctcg ccgcaagttc aagttcgtca tctcgatgca gcggtactcc aagttcaaca    3120
aggaggagca ggagaacgcc gagttccttc tgcgcgcgta cccggatttg cagatcgcgt    3180
acctcgatga agagcccggt cccagcaaga gcgacgaggt tcggttgttt tcgacactca    3240
tcgacggaca ctccgaggtg gacgagaaga cgggccgccg caagcccaag ttccgcatcg    3300
agctgcccgg taacccatc ctcggtgacg ggaagtcgga taaccagaac cacgccatcg     3360
tcttctaccg cggcgagtac attcaggtca ttgacgctaa ccaggacaat tacctggaag    3420
agtgtctcaa gatccgtaat gtcctgggcg agtttgagga atactccgtg tcgagccaga    3480
gcccgtacgc gcagtggggc cacaaggagt tcaacaagtg ccccgtcgct atcctgggtt    3540
cccgcgagta catcttctcg gagaaacatc gtatcctcgg tgacatcgct gccggcaagg    3600
aacagacgtt cggtaccatt acggcgcgtg cgcttgcgtg gatcggcggc aagctgcatt    3660
```

-continued

```
acggtcaccc ggatttcctc aatgcgacgt tcatgacgac gcgtggtggc gtgtcaaaag    3720
cgcagaaggg cttgcatctt aacgaggata tcttcgctgg tatgaccgcc gtgtcccgcg    3780
gagggcgcat caagcacatg gagtactacc agtgcggcaa aggtcgtgat ctcggattcg    3840
gcacgatctt gaacttccag accaagatcg gtactggtat gggcgagcag ctgctctcgc    3900
gcgagtacta ctatctgggc acgcaattgc ctatcgaccg gttcttgacg ttctactacg    3960
cgcacgctgg tttccatgtc aacaacatcc tggtcatcta ctccatccag gtcttcatgg    4020
tcacccgtaa gtgcaggccc tcatgaccgc cgagcaagca gtctaacgga tgtgcagtgc    4080
tgtacctggg cacattgaac aagcagctgt tcatctgcaa ggtcaactcc aatggccagg    4140
ttcttagtgg acaagctggg tgctacaacc tcatcccggt cttcgagtgg attcgccgga    4200
gtatcatctc catcttcttg gtgttcttca tcgccttctt gccgttgttc ttgcaaggta    4260
tgttcacttc tcatgtgcca tttgtcaatc gctcactcgt acgacagagc tttgcgaacg    4320
cggaacagga aaggcgttgc tgcgtctcgg aagcacttc ctgtcactgt cgcccatctt    4380
cgaagtgttc tccacccaaa tctactcgca ggcgctcttg aacaacatga gtttcggtgg    4440
tgcgcgctac atcgctacag gacgcggttt cgcgacgagt cggataccct tcaacatcct    4500
ctactcgcgt ttcgcgccgc cgagcatcta catgggcatg cgtaatctgc tgctcttgct    4560
gtacgcgacg atggccattt ggatcccaca cctgatctac ttctggttct ccgtcctctc    4620
cctctgcatc gcgccattca tgttcaatcc gcatcaattc tcgtacgctg acttcatcat    4680
cgactaccgg gagttcttgc gctggatgtc gcgcggtaac tcgcggacga aggcgagtag    4740
ctggtacgga tattgccgtc tgtcgcgtac cgcgattact gggtacaaga agaagaaact    4800
gggacacccg tcggagaagc tgtcgggcga tgtgccgcgt gcgccgtgga ggaacgtcat    4860
cttctcggag atcctttggc ccatcggcgc gtgcatcatc ttcatcgtcg cgtacatgtt    4920
cgtcaaatcg ttccctgacg agcagggcaa cgcgccgccg agcccgctgg tccgcattct    4980
gctcatcgcg gttgggccta ctgtgtggaa cgcggcggtg ctcatcacgc tgttcttcct    5040
gtcgctcttc ctgggcccga tgatggatgg ctgggtcaag ttcggctcag tcatggcggc    5100
acttgcgcat ggtctagcgc tcataggcat gctcacgttc ttcgagttct tcgtacgtcc    5160
ttcgcgttgt tgtggtcgag tgctttgcta acaccgcctt cagtggttcc tcgagctctg    5220
ggatgcctcg cacgccgtgc tcggcgtcat cgccattatt gccgttcagc gcggatccaa    5280
gaagatcctc attgccgtct tcctgacgcg tgagtacaag cacgacgaga cgaaccgcgc    5340
gtggtggaca ggtaaatggt atggacgcgg gctgggtacc tcggccatgt cccagccggc    5400
gcgcgagttc atcgtgaaga tcgtggagat gtcgctgtgg acgtcggact tcctgcttgc    5460
gcacctgttg ctcatcatct tgacggtgcc gctactgctg ccgttcttca actcgatcca    5520
ttcgacgatg ctttgtgagt gatttgtagt cgttggtcac ggatgattgc tgactcgcgt    5580
gcagtctggt tgcgcccttc gaagcagatt aggcaacctc tgttctccac taagcagaag    5640
cggcaacggc gatggattgt aagttccttt gattgctctg gctaccgacc ttcgctcacc    5700
tgtctcaggt catgaagtat accgtggtat atctcgtggt ggtggctttc ctcgttgcgc    5760
tcatcgctct gcgtacgttt tctgtcgcgc tcaccctcta ttttcactaa cgtttcctcc    5820
agccgcgctc ttccgcgaga gcatccactt caactgcgag atctgccaga gtatatagtc    5880
atataacgac gtctatcgta tcgccggacg agagccccgt cgcctacaca ctgacatgga    5940
attgctgtgt atacaatcga tcttctgacc gcgtcggggg cgttgccgtc tttctactat    6000
caacttgctt gtgtatcaac atttcttctc tccaagccta cattgacata gagtaatagc    6060
```

```
ccatgttcat acaacaatcg catagcattg catataccat                 6100
```

<210> SEQ ID NO 2
<211> LENGTH: 1740
<212> TYPE: PRT
<213> ORGANISM: Schizophyllum commune

<400> SEQUENCE: 2

```
Met Ser Gly Pro Gly Tyr Gly Arg Asn Pro Phe Asp Asn Pro Pro Pro
1               5                   10                  15

Asn Arg Gly Pro Tyr Gly Gln Gln Pro Gly Phe Pro Gly Pro Gly Pro
            20                  25                  30

Arg Pro Tyr Asp Ser Asp Ala Asp Met Ser Gln Thr Tyr Gly Ser Thr
        35                  40                  45

Thr Arg Leu Ala Gly Ser Ala Gly Tyr Ser Asp Arg Asn Gly Ser Phe
    50                  55                  60

Asp Gly Asp Arg Ser Tyr Ala Pro Ser Ile Asp Ser Arg Ala Ser Val
65                  70                  75                  80

Pro Ser Ile Ser Pro Phe Ala Asp Pro Gly Ile Gly Ser Asn Glu Pro
                85                  90                  95

Tyr Pro Ala Trp Ser Val Glu Arg Gln Ile Pro Met Ser Thr Glu Glu
            100                 105                 110

Ile Glu Asp Ile Phe Leu Asp Leu Thr Gln Lys Phe Gly Phe Gln Arg
        115                 120                 125

Asp Ser Met Arg Asn Thr Phe Asp Phe Met Met His Leu Leu Asp Ser
    130                 135                 140

Arg Ala Ser Arg Met Thr Pro Asn Gln Ala Leu Leu Thr Leu His Ala
145                 150                 155                 160

Asp Tyr Ile Gly Gly Gln His Ala Asn Tyr Arg Lys Trp Tyr Phe Ala
                165                 170                 175

Ala Gln Leu Asn Leu Asp Asp Ala Val Gly Gln Thr Asn Asn Pro Gly
            180                 185                 190

Ile Gln Arg Leu Lys Thr Ile Lys Gly Ala Thr Lys Thr Lys Ser Leu
        195                 200                 205

Asp Ser Ala Leu Asn Arg Trp Arg Asn Ala Met Asn Asn Met Ser Gln
    210                 215                 220

Tyr Asp Arg Leu Arg Gln Ile Ala Leu Tyr Leu Leu Cys Trp Gly Glu
225                 230                 235                 240

Ala Gly Asn Ile Arg Leu Ala Pro Glu Cys Leu Cys Phe Ile Phe Lys
                245                 250                 255

Cys Ala Asp Asp Tyr Tyr Arg Ser Pro Glu Cys Gln Asn Arg Met Asp
            260                 265                 270

Pro Val Pro Glu Gly Leu Tyr Leu Gln Thr Val Ile Lys Pro Leu Tyr
        275                 280                 285

Arg Phe Leu Arg Asp Gln Ala Tyr Glu Val Val Asp Gly Lys Gln Val
    290                 295                 300

Lys Arg Glu Lys Asp His Asp Gln Ile Ile Gly Tyr Asp Asp Val Asn
305                 310                 315                 320

Gln Leu Phe Trp Tyr Pro Glu Gly Leu Ala Lys Ile Val Met Ser Asp
                325                 330                 335

Asn Thr Arg Leu Val Asp Val Pro Pro Ala Gln Arg Phe Met Lys Phe
            340                 345                 350

Ala Lys Ile Glu Trp Asn Arg Val Phe Phe Lys Thr Tyr Phe Glu Lys
        355                 360                 365
```

-continued

Arg Ser Thr Ala His Leu Leu Val Asn Phe Asn Arg Ile Trp Ile Leu
    370                 375                 380

His Val Ser Met Tyr Phe Phe Tyr Thr Ala Phe Asn Ser Pro Arg Val
385                 390                 395                 400

Tyr Ala Pro His Gly Lys Leu Asp Pro Ser Pro Glu Met Thr Trp Ser
            405                 410                 415

Ala Thr Ala Leu Gly Gly Ala Val Ser Thr Met Ile Met Ile Leu Ala
                420                 425                 430

Thr Ile Ala Glu Tyr Thr Tyr Ile Pro Thr Thr Trp Asn Asn Ala Ser
        435                 440                 445

His Leu Thr Thr Arg Leu Ile Phe Leu Leu Val Ile Leu Ala Leu Thr
    450                 455                 460

Ala Gly Pro Thr Phe Tyr Ile Ala Met Ile Asp Gly Arg Thr Asp Ile
465                 470                 475                 480

Gly Gln Val Pro Leu Ile Val Ala Ile Val Gln Phe Phe Ile Ser Val
            485                 490                 495

Val Ala Thr Leu Ala Phe Ala Thr Ile Pro Ser Gly Arg Met Phe Gly
                500                 505                 510

Asp Arg Val Ala Gly Lys Ser Arg Lys His Met Ala Ser Gln Thr Phe
        515                 520                 525

Thr Ala Ser Tyr Pro Ser Met Lys Arg Ser Ser Arg Val Ala Ser Ile
    530                 535                 540

Met Leu Trp Leu Leu Val Phe Gly Cys Lys Tyr Val Glu Ser Tyr Phe
545                 550                 555                 560

Phe Leu Thr Ser Ser Phe Ser Ser Pro Ile Ala Val Met Ala Arg Thr
            565                 570                 575

Lys Val Gln Gly Cys Asn Asp Arg Ile Phe Gly Ser Gln Leu Cys Thr
                580                 585                 590

Asn Gln Val Pro Phe Ala Leu Ala Ile Met Tyr Val Met Asp Leu Val
        595                 600                 605

Leu Phe Phe Leu Asp Thr Tyr Leu Trp Tyr Ile Ile Trp Leu Val Ile
    610                 615                 620

Phe Ser Met Val Arg Ala Phe Lys Leu Gly Ile Ser Ile Trp Thr Pro
625                 630                 635                 640

Trp Ser Glu Ile Phe Thr Arg Met Pro Lys Arg Ile Tyr Ala Lys Leu
            645                 650                 655

Leu Ala Thr Ala Glu Met Glu Val Lys Tyr Lys Pro Lys Val Leu Val
                660                 665                 670

Ser Gln Ile Trp Asn Ala Val Ile Ile Ser Met Tyr Arg Glu His Leu
        675                 680                 685

Leu Ser Ile Glu His Val Gln Arg Leu Leu Tyr His Gln Val Asp Gly
    690                 695                 700

Pro Asp Gly Arg Arg Thr Leu Arg Ala Pro Phe Phe Thr Ser Gln
705                 710                 715                 720

Arg Thr Ala Lys Pro Gly Leu Phe Phe Pro Gly Gly Glu Ala Glu
            725                 730                 735

Arg Arg Ile Ser Phe Phe Ala Ser Ser Leu Thr Thr Ala Leu Pro Glu
                740                 745                 750

Pro Leu Pro Ile Asp Ala Met Pro Thr Phe Thr Val Leu Val Pro His
        755                 760                 765

Tyr Ser Glu Lys Ile Leu Leu Ser Leu Arg Glu Ile Ile Arg Glu Glu
    770                 775                 780

```
Asp Gln Asn Thr Arg Val Thr Leu Leu Glu Tyr Leu Lys Gln Leu His
785                 790                 795                 800

Pro Val Glu Trp Asp Asn Phe Val Lys Asp Thr Lys Ile Leu Ala Glu
                805                 810                 815

Glu Ser Gly Asp Val Gln Asp Glu Lys Arg Ala Arg Thr Asp Asp Leu
            820                 825                 830

Pro Phe Tyr Cys Ile Gly Phe Lys Thr Ser Ser Pro Glu Tyr Thr Leu
            835                 840                 845

Arg Thr Arg Ile Trp Ala Ser Leu Arg Ala Gln Thr Leu Tyr Arg Thr
        850                 855                 860

Val Ser Gly Met Met Asn Tyr Ser Lys Ala Ile Lys Leu Leu Tyr Arg
865                 870                 875                 880

Val Glu Asn Pro Asp Val Val His Ala Phe Gly Gly Asn Thr Glu Arg
                885                 890                 895

Leu Glu Arg Glu Leu Glu Arg Met Ser Arg Arg Lys Phe Lys Phe Val
            900                 905                 910

Ile Ser Met Gln Arg Tyr Ser Lys Phe Asn Lys Glu Glu Gln Glu Asn
        915                 920                 925

Ala Glu Phe Leu Leu Arg Ala Tyr Pro Asp Leu Gln Ile Ala Tyr Leu
930                 935                 940

Asp Glu Glu Pro Gly Pro Ser Lys Ser Asp Glu Val Arg Leu Phe Ser
945                 950                 955                 960

Thr Leu Ile Asp Gly His Ser Glu Val Asp Glu Lys Thr Gly Arg Arg
                965                 970                 975

Lys Pro Lys Phe Arg Ile Glu Leu Pro Gly Asn Pro Ile Leu Gly Asp
            980                 985                 990

Gly Lys Ser Asp Asn Gln Asn His Ala Ile Val Phe Tyr Arg Gly Glu
        995                 1000                1005

Tyr Ile Gln Val Ile Asp Ala Asn Gln Asp Asn Tyr Leu Glu Glu
    1010                1015                1020

Cys Leu Lys Ile Arg Asn Val Leu Gly Glu Phe Glu Glu Tyr Ser
    1025                1030                1035

Val Ser Ser Gln Ser Pro Tyr Ala Gln Trp Gly His Lys Glu Phe
    1040                1045                1050

Asn Lys Cys Pro Val Ala Ile Leu Gly Ser Arg Glu Tyr Ile Phe
    1055                1060                1065

Ser Glu Asn Ile Gly Ile Leu Gly Asp Ile Ala Ala Gly Lys Glu
    1070                1075                1080

Gln Thr Phe Gly Thr Ile Thr Ala Arg Ala Leu Ala Trp Ile Gly
    1085                1090                1095

Gly Lys Leu His Tyr Gly His Pro Asp Phe Leu Asn Ala Thr Phe
    1100                1105                1110

Met Thr Thr Arg Gly Gly Val Ser Lys Ala Gln Lys Gly Leu His
    1115                1120                1125

Leu Asn Glu Asp Ile Phe Ala Gly Met Thr Ala Val Ser Arg Gly
    1130                1135                1140

Gly Arg Ile Lys His Met Glu Tyr Tyr Gln Cys Gly Lys Gly Arg
    1145                1150                1155

Asp Leu Gly Phe Gly Thr Ile Leu Asn Phe Gln Thr Lys Ile Gly
    1160                1165                1170

Thr Gly Met Gly Glu Gln Leu Leu Ser Arg Glu Tyr Tyr Tyr Leu
    1175                1180                1185

Gly Thr Gln Leu Pro Ile Asp Arg Phe Leu Thr Phe Tyr Tyr Ala
```

```
                    1190                1195                1200

His Ala Gly Phe His Val Asn Asn Ile Leu Val Ile Tyr Ser Ile
            1205                1210                1215

Gln Val Phe Met Val Thr Leu Leu Tyr Leu Gly Thr Leu Asn Lys
            1220                1225                1230

Gln Leu Phe Ile Cys Lys Val Asn Ser Asn Gly Gln Val Leu Ser
            1235                1240                1245

Gly Gln Ala Gly Cys Tyr Asn Leu Ile Pro Val Phe Glu Trp Ile
            1250                1255                1260

Arg Arg Ser Ile Ile Ser Ile Phe Leu Val Phe Phe Ile Ala Phe
            1265                1270                1275

Leu Pro Leu Phe Leu Gln Glu Leu Cys Glu Arg Gly Thr Gly Lys
            1280                1285                1290

Ala Leu Leu Arg Leu Gly Lys His Phe Leu Ser Leu Ser Pro Ile
            1295                1300                1305

Phe Glu Val Phe Ser Thr Gln Ile Tyr Ser Gln Ala Leu Leu Asn
            1310                1315                1320

Asn Met Ser Phe Gly Gly Ala Arg Tyr Ile Ala Thr Gly Arg Gly
            1325                1330                1335

Phe Ala Thr Ser Arg Ile Pro Phe Asn Ile Leu Tyr Ser Arg Phe
            1340                1345                1350

Ala Pro Pro Ser Ile Tyr Met Gly Met Arg Asn Leu Leu Leu Leu
            1355                1360                1365

Leu Tyr Ala Thr Met Ala Ile Trp Ile Pro His Leu Ile Tyr Phe
            1370                1375                1380

Trp Phe Ser Val Leu Ser Leu Cys Ile Ala Pro Phe Met Phe Asn
            1385                1390                1395

Pro His Gln Phe Ser Tyr Ala Asp Phe Ile Ile Asp Tyr Arg Glu
            1400                1405                1410

Phe Leu Arg Trp Met Ser Arg Gly Asn Ser Arg Thr Lys Ala Ser
            1415                1420                1425

Ser Trp Tyr Gly Tyr Cys Arg Leu Ser Arg Thr Ala Ile Thr Gly
            1430                1435                1440

Tyr Lys Lys Lys Lys Leu Gly His Pro Ser Glu Lys Leu Ser Gly
            1445                1450                1455

Asp Val Pro Arg Ala Pro Trp Arg Asn Val Ile Phe Ser Glu Ile
            1460                1465                1470

Leu Trp Pro Ile Gly Ala Cys Ile Ile Phe Ile Val Ala Tyr Met
            1475                1480                1485

Phe Val Lys Ser Phe Pro Asp Glu Gln Gly Asn Ala Pro Pro Ser
            1490                1495                1500

Pro Leu Val Arg Ile Leu Ile Ala Val Gly Pro Thr Val Trp
            1505                1510                1515

Asn Ala Ala Val Leu Ile Thr Leu Phe Phe Leu Ser Leu Phe Leu
            1520                1525                1530

Gly Pro Met Met Asp Gly Trp Val Lys Phe Gly Ser Val Met Ala
            1535                1540                1545

Ala Leu Ala His Gly Leu Ala Leu Ile Gly Met Leu Thr Phe Phe
            1550                1555                1560

Glu Phe Phe Trp Phe Leu Glu Leu Trp Asp Ala Ser His Ala Val
            1565                1570                1575

Leu Gly Val Ile Ala Ile Ile Ala Val Gln Arg Gly Ile Gln Lys
            1580                1585                1590
```

-continued

```
Ile Leu Ile Ala Val Phe Leu Thr Arg Glu Tyr Lys His Asp Glu
    1595                1600                1605

Thr Asn Arg Ala Trp Trp Thr Gly Lys Trp Tyr Gly Arg Gly Leu
    1610                1615                1620

Gly Thr Ser Ala Met Ser Gln Pro Ala Arg Glu Phe Ile Val Lys
    1625                1630                1635

Ile Val Glu Met Ser Leu Trp Thr Ser Asp Phe Leu Leu Ala His
    1640                1645                1650

Leu Leu Leu Ile Ile Leu Thr Val Pro Leu Leu Pro Phe Phe
    1655                1660                1665

Asn Ser Ile His Ser Thr Met Leu Phe Trp Leu Arg Pro Ser Lys
    1670                1675                1680

Gln Ile Arg Gln Pro Leu Phe Ser Thr Lys Gln Lys Arg Gln Arg
    1685                1690                1695

Arg Trp Ile Val Met Lys Tyr Thr Val Val Tyr Leu Val Val Val
    1700                1705                1710

Ala Phe Leu Val Ala Leu Ile Ala Leu Pro Ala Leu Phe Arg Glu
    1715                1720                1725

Ser Ile His Phe Asn Cys Glu Ile Cys Gln Ser Ile
    1730                1735                1740

<210> SEQ ID NO 3
<211> LENGTH: 5770
<212> TYPE: DNA
<213> ORGANISM: Schizophyllum commune

<400> SEQUENCE: 3
ctgtccaaag aagagatcga ggacatcttc ctcgatctga cgcagaagtt tggctttcag      60
cgggattcca tgcggaacat ggtacgtggc gtatgcccat gtgcggcgtt ctgaggccta     120
aacgttttcc gccagttcga cttcaccatg cagctgcttg acagccgagc gtctcgtatg     180 accccccaacc aggcgctcct caccctccac gccgactaca ttggtggcca gcatgcgaac     240
taccggaagt ggtacttcgc ggcgcagctc gaccttgacg acgccgtggg acaaactcag     300
aatccgggtc tcaaccgcct caagtccact cgcggatcgg gcaagcgacc acgccatgaa     360
aagtcgctga cacggcatt ggagcgctgg cggcaagcca tgaacaacat gtcgcagtat     420
gaccgcttac gccagatcgc gctctacctg ctctgctggg gcgaagcggc gcaagtgcga     480
ttcatgcccg agtgcttgtg cttcatcttc aagtgcgccg acgactatta tcgttcgccg     540
gagtgccaga acaggatgga gccggtaccg gagggtctct acctgaggac ggtcgtaaag     600
ccgctctaca gatttgtccg ggatcaaggc tatgaggtgg tggagggaaa attcgtacgg     660
cgggaacggg atcacgacca aatcattggt tacgatgacg tgaatcagct gttctggtac     720
ccggagggca ttgcccgtat cgtcctgtcg gacaaggtaa gcacctctgt gcatcttctg     780
tgacatacag ggctaattgt cgagcagagt cgtctggtcg acctccctcc agcacagcgc     840
ttcatgaagt tcgaccgtat cgagtggaat cgcgtcttct tcaagacgtt ctacgagact     900
cgatccttta cgcatctttt ggtcgacttc aaccgtatct gggtcgtgca catcgctctc     960
tacttcttct acaccgcata caactccccc acgatctacg ccatcaacgg caacactccg    1020
acgtctctgg cttggagcgc gactgcgctc ggcggtgcgg tagcgacagg tatcatgatc    1080
ctcgccacga tcgccgagtt ctcgcacatc cccacgacat ggaacaacac ctcgcatctg    1140
actcgccgcc tcgccttcct cctcgtcacg ctcggcctca catgtggtcc gacgttctac    1200
```

```
gtcgcgattg cagagagcaa cgggagcggc ggctctttgg ccttgattct cggcatcgtc    1260
cagttcttca tctccgtcgt agcgactgcg ctcttcacta tcatgccttc tggtcgtatg    1320
ttcggcgacc gcgtcgcagg caagagtcgc aagtatctcg ccagccagac gttcacggcc    1380
agctacccgt cgttgcccaa gcaccagcgg ttcgcatcac tcctgatgtg gttcctcatc    1440
ttcgggtgca agttgacgga gagttacttc ttcctgacgt tgtccttccg cgaccctatt    1500
cgcgtcatgg tcggcatgaa gatccagaac tgcgaggaca agattttcgg cagcggcctt    1560
tgcaggaatc acgcagcatt caccctcacg atcatgtaca tcatggacct cgtcttgttc    1620
ttcctcgaca ccttcctttg gtatgtcatc tggaactcgg ttttcagtat cgcacgctct    1680
ttcgtactcg gcctttcgat ctggacacca tggagggaca tcttccagcg tctgccgaag    1740
cgtatctacg cgaagcttct agcgaccggc gacatggagg tcaagtacaa gcccaaggtg    1800
tgtgaatagc tcgctgtaag gttcttgatt ctgactcatt cgcaggtctt ggtttcgcaa    1860
atctggaacg ccatcatcat ctccatgtac cgcgagcact tgctctctat cgagcacgtt    1920
caaaagctcc tgtaccatca agtggacact ggcgaagccg gcaagcggag tcttcgcgcg    1980
cctccgttct tcgtcgcgca gggcagcagc ggtggctcgg gcgagttctt cccgcctggt    2040
agcgaggctg agcgtcgtat ctctttcttc gcgcagtctc tatctacgga gattcctcag    2100
cccatcccgg ttgacgccat gccgacgttc acagtgctta cgcctcacta cagcgagaag    2160
gtgcgctttt tcctgggcgc attcaacatt agctgactgt cgtgcacaga tccttctttc    2220
gctccgtgag attatccgcg aggaggacca gaacacccgc gtgacattgc ttgagtatct    2280
caagcagctt cacccggtcg agtgggagaa cttcgtcaag gacaccaaga tttggccga    2340 ggagtccgct atgttcaacg gtccaagtcc tttcggcaac gatgagaagg gtcagtccaa    2400
gatggacgat cttcctttct actgcatcgg tttcaagagc gccgcgcccg agtacaccct    2460
ccgcacccgt atctgggcgt ccttgcgcgc gcagaccctc taccgcacgg tctccggcat    2520
gatgaactat gcgaaggcga ttaagctgct ctaccgcgtc gagaacccg aggtcgtgca    2580 gcagttcggc ggtaacacgg acaagctcga gcgcgagttg gagcggatgg cccggcggaa    2640
gttcaagttc ctggtgtcca tgcagcgcta ctcgaagttc aacaaggagg agcacgagaa    2700
cgccgagttc ttgctccgcg cgtacccgga cctgcagatc gcgtacctgg aggaagagcc    2760
tcctcgcaag gagggtggcg atccacgcat cttctctgcc ctcgtcgacg gccacagcga    2820
catcatcccg gagaccggca agcggcgccc caagttccgc atcgagctgc ccggcaaccc    2880
cattctcggt gacggcaagt cggacaacca gaaccacgcc atcgtcttct accgcggcga    2940
gtacctccag cttatcgacg ccaaccagga caactacctc gaggagtgct tgaagatccg    3000
taacgtactc gccgagttcg aggagtacga cgtctctagc cagagtccgt acgcgcagtg    3060
gagtgtcaag gagttcaagc gctccccggt cgccatcgtc ggtgcacgcg agtatatctt    3120
ctcggagcac atcggtattc tcggtgattt ggcggctggc aaggaacaga cgttcggtac    3180
gctcacggca cgcaacaacg ccttccttgg cggcaagctg cactacggtc acccggattt    3240
cctcaacgcc ctctacatga acacgcgcgg tggtgtctcc aaggcgcaga agggtctcca    3300
tctcaacgag gatatttacg ccggtatgaa cgcggtcggt cgcggtggac gcatcaagca    3360
tagcgaatac taccagtgcg gcaagggtcg tgacctcggt tttggcacca tcttgaactt    3420
ccagaccaag atcggtacgg gtatgggcga gcagatcctc tcgcgcgagt actactacct    3480
cggaacccaa ttgcccatcg atcgcttcct cacgttctac tacgcgcacc caggtttcca    3540
gatcaacaac atgctggtta tcctatccgt gcaggtcttc atcgttacca gtacgttgat    3600
```

```
tgcatatcgt tagcctgaca gcgtctgacg aattcccagt ggtcttcctc ggtaccttga    3660
agtcttcggt cacgatctgc aagtacacgt ccagcggtca gtacatcggt ggtcaatccg    3720
gttgctacaa cctcgtcccg gtcttccagt ggatcgagcg ctgcatcatc agcatcttct    3780
tggtgttcat gatcgctttc atgccgctct tcctgcaagg taagagctcg tcaacctgct    3840
caagggcctt gcgctgatca tcatctcaga actcgtcgag cgcggtacct ggagtgccat    3900
ctggcgtctg ctcaagcagt ttatgtcgct gtcgcctgtc ttcgaggtgt tctccaccca    3960
gattcagaca cactccgtgt tgagcaactt gacgttcggt ggtgcgcgtt acatcgctac    4020
cggtcgtggg ttcgccacca gtcgtatcag cttcagcatc ttgttctcgc gtttcgcagg    4080
cccgagtatc tacctcggca tgcgcacgct cattatgctg ctctacgtga cgttgacgat    4140
ctggacgcca tgggtcattt acttctgggt ttccattctc tcgctctgca tcgcgccgtt    4200
cttgttcaat ccgcatcaat tcgtcttctc ggatttcctc atcgactaca ggtacgtcgg    4260
acgagcgctg ttccgcgacg taagctgacc ggttatacag ggaataccrc cggtggatgt    4320
cgcgtggtaa ctcgcgctcg cacaacaact cctggattgg gtactgccgg ttgtcccgca    4380
cgatgatcac tgggtacaag aagaagaagc tgggccaccc gtcggagaag ctttccggcg    4440
acgttcctcg tgcaggctgg cgcgccgtct tattctcgga gatcatcttc ccggcatgca    4500
tggccatcct cttcatcatc gcgtacatgt tcgtcaagtc gttccctctc gacggcaagc    4560
agcctccctc cggcctcgtt cgcatcgccg tcgtgtctat cggccccatc gtgtggaacg    4620
ccgccatcct gttgacgctc ttccttgtgt cgttgttcct cggccccatg ctcgacccgg    4680
tcttccccct cttcggttcc gttatggcct tcatcgcgca tttcctcggc acaatcggaa    4740
tgattgggtt cttcgagttc ctggtatgtg cccatacctt tcattcgtct tcaactatct    4800
aacagattca tagtggttcc tcgagtcctg ggaggcgtcg catgccgtgc tgggtctcat    4860
cgccgtcatc tccatccagc gcgccattca caaaattctt atcgccgttt cctcagtcg    4920 cgagttcaag cacgacgaga cgaacagggc ttggtggact ggtcgctggt atggccgtgg    4980
cctcggcacg cacgccatgt cgcagccggc gcgtgagttc gcgtcaaga tcatcgagtt    5040 gtcgctctgg agctcggatc tcatactcgg ccacatcctg ctgttcatgc ttactccggc    5100
tgtcctcatc ccgtacttcg accgtctgca cgccatgatg ctctgtacgt cgtgtctcat    5160
tgtttgtgtt ggtcatactc ttaccctctc ttagtctggc tgcgcccctc aaagcaaatc    5220
cgcgcgcctc tgtactcaat caagcagaag aggcaaagac gctggattgt cagtgttcag    5280
tgccttattc tatcagctct tactgacgtc ttcatagatc atgaagtacg gtactgtata    5340
cgttaccgtc atcgcgatct tcgtcgcgct catcgcgctt cgtgagtacc cttgctatct    5400
ttcgtacctg agcgtcgctg accccttcc cagcccttgt cttccgacac actctaaagg    5460
tcgagtgctc cctttgcgac agcttgtaat atcggactcg tatatatcta gacttctccg    5520
caccatgtgt agctgacgct tgggtatact tcgcggtgcc gagctaattg tcgacggaca    5580
ttctccatcg ttgagtgcag cgacatcggg tggtttacga cacggacact tttcattgta    5640
ccctctacga atgcaagaac tctcttacga ccagtaccta tgtgctaagc cgtcgcctgt    5700
tcaggatcat acatacatac gtttctagat accttacagt taggcctatt cagggagagt    5760
ctgcataaaa                                                            5770
```

<210> SEQ ID NO 4
<211> LENGTH: 1622
<212> TYPE: PRT

<213> ORGANISM: Schizophyllum commune

<400> SEQUENCE: 4

```
Met Arg Asn Met Phe Asp Phe Thr Met Gln Leu Leu Asp Ser Arg Ala
 1               5                  10                  15

Ser Arg Met Thr Pro Asn Gln Ala Leu Leu Thr Leu His Ala Asp Tyr
            20                  25                  30

Ile Gly Gly Gln His Ala Asn Tyr Arg Lys Trp Tyr Phe Ala Ala Gln
        35                  40                  45

Leu Asp Leu Asp Asp Ala Val Gly Gln Thr Gln Asn Pro Gly Leu Asn
    50                  55                  60

Arg Leu Lys Ser Thr Arg Gly Ser Gly Lys Arg Pro Arg His Glu Lys
65                  70                  75                  80

Ser Leu Asn Thr Ala Leu Glu Arg Trp Arg Gln Ala Met Asn Asn Met
                85                  90                  95

Ser Gln Tyr Asp Arg Leu Arg Gln Ile Ala Leu Tyr Leu Leu Cys Trp
            100                 105                 110

Gly Glu Ala Ala Gln Val Arg Phe Met Pro Glu Cys Leu Cys Phe Ile
        115                 120                 125

Phe Lys Cys Ala Asp Asp Tyr Tyr Arg Ser Pro Glu Cys Gln Asn Arg
    130                 135                 140

Met Glu Pro Val Pro Glu Gly Leu Tyr Leu Arg Thr Val Val Lys Pro
145                 150                 155                 160

Leu Tyr Arg Phe Val Arg Asp Gln Gly Tyr Glu Val Val Glu Gly Lys
                165                 170                 175

Phe Val Arg Arg Glu Arg Asp His Asp Gln Ile Ile Gly Tyr Asp Asp
            180                 185                 190

Val Asn Gln Leu Phe Trp Tyr Pro Glu Gly Ile Ala Arg Ile Val Leu
        195                 200                 205

Ser Asp Lys Ser Arg Leu Val Asp Leu Pro Pro Ala Gln Arg Phe Met
    210                 215                 220

Lys Phe Asp Arg Ile Glu Trp Asn Arg Val Phe Phe Lys Thr Phe Tyr
225                 230                 235                 240

Glu Thr Arg Ser Phe Thr His Leu Leu Val Asp Phe Asn Arg Ile Trp
                245                 250                 255

Val Val His Ile Ala Leu Tyr Phe Phe Tyr Thr Ala Tyr Asn Ser Pro
            260                 265                 270

Thr Ile Tyr Ala Ile Asn Gly Asn Thr Pro Thr Ser Leu Ala Trp Ser
        275                 280                 285

Ala Thr Ala Leu Gly Gly Ala Val Ala Thr Gly Ile Met Ile Leu Ala
    290                 295                 300

Thr Ile Ala Glu Phe Ser His Ile Pro Thr Thr Trp Asn Asn Thr Ser
305                 310                 315                 320

His Leu Thr Arg Arg Leu Ala Phe Leu Leu Val Thr Leu Gly Leu Thr
                325                 330                 335

Cys Gly Pro Thr Phe Tyr Val Ala Ile Ala Glu Ser Asn Gly Ser Gly
            340                 345                 350

Gly Ser Leu Ala Leu Ile Leu Gly Ile Val Gln Phe Phe Ile Ser Val
        355                 360                 365

Val Ala Thr Ala Leu Phe Thr Ile Met Pro Ser Gly Arg Met Phe Gly
    370                 375                 380

Asp Arg Val Ala Gly Lys Ser Arg Lys Tyr Leu Ala Ser Gln Thr Phe
385                 390                 395                 400
```

```
Thr Ala Ser Tyr Pro Ser Leu Pro Lys His Gln Arg Phe Ala Ser Leu
                405                 410                 415
Leu Met Trp Phe Leu Ile Phe Gly Cys Lys Leu Thr Glu Ser Tyr Phe
            420                 425                 430
Phe Leu Thr Leu Ser Phe Arg Asp Pro Ile Arg Val Met Val Gly Met
            435                 440                 445
Lys Ile Gln Asn Cys Glu Asp Lys Ile Phe Gly Ser Gly Leu Cys Arg
        450                 455                 460
Asn His Ala Ala Phe Thr Leu Thr Ile Met Tyr Ile Met Asp Leu Val
465                 470                 475                 480
Leu Phe Phe Leu Asp Thr Phe Leu Trp Tyr Val Ile Trp Asn Ser Val
                485                 490                 495
Phe Ser Ile Ala Arg Ser Phe Val Leu Gly Leu Ser Ile Trp Thr Pro
            500                 505                 510
Trp Arg Asp Ile Phe Gln Arg Leu Pro Lys Arg Ile Tyr Ala Lys Leu
            515                 520                 525
Leu Ala Thr Gly Asp Met Glu Val Lys Tyr Lys Pro Lys Val Leu Val
        530                 535                 540
Ser Gln Ile Trp Asn Ala Ile Ile Ile Ser Met Tyr Arg Glu His Leu
545                 550                 555                 560
Leu Ser Ile Glu His Val Gln Lys Leu Leu Tyr His Gln Val Asp Thr
                565                 570                 575
Gly Glu Ala Gly Lys Arg Ser Leu Arg Ala Pro Pro Phe Phe Val Ala
            580                 585                 590
Gln Gly Ser Ser Gly Ser Gly Glu Phe Phe Pro Pro Gly Ser Glu
            595                 600                 605
Ala Glu Arg Arg Ile Ser Phe Phe Ala Gln Ser Leu Ser Thr Glu Ile
        610                 615                 620
Pro Gln Pro Ile Pro Val Asp Ala Met Pro Thr Phe Thr Val Leu Thr
625                 630                 635                 640
Pro His Tyr Ser Glu Lys Ile Leu Leu Ser Leu Arg Glu Ile Ile Arg
                645                 650                 655
Glu Glu Asp Gln Asn Thr Arg Val Thr Leu Leu Glu Tyr Leu Lys Gln
            660                 665                 670
Leu His Pro Val Glu Trp Glu Asn Phe Val Lys Asp Thr Lys Ile Leu
            675                 680                 685
Ala Glu Glu Ser Ala Met Phe Asn Gly Pro Ser Pro Phe Gly Asn Asp
        690                 695                 700
Glu Lys Gly Gln Ser Lys Met Asp Asp Leu Pro Phe Tyr Cys Ile Gly
705                 710                 715                 720
Phe Lys Ser Ala Ala Pro Glu Tyr Thr Leu Arg Thr Arg Ile Trp Ala
                725                 730                 735
Ser Leu Arg Ala Gln Thr Leu Tyr Arg Thr Val Ser Gly Met Met Asn
            740                 745                 750
Tyr Ala Lys Ala Ile Lys Leu Leu Tyr Arg Val Glu Asn Pro Glu Val
            755                 760                 765
Val Gln Gln Phe Gly Gly Asn Thr Asp Lys Leu Glu Arg Glu Leu Glu
        770                 775                 780
Arg Met Ala Arg Arg Lys Phe Lys Phe Leu Val Ser Met Gln Arg Tyr
785                 790                 795                 800
Ser Lys Phe Asn Lys Glu Glu His Glu Asn Ala Glu Phe Leu Leu Arg
                805                 810                 815
Ala Tyr Pro Asp Leu Gln Ile Ala Tyr Leu Glu Glu Glu Pro Pro Arg
```

-continued

```
                820                 825                 830
Lys Glu Gly Gly Asp Pro Arg Ile Phe Ser Ala Leu Val Asp Gly His
            835                 840                 845
Ser Asp Ile Ile Pro Glu Thr Gly Lys Arg Arg Pro Lys Phe Arg Ile
850                 855                 860
Glu Leu Pro Gly Asn Pro Ile Leu Gly Asp Gly Lys Ser Asp Asn Gln
865                 870                 875                 880
Asn His Ala Ile Val Phe Tyr Arg Gly Glu Tyr Leu Gln Leu Ile Asp
            885                 890                 895
Ala Asn Gln Asp Asn Tyr Leu Glu Glu Cys Leu Lys Ile Arg Asn Val
            900                 905                 910
Leu Ala Glu Phe Glu Glu Tyr Asp Val Ser Ser Gln Ser Pro Tyr Ala
            915                 920                 925
Gln Trp Ser Val Lys Glu Phe Lys Arg Ser Pro Val Ala Ile Val Gly
            930                 935                 940
Ala Arg Glu Tyr Ile Phe Ser Glu His Ile Gly Ile Leu Gly Asp Leu
945                 950                 955                 960
Ala Ala Gly Lys Glu Gln Thr Phe Gly Thr Leu Thr Ala Arg Asn Asn
            965                 970                 975
Ala Phe Leu Gly Gly Lys Leu His Tyr Gly His Pro Asp Phe Leu Asn
            980                 985                 990
Ala Leu Tyr Met Asn Thr Arg Gly Gly Val Ser Lys Ala Gln Lys Gly
            995                 1000                1005
Leu His Leu Asn Glu Asp Ile Tyr Ala Gly Met Asn Ala Val Gly
            1010                1015                1020
Arg Gly Gly Arg Ile Lys His Ser Glu Tyr Tyr Gln Cys Gly Lys
            1025                1030                1035
Gly Arg Asp Leu Gly Phe Gly Thr Ile Leu Asn Phe Gln Thr Lys
            1040                1045                1050
Ile Gly Thr Gly Met Gly Glu Gln Ile Leu Ser Arg Glu Tyr Tyr
            1055                1060                1065
Tyr Leu Gly Thr Gln Leu Pro Ile Asp Arg Phe Leu Thr Phe Tyr
            1070                1075                1080
Tyr Ala His Pro Gly Phe Gln Ile Asn Asn Met Leu Val Ile Leu
            1085                1090                1095
Ser Val Gln Val Phe Ile Val Thr Met Val Phe Leu Gly Thr Leu
            1100                1105                1110
Lys Ser Ser Val Thr Ile Cys Lys Tyr Thr Ser Ser Gly Gln Tyr
            1115                1120                1125
Ile Gly Gly Gln Ser Gly Cys Tyr Asn Leu Val Pro Val Phe Gln
            1130                1135                1140
Trp Ile Glu Arg Cys Ile Ile Ser Ile Phe Leu Val Phe Met Ile
            1145                1150                1155
Ala Phe Met Pro Leu Phe Leu Gln Glu Leu Val Glu Arg Gly Thr
            1160                1165                1170
Trp Ser Ala Ile Trp Arg Leu Leu Lys Gln Phe Met Ser Leu Ser
            1175                1180                1185
Pro Val Phe Glu Val Phe Ser Thr Gln Ile Gln Thr His Ser Val
            1190                1195                1200
Leu Ser Asn Leu Thr Phe Gly Gly Ala Arg Tyr Ile Ala Thr Gly
            1205                1210                1215
Arg Gly Phe Ala Thr Ser Arg Ile Ser Phe Ser Ile Leu Phe Ser
            1220                1225                1230
```

-continued

```
Arg Phe Ala Gly Pro Ser Ile Tyr Leu Gly Met Arg Thr Leu Ile
    1235                1240                1245

Met Leu Leu Tyr Val Thr Leu Thr Ile Trp Thr Pro Trp Val Ile
    1250                1255                1260

Tyr Phe Trp Val Ser Ile Leu Ser Leu Cys Ile Ala Pro Phe Leu
    1265                1270                1275

Phe Asn Pro His Gln Phe Val Phe Ser Asp Phe Leu Ile Asp Tyr
    1280                1285                1290

Arg Glu Tyr Leu Arg Trp Met Ser Arg Gly Asn Ser Arg Ser His
    1295                1300                1305

Asn Asn Ser Trp Ile Gly Tyr Cys Arg Leu Ser Arg Thr Met Ile
    1310                1315                1320

Thr Gly Tyr Lys Lys Lys Leu Gly His Pro Ser Glu Lys Leu
    1325                1330                1335

Ser Gly Asp Val Pro Arg Ala Gly Trp Arg Ala Val Leu Phe Ser
    1340                1345                1350

Glu Ile Ile Phe Pro Ala Cys Met Ala Ile Leu Phe Ile Ile Ala
    1355                1360                1365

Tyr Met Phe Val Lys Ser Phe Pro Leu Asp Gly Lys Gln Pro Pro
    1370                1375                1380

Ser Gly Leu Val Arg Ile Ala Val Val Ser Ile Gly Pro Ile Val
    1385                1390                1395

Trp Asn Ala Ala Ile Leu Leu Thr Leu Phe Leu Val Ser Leu Phe
    1400                1405                1410

Leu Gly Pro Met Leu Asp Pro Val Phe Pro Leu Phe Gly Ser Val
    1415                1420                1425

Met Ala Phe Ile Ala His Phe Leu Gly Thr Ile Gly Met Ile Gly
    1430                1435                1440

Phe Phe Glu Phe Leu Trp Phe Leu Glu Ser Trp Glu Ala Ser His
    1445                1450                1455

Ala Val Leu Gly Leu Ile Ala Val Ile Ser Ile Gln Arg Ala Ile
    1460                1465                1470

His Lys Ile Leu Ile Ala Val Phe Leu Ser Arg Glu Phe Lys His
    1475                1480                1485

Asp Glu Thr Asn Arg Ala Trp Trp Thr Gly Arg Trp Tyr Gly Arg
    1490                1495                1500

Gly Leu Gly Thr His Ala Met Ser Gln Pro Ala Arg Glu Phe Val
    1505                1510                1515

Val Lys Ile Ile Glu Leu Ser Leu Trp Ser Ser Asp Leu Ile Leu
    1520                1525                1530

Gly His Ile Leu Leu Phe Met Leu Thr Pro Ala Val Leu Ile Pro
    1535                1540                1545

Tyr Phe Asp Arg Leu His Ala Met Met Leu Phe Trp Leu Arg Pro
    1550                1555                1560

Ser Lys Gln Ile Arg Ala Pro Leu Tyr Ser Ile Lys Gln Lys Arg
    1565                1570                1575

Gln Arg Arg Trp Ile Ile Met Lys Tyr Gly Thr Val Tyr Val Thr
    1580                1585                1590

Val Ile Ala Ile Phe Val Ala Leu Ile Ala Leu Pro Leu Val Phe
    1595                1600                1605

Arg His Thr Leu Lys Val Glu Cys Ser Leu Cys Asp Ser Leu
    1610                1615                1620
```

<210> SEQ ID NO 5
<211> LENGTH: 5223
<212> TYPE: DNA
<213> ORGANISM: Schizophyllum commune

<400> SEQUENCE: 5

```
atgtccggcc caggatatgg caggaatcca ttcgacaatc ccccgcccaa cagaggtccc      60
tatggccagc agccaggttt cccggggccc ggccctcggc cttacgactc ggacgcggac     120
atgagccaga cctatggcag cacaaccagg ctcgccggca gtgccggtta cagcgacaga     180
aacggcagct cgacggcga ccgctcctac gcgccctcaa ttgactcgcg cgccagcgtg      240
cccagcatat cgcccttcgc agacccgggt atcggctcta atgagccgta tcccgcttgg     300
tcggtcgaac gccagattcc catgtccacg gaggagattg aggacatctt cctcgacctc     360
acccaaaagt ttggcttcca gcgcgactcc atgcggaata cgttcgactt catgatgcac     420
ctcctcgatt cccgtgcctc gcgcatgacg cccaaccaag ctctgctcac gcttcacgcc     480
gactacattg gtggccagca tgccaattac cggaagtggt atttcgccgc acagctcaac     540
ctcgatgacg cggtcgggca aaccaataac cccggtatcc agcgcttgaa gaccatcaag     600
ggcgctacga agaccaagtc gctcgacagc gcactcaacc gctggcgcaa cgcgatgaac     660
aacatgagcc agtacgatcg cctccggcaa attgcgctct acctcctctg ctggggtgaa     720
gcaggcaaca tccgtctggc gcccgagtgc ttgtgcttca tcttcaagtg cgcggacgac     780
tactacagaa gtcccgagtg tcagaaccgg atggacccg tgccggaagg ctgtacctg       840
cagacggtca tcaagccgct ctatcgcttc tacgtgatc aggcgtacga agtcgttgat      900
gggaagcaag tgaagcgcga aaggaccac gaccagatta tcggttatga cgacgtcaac      960
cagttattct ggtatccgga aggtttggct aagatcgtca tgtcggacaa cacacgactt    1020
gtagatgtac ctccggcgca gcggttcatg aagttcgcca agatcgagtg gaaccgcgtc    1080
ttcttcaaga cgtactttga gaagcgctct actgcccatc tcctggtcaa cttcaaccgt    1140
atatggatcc tccacgtctc gatgtacttc ttctacacgg cattcaactc tccacgagtc    1200
tacgcgccgc acggcaaact cgaccccctcc cctgagatga cctggtccgc gactgccctt    1260
ggaggcgctg tgtccaccat gatcatgatc cttgccacta tcgcggagta cacctacatc    1320
cccacgacat ggaacaatgc gtcgcacctc accacgcggc tcattttcct cctggtcatc    1380
ctcgcgctca ctgctggccc aacattctat atcgccatga tagacggacg cacggacatc    1440
ggccaagtac cactcatcgt ggccatagtg cagttcttca tctccgtcgt cgccaccctc    1500
gctttcgcta ccatcccttc tggtcgcatg ttcggcgacc gtgtggctgg caagtcaaga    1560
aagcacatgg catcgcagac gttcacagcg tcgtacccgt ccatgaagcg gtcatctcgc    1620
gtagcgagta tcatgctgtg gctttttggtc tttggctgca aatacgtcga gtcttacttc    1680
ttcttgacgt cctccttctc cagcccgatc gcggtcatgg cgcgtacgaa ggtacagggc    1740
tgcaacgacc gtatcttcgg cagccagctg tgcacgaatc aggtcccgtt cgcgctggca    1800
atcatgtacg tgatggacct ggtactgttc ttcctggaca cgtacctgtg gtacatcatc    1860
tggctggtga tcttctcgat ggtgcgcgcg ttcaagcttg gtatctcgat ctggacgccc    1920
tggagcgaga tcttcacccg catgccgaag cgtatttacg caaagctgct ggcgacggcc    1980
gagatggagg tcaagtataa gcccaaggtg ctcgtctcac aaatctggaa gcggtcatc     2040
atctccatgt accgggagca tctcttgtcc atcgagcacg tccagcgctt gctttaccac    2100
caggttgatg gtcccgatgg ccgccgcacc ctcagggcac cgccgttctt caccagccag    2160
```

```
cgaactgcga agccaggcct gttcttccct cctggtggcg aggctgagcg ccgcatctcg    2220
ttctttgcct catcgctgac gaccgcgctc ccggagcctc tgccgatcga cgccatgccc    2280
accttcaccg tgctcgttcc ccattactcc gagaagattc tgctcagtct gcgcgagatt    2340
atccgcgagg aggaccagaa cacccgcgtt accttactgg agtacctcaa gcagctccac    2400
cctgtcgaat gggacaattt cgtcaaggac accaagatct ggcggaaga gtcgggagac    2460 gtccaggacg agaagcgcgc gcgcacggac gacttgccgt tctattgcat cgggttcaag    2520
acctcgtcac cagagtacac cctgcgtacg cgtatctggg cctcactgcg cgcacagacg    2580
ctgtaccgca cggtctccgg tatgatgaac tactccaagg cgattaagct cctctatcgc    2640
gtcgagaacc cggatgtcgt tcatgccttc ggtgggaaca cggaacgtct tgaacgcgag    2700
cttgagcgca tgtctcgccg caagttcaag ttcgtcatct cgatgcagcg gtactccaag    2760
ttcaacaagg aggagcagga gaacgccgag ttccttctgc gcgcgtaccc ggatttgcag    2820
atcgcgtacc tcgatgaaga gcccggtccc agcaagagcg acgaggttcg gttgttttcg    2880
acactcatcg acggacactc cgaggtggac gagaagacgg gccgccgcaa gcccaagttc    2940
cgcatcgagc tgcccggtaa ccccatcctc ggtgacggga agtcggataa ccagaaccac    3000
gccatcgtct tctaccgcgg cgagtacatt caggtcattg acgctaacca ggacaattac    3060
ctggaagagt gtctcaagat ccgtaatgtc ctgggcgagt ttgaggaata ctccgtgtcg    3120
agccagagcc cgtacgcgca gtggggccac aaggagttca caagtgccc cgtcgctatc    3180 ctgggttccc gcgagtacat cttctcggag aacatcggta tcctcggtga catcgctgcc    3240
ggcaaggaac agacgttcgg taccattacg gcgcgtgcgc ttgcgtggat cggcggcaag    3300
ctgcattacg gtcaccccga tttcctcaat gcgacgttca tgacgacgcg tggtggcgtg    3360
tcaaaagcgc agaagggctt gcatcttaac gaggatatct tcgctggtat gaccgccgtg    3420
tcccgcggag ggcgcatcaa gcacatggag tactaccagt gcggcaaagg tcgtgatctc    3480
ggattcggca cgatcttgaa cttccagacc aagatcggta ctggtatggg cgagcagctg    3540
ctctcgcgcg agtactacta tctgggcacg caattgccta tcgaccggtt cttgacgttc    3600
tactacgcgc acgctggttt ccatgtcaac aacatcctgg tcatctactc catccaggtc    3660
ttcatggtca ccctgctgta cctgggcaca ttgaacaagc agctgttcat ctgcaaggtc    3720
aactccaatg ccaggttcct tagtggacaa gctgggtgct acaacctcat cccggtcttc    3780
gagtggattc gccggagtat catctccatc ttcttggtgt tcttcatcgc cttcttgccg    3840
ttgttcttgc aagagctttg cgaacgcgga acaggaaagg cgttgctgcg tctcgggaag    3900
cacttcctgt cactgtcgcc catcttcgaa gtgttctcca cccaaatcta ctcgcaggcg    3960
ctcttgaaca acatgagttt cggtggtgcg cgctacatcg ctacaggacg cggtttcgcg    4020
acgagtcgga taccttcaa catcctctac tcgcgtttcg cgccgccgag catctacatg    4080
ggcatgcgta atctgctgct cttgctgtac gcgacgatgg ccatttggat cccacacctg    4140
atctacttct ggttctccgt cctctccctc tgcatcgcgc cattcatgtt caatccgcat    4200
caattctcgt acgctgactt catcatcgac taccgggagt tcttgcgctg gatgtcgcgc    4260
ggtaactcgc ggacgaaggc gagtagctgg tacggatatt gccgtctgtc gcgtaccgcg    4320
attactgggt acaagaagaa gaaactggga cacccgtcgg agaagctgtc gggcgatgtg    4380
ccgcgtgcgc cgtggaggaa cgtcatcttc tcggagatcc tttggcccat cggcgcgtgc    4440
atcatcttca tcgtcgcgta catgttcgtc aaatcgttcc ctgacgagca gggcaacgcg    4500
```

-continued

```
ccgccgagcc cgctggtccg cattctgctc atcgcggttg gccctactgt gtggaacgcg    4560
gcggtgctca tcacgctgtt cttcctgtcg ctcttcctgg cccgatgat  ggatggctgg    4620 gtcaagttcg gctcagtcat ggcggcactt gcgcatggtc tagcgctcat aggcatgctc    4680
acgttcttcg agttcttctg gttcctcgag ctctgggatg cctcgcacgc cgtgctcggc    4740
gtcatcgcca ttattgccgt tcagcgcggg atccagaaga tcctcattgc cgtcttcctg    4800
acgcgtgagt acaagcacga cgagacgaac cgcgcgtggt ggacaggtaa atggtatgga    4860
cgcgggctgg gtacctcggc catgtcccag ccggcgcgcg agttcatcgt gaagatcgtg    4920
gagatgtcgc tgtggacgtc ggacttcctg cttgcgcacc tgttgctcat catcttgacg    4980
gtgccgctac tgctgccgtt cttcaactcg atccattcga cgatgctttt ctggttgcgc    5040
ccttcgaagc agattaggca acctctgttc tccactaagc agaagcggca acggcgatgg    5100
attgtcatga agtataccgt ggtatatctc gtggtggtgg cttt cctcgt tgcgctcatc    5160 gctctgcccg cgctcttccg cgagagcatc cacttcaact gcgagatctg ccagagtata    5220
tag                                                                  5223
```

<210> SEQ ID NO 6
<211> LENGTH: 1740
<212> TYPE: PRT
<213> ORGANISM: Schizophyllum commune

<400> SEQUENCE: 6

```
Met Ser Gly Pro Gly Tyr Gly Arg Asn Pro Phe Asp Asn Pro Pro Pro
 1               5                  10                  15

Asn Arg Gly Pro Tyr Gly Gln Gln Pro Gly Phe Pro Gly Pro Gly Pro
             20                  25                  30

Arg Pro Tyr Asp Ser Asp Ala Asp Met Ser Gln Thr Tyr Gly Ser Thr
         35                  40                  45

Thr Arg Leu Ala Gly Ser Ala Gly Tyr Ser Arg Asn Gly Ser Phe
     50                  55                  60

Asp Gly Asp Arg Ser Tyr Ala Pro Ser Ile Asp Ser Arg Ala Ser Val
 65                  70                  75                  80

Pro Ser Ile Ser Pro Phe Ala Asp Pro Gly Ile Gly Ser Asn Glu Pro
                 85                  90                  95

Tyr Pro Ala Trp Ser Val Glu Arg Gln Ile Pro Met Ser Thr Glu Glu
            100                 105                 110

Ile Glu Asp Ile Phe Leu Asp Leu Thr Gln Lys Phe Gly Phe Gln Arg
        115                 120                 125

Asp Ser Met Arg Asn Thr Phe Asp Phe Met Met His Leu Leu Asp Ser
    130                 135                 140

Arg Ala Ser Arg Met Thr Pro Asn Gln Ala Leu Leu Thr Leu His Ala
145                 150                 155                 160

Asp Tyr Ile Gly Gly Gln His Ala Asn Tyr Arg Lys Trp Tyr Phe Ala
                165                 170                 175

Ala Gln Leu Asn Leu Asp Asp Ala Val Gly Gln Thr Asn Asn Pro Gly
            180                 185                 190

Ile Gln Arg Leu Lys Thr Ile Lys Gly Ala Thr Lys Thr Lys Ser Leu
        195                 200                 205

Asp Ser Ala Leu Asn Arg Trp Arg Asn Ala Met Asn Asn Met Ser Gln
    210                 215                 220

Tyr Asp Arg Leu Arg Gln Ile Ala Leu Tyr Leu Leu Cys Trp Gly Glu
225                 230                 235                 240
```

```
Ala Gly Asn Ile Arg Leu Ala Pro Glu Cys Leu Cys Phe Ile Phe Lys
            245                 250                 255
Cys Ala Asp Asp Tyr Tyr Arg Ser Pro Glu Cys Gln Asn Arg Met Asp
        260                 265                 270
Pro Val Pro Glu Gly Leu Tyr Leu Gln Thr Val Ile Lys Pro Leu Tyr
    275                 280                 285
Arg Phe Leu Arg Asp Gln Ala Tyr Glu Val Val Asp Gly Lys Gln Val
290                 295                 300
Lys Arg Glu Lys Asp His Asp Gln Ile Ile Gly Tyr Asp Asp Val Asn
305                 310                 315                 320
Gln Leu Phe Trp Tyr Pro Glu Gly Leu Ala Lys Ile Val Met Ser Asp
                325                 330                 335
Asn Thr Arg Leu Val Asp Val Pro Pro Ala Gln Arg Phe Met Lys Phe
            340                 345                 350
Ala Lys Ile Glu Trp Asn Arg Val Phe Phe Lys Thr Tyr Phe Glu Lys
        355                 360                 365
Arg Ser Thr Ala His Leu Leu Val Asn Phe Asn Arg Ile Trp Ile Leu
    370                 375                 380
His Val Ser Met Tyr Phe Phe Tyr Thr Ala Phe Asn Ser Pro Arg Val
385                 390                 395                 400
Tyr Ala Pro His Gly Lys Leu Asp Pro Ser Pro Glu Met Thr Trp Ser
                405                 410                 415
Ala Thr Ala Leu Gly Gly Ala Val Ser Thr Met Ile Met Ile Leu Ala
            420                 425                 430
Thr Ile Ala Glu Tyr Thr Tyr Ile Pro Thr Thr Trp Asn Asn Ala Ser
        435                 440                 445
His Leu Thr Thr Arg Leu Ile Phe Leu Leu Val Ile Leu Ala Leu Thr
    450                 455                 460
Ala Gly Pro Thr Phe Tyr Ile Ala Met Ile Asp Gly Arg Thr Asp Ile
465                 470                 475                 480
Gly Gln Val Pro Leu Ile Val Ala Ile Val Gln Phe Phe Ile Ser Val
                485                 490                 495
Val Ala Thr Leu Ala Phe Ala Thr Ile Pro Ser Gly Arg Met Phe Gly
            500                 505                 510
Asp Arg Val Ala Gly Lys Ser Arg Lys His Met Ala Ser Gln Thr Phe
        515                 520                 525
Thr Ala Ser Tyr Pro Ser Met Lys Arg Ser Ser Arg Val Ala Ser Ile
    530                 535                 540
Met Leu Trp Leu Leu Val Phe Gly Cys Lys Tyr Val Glu Ser Tyr Phe
545                 550                 555                 560
Phe Leu Thr Ser Ser Phe Ser Ser Pro Ile Ala Val Met Ala Arg Thr
                565                 570                 575
Lys Val Gln Gly Cys Asn Asp Arg Ile Phe Gly Ser Gln Leu Cys Thr
            580                 585                 590
Asn Gln Val Pro Phe Ala Leu Ala Ile Met Tyr Val Met Asp Leu Val
        595                 600                 605
Leu Phe Phe Leu Asp Thr Tyr Leu Trp Tyr Ile Ile Trp Leu Val Ile
    610                 615                 620
Phe Ser Met Val Arg Ala Phe Lys Leu Gly Ile Ser Ile Trp Thr Pro
625                 630                 635                 640
Trp Ser Glu Ile Phe Thr Arg Met Pro Lys Arg Ile Tyr Ala Lys Leu
                645                 650                 655
Leu Ala Thr Ala Glu Met Glu Val Lys Tyr Lys Pro Lys Val Leu Val
```

-continued

```
                660                 665                 670
Ser Gln Ile Trp Asn Ala Val Ile Ser Met Tyr Arg Glu His Leu
            675                 680                 685

Leu Ser Ile Glu His Val Gln Arg Leu Leu Tyr His Gln Val Asp Gly
            690                 695                 700

Pro Asp Gly Arg Arg Thr Leu Arg Ala Pro Pro Phe Phe Thr Ser Gln
705                 710                 715                 720

Arg Thr Ala Lys Pro Gly Leu Phe Phe Pro Pro Gly Gly Glu Ala Glu
                725                 730                 735

Arg Arg Ile Ser Phe Phe Ala Ser Ser Leu Thr Thr Ala Leu Pro Glu
            740                 745                 750

Pro Leu Pro Ile Asp Ala Met Pro Thr Phe Thr Val Leu Val Pro His
            755                 760                 765

Tyr Ser Glu Lys Ile Leu Leu Ser Leu Arg Glu Ile Ile Arg Glu Glu
            770                 775                 780

Asp Gln Asn Thr Arg Val Thr Leu Leu Glu Tyr Leu Lys Gln Leu His
785                 790                 795                 800

Pro Val Glu Trp Asp Asn Phe Val Lys Asp Thr Lys Ile Leu Ala Glu
                805                 810                 815

Glu Ser Gly Asp Val Gln Asp Glu Lys Arg Ala Arg Thr Asp Leu
            820                 825                 830

Pro Phe Tyr Cys Ile Gly Phe Lys Thr Ser Ser Pro Gly Tyr Thr Leu
            835                 840                 845

Arg Thr Arg Ile Trp Ala Ser Leu Arg Ala Gln Thr Leu Tyr Arg Thr
850                 855                 860

Val Ser Gly Met Met Asn Tyr Ser Lys Ala Ile Lys Leu Leu Tyr Arg
865                 870                 875                 880

Val Glu Asn Pro Asp Val Val His Ala Phe Gly Gly Asn Thr Glu Arg
                885                 890                 895

Leu Glu Arg Glu Leu Glu Arg Met Ser Arg Arg Lys Phe Lys Phe Val
            900                 905                 910

Ile Ser Met Gln Arg Tyr Ser Lys Phe Asn Lys Glu Glu Gln Glu Asn
            915                 920                 925

Ala Glu Phe Leu Leu Arg Ala Tyr Pro Asp Leu Gln Ile Ala Tyr Leu
            930                 935                 940

Asp Glu Glu Pro Gly Pro Ser Lys Ser Asp Glu Val Arg Leu Phe Ser
945                 950                 955                 960

Thr Leu Ile Asp Gly His Ser Glu Val Asp Glu Lys Thr Gly Arg Arg
                965                 970                 975

Lys Pro Lys Phe Arg Ile Glu Leu Pro Gly Asn Pro Ile Leu Gly Asp
            980                 985                 990

Gly Lys Ser Asp Asn Gln Asn His Ala Ile Val Phe Tyr Arg Gly Glu
            995                1000                1005

Tyr Ile Gln Val Ile Asp Ala Asn Gln Asp Asn Tyr Leu Glu Glu
            1010                1015                1020

Cys Leu Lys Ile Arg Asn Val Leu Gly Glu Phe Glu Glu Tyr Ser
            1025                1030                1035

Val Ser Ser Gln Ser Pro Tyr Ala Gln Trp Gly His Lys Glu Phe
            1040                1045                1050

Asn Lys Cys Pro Val Ala Ile Leu Gly Ser Arg Glu Tyr Ile Phe
            1055                1060                1065

Ser Glu Asn Ile Gly Ile Leu Gly Asp Ile Ala Ala Gly Lys Glu
            1070                1075                1080
```

```
Gln Thr Phe Gly Thr Ile Thr Ala Arg Ala Leu Ala Trp Ile Gly
1085                1090                1095

Gly Lys Leu His Tyr Gly His Pro Asp Phe Leu Asn Ala Thr Phe
    1100                1105                1110

Met Thr Thr Arg Gly Gly Val Ser Lys Ala Gln Lys Gly Leu His
1115                1120                1125

Leu Asn Glu Asp Ile Phe Ala Gly Met Thr Ala Val Ser Arg Gly
    1130                1135                1140

Gly Arg Ile Lys His Met Glu Tyr Tyr Gln Cys Gly Lys Gly Arg
1145                1150                1155

Asp Leu Gly Phe Gly Thr Ile Leu Asn Phe Gln Thr Lys Ile Gly
    1160                1165                1170

Thr Gly Met Gly Glu Gln Leu Leu Ser Arg Glu Tyr Tyr Tyr Leu
1175                1180                1185

Gly Thr Gln Leu Pro Ile Asp Arg Phe Leu Thr Phe Tyr Tyr Ala
    1190                1195                1200

His Ala Gly Phe His Val Asn Asn Ile Leu Val Ile Tyr Ser Ile
1205                1210                1215

Gln Val Phe Met Val Thr Leu Leu Tyr Leu Gly Thr Leu Asn Lys
    1220                1225                1230

Gln Leu Phe Ile Cys Lys Val Asn Ser Asn Gly Gln Val Leu Ser
1235                1240                1245

Gly Gln Ala Gly Cys Tyr Asn Leu Ile Pro Val Phe Glu Trp Ile
    1250                1255                1260

Arg Arg Ser Ile Ile Ser Ile Phe Leu Val Phe Phe Ile Ala Phe
1265                1270                1275

Leu Pro Leu Phe Leu Gln Glu Leu Cys Glu Arg Gly Thr Gly Lys
    1280                1285                1290

Ala Leu Leu Arg Leu Gly Lys His Phe Leu Ser Leu Ser Pro Ile
1295                1300                1305

Phe Glu Val Phe Ser Thr Gln Ile Tyr Ser Gln Ala Leu Leu Asn
    1310                1315                1320

Asn Met Ser Phe Gly Gly Ala Arg Tyr Ile Ala Thr Gly Arg Gly
1325                1330                1335

Phe Ala Thr Ser Arg Ile Pro Phe Asn Ile Leu Tyr Ser Arg Phe
    1340                1345                1350

Ala Pro Pro Ser Ile Tyr Met Gly Met Arg Asn Leu Leu Leu Leu
1355                1360                1365

Leu Tyr Ala Thr Met Ala Ile Trp Ile Pro His Leu Ile Tyr Phe
    1370                1375                1380

Trp Phe Ser Val Leu Ser Leu Cys Ile Ala Pro Phe Met Phe Asn
1385                1390                1395

Pro His Gln Phe Ser Tyr Ala Asp Phe Ile Ile Asp Tyr Arg Glu
    1400                1405                1410

Phe Leu Arg Trp Met Ser Arg Gly Asn Ser Arg Thr Lys Ala Ser
1415                1420                1425

Ser Trp Tyr Gly Tyr Cys Arg Leu Ser Arg Thr Ala Ile Thr Gly
    1430                1435                1440

Tyr Lys Lys Lys Lys Leu Gly His Pro Ser Glu Lys Leu Ser Gly
1445                1450                1455

Asp Val Pro Arg Ala Pro Trp Arg Asn Val Ile Phe Ser Glu Ile
    1460                1465                1470
```

| | | | | | | | | | | |
|---|---|---|---|---|---|---|---|---|---|---|
| Leu | Trp | Pro | Ile | Gly | Ala | Cys | Ile | Ile | Phe | Ile | Val | Ala | Tyr | Met |
| | 1475 | | | | 1480 | | | | | 1485 | | | | |

Phe Val Lys Ser Phe Pro Asp Glu Gln Gly Asn Ala Pro Pro Ser
    1490                1495                1500

Pro Leu Val Arg Ile Leu Leu Ile Ala Val Gly Pro Thr Val Trp
    1505                1510                1515

Asn Ala Ala Val Leu Ile Thr Leu Phe Phe Leu Ser Leu Phe Leu
    1520                1525                1530

Gly Pro Met Met Asp Gly Trp Val Lys Phe Gly Ser Val Met Ala
    1535                1540                1545

Ala Leu Ala His Gly Leu Ala Leu Ile Gly Met Leu Thr Phe Phe
    1550                1555                1560

Glu Phe Phe Trp Phe Leu Glu Leu Trp Asp Ala Ser His Ala Val
    1565                1570                1575

Leu Gly Val Ile Ala Ile Ile Ala Val Gln Arg Gly Ile Gln Lys
    1580                1585                1590

Ile Leu Ile Ala Val Phe Leu Thr Arg Glu Tyr Lys His Asp Glu
    1595                1600                1605

Thr Asn Arg Ala Trp Trp Thr Gly Lys Trp Tyr Gly Arg Gly Leu
    1610                1615                1620

Gly Thr Ser Ala Met Ser Gln Pro Ala Arg Glu Phe Ile Val Lys
    1625                1630                1635

Ile Val Glu Met Ser Leu Trp Thr Ser Asp Phe Leu Leu Ala His
    1640                1645                1650

Leu Leu Leu Ile Ile Leu Thr Val Pro Leu Leu Leu Pro Phe Phe
    1655                1660                1665

Asn Ser Ile His Ser Thr Met Leu Phe Trp Leu Arg Pro Ser Lys
    1670                1675                1680

Gln Ile Arg Gln Pro Leu Phe Ser Thr Lys Gln Lys Arg Gln Arg
    1685                1690                1695

Arg Trp Ile Val Met Lys Tyr Thr Val Val Tyr Leu Val Val Val
    1700                1705                1710

Ala Phe Leu Val Ala Leu Ile Ala Leu Pro Ala Leu Phe Arg Glu
    1715                1720                1725

Ser Ile His Phe Asn Cys Glu Ile Cys Gln Ser Ile
    1730                1735                1740

<210> SEQ ID NO 7
<211> LENGTH: 4869
<212> TYPE: DNA
<213> ORGANISM: Schizophyllum commune

<400> SEQUENCE: 7

```
atgcggaaca tgttcgactt caccatgcag ctgcttgaca gccgagcgtc tcgtatgacc    60
cccaaccagg cgctcctcac cctccacgcc gactacattg gtggccagca tgcgaactac   120
cggaagtggt acttcgcggc gcagctcgac cttgacgacg ccgtgggaca aactcagaat   180
ccgggtctca accgcctcaa gtccactcgc ggatcgggca agcgaccacg ccatgaaaag   240
tcgctgaaca cggcattgga gcgctggcgg caagccatga caacatgtc gcagtatgac   300
cgcttacgcc agatcgcgct ctacctgctc tgctggggcg aagcggcgca agtgcgattc   360
atgcccgagt gcttgtgctt catcttcaag tgcgccgacg actattatcg ttcgccggag   420
tgccagaaca ggatggagcc ggtaccggag ggtctctacc tgaggacggt cgtaaagccg   480
ctctacagat ttgtccggga tcaaggctat gaggtggtgg agggaaaatt cgtacggcgg   540
```

```
gaacgggatc acgaccaaat cattggttac gatgacgtga atcagctgtt ctggtacccg      600
gagggcattg cccgtatcgt cctgtcggac aagagtcgtc tggtcgacct ccctccagca      660
cagcgcttca tgaagttcga ccgtatcgag tggaatcgcg tcttcttcaa gacgttctac      720
gagactcgat cctttacgca tcttttggtc gacttcaacc gtatctgggt cgtgcacatc      780
gctctctact tcttctacac cgcatacaac tcccccacga tctacgccat caacggcaac      840
actccgacgt ctctggcttg gagcgcgact gcgctcggcg gtgcggtagc gacaggtatc      900
atgatcctcg ccacgatcgc cgagttctcg cacatcccca cgacatggaa caacacctcg      960
catctgactc gccgcctcgc cttcctcctc gtcacgctcg gcctcacatg tggtccgacg     1020
ttctacgtcg cgattgcaga gagcaacggg agcggcggct ctttggcctt gattctcggc     1080
atcgtccagt tcttcatctc cgtcgtagcg actgcgctct tcactatcat gccttctggt     1140
cgtatgttcg gcgaccgcgt cgcaggcaag agtcgcaagt atctcgccag ccagacgttc     1200
acggccagct acccgtcgtt gcccaagcac cagcggttcg catcactcct gatgtggttc     1260
ctcatcttcg ggtgcaagtt gacggagagt tacttcttcc tgacgttgtc cttccgcgac     1320
cctattcgcg tcatggtcgg catgaagatc cagaactgcg aggacaagat tttcggcagc     1380
ggcctttgca ggaatcacgc agcattcacc ctcacgatca tgtacatcat ggacctcgtc     1440
ttgttcttcc tcgacacctt cctttggtat gtcatctgga actcggtttt cagtatcgca     1500
cgctctttcg tactcggcct ttcgatctgg acaccatgga gggacatctt ccagcgtctg     1560
ccgaagcgta tctacgcgaa gcttctagcg accggcgaca tggaggtcaa gtacaagccc     1620
aaggtcttgg tttcgcaaat ctggaacgcc atcatcatct ccatgtaccg cgagcacttg     1680
ctctctatcg agcacgttca aaagctcctg taccatcaag tggacactgg cgaagcggc     1740 aagcggagtc ttcgcgcgcc tccgttcttc gtcgcgcagg gcagcagcgg tggctcgggc     1800
gagttcttcc cgcctggtag cgaggctgag cgtcgtatct cttttcttcgc gcagtctcta     1860 tctacggaga ttcctcagcc catcccggtt gacgccatgc cgacgttcac agtgcttacg     1920
cctcactaca gcgagaagat ccttctttcg ctccgtgaga ttatccgcga ggaggaccag     1980
aacacccgcg tgacattgct tgagtatctc aagcagcttc acccggtcga gtgggagaac     2040
ttcgtcaagg acaccaagat tttggccgag gagtccgcta tgttcaacgg tccaagtcct     2100
ttcggcaacg atgagaaggg tcagtccaag atggacgatc ttcctttcta ctgcatcggt     2160
ttcaagagcg ccgcgcccga gtacaccctc cgcacccgta tctgggcgtc cttgcgcgcg     2220
cagaccctct accgcacggt ctccggcatg atgaactatg cgaaggcgat taagctgctc     2280
taccgcgtcg agaaccccga ggtcgtgcag cagttcggcg gtaacacgga caagctcgag     2340
cgcgagttgg agcggatggc ccggcggaag ttcaagttcc tggtgtccat gcagcgctac     2400
tcgaagttca acaaggagga gcacgagaac gccgagttct gctccgcgc gtacccggac     2460 ctgcagatcg cgtacctgga ggaagagcct cctcgcaagg agggtggcga tccacgcatc     2520
ttctctgccc tcgtcgacgg ccacagcgac atcatcccgg agaccggcaa gcggcgcccc     2580
aagttccgca tcgagctgcc cggcaacccc attctcggtg acggcaagtc ggacaaccag     2640
aaccacgcca tcgtcttcta ccgcggcgag tacctccagc ttatcgacgc caaccaggac     2700
aactacctcg aggagtgctt gaagatccgt aacgtactcg ccgagttcga ggagtacgac     2760
gtctctagcc agagtccgta cgcgcagtgg agtgtcaagg agttcaagcg ctccccggtc     2820
gccatcgtcg gtgcacgcga gtatatcttc tcggagcaca tcggtattct cggtgatttg     2880
```

-continued

| | |
|---|---|
| gcggctggca aggaacagac gttcggtacg ctcacggcac gcaacaacgc cttccttggc | 2940 |
| ggcaagctgc actacggtca cccggatttc ctcaacgccc tctacatgaa cacgcgcggt | 3000 |
| ggtgtctcca aggcgcagaa gggtctccat ctcaacgagg atatttacgc cggtatgaac | 3060 |
| gcggtcggtc gcggtggacg catcaagcat agcgaatact accagtgcgg caagggtcgt | 3120 |
| gacctcggtt ttggcaccat cttgaacttc cagaccaaga tcggtacggg tatgggcgag | 3180 |
| cagatcctct cgcgcgagta ctactacctc ggaacccaat tgcccatcga tcgcttcctc | 3240 |
| acgttctact acgcgcaccc aggtttccag atcaacaaca tgctggttat cctatccgtg | 3300 |
| caggtcttca tcgttaccat ggtcttcctc ggtaccttga agtcttcggt cacgatctgc | 3360 |
| aagtacacgt ccagcggtca gtacatcggt ggtcaatccg gttgctacaa cctcgtcccg | 3420 |
| gtcttccagt ggatcgagcg ctgcatcatc agcatcttct tggtgttcat gatcgctttc | 3480 |
| atgccgctct tcctgcaaga actcgtcgag cgcggtacct ggagtgccat ctggcgtctg | 3540 |
| ctcaagcagt ttatgtcgct gtcgcctgtc ttcgaggtgt tctccaccca gattcagaca | 3600 |
| cactccgtgt tgagcaactt gacgttcggt ggtgcgcgtt acatcgctac cggtcgtggg | 3660 |
| ttcgccacca gtcgtatcag cttcagcatc ttgttctcgc gtttcgcagg cccgagtatc | 3720 |
| tacctcggca tgcgcacgct cattatgctg ctctacgtga cgttgacgat ctggacgcca | 3780 |
| tgggtcattt acttctgggt tccattctc tcgctctgca tcgcgccgtt cttgttcaat | 3840 |
| ccgcatcaat tcgtcttctc ggatttcctc atcgactaca gggaataccrt ccggtggatg | 3900 |
| tcgcgtggta actcgcgctc gcacaacaac tcctggattg ggtactgccg gttgtcccgc | 3960 |
| acgatgatca ctgggtacaa gaagaagaag ctgggccacc gtcggagaa gctttccggc | 4020 |
| gacgttcctc gtgcaggctg gcgcgccgtc ttattctcgg agatcatctt cccggcatgc | 4080 |
| atggccatcc tcttcatcat cgcgtacatg ttcgtcaagt cgttccctct cgacggcaag | 4140 |
| cagcctccct ccggcctcgt tcgcatcgcc gtcgtgtcta tcggccccat cgtgtggaac | 4200 |
| gccgccatcc tgttgacgct cttccttgtg tcgttgttcc tcggcccccat gctcgacccg | 4260 |
| gtcttccccc tcttcggttc cgttatggcc ttcatcgcgc atttcctcgg cacaatcgga | 4320 |
| atgattgggt tcttcgagtt cctgtggttc ctcgagtcct gggaggcgtc gcatgccgtg | 4380 |
| ctgggtctca tcgccgtcat ctccatccag cgcgccattc acaaaattct tatcgccgtt | 4440 |
| ttcctcagtc gcgagttcaa gcacgacgag acgaacaggg cttggtggac tggtcgctgg | 4500 |
| tatggccgtg gcctcggcac gcacgccatg tcgcagccgg cgcgtgagtt cgtcgtcaag | 4560 |
| atcatcgagt tgtcgctctg gagctcggat tcatactcg gccacatcct gctgttcatg | 4620 |
| cttactccgg ctgtcctcat cccgtacttc gaccgtctgc acgccatgat gctcttctgg | 4680 |
| ctgcgcccct caaagcaaat ccgcgcgcct ctgtactcaa tcaagcagaa gaggcaaaga | 4740 |
| cgctggatta tcatgaagta cggtactgta tacgttaccg tcatcgcgat cttcgtcgcg | 4800 |
| ctcatcgcgc ttcccctcgt cttccgacac actctaaagg tcgagtgctc cctttgcgac | 4860 |
| agcttgtaa | 4869 |

<210> SEQ ID NO 8
<211> LENGTH: 1622
<212> TYPE: PRT
<213> ORGANISM: Schizophyllum commune

<400> SEQUENCE: 8

Met Arg Asn Met Phe Asp Phe Thr Met Gln Leu Leu Asp Ser Arg Ala
1               5                   10                  15

```
Ser Arg Met Thr Pro Asn Gln Ala Leu Leu Thr Leu His Ala Asp Tyr
            20                  25                  30

Ile Gly Gly Gln His Ala Asn Tyr Arg Lys Trp Tyr Phe Ala Ala Gln
        35                  40                  45

Leu Asp Leu Asp Asp Ala Val Gly Gln Thr Gln Asn Pro Gly Leu Asn
    50                  55                  60

Arg Leu Lys Ser Thr Arg Gly Ser Gly Lys Arg Pro Arg His Glu Lys
65                  70                  75                  80

Ser Leu Asn Thr Ala Leu Glu Arg Trp Arg Gln Ala Met Asn Asn Met
                85                  90                  95

Ser Gln Tyr Asp Arg Leu Arg Gln Ile Ala Leu Tyr Leu Leu Cys Trp
            100                 105                 110

Gly Glu Ala Ala Gln Val Arg Phe Met Pro Glu Cys Leu Cys Phe Ile
        115                 120                 125

Phe Lys Cys Ala Asp Asp Tyr Tyr Arg Ser Pro Glu Cys Gln Asn Arg
    130                 135                 140

Met Glu Pro Val Pro Glu Gly Leu Tyr Leu Arg Thr Val Val Lys Pro
145                 150                 155                 160

Leu Tyr Arg Phe Val Arg Asp Gln Gly Tyr Glu Val Val Glu Gly Lys
                165                 170                 175

Phe Val Arg Arg Glu Arg Asp His Asp Gln Ile Ile Gly Tyr Asp Asp
            180                 185                 190

Val Asn Gln Leu Phe Trp Tyr Pro Glu Gly Ile Ala Arg Ile Val Leu
        195                 200                 205

Ser Asp Lys Ser Arg Leu Val Asp Leu Pro Pro Ala Gln Arg Phe Met
    210                 215                 220

Lys Phe Asp Arg Ile Glu Trp Asn Arg Val Phe Phe Lys Thr Phe Tyr
225                 230                 235                 240

Glu Thr Arg Ser Phe Thr His Leu Leu Val Asp Phe Asn Arg Ile Trp
                245                 250                 255

Val Val His Ile Ala Leu Tyr Phe Phe Tyr Thr Ala Tyr Asn Ser Pro
            260                 265                 270

Thr Ile Tyr Ala Ile Asn Gly Asn Thr Pro Thr Ser Leu Ala Trp Ser
        275                 280                 285

Ala Thr Ala Leu Gly Gly Ala Val Ala Thr Gly Ile Met Ile Leu Ala
    290                 295                 300

Thr Ile Ala Glu Phe Ser His Ile Pro Thr Thr Trp Asn Asn Thr Ser
305                 310                 315                 320

His Leu Thr Arg Arg Leu Ala Phe Leu Leu Val Thr Leu Gly Leu Thr
                325                 330                 335

Cys Gly Pro Thr Phe Tyr Val Ala Ile Ala Glu Ser Asn Gly Ser Gly
            340                 345                 350

Gly Ser Leu Ala Leu Ile Leu Gly Ile Val Gln Phe Phe Ile Ser Val
        355                 360                 365

Val Ala Thr Ala Leu Phe Thr Ile Met Pro Ser Gly Arg Met Phe Gly
    370                 375                 380

Asp Arg Val Ala Gly Lys Ser Arg Lys Tyr Leu Ala Ser Gln Thr Phe
385                 390                 395                 400

Thr Ala Ser Tyr Pro Ser Leu Pro Lys His Gln Arg Phe Ala Ser Leu
                405                 410                 415

Leu Met Trp Phe Leu Ile Phe Gly Cys Lys Leu Thr Glu Ser Tyr Phe
            420                 425                 430

Phe Leu Thr Leu Ser Phe Arg Asp Pro Ile Arg Val Met Val Gly Met
```

```
                435                 440                 445
Lys Ile Gln Asn Cys Glu Asp Lys Ile Phe Gly Ser Gly Leu Cys Arg
450                 455                 460
Asn His Ala Ala Phe Thr Leu Thr Ile Met Tyr Ile Met Asp Leu Val
465                 470                 475                 480
Leu Phe Phe Leu Asp Thr Phe Leu Trp Tyr Val Ile Trp Asn Ser Val
                485                 490                 495
Phe Ser Ile Ala Arg Ser Phe Val Leu Gly Leu Ser Ile Trp Thr Pro
                500                 505                 510
Trp Arg Asp Ile Phe Gln Arg Leu Pro Lys Arg Ile Tyr Ala Lys Leu
            515                 520                 525
Leu Ala Thr Gly Asp Met Glu Val Lys Tyr Lys Pro Lys Val Leu Val
530                 535                 540
Ser Gln Ile Trp Asn Ala Ile Ile Ile Ser Met Tyr Arg Glu His Leu
545                 550                 555                 560
Leu Ser Ile Glu His Val Gln Lys Leu Leu Tyr His Gln Val Asp Thr
                565                 570                 575
Gly Glu Ala Gly Lys Arg Ser Leu Arg Ala Pro Pro Phe Phe Val Ala
                580                 585                 590
Gln Gly Ser Ser Gly Ser Gly Glu Phe Phe Pro Pro Gly Ser Glu
                595                 600                 605
Ala Glu Arg Arg Ile Ser Phe Phe Ala Gln Ser Leu Ser Thr Glu Ile
610                 615                 620
Pro Gln Pro Ile Pro Val Asp Ala Met Pro Thr Phe Thr Val Leu Thr
625                 630                 635                 640
Pro His Tyr Ser Glu Lys Ile Leu Leu Ser Leu Arg Glu Ile Ile Arg
                645                 650                 655
Glu Glu Asp Gln Asn Thr Arg Val Thr Leu Leu Glu Tyr Leu Lys Gln
                660                 665                 670
Leu His Pro Val Glu Trp Glu Asn Phe Val Lys Asp Thr Lys Ile Leu
            675                 680                 685
Ala Glu Glu Ser Ala Met Phe Asn Gly Pro Ser Pro Phe Gly Asn Asp
            690                 695                 700
Glu Lys Gly Gln Ser Lys Met Asp Asp Leu Pro Phe Tyr Cys Ile Gly
705                 710                 715                 720
Phe Lys Ser Ala Ala Pro Glu Tyr Thr Leu Arg Thr Arg Ile Trp Ala
                725                 730                 735
Ser Leu Arg Ala Gln Thr Leu Tyr Arg Thr Val Ser Gly Met Met Asn
                740                 745                 750
Tyr Ala Lys Ala Ile Lys Leu Leu Tyr Arg Val Glu Asn Pro Glu Val
            755                 760                 765
Val Gln Gln Phe Gly Gly Asn Thr Asp Lys Leu Glu Arg Glu Leu Glu
            770                 775                 780
Arg Met Ala Arg Arg Lys Phe Lys Phe Leu Val Ser Met Gln Arg Tyr
785                 790                 795                 800
Ser Lys Phe Asn Lys Glu Glu His Glu Asn Ala Glu Phe Leu Leu Arg
                805                 810                 815
Ala Tyr Pro Asp Leu Gln Ile Ala Tyr Leu Glu Glu Pro Pro Arg
                820                 825                 830
Lys Glu Gly Gly Asp Pro Arg Ile Phe Ser Ala Leu Val Asp Gly His
            835                 840                 845
Ser Asp Ile Ile Pro Glu Thr Gly Lys Arg Arg Pro Lys Phe Arg Ile
850                 855                 860
```

```
Glu Leu Pro Gly Asn Pro Ile Leu Gly Asp Gly Lys Ser Asp Asn Gln
865                 870                 875                 880

Asn His Ala Ile Val Phe Tyr Arg Gly Glu Tyr Leu Gln Leu Ile Asp
                885                 890                 895

Ala Asn Gln Asp Asn Tyr Leu Glu Cys Leu Lys Ile Arg Asn Val
            900                 905                 910

Leu Ala Glu Phe Glu Glu Tyr Asp Val Ser Ser Gln Ser Pro Tyr Ala
            915                 920                 925

Gln Trp Ser Val Lys Glu Phe Lys Arg Ser Pro Val Ala Ile Val Gly
            930                 935                 940

Ala Arg Glu Tyr Ile Phe Ser Glu His Ile Gly Ile Leu Gly Asp Leu
945                 950                 955                 960

Ala Ala Gly Lys Glu Gln Thr Phe Gly Thr Leu Thr Ala Arg Asn Asn
                965                 970                 975

Ala Phe Leu Gly Gly Lys Leu His Tyr Gly His Pro Asp Phe Leu Asn
            980                 985                 990

Ala Leu Tyr Met Asn Thr Arg Gly Gly Val Ser Lys Ala Gln Lys Gly
            995                 1000                1005

Leu His Leu Asn Glu Asp Ile Tyr Ala Gly Met Asn Ala Val Gly
    1010                1015                1020

Arg Gly Gly Arg Ile Lys His Ser Glu Tyr Tyr Gln Cys Gly Lys
    1025                1030                1035

Gly Arg Asp Leu Gly Phe Gly Thr Ile Leu Asn Phe Gln Thr Lys
    1040                1045                1050

Ile Gly Thr Gly Met Gly Glu Gln Ile Leu Ser Arg Glu Tyr Tyr
    1055                1060                1065

Tyr Leu Gly Thr Gln Leu Pro Ile Asp Arg Phe Leu Thr Phe Tyr
    1070                1075                1080

Tyr Ala His Pro Gly Phe Gln Ile Asn Asn Met Leu Val Ile Leu
    1085                1090                1095

Ser Val Gln Val Phe Ile Val Thr Met Val Phe Leu Gly Thr Leu
    1100                1105                1110

Lys Ser Ser Val Thr Ile Cys Lys Tyr Thr Ser Ser Gly Gln Tyr
    1115                1120                1125

Ile Gly Gly Gln Ser Gly Cys Tyr Asn Leu Val Pro Val Phe Gln
    1130                1135                1140

Trp Ile Glu Arg Cys Ile Ile Ser Ile Phe Leu Val Phe Met Ile
    1145                1150                1155

Ala Phe Met Pro Leu Phe Leu Gln Glu Leu Val Glu Arg Gly Thr
    1160                1165                1170

Trp Ser Ala Ile Trp Arg Leu Leu Lys Gln Phe Met Ser Leu Ser
    1175                1180                1185

Pro Val Phe Glu Val Phe Ser Thr Gln Ile Gln Thr His Ser Val
    1190                1195                1200

Leu Ser Asn Leu Thr Phe Gly Gly Ala Arg Tyr Ile Ala Thr Gly
    1205                1210                1215

Arg Gly Phe Ala Thr Ser Arg Ile Ser Phe Ser Ile Leu Phe Ser
    1220                1225                1230

Arg Phe Ala Gly Pro Ser Ile Tyr Leu Gly Met Arg Thr Leu Ile
    1235                1240                1245

Met Leu Leu Tyr Val Thr Leu Thr Ile Trp Thr Pro Trp Val Ile
    1250                1255                1260
```

| | | | | | | | | | | |
|---|---|---|---|---|---|---|---|---|---|---|
| Tyr | Phe | Trp | Val | Ser | Ile | Leu | Ser | Leu | Cys | Ile | Ala | Pro | Phe | Leu |
| 1265 | | | | | 1270 | | | | | 1275 | | | | |
| Phe | Asn | Pro | His | Gln | Phe | Val | Phe | Ser | Asp | Phe | Leu | Ile | Asp | Tyr |
| 1280 | | | | | 1285 | | | | | 1290 | | | | |
| Arg | Glu | Tyr | Leu | Arg | Trp | Met | Ser | Arg | Gly | Asn | Ser | Arg | Ser | His |
| 1295 | | | | | 1300 | | | | | 1305 | | | | |
| Asn | Asn | Ser | Trp | Ile | Gly | Tyr | Cys | Arg | Leu | Ser | Arg | Thr | Met | Ile |
| 1310 | | | | | 1315 | | | | | 1320 | | | | |
| Thr | Gly | Tyr | Lys | Lys | Lys | Leu | Gly | His | Pro | Ser | Glu | Lys | Leu |
| 1325 | | | | | 1330 | | | | | 1335 | | | | |
| Ser | Gly | Asp | Val | Pro | Arg | Ala | Gly | Trp | Arg | Ala | Val | Leu | Phe | Ser |
| 1340 | | | | | 1345 | | | | | 1350 | | | | |
| Glu | Ile | Ile | Phe | Pro | Ala | Cys | Met | Ala | Ile | Leu | Phe | Ile | Ile | Ala |
| 1355 | | | | | 1360 | | | | | 1365 | | | | |
| Tyr | Met | Phe | Val | Lys | Ser | Phe | Pro | Leu | Asp | Gly | Lys | Gln | Pro | Pro |
| 1370 | | | | | 1375 | | | | | 1380 | | | | |
| Ser | Gly | Leu | Val | Arg | Ile | Ala | Val | Val | Ser | Ile | Gly | Pro | Ile | Val |
| 1385 | | | | | 1390 | | | | | 1395 | | | | |
| Trp | Asn | Ala | Ala | Ile | Leu | Leu | Thr | Leu | Phe | Leu | Val | Ser | Leu | Phe |
| 1400 | | | | | 1405 | | | | | 1410 | | | | |
| Leu | Gly | Pro | Met | Leu | Asp | Pro | Val | Phe | Pro | Leu | Phe | Gly | Ser | Val |
| 1415 | | | | | 1420 | | | | | 1425 | | | | |
| Met | Ala | Phe | Ile | Ala | His | Phe | Leu | Gly | Thr | Ile | Gly | Met | Ile | Gly |
| 1430 | | | | | 1435 | | | | | 1440 | | | | |
| Phe | Phe | Glu | Phe | Leu | Trp | Phe | Leu | Glu | Ser | Trp | Glu | Ala | Ser | His |
| 1445 | | | | | 1450 | | | | | 1455 | | | | |
| Ala | Val | Leu | Gly | Leu | Ile | Ala | Val | Ile | Ser | Ile | Gln | Arg | Ala | Ile |
| 1460 | | | | | 1465 | | | | | 1470 | | | | |
| His | Lys | Ile | Leu | Ile | Ala | Val | Phe | Leu | Ser | Arg | Glu | Phe | Lys | His |
| 1475 | | | | | 1480 | | | | | 1485 | | | | |
| Asp | Glu | Thr | Asn | Arg | Ala | Trp | Trp | Thr | Gly | Arg | Trp | Tyr | Gly | Arg |
| 1490 | | | | | 1495 | | | | | 1500 | | | | |
| Gly | Leu | Gly | Thr | His | Ala | Met | Ser | Gln | Pro | Ala | Arg | Glu | Phe | Val |
| 1505 | | | | | 1510 | | | | | 1515 | | | | |
| Val | Lys | Ile | Ile | Glu | Leu | Ser | Leu | Trp | Ser | Ser | Asp | Leu | Ile | Leu |
| 1520 | | | | | 1525 | | | | | 1530 | | | | |
| Gly | His | Ile | Leu | Leu | Phe | Met | Leu | Thr | Pro | Ala | Val | Leu | Ile | Pro |
| 1535 | | | | | 1540 | | | | | 1545 | | | | |
| Tyr | Phe | Asp | Arg | Leu | His | Ala | Met | Met | Leu | Phe | Trp | Leu | Arg | Pro |
| 1550 | | | | | 1555 | | | | | 1560 | | | | |
| Ser | Lys | Gln | Ile | Arg | Ala | Pro | Leu | Tyr | Ser | Ile | Lys | Gln | Lys | Arg |
| 1565 | | | | | 1570 | | | | | 1575 | | | | |
| Gln | Arg | Arg | Trp | Ile | Ile | Met | Lys | Tyr | Gly | Thr | Val | Tyr | Val | Thr |
| 1580 | | | | | 1585 | | | | | 1590 | | | | |
| Val | Ile | Ala | Ile | Phe | Val | Ala | Leu | Ile | Ala | Leu | Pro | Leu | Val | Phe |
| 1595 | | | | | 1600 | | | | | 1605 | | | | |
| Arg | His | Thr | Leu | Lys | Val | Glu | Cys | Ser | Leu | Cys | Asp | Ser | Leu |
| 1610 | | | | | 1615 | | | | | 1620 | | | | |

<210> SEQ ID NO 9
<211> LENGTH: 6098
<212> TYPE: DNA
<213> ORGANISM: Schizophyllum commune

<400> SEQUENCE: 9

```
cccgtccctc aaggccgttc tttcgctggc gaccgacccg gtgttcgcga gaacctgttg    60
tttctgacga tcatcaaccc tttcttctcg tcgctcttta gctctcccta gaccgtcttt   120
tactctactc ttcgacgcac gccatgtccg gtccaggata tggcaggaat ccattcgaca   180 atccccgcc caacagaggt ccctatggcc agcagccagg tttcccgggg cccggccctc   240
ggccttacga ctcggacgcg gacatgagcc agacctatgg cagcacaacc aggctcgccg   300
gcagtgccgg ttacagcgac agaaacggtg cgaacgtcgc taccgtactt cctcgatcgt   360
cgactcacat atcacgcagg cagcttcgac ggcgaccgct cctacgcgcc ctcaattgac   420
tcgcgcgcca gcgtgcccag catatcgccc ttcgcagacc cgggtatcgg ctctaatgag   480
ccgtatcccg cttggtcggt cgaacgccag atccccatgt ccacggagga gattgaggat   540
atcttcctcg acctcaccca aaagtttggc ttccagcgcg actccatgcg gaatacggtg   600
cgtgaataag cagcccactc gaccgcggga acagctcaat tgacctgtca cccagttcga   660
cttcatgatg cacctccttg attcccgtgc ctcgcgcatg acgcccaacc aagctctgct   720
cacgcttcac gccgactaca ttggtggcca gcacgccaac tataggaagt ggtatttcgc   780
cgctcagctc aacctcgatg acgcggtcgg gcaaaccaat aaccccggta tccagcgctt   840
gaagaccatc aagggcgcta cgaagaccaa gtcgctcgac agcgcactca accgctggcg   900
caatgcgatg aacaacatga gccagtacga tcgcctccgg caaattgcgc tctatctcct  960
ctgctgggga gaagcaggca acatccgtct ggcgcccgag tgcttgtgct tcatcttcaa  1020
gtgcgcggac gactactaca gaagtcccga gtgtcagaac cggatggacc ccgtgccgga  1080
agggctgtac ctccagacgg tcatcaagcc gctctatcgc ttcctacgtg atcaggcgta  1140
cgaagtcgtt gatgggaagc aagtgaagcg cgagaaggac cacgaccaga ttatcggtta  1200
tgacgacgtc aaccagttat tctggtatcc ggaaggtttg gctaagatcg tcatgtcgga  1260
caacgtgcgt atgatcttat cggttacaat tcgtccgctc acatctttcc agacacgact  1320
tgtagatgta cctccggcgc agcggttcat gaagttcgcc aagatcgagt ggaaccgcgt  1380
cttcttcaag acgtactttg agaagcgctc tactgcccat ctcctggtca acttcaaccg  1440
tatatggatc ctccacgtct cgatgtactt cttctacacg gcattcaact ctccacgagt  1500
ctacgcgccg cacggcaaac tcgacccctc ccctgagatg acctggtccg cgactgccct  1560
tggaggcgct gtgtccacca tgatcatgat ccttgccact atcgcggagt acacctacat  1620
ccccacgaca tggaacaatg cgtcgcacct caccacgcgg ctcatttccc tcctggtcat  1680
cctcgcgctc actgctggac caacattcta tatcgccatg atagacggac gcacggacat  1740
cggccaagta ccactcatcg tggccatagt gcagttcttc atctccgtcg tcgccaccct  1800
cgctttcgct accatcccct ctggtcgcat gttcggcgac cgtgtggctg gcaagtcaag  1860
aaagcacatg gcatcgcaga cgttcacagc gtcgtacccg tccatgaagc ggtcatctcg  1920
cgtagcgagt atcatgctgt ggcttttggt ctttggctgc aaatacgtcg agtcttactt  1980
cttcttgacg tcctccttct ccagcccgat cgcggtcatg gcgcgtacga aggtacaggg  2040
ctgcaacgac cgtatcttcg gcagccagct gtgcacgaat caggtcccgt tcgcgctggc  2100
aatcatgtac gtgatggacc tggtactgtt cttcctggac acgtacctgt ggtacatcat  2160
ctggctggtg atcttctcga tggtgcgcgc gttcaagctt ggtatctcga tctggacgcc  2220
ctggagcgag atcttcaccc gcatgccgaa gcgtatctac gcgaagctgc tggcgacggc  2280
cgagatggag gtcaagtata agcccaaggt atgctgaatg caatctggtc aggtgaattc  2340
```

```
accctcatat tgttgtgcag gtgctcgtct cgcaaatctg gaacgcggtc atcatctcca    2400
tgtaccggga gcatctcttg tccatcgagc acgtccagcg cctgctatac caccaggttg    2460
atggtccaga cggtcgccgc accctcaggg caccgccgtt cttcaccagc cagcgaactg    2520
cgaagccagg cctgttcttc cctcctggtg gcgaggctga gcgccgtatc tcgttctttg    2580
cctcatcgct gacgaccgcg ctccctgagc ctctgccgat cgacgccatg cccaccttca    2640
ccgtgctcgt tccccattac tcggagaaga ttctgctcag tctgcgcgag attattcgcg    2700
aggaggacca gaacacccgc gtcaccttgc tggagtacct caagcagctc caccctgtcg    2760
aatgggacaa cttcgtcaag gacaccaaga tcttggcgga agagtcgggc gacgtccagg    2820
acgagaagcg cgcgcgcacg gacgacttgc cgttctactg catcgggttc aagacctcgt    2880
caccagagta caccctgcgt acgcgtatct gggcttcact gcgcgcacag acgctgtacc    2940
gcacggtctc cggtatgatg aactactcca aggcgatcaa gctcctctat cgcgtcgaga    3000
acccggatgt cgttcatgcc ttcggtggga acacggaacg tcttgaacgc gagcttgagc    3060
gcatgtctcg ccgcaagttc aagttcgtca tctcgatgca gcggtactct aagttcaaca    3120
aggaggagca agagaacgcc gaattccttc tgcgcgcgta cccggatttg cagatcgcgt    3180
acctcgatga agagcccggt cccagcaaga gcgacgaggt tcggttgttt tcgacactca    3240
tcgatggaca ctccgaggtg gatgagaaga ccggccgccg caagcccaag ttccgcattg    3300
agctgcccgg taaccccatc ctcggtgacg ggaagtcgga taaccagaac cacgccattg    3360
tcttctaccg cggcgagtac atccaggtca tcgacgctaa ccaggacaat tacctggaag    3420
agtgtctcaa gatccgtaac gtcctgggcg agtttgagga atactccgtg tcgagccaga    3480
gcccgtacgc acagtggggc cacaaggagt tcaacaagtg ccccgtcgct atcctgggtt    3540
ctcgcgagta catcttctcg gagaacatcg gtatcctcgg tgacatcgcc gccggcaagg    3600
aacagacgtt cggtaccatt acggcgcgtg cgcttgcgtg gatcggcggc aagctgcatt    3660
acggtcaccc ggatttcctc aatgcgacgt tcatgacgac gcgtggtggc gtgtcaaaag    3720
cgcagaaggg cttgcatctc aacgaggata tcttcgctgg tatgaccgcc gtgtcccgcg    3780
gagggcgcat caagcacatg gagtactacc agtgcggcaa aggtcgtgat tcggtttcg    3840
gcacgatctt gaacttccag acgaagatcg gtactggtat gggcgagcag ctcctctcgc    3900
gcgagtacta ctacctgggc acgcaattgc ctatcgaccg gttcttgacg ttctactacg    3960
cgcacgctgg tttccacgtc aacaacatcc tggtcatcta ctccatccag gtcttcatgg    4020
tcacctgtaa gtgcaggcgc tcatgaccgc cgagaacgta gtctgacgga tgtgcagtgc    4080
tgtacctggg cacattgaac aagcagctgt tcatctgcaa ggtcaactcc aatggccagg    4140
ttcttagtgg acaagctggg tgctacaacc tcatcccggt cttcgagtgg attgccggga    4200
gtatcatctc catcttcttg gtgttcttca tcgccttctt gcctctattc ttgcaaggta    4260
tgttcacttt ccatgtgtca tccgttagcc gctcaccata cgacagagct gtgcgagcgc    4320
ggaacgggaa aggcgttgct gcgtctcggg aagcacttct tgtcactgtc gcccatttc    4380
gaagtgttct ccacccagat ttactcgcag gcgctcttga caacatgag cttcggtggt    4440
gcgcgctaca tcgccacagg tcgtggtttc gcgactagtc gcatacccct caacatcctc    4500
tactcgcgtt tcgcgccgcc aagcatctac atgggcatgc gtaacctgct gctcctgctg    4560
tacgcgacga tggccatttg gatcccgcac ctgatctact tctggttctc cgtcctctcc    4620
ctctgcatcg cgccattcat gttcaatccg catcaattct cgtacgccga cttcatcatc    4680
gactaccggg agttcttgcg ctggatgtcg cgcggtaact cgcgaacgaa ggcgagcagc    4740
```

-continued

```
tggtacggat actgccgtct gtcgcgtacc gcgattactg ggtacaagaa gaagaagctg    4800
ggacacccgt cggagaagct gtcgggcgac gtaccgcgtg cgccgtggag gaacgttatc    4860
ttctcggaga tcctgtggcc catcggcgcg tgcatcatct tcatcgtcgc gtacatgttc    4920
gtcaagtcgt tccccgacga gcagggcaac gcgccgccga gcccgctggt ccggattctg    4980
ctcatcgcgg ttggccctac tgtgtggaac gcggcggtgc tcataacgct gttcttcctg    5040
tcgctcttcc tgggcccgat gatggatggc tgggtcaagt tcggctcggt catggcggcc    5100
cttgcgcatg gcctggcgct tataggcatg ctcacgttct ttgagttctt cgtacgtcct    5160
tcgcgttgtg tcgtcaagtg ctctgctaac gccgtcttca gtggttcctt gagctctggg    5220
atgcctcgca cgccgtgctc ggcgtcatcg ctatcattgc cgttcagcgc gggatccaga    5280
agatcctcat tgccgtcttc ctgacgcgtg agtacaagca cgacgagacg aaccgcgcgt    5340
ggtggacagg taaatggtat ggacgcgggc tgggtacctc ggccatgtcc cagccggcgc    5400
gcgagttcat cgtgaagatc gtggagatgt cgttgtggac gtcggacttc ctgcttgcgc    5460
acctgttgct catcatcttg acggtgccgc tactgctgcc gttcttcaac tcaattcatt    5520
cgacgatgct ttgtgagtgg tttgtagtcg ttggtcatgg atgatttctg actcgcgtgc    5580
agtctggttg cgcccttcga agcagattag gcaacctctg ttctccacca gcagaagcg    5640 gcaacggcga tggattgtga gttcctttga ttgctctggg taccgacctt cgctcacctt    5700
tcttaggtca tgaagtatac cgtggtatat ctcgtggtgg tggctttcct cgtcgcgctc    5760
atcgctctgc gtacgttttc cctcgcgctc accctgtatt ttcactaacg tttcctccag    5820
ccgccctctt ccgcgagagc atccacttca actgcgagat ctgccagagt atatagtcat    5880
ataacgacgt ctatcgtatc gccggacgag agccccgtcg cctacacact gacatggaat    5940
cgctgtgtat acaatcgatc ttctgaccgc gtcggggggcg ttgccgtctt tctactatca    6000
atttgcttgt gtatcaacat ttcttctctc caagcctaca ttgacataga gtaatagccc    6060
atgttcatac aacaatcgca tagcattgca tataccat                            6098
```

<210> SEQ ID NO 10
<211> LENGTH: 1726
<212> TYPE: PRT
<213> ORGANISM: Schizophyllum commune

<400> SEQUENCE: 10

```
Met Ser Gly Pro Gly Tyr Gly Arg Asn Pro Phe Asp Asn Pro Pro
1               5                   10                  15

Asn Arg Gly Pro Tyr Gly Gln Gln Pro Gly Phe Pro Gly Pro Gly Pro
                20                  25                  30

Arg Pro Tyr Asp Ser Asp Ala Asp Met Ser Gln Thr Tyr Gly Ser Thr
            35                  40                  45

Thr Arg Leu Ala Gly Ser Ala Gly Tyr Ser Asp Arg Asn Gly Ser Phe
        50                  55                  60

Asp Gly Asp Arg Ser Tyr Ala Pro Ser Ile Asp Ser Arg Ala Ser Val
65                  70                  75                  80

Pro Ser Ile Ser Pro Phe Ala Asp Pro Gly Ile Gly Ser Asn Glu Pro
                85                  90                  95

Tyr Pro Ala Trp Ser Val Glu Arg Gln Ile Pro Met Ser Thr Glu Glu
            100                 105                 110

Ile Glu Asp Ile Phe Leu Asp Leu Thr Gln Lys Phe Gly Phe Gln Arg
        115                 120                 125
```

```
Asp Ser Met Arg Asn Thr Phe Asp Phe Met Met His Leu Leu Asp Ser
    130                 135                 140
Arg Ala Ser Arg Met Thr Pro Asn Gln Ala Leu Leu Thr Leu His Ala
145                 150                 155                 160
Asp Tyr Ile Gly Gly Gln His Ala Asn Tyr Arg Lys Trp Tyr Phe Ala
                165                 170                 175
Ala Gln Leu Asn Leu Asp Asp Ala Val Gly Gln Thr Asn Asn Pro Gly
            180                 185                 190
Ile Gln Arg Leu Lys Thr Ile Lys Gly Ala Thr Lys Thr Lys Ser Leu
        195                 200                 205
Asp Ser Ala Leu Asn Arg Trp Arg Asn Ala Met Asn Asn Met Ser Gln
    210                 215                 220
Tyr Asp Arg Leu Arg Gln Ile Ala Leu Tyr Leu Leu Cys Trp Gly Glu
225                 230                 235                 240
Ala Gly Asn Ile Arg Leu Ala Pro Glu Cys Leu Cys Phe Ile Phe Lys
                245                 250                 255
Cys Ala Asp Asp Tyr Tyr Arg Ser Pro Glu Cys Gln Asn Arg Met Asp
            260                 265                 270
Pro Val Pro Glu Gly Leu Tyr Leu Gln Thr Val Ile Lys Pro Leu Tyr
        275                 280                 285
Arg Phe Leu Arg Asp Gln Ala Tyr Glu Val Val Asp Gly Lys Gln Val
    290                 295                 300
Lys Arg Glu Lys Asp His Asp Gln Ile Ile Gly Tyr Asp Asp Val Asn
305                 310                 315                 320
Gln Leu Phe Trp Tyr Pro Glu Gly Leu Ala Lys Ile Val Met Ser Asp
                325                 330                 335
Asn Thr Arg Leu Val Asp Val Pro Pro Ala Gln Arg Phe Met Lys Phe
            340                 345                 350
Ala Lys Ile Glu Trp Asn Arg Val Phe Phe Lys Thr Tyr Phe Glu Lys
        355                 360                 365
Arg Ser Thr Ala His Leu Leu Val Asn Phe Asn Arg Ile Trp Ile Leu
    370                 375                 380
His Val Ser Met Tyr Phe Phe Tyr Thr Ala Phe Asn Ser Pro Arg Val
385                 390                 395                 400
Tyr Ala Pro His Gly Lys Leu Asp Pro Ser Pro Glu Met Thr Trp Ser
                405                 410                 415
Ala Thr Ala Leu Gly Gly Ala Val Ser Thr Met Ile Met Ile Leu Ala
            420                 425                 430
Thr Ile Ala Glu Tyr Thr Tyr Ile Pro Thr Thr Trp Asn Asn Ala Ser
        435                 440                 445
His Leu Thr Thr Arg Leu Ile Phe Leu Leu Val Ile Leu Ala Leu Thr
    450                 455                 460
Ala Gly Pro Thr Phe Tyr Ile Ala Met Ile Asp Gly Arg Thr Asp Ile
465                 470                 475                 480
Gly Gln Val Pro Leu Ile Val Ala Ile Val Gln Phe Phe Ile Ser Val
                485                 490                 495
Val Ala Thr Leu Ala Phe Ala Thr Ile Pro Ser Gly Arg Met Phe Gly
            500                 505                 510
Asp Arg Val Ala Gly Lys Ser Arg Lys His Met Ala Ser Gln Thr Phe
        515                 520                 525
Thr Ala Ser Tyr Pro Ser Met Lys Arg Ser Ser Arg Val Ala Ser Ile
    530                 535                 540
Met Leu Trp Leu Leu Val Phe Gly Cys Lys Tyr Val Glu Ser Tyr Phe
```

```
                545                 550                 555                 560
            Phe Leu Thr Ser Ser Phe Ser Ser Pro Ile Ala Val Met Ala Arg Thr
                            565                 570                 575
            Lys Val Gln Gly Cys Asn Asp Arg Ile Phe Gly Ser Gln Leu Cys Thr
                            580                 585                 590
            Asn Gln Val Pro Phe Ala Leu Ala Ile Met Tyr Val Met Asp Leu Val
                            595                 600                 605
            Leu Phe Phe Leu Asp Thr Tyr Leu Trp Tyr Ile Ile Trp Leu Val Ile
                            610                 615                 620
            Phe Ser Met Val Arg Ala Phe Lys Leu Gly Ile Ser Ile Trp Thr Pro
            625                 630                 635                 640
            Trp Ser Glu Ile Phe Thr Arg Met Pro Lys Arg Ile Tyr Ala Lys Leu
                            645                 650                 655
            Leu Ala Thr Ala Glu Met Glu Val Lys Tyr Lys Pro Lys Val Leu Val
                            660                 665                 670
            Ser Gln Ile Trp Asn Ala Val Ile Ile Ser Met Tyr Arg Glu His Leu
                            675                 680                 685
            Leu Ser Ile Glu His Val Gln Arg Leu Leu Tyr His Gln Val Asp Gly
                            690                 695                 700
            Pro Asp Gly Arg Arg Thr Leu Arg Ala Pro Pro Phe Phe Thr Ser Gln
            705                 710                 715                 720
            Arg Thr Ala Lys Pro Gly Leu Phe Phe Pro Pro Gly Gly Glu Ala Glu
                            725                 730                 735
            Arg Arg Ile Ser Phe Phe Ala Ser Ser Leu Thr Thr Ala Leu Pro Glu
                            740                 745                 750
            Pro Leu Pro Ile Asp Ala Met Pro Thr Phe Thr Val Leu Val Pro His
                            755                 760                 765
            Tyr Ser Glu Lys Ile Leu Leu Ser Leu Arg Glu Ile Ile Arg Glu Glu
                            770                 775                 780
            Asp Gln Asn Thr Arg Val Thr Leu Leu Glu Tyr Leu Lys Gln Leu His
            785                 790                 795                 800
            Pro Val Glu Trp Asp Asn Phe Val Lys Asp Thr Lys Ile Leu Ala Glu
                            805                 810                 815
            Glu Ser Gly Asp Val Gln Asp Glu Lys Arg Ala Arg Thr Asp Asp Leu
                            820                 825                 830
            Pro Phe Tyr Cys Ile Gly Phe Lys Thr Ser Ser Pro Glu Tyr Thr Leu
                            835                 840                 845
            Arg Thr Arg Ile Trp Ala Ser Leu Arg Ala Gln Thr Leu Tyr Arg Thr
                            850                 855                 860
            Val Ser Gly Met Met Asn Tyr Ser Lys Ala Ile Lys Leu Leu Tyr Arg
            865                 870                 875                 880
            Val Glu Asn Pro Asp Val Val His Ala Phe Gly Gly Asn Thr Glu Arg
                            885                 890                 895
            Leu Glu Arg Glu Leu Glu Arg Met Ser Arg Arg Lys Phe Lys Phe Val
                            900                 905                 910
            Ile Ser Met Gln Arg Tyr Ser Lys Phe Asn Lys Glu Glu Gln Glu Asn
                            915                 920                 925
            Ala Glu Phe Leu Leu Arg Ala Tyr Pro Asp Leu Gln Ile Ala Tyr Leu
                            930                 935                 940
            Asp Glu Glu Pro Gly Pro Ser Lys Ser Asp Glu Val Arg Leu Phe Ser
            945                 950                 955                 960
            Thr Leu Ile Asp Gly His Ser Glu Val Asp Glu Lys Thr Gly Arg Arg
                            965                 970                 975
```

-continued

```
Lys Pro Lys Phe Arg Ile Glu Leu Pro Gly Asn Pro Ile Leu Gly Asp
            980                 985                 990

Gly Lys Ser Asp Asn Gln Asn His  Ala Ile Val Phe Tyr  Arg Gly Glu
            995                1000                1005

Tyr Ile Gln Val Ile Asp Ala  Asn Gln Asp Asn Tyr  Leu Glu Glu
        1010                1015                1020

Cys Leu Lys Ile Arg Asn Val  Leu Gly Glu Phe Glu  Glu Tyr Ser
        1025                1030                1035

Val Ser Ser Gln Ser Pro Tyr  Ala Gln Trp Gly His  Lys Glu Phe
        1040                1045                1050

Asn Lys Cys Pro Val Ala Ile  Leu Gly Ser Arg Glu  Tyr Ile Phe
        1055                1060                1065

Ser Glu Asn Ile Gly Ile Leu  Gly Asp Ile Ala Ala  Gly Lys Glu
        1070                1075                1080

Gln Thr Phe Gly Thr Ile Thr  Ala Arg Ala Leu Ala  Trp Ile Gly
        1085                1090                1095

Gly Lys Leu His Tyr Gly His  Pro Asp Phe Leu Asn  Ala Thr Phe
        1100                1105                1110

Met Thr Thr Arg Gly Gly Val  Ser Lys Ala Gln Lys  Gly Leu His
        1115                1120                1125

Leu Asn Glu Asp Ile Phe Ala  Gly Met Thr Ala Val  Ser Arg Gly
        1130                1135                1140

Gly Arg Ile Lys His Met Glu  Tyr Tyr Gln Cys Gly  Lys Gly Arg
        1145                1150                1155

Asp Leu Gly Phe Gly Thr Ile  Leu Asn Phe Gln Thr  Lys Ile Gly
        1160                1165                1170

Thr Gly Met Gly Glu Gln Leu  Leu Ser Arg Glu Tyr  Tyr Tyr Leu
        1175                1180                1185

Gly Thr Gln Leu Pro Ile Asp  Arg Phe Leu Thr Phe  Tyr Tyr Ala
        1190                1195                1200

His Ala Gly Phe His Val Asn  Asn Ile Leu Val Ile  Tyr Ser Ile
        1205                1210                1215

Gln Val Phe Met Val Thr Leu  Leu Tyr Leu Gly Thr  Leu Asn Lys
        1220                1225                1230

Gln Leu Phe Ile Cys Lys Val  Asn Ser Asn Gly Gln  Val Leu Ser
        1235                1240                1245

Gly Gln Ala Gly Cys Tyr Asn  Leu Ile Pro Val Phe  Glu Trp Ile
        1250                1255                1260

Arg Arg Ser Ile Ile Ser Ile  Phe Leu Val Phe Phe  Ile Ala Phe
        1265                1270                1275

Leu Pro Leu Phe Leu Gln Glu  Leu Cys Glu Arg Gly  Thr Gly Lys
        1280                1285                1290

Ala Leu Leu Arg Leu Gly Lys  His Phe Leu Ser Leu  Ser Pro Ile
        1295                1300                1305

Phe Glu Val Phe Ser Thr Gln  Ile Tyr Ser Gln Ala  Leu Leu Asn
        1310                1315                1320

Asn Met Ser Phe Gly Gly Ala  Arg Tyr Ile Ala Thr  Gly Arg Gly
        1325                1330                1335

Phe Ala Thr Ser Arg Ile Pro  Phe Asn Ile Leu Tyr  Ser Arg Phe
        1340                1345                1350

Ala Pro Pro Ser Ile Tyr Met  Gly Met Arg Asn Leu  Leu Leu Leu
        1355                1360                1365
```

-continued

| Leu | Tyr | Ala | Thr | Met | Ala | Ile | Trp | Ile | Pro | His | Leu | Ile | Tyr | Phe |
| | 1370 | | | | 1375 | | | | 1380 | | | | | |

| Trp | Phe | Ser | Val | Leu | Ser | Leu | Cys | Ile | Ala | Pro | Phe | Met | Phe | Asn |
| 1385 | | | | | 1390 | | | | | 1395 | | | | |

| Pro | His | Gln | Phe | Ser | Tyr | Ala | Asp | Phe | Ile | Ile | Asp | Tyr | Arg | Glu |
| 1400 | | | | | 1405 | | | | | 1410 | | | | |

| Phe | Leu | Arg | Trp | Met | Ser | Arg | Gly | Asn | Ser | Arg | Thr | Lys | Ala | Ser |
| 1415 | | | | | 1420 | | | | | 1425 | | | | |

| Ser | Trp | Tyr | Gly | Tyr | Cys | Arg | Leu | Ser | Arg | Thr | Ala | Ile | Thr | Gly |
| 1430 | | | | | 1435 | | | | | 1440 | | | | |

| Tyr | Lys | Lys | Lys | Leu | Gly | His | Pro | Ser | Glu | Lys | Leu | Ser | Gly |
| 1445 | | | | | 1450 | | | | | 1455 | | | | |

| Asp | Val | Pro | Arg | Ala | Pro | Trp | Arg | Asn | Val | Ile | Phe | Ser | Glu | Ile |
| 1460 | | | | | 1465 | | | | | 1470 | | | | |

| Leu | Trp | Pro | Ile | Gly | Ala | Cys | Ile | Ile | Phe | Ile | Val | Ala | Tyr | Met |
| 1475 | | | | | 1480 | | | | | 1485 | | | | |

| Phe | Val | Lys | Ser | Phe | Pro | Asp | Glu | Gln | Gly | Asn | Ala | Pro | Pro | Ser |
| 1490 | | | | | 1495 | | | | | 1500 | | | | |

| Pro | Leu | Val | Arg | Ile | Leu | Leu | Ile | Ala | Val | Gly | Pro | Thr | Val | Trp |
| 1505 | | | | | 1510 | | | | | 1515 | | | | |

| Asn | Ala | Ala | Val | Leu | Ile | Thr | Leu | Phe | Phe | Leu | Ser | Leu | Phe | Leu |
| 1520 | | | | | 1525 | | | | | 1530 | | | | |

| Gly | Pro | Met | Met | Asp | Gly | Trp | Val | Lys | Phe | Gly | Ser | Val | Met | Ala |
| 1535 | | | | | 1540 | | | | | 1545 | | | | |

| Ala | Leu | Ala | His | Gly | Leu | Ala | Leu | Ile | Gly | Met | Leu | Thr | Phe | Phe |
| 1550 | | | | | 1555 | | | | | 1560 | | | | |

| Glu | Phe | Phe | Trp | Phe | Leu | Glu | Leu | Trp | Asp | Ala | Ser | His | Ala | Val |
| 1565 | | | | | 1570 | | | | | 1575 | | | | |

| Leu | Gly | Val | Ile | Ala | Ile | Ala | Val | Gln | Arg | Gly | Ile | Gln | Lys |
| 1580 | | | | | 1585 | | | | | 1590 | | | | |

| Ile | Leu | Ile | Ala | Val | Phe | Leu | Thr | Arg | Lys | Trp | Tyr | Gly | Arg | Gly |
| 1595 | | | | | 1600 | | | | | 1605 | | | | |

| Leu | Gly | Thr | Ser | Ala | Met | Ser | Gln | Pro | Ala | Arg | Glu | Phe | Ile | Val |
| 1610 | | | | | 1615 | | | | | 1620 | | | | |

| Lys | Ile | Val | Glu | Met | Ser | Leu | Trp | Thr | Ser | Asp | Phe | Leu | Leu | Ala |
| 1625 | | | | | 1630 | | | | | 1635 | | | | |

| His | Leu | Leu | Leu | Ile | Ile | Leu | Thr | Val | Pro | Leu | Leu | Leu | Pro | Phe |
| 1640 | | | | | 1645 | | | | | 1650 | | | | |

| Phe | Asn | Ser | Ile | His | Ser | Thr | Met | Leu | Phe | Trp | Leu | Arg | Pro | Ser |
| 1655 | | | | | 1660 | | | | | 1665 | | | | |

| Lys | Gln | Ile | Arg | Gln | Pro | Leu | Phe | Ser | Thr | Lys | Gln | Lys | Arg | Gln |
| 1670 | | | | | 1675 | | | | | 1680 | | | | |

| Arg | Arg | Trp | Ile | Val | Met | Lys | Tyr | Thr | Val | Val | Tyr | Leu | Val | Val |
| 1685 | | | | | 1690 | | | | | 1695 | | | | |

| Val | Ala | Phe | Leu | Val | Ala | Leu | Ile | Ala | Leu | Pro | Ala | Leu | Phe | Arg |
| 1700 | | | | | 1705 | | | | | 1710 | | | | |

| Glu | Ser | Ile | His | Phe | Asn | Cys | Glu | Ile | Cys | Gln | Ser | Ile |
| 1715 | | | | | 1720 | | | | | 1725 | | | | |

<210> SEQ ID NO 11
<211> LENGTH: 5771
<212> TYPE: DNA
<213> ORGANISM: Schizophyllum commune

<400> SEQUENCE: 11

-continued

| | |
|---|---|
| ctgtccaagg aggagatcga ggacatcttc ctcgatttga cgcagaagtt tggctttcag | 60 |
| cgggattcca tgcggaatat ggtacgtggc gtgtgcccat gtgcggcgtt ctgaggccta | 120 |
| acgttttccg ccagttcgac ttcaccatgc agctgcttga cagccgagcg tctcgtatga | 180 |
| cccccaacca ggcgctcctc accctccacg ccgactacta tggtggccag catgcgaact | 240 |
| accggaagtg gtacttcgcg gcgcagctcg accttgacga cgccgtggga caaactcaga | 300 |
| atccgggtct caaccgcctc aagtccactc gcggatcggg caagcgacca cgccatgaaa | 360 |
| agtcgctgaa cacggcattg gagcgctggc ggcaagccat gaacaacatg tcgcagtatg | 420 |
| accgcttacg ccagatcgcg ctctacctgc tctgctgggg cgaagcggcg caagtgcgat | 480 |
| tcatgcccga gtgcttgtgc ttcatcttca agtgcgccga cgactactat cgttcgccgg | 540 |
| agtgccagaa caggatggag ccggtaccgg agggtctcta cctgaggacg gtcgtaaagc | 600 |
| cgctctacag atttgtccgg gatcaaggct atgaggtggt ggagggaaaa ttcgtacggc | 660 |
| gggaacggga tcacgaccaa atcattggtt acgatgacga gaatcagctg ttctggtacc | 720 |
| cggagggaat tgcccgtatc gtcctgtcgg acaaggtaag cacctctgtg catcttctgt | 780 |
| gacatacagg gctaattgtc gagcagagtc gtcagtcga cctcccccca gcacagcgct | 840 |
| tcatgaagtt cgaccgtatc gagtggaatc gcgtcttctt caagacgttt tacgagactc | 900 |
| gatccttcac gcatcttttg gtcgacttca accgtatctg ggtcgtgcac atcgctctct | 960 |
| acttcttcta cactgcatac aactccccca cgatctacgc catcaacggc aacacaccga | 1020 |
| cgtctctggc ttggagcgcg actgcgctcg cggtgcggt agcgacaggt atcatgatcc | 1080 |
| tcgccacgat cgccgagttc tcgcacatcc ccacgacatg gaacaacacc tcgcatctga | 1140 |
| ctcgccgcct cgccttcctc ctcgtcacgc tcggcctcac atgtggtccg acgttctacg | 1200 |
| tcgcgattgc agagagcaac gggagcggcg gctcttggc cttgattctc ggtatcgtcc | 1260 |
| agttcttcat ctccgtcgtg gcaactgcgc tcttcactat catgccttct ggtcgtatgt | 1320 |
| tcggcgaccg tgtcgcaggc aagagtcgca agtatctcgc cagccagacg ttcacggcca | 1380 |
| gctaccgtc gttgcccaag caccagcggt tcgcctcact cctgatgtgg ttcctcatct | 1440 |
| tcgggtgcaa gttgacggag agttacttct ttctgacgct gtccttccgc gaccctatcc | 1500 |
| gcgtcatggt cggcatgaag atccagaact gcgaggacaa gattttcggc agcggccttt | 1560 |
| gcaggaatca cgcagcattc accctcacga tcatgtacat catggacctc gtcttgttct | 1620 |
| tcctcgacac cttcctttgg tatgtcatct ggaactcggt tttcagtatc gcacgctctt | 1680 |
| tcgtactcgg ccttcgatc tggacaccgt ggagagacat cttccagcgt ctgccgaagc | 1740 |
| ggatctacgc gaagcttctg gcgactggcg acatggaggt caagtacaag cccaaggtat | 1800 |
| gcgttgagct cgccgtaaat ccacttaagg ctaacacgtt cgcaggtctt ggtctcgcaa | 1860 |
| atctggaacg ccatcatcat ctccatgtac cgcgagcact tgctctctat tgagcacgtc | 1920 |
| cagaagctcc tgtaccacca agtggacact ggcgaagccg gcaagcggag tcttcgcgcg | 1980 |
| cctccgttct tcgtcgcgca gggcagcagc ggtggctcgg gcgagttctt cccgcctggc | 2040 |
| agcgaggccg agcgtcgtat ctctttcttc gcgcagtcgc tttctacgga gattcctcag | 2100 |
| cccatcccgg tcgacgccat gccgacgttc acggtgctta cgcctcacta cagcgagaag | 2160 |
| gtacatgctc cccttgtagc catatgacat cagctgactg tcgtgcacag atccttctct | 2220 |
| ctctccgtga aattatccgc gaggaggacc agaacactcg cgttacgttg ctcgagtacc | 2280 |
| tgaagcagct gcatccggtc gagtgggaga atttcgtcaa ggacactaaa attttggccg | 2340 |

```
aggagtccgc tatgtttaac ggtccgagtc ctttcggcaa cgacgagaag ggtcagtcca    2400
agatggacga tctaccgttc tactgcatcg gtttcaagag cgccgcgccc gagtacaccc    2460
tccgcacccg tatctgggcg tccctgcgcg cgcagacgct gtaccgcacg gtctccggca    2520
tgatgaacta tgcgaaggcg atcaagctgc tctaccgcgt tgagaacccg gaggtcgtac    2580
aacagttcgg cggcaacacg gacaagctcg agcgcgagtt ggagcggatg gcgcgacgga    2640
agttcaagtt cctcgtgtcc atgcagcgct actcgaagtt caacaaggag gagcacgaga    2700
acgccgagtt cttgctccgc gcgtacccgg acttgcagat cgcgtacctc gaggaagagc    2760
cccctcgcaa ggagggcggc gatccacgca tcttctctgc cctcgtcgac ggccacagcg    2820
acatcatccc ggagaccggc aagcggcgcc ccaagttccg tatcgagctg cccggtaacc    2880
ccattctcgg tgacggtaaa tccgacaatc agaaccacgc tatcgtcttc taccgcggcg    2940
agtacctcca gcttatcgac gccaaccagg acaactacct cgaggagtgc ttgaagatcc    3000
gtaacgtgct cgccgagttt gaggagtacg acgtctccag ccagagcccg tacgcgcagt    3060
ggagtgtcaa ggagttcaag cgctctccgg tcgccatcgt cggtgcacgc gagtacatct    3120
tctcagagca catcggtatc ctcggtgatc tggcggctgg caaggaacag acgttcggta    3180
cgctcacggc acgcaacaac gccttccttg gcggcaagct gcactacggt caccccgatt    3240
tcctcaacgc cctctacatg aacacgcgcg gtggtgtctc caaggcgcag aagggtctcc    3300
atctcaacga ggatatctac gccggtatga acgcggtcgg tcgcggtgga cgcattaagc    3360
acagcgagta ctatcagtgc ggcaagggtc gtgacctcgg tttcggcacc atcttgaact    3420
tccagaccaa gatcggtacg ggtatgggcg agcagatcct ctcgcgcgag tactactatc    3480
tcggaacaca actgcccatc gatcgcttcc tcacgttcta ctacgcgcac ccgggttttcc    3540
agatcaacaa catgctggtc atcctctccg tgcaggtctt catcgttacc agtacgttca    3600
atgcatattg ttagcctgac aacgtctgac gaatttccag tggtcttcct cggtaccttg    3660
aagtcttcgg tcacgatctg caagtacacg tccagcggtc agtacatcgg tggtcaatcc    3720
ggttgctaca acctcgtccc ggtcttccag tggatcgagc gctgcatcat cagcatcttc    3780
ttggtgttca tgatcgcttt catgccgctc ttcctgcaag gtaagagctt gtcaacctgc    3840
tcaaggggct tgcgctgatc atcatctcag aactcgtcga gcgcggtacc tggagtgcca    3900
tctggcgtct gctcaagcag tttatgtcgc tgtcgcctgt cttcgaggtg ttctccaccc    3960
agattcagac gcactccgtg ttgagcaact tgacgttcgg tggtgcgcgt tacatcgcta    4020
ccggtcgtgg gttcgccacc agtcgtatca gcttcagcat cttgttctcg cgtttcgcag    4080
gcccgagtat ctacctcggc atgcgcacgc tcattatgct gctctacgtg acgttgacga    4140
tctgacgcc atgggtcatt tacttctggg tttccattct ctcgctctgc atcgcgccgt    4200
tcttgttcaa cccgcatcaa ttcgtattct cggacttcct catcgactac aggtacgtcg    4260
gacgagcgct gttccgcgac gtaagctgac cggttataca gggaataccct gcggtggatg    4320
tcgcgtggca actcgcgctc gcacaacaac tcctggattg ggtactgccg gttgtcccgc    4380
acgatgatca ctgggtacaa gaagaagaag ctgggccacc cgtcggagaa gctttccggc    4440
gacgttcctc gtgcaggctg gcgcgccgtc ttgttctcgg agatcatctt cccggcgtgc    4500
atggccatcc tcttcatcat cgcgtacatg ttcgtcaagt cgttccctct cgacggcaag    4560
cagcctccct ccggcctcgt tcgcatcgcc gtcgtgtcta tcggcccccat cgtgtggaac    4620
gccgccatcc tgttgacgct cttccttgtg tcgttgttcc tcggcccccat gctcgacccg    4680
gtcttcccccc tcttcggttc cgttatggcc ttcatcgcgc atttccttgg cacaatcgga    4740
```

```
atgattgggt tcttcgagtt cctggtatgt gcccatacct ttcattcgac ttcaactatc    4800
taacagattc atagtggttc ctcgagtcct gggaggcgtc gcatgccgtg ctgggtctca    4860
tcgccgtcat ctccatccag cgcgccattc acaagatcct tatcgccgtt ttcctcagtc    4920
gcgagttcaa gcacgacgag acgaacaggg cctggtggac tggtcgctgg tatggccgtg    4980
gcctcggcac gcacgccatg tcgcagccgg cgcgtgagtt cgtcgtcaag atcatcgagt    5040
tgtcgctttg gagctcggat tcatactcg gccacatcct gctgttcatg cttactccgg      5100
ccgtcctcat cccgtacttc gaccgtttgc acgccatgat gctctgtacg tcgtgtctca    5160
ttgtctgtgt tggtcatact cttaccctct cttagtctgg ctgcgtccct cgaagcaaat    5220
ccgcgcgcct ctgtactcga tcaagcagaa gaggcaaaga cgctggattg tcagtgttca    5280
gtgccttatt ctatcagctc ttactaacgt cttcatagat catgaagtac ggtactgtat    5340
acgttaccgt catcgcgatc ttcgtcgcgc tcatcgcgct tcgtgagttt ccttgctatt    5400
tttcgtacct gagcgtcgct gacccctttc ccagccctcg tattccgaca cactctaaag    5460
gtcgagtgct ccctttgcga cagcttgtaa tatcggactc gtatatatct agacttctcc    5520
gcaccatgtg tagctgacgc ttgggtatac ttcgcggtgc cgagctaatt gtcgacggac    5580
attctccatc gttgagtgca gcgacgtcgg gtggtttacg acacggacac ttttcattgt    5640
accctctacg aatgcaagaa ctctcttacg accagtacct atgtgctaag ccgtcgcctg    5700
ttcaggatca tacatacata cgtttctaga taccttacag ttaggcctat tcagggagag    5760
tctgcataaa a                                                         5771

<210> SEQ ID NO 12
<211> LENGTH: 1783
<212> TYPE: PRT
<213> ORGANISM: Schizophyllum commune

<400> SEQUENCE: 12

Met Pro Arg Pro Gly Gly Thr Ser Ala Glu Gly Gly Tyr Ala Ser Ser
1               5                   10                  15

Pro Ser Met Glu Thr Thr Pro Ser Asp Pro Phe Gly Thr Ala Asn Gly
            20                  25                  30

Ala Pro Arg Arg Tyr Tyr Asp Asn Asp Ser Glu Glu Tyr Gly Pro Gly
        35                  40                  45

Arg Arg Asp Thr Tyr Ala Ser Asp Ser Ser Asn Gln Gly Leu Thr Asp
    50                  55                  60

Pro Gly Tyr Tyr Asp Gln Asn Gly Ala Tyr Asp Pro Tyr Pro Thr Gly
65                  70                  75                  80

Asp Thr Asp Ser Asp Gly Asp Val Tyr Gly Gln Arg Tyr Gly Pro Ser
                85                  90                  95

Ala Glu Ser Leu Gly Thr His Lys Phe Gly His Ser Asp Ser Ser Thr
            100                 105                 110

Pro Thr Phe Val Asp Tyr Ser Ala Ser Ser Gly Gly Arg Asp Ser Tyr
        115                 120                 125

Pro Ala Trp Thr Ala Glu Arg Asn Ile Pro Leu Ser Lys Glu Glu Ile
    130                 135                 140

Glu Asp Ile Phe Leu Asp Leu Thr Gln Lys Phe Gly Phe Gln Arg Asp
145                 150                 155                 160

Ser Met Arg Asn Met Phe Asp Phe Thr Met Gln Leu Leu Asp Ser Arg
                165                 170                 175

Ala Ser Arg Met Thr Pro Asn Gln Ala Leu Leu Thr Leu His Ala Asp
```

```
                180                 185                 190
Tyr Ile Gly Gly Gln His Ala Asn Tyr Arg Lys Trp Tyr Phe Ala Ala
            195                 200                 205
Gln Leu Asp Leu Asp Asp Ala Val Gly Gln Thr Gln Asn Pro Gly Leu
            210                 215                 220
Asn Arg Leu Lys Ser Thr Arg Gly Ser Gly Lys Arg Pro Arg His Glu
225                 230                 235                 240
Lys Ser Leu Asn Thr Ala Leu Glu Arg Trp Arg Gln Ala Met Asn Asn
                245                 250                 255
Met Ser Gln Tyr Asp Arg Leu Arg Gln Ile Ala Leu Tyr Leu Leu Cys
            260                 265                 270
Trp Gly Glu Ala Ala Gln Val Arg Phe Met Pro Glu Cys Leu Cys Phe
            275                 280                 285
Ile Phe Lys Cys Ala Asp Asp Tyr Tyr Arg Ser Pro Glu Cys Gln Asn
            290                 295                 300
Arg Met Glu Pro Val Pro Glu Gly Leu Tyr Leu Arg Thr Val Val Lys
305                 310                 315                 320
Pro Leu Tyr Arg Phe Val Arg Asp Gln Gly Tyr Glu Val Val Glu Gly
                325                 330                 335
Lys Phe Val Arg Arg Glu Arg Asp His Asp Gln Ile Ile Gly Tyr Asp
                340                 345                 350
Asp Val Asn Gln Leu Phe Trp Tyr Pro Glu Gly Ile Ala Arg Ile Val
            355                 360                 365
Leu Ser Asp Lys Ser Arg Leu Val Asp Leu Pro Pro Ala Gln Arg Phe
            370                 375                 380
Met Lys Phe Asp Arg Ile Glu Trp Asn Arg Val Phe Phe Lys Thr Phe
385                 390                 395                 400
Tyr Glu Thr Arg Ser Phe Thr His Leu Leu Val Asp Phe Asn Arg Ile
                405                 410                 415
Trp Val Val His Ile Ala Leu Tyr Phe Phe Tyr Thr Ala Tyr Asn Ser
                420                 425                 430
Pro Thr Ile Tyr Ala Ile Asn Gly Asn Thr Pro Thr Ser Leu Ala Trp
            435                 440                 445
Ser Ala Thr Ala Leu Gly Gly Ala Val Ala Thr Gly Ile Met Ile Leu
            450                 455                 460
Ala Thr Ile Ala Glu Phe Ser His Ile Pro Thr Thr Trp Asn Asn Thr
465                 470                 475                 480
Ser His Leu Thr Arg Arg Leu Ala Phe Leu Leu Val Thr Leu Gly Leu
                485                 490                 495
Thr Cys Gly Pro Thr Phe Tyr Val Ala Ile Ala Glu Ser Asn Gly Ser
            500                 505                 510
Gly Gly Ser Leu Ala Leu Ile Leu Gly Ile Val Gln Phe Phe Ile Ser
            515                 520                 525
Val Val Ala Thr Ala Leu Phe Thr Ile Met Pro Ser Gly Arg Met Phe
            530                 535                 540
Gly Asp Arg Val Ala Gly Lys Ser Arg Lys Tyr Leu Ala Ser Gln Thr
545                 550                 555                 560
Phe Thr Ala Ser Tyr Pro Ser Leu Pro Lys His Gln Arg Phe Ala Ser
                565                 570                 575
Leu Leu Met Trp Phe Leu Ile Phe Gly Cys Lys Leu Thr Glu Ser Tyr
            580                 585                 590
Phe Phe Leu Thr Leu Ser Phe Arg Asp Pro Ile Arg Val Met Val Gly
            595                 600                 605
```

```
Met Lys Ile Gln Asn Cys Glu Asp Lys Ile Phe Gly Ser Gly Leu Cys
    610                 615                 620

Arg Asn His Ala Ala Phe Thr Leu Thr Ile Met Tyr Ile Met Asp Leu
625                 630                 635                 640

Val Leu Phe Phe Leu Asp Thr Phe Leu Trp Tyr Val Ile Trp Asn Ser
                    645                 650                 655

Val Phe Ser Ile Ala Arg Ser Phe Val Leu Gly Leu Ser Ile Trp Thr
                660                 665                 670

Pro Trp Arg Asp Ile Phe Gln Arg Leu Pro Lys Arg Ile Tyr Ala Lys
            675                 680                 685

Leu Leu Ala Thr Gly Asp Met Glu Val Lys Tyr Lys Pro Lys Val Leu
    690                 695                 700

Val Ser Gln Ile Trp Asn Ala Ile Ile Ile Ser Met Tyr Arg Glu His
705                 710                 715                 720

Leu Leu Ser Ile Glu His Val Gln Lys Leu Leu Tyr His Gln Val Asp
                    725                 730                 735

Thr Gly Glu Ala Gly Lys Arg Ser Leu Arg Ala Pro Pro Phe Phe Val
                740                 745                 750

Ala Gln Gly Ser Ser Gly Gly Ser Gly Glu Phe Phe Pro Pro Gly Ser
            755                 760                 765

Glu Ala Glu Arg Arg Ile Ser Phe Phe Ala Gln Ser Leu Ser Thr Glu
    770                 775                 780

Ile Pro Gln Pro Ile Pro Val Asp Ala Met Pro Thr Phe Thr Val Leu
785                 790                 795                 800

Thr Pro His Tyr Ser Glu Lys Ile Leu Leu Ser Leu Arg Glu Ile Ile
                    805                 810                 815

Arg Glu Glu Asp Gln Asn Thr Arg Val Thr Leu Leu Gly Tyr Leu Lys
                820                 825                 830

Gln Leu His Pro Val Glu Trp Glu Asn Phe Val Lys Asp Thr Lys Ile
            835                 840                 845

Leu Ala Glu Glu Ser Ala Met Phe Asn Gly Pro Ser Pro Phe Gly Asn
    850                 855                 860

Asp Glu Lys Gly Gln Ser Lys Met Asp Asp Leu Pro Phe Tyr Cys Ile
865                 870                 875                 880

Gly Phe Lys Ser Ala Ala Pro Glu Tyr Thr Leu Arg Thr Arg Ile Trp
                    885                 890                 895

Ala Ser Leu Arg Ala Gln Thr Leu Tyr Arg Thr Val Ser Gly Met Met
                900                 905                 910

Asn Tyr Ala Lys Ala Ile Lys Leu Leu Tyr Arg Val Glu Asn Pro Glu
            915                 920                 925

Val Val Gln Gln Phe Gly Gly Asn Thr Asp Lys Leu Glu Arg Glu Leu
    930                 935                 940

Glu Arg Met Ala Arg Arg Lys Phe Lys Phe Leu Val Ser Met Gln Arg
945                 950                 955                 960

Tyr Ser Lys Phe Asn Lys Glu Glu His Glu Asn Ala Glu Phe Leu Leu
                    965                 970                 975

Arg Ala Tyr Pro Asp Leu Gln Ile Ala Tyr Leu Glu Glu Pro Pro
                980                 985                 990

Arg Lys Glu Gly Gly Asp Pro Arg Ile Phe Ser Ala Leu Val Asp Gly
            995                1000                1005

His Ser Asp Ile Ile Pro Glu Thr Gly Lys Arg Arg Pro Lys Phe
    1010                1015                1020
```

```
Arg Ile Glu Leu Pro Gly Asn Pro Ile Leu Gly Asp Gly Lys Ser
    1025                1030                1035

Asp Asn Gln Asn His Ala Ile Val Phe Tyr Arg Gly Glu Tyr Leu
    1040                1045                1050

Gln Leu Ile Asp Ala Asn Gln Asp Asn Tyr Leu Glu Glu Cys Leu
    1055                1060                1065

Lys Ile Arg Asn Val Leu Ala Glu Phe Glu Glu Tyr Asp Val Ser
    1070                1075                1080

Ser Gln Ser Pro Tyr Ala Gln Trp Ser Val Lys Glu Phe Lys Arg
    1085                1090                1095

Ser Pro Val Ala Ile Val Gly Ala Arg Glu Tyr Ile Phe Ser Glu
    1100                1105                1110

His Ile Gly Ile Leu Gly Asp Leu Ala Ala Gly Lys Glu Gln Thr
    1115                1120                1125

Phe Gly Thr Leu Thr Ala Arg Asn Asn Ala Phe Leu Gly Gly Lys
    1130                1135                1140

Leu His Tyr Gly His Pro Asp Phe Leu Asn Ala Leu Tyr Met Asn
    1145                1150                1155

Thr Arg Gly Gly Val Ser Lys Ala Gln Lys Gly Leu His Leu Asn
    1160                1165                1170

Glu Asp Ile Tyr Ala Gly Met Asn Ala Val Gly Arg Gly Gly Arg
    1175                1180                1185

Ile Lys His Ser Glu Tyr Tyr Gln Cys Gly Lys Gly Arg Asp Leu
    1190                1195                1200

Gly Phe Gly Thr Ile Leu Asn Phe Gln Thr Lys Ile Gly Thr Gly
    1205                1210                1215

Met Gly Glu Gln Ile Leu Ser Arg Glu Tyr Tyr Tyr Leu Gly Thr
    1220                1225                1230

Gln Leu Pro Ile Asp Arg Phe Leu Thr Phe Tyr Tyr Ala His Pro
    1235                1240                1245

Gly Phe Gln Ile Asn Asn Met Leu Val Ile Leu Ser Val Gln Val
    1250                1255                1260

Phe Ile Val Thr Met Val Phe Leu Gly Thr Leu Lys Ser Ser Val
    1265                1270                1275

Thr Ile Cys Lys Tyr Thr Ser Ser Gly Gln Tyr Ile Gly Gly Gln
    1280                1285                1290

Ser Gly Cys Tyr Asn Leu Val Pro Val Phe Gln Trp Ile Glu Arg
    1295                1300                1305

Cys Ile Ile Ser Ile Phe Leu Val Phe Met Ile Ala Phe Met Pro
    1310                1315                1320

Leu Phe Leu Gln Glu Leu Val Glu Arg Gly Thr Trp Ser Ala Ile
    1325                1330                1335

Trp Arg Leu Leu Lys Gln Phe Met Ser Leu Ser Pro Val Phe Glu
    1340                1345                1350

Val Phe Ser Thr Gln Ile Gln Thr His Ser Val Leu Ser Asn Leu
    1355                1360                1365

Thr Phe Gly Gly Ala Arg Tyr Ile Ala Thr Gly Arg Gly Phe Ala
    1370                1375                1380

Thr Ser Arg Ile Ser Phe Ser Ile Leu Phe Ser Arg Phe Ala Gly
    1385                1390                1395

Pro Ser Ile Tyr Leu Gly Met Arg Thr Leu Ile Met Leu Leu Tyr
    1400                1405                1410

Val Thr Leu Thr Ile Trp Thr Pro Trp Val Ile Tyr Phe Trp Val
```

```
            1415                1420                1425

Ser Ile Leu Ser Leu Cys Ile Ala Pro Phe Leu Phe Asn Pro His
    1430                1435                1440

Gln Phe Val Phe Ser Asp Phe Leu Ile Asp Tyr Arg Glu Tyr Leu
    1445                1450                1455

Arg Trp Met Ser Arg Gly Asn Ser Arg Ser His Asn Asn Ser Trp
    1460                1465                1470

Ile Gly Tyr Cys Arg Leu Ser Arg Thr Met Ile Thr Gly Tyr Lys
    1475                1480                1485

Lys Lys Lys Leu Gly His Pro Ser Glu Lys Leu Ser Gly Asp Val
    1490                1495                1500

Pro Arg Ala Gly Trp Arg Ala Val Leu Phe Ser Glu Ile Ile Phe
    1505                1510                1515

Pro Ala Cys Met Ala Ile Leu Phe Ile Ile Ala Tyr Met Phe Val
    1520                1525                1530

Lys Ser Phe Pro Leu Asp Gly Lys Gln Pro Pro Ser Gly Leu Val
    1535                1540                1545

Arg Ile Ala Val Val Ser Ile Gly Pro Ile Val Trp Asn Ala Ala
    1550                1555                1560

Ile Leu Leu Thr Leu Phe Leu Val Ser Leu Phe Leu Gly Pro Met
    1565                1570                1575

Leu Asp Pro Val Phe Pro Leu Phe Gly Ser Val Met Ala Phe Ile
    1580                1585                1590

Ala His Phe Leu Gly Thr Ile Gly Met Ile Gly Phe Phe Glu Phe
    1595                1600                1605

Leu Trp Phe Leu Glu Ser Trp Glu Ala Ser His Ala Val Leu Gly
    1610                1615                1620

Leu Ile Ala Val Ile Ser Ile Gln Arg Ala Ile His Lys Ile Leu
    1625                1630                1635

Ile Ala Val Phe Leu Ser Arg Glu Phe Lys His Asp Glu Thr Asn
    1640                1645                1650

Arg Ala Trp Trp Thr Gly Arg Trp Tyr Gly Arg Gly Leu Gly Thr
    1655                1660                1665

His Ala Met Ser Gln Pro Ala Arg Glu Phe Val Val Lys Ile Ile
    1670                1675                1680

Glu Leu Ser Leu Trp Ser Ser Asp Leu Ile Leu Gly His Ile Leu
    1685                1690                1695

Leu Phe Met Leu Thr Pro Ala Val Leu Ile Pro Tyr Phe Asp Arg
    1700                1705                1710

Leu His Ala Met Met Leu Phe Trp Leu Arg Pro Ser Lys Gln Ile
    1715                1720                1725

Arg Ala Pro Leu Tyr Ser Ile Lys Gln Lys Arg Gln Arg Arg Trp
    1730                1735                1740

Ile Ile Met Lys Tyr Gly Thr Val Tyr Val Thr Val Ile Ala Ile
    1745                1750                1755

Phe Val Ala Leu Ile Ala Leu Pro Leu Val Phe Arg His Thr Leu
    1760                1765                1770

Lys Val Glu Cys Ser Leu Cys Asp Ser Leu
    1775                1780

<210> SEQ ID NO 13
<211> LENGTH: 5223
<212> TYPE: DNA
<213> ORGANISM: Schizophyllum commune
```

<400> SEQUENCE: 13

```
atgtccggtc caggatatgg caggaatcca ttcgacaatc ccccgcccaa cagaggtccc      60
tatggccagc agccaggttt cccggggccc ggccctcggc cttacgactc ggacgcggac     120
atgagccaga cctatggcag cacaaccagg ctcgccggca gtgccggtta cagcgacaga     180
aacggcagct tcgacggcga ccgctcctac gcgccctcaa ttgactcgcg cgccagcgtg     240
cccagcatat cgcccttcgc agacccgggt atcggctcta atgagccgta tcccgcttgg     300
tcggtcgaac gccagatccc catgtccacg gaggagattg aggatatctt cctcgacctc     360
acccaaaagt ttggcttcca gcgcgactcc atgcggaata cgttcgactt catgatgcac     420
ctccttgatt cccgtgcctc gcgcatgacg cccaaccaag ctctgctcac gcttcacgcc     480
gactacattg gtggccagca cgccaactat aggaagtggt atttcgccgc tcagctcaac     540
ctcgatgacg cggtcgggca aaccaataac cccggtatcc agcgcttgaa gaccatcaag     600
ggcgctacga agaccaagtc gctcgacagc gcactcaacc gctggcgcaa tgcgatgaac     660
aacatgagcc agtacgatcg cctccggcaa attgcgctct atctcctctg ctggggagaa     720
gcaggcaaca tccgtctggc gcccgagtgc ttgtgcttca tcttcaagtg cgcggacgac     780
tactacagaa gtcccgagtg tcagaaccgg atggaccccg tgccggaagg gctgtacctc     840
cagacggtca tcaagccgct ctatcgcttc tacgtgatca aggcgtacga agtcgttgat     900
gggaagcaag tgaagcgcga aaggaccac gaccagatta tcggttatga cgacgtcaac     960
cagttattct ggtatccgga aggtttggct aagatcgtca tgtcggacaa cacacgactt    1020
gtagatgtac ctccggcgca gcggttcatg aagttcgcca agatcgagtg gaaccgcgtc    1080
ttcttcaaga cgtactttga gaagcgctct actgcccatc tcctggtcaa cttcaaccgt    1140
atatggatcc tccacgtctc gatgtacttc ttctacacgg cattcaactc tccacgagtc    1200
tacgcgccgc acggcaaact cgaccgctcc cctgagatga cctggtccgc gactgccctt    1260
ggaggcgctg tgtccaccat gatcatgatc cttgccacta tcgcggagta cctacatc     1320
cccacgacat ggaacaatgc gtcgcacctc accacgcggc tcattttcct cctggtcatc    1380
ctcgcgctca ctgctggacc aacattctat atcgccatga tagacggacg cacggacatc    1440
ggccaagtac cactcatcgt ggccatagtg cagttcttca tctccgtcgt cgccacccta    1500
gctttcgcta ccatcccttc tggtcgcatg ttcggcgacc gtgtggctgg caagtcaaga    1560
aagcacatgg catcgcagac gttcacagcg tcgtacccgt ccatgaagcg gtcatctcgc    1620
gtagcgagta tcatgctgtg gcttttggtc tttggctgca aatacgtcga gtcttacttc    1680
ttcttgacgt cctccttctc cagcccgatc gcggtcatgg cgcgtacgaa ggtacagggc    1740
tgcaacgacc gtatcttcgg cagccagctg tgcacgaatc aggtcccgtt cgcgctggca    1800
atcatgtacg tgatggacct ggtactgttc ttcctggaca cgtacctgtg gtacatcatc    1860
tggctggtga tcttctcgat ggtgcgcgcg ttcaagcttg gtatctcgat ctggacgccc    1920
tggagcgaga tcttcacccg catgccgaag cgtatctacg cgaagctgct ggcgacggcc    1980
gagatggagg tcaagtataa gcccaaggtg ctcgtctcgc aaatctggaa cgcggtcatc    2040
atctccatgt accgggagca tctcttgtcc atcgagcacg tccagcgcct gctataccac    2100
caggttgatg gtccagacgg tcgccgcacc ctcagggcac cgccgttctt caccagccag    2160
cgaactgcga agccaggcct gttcttccct cctggtggcg aggctgagcg ccgtatctcg    2220
ttctttgcct catcgctgac gaccgcgctc cctgagcctc tgccgatcga cgccatgccc    2280
```

```
accttcaccg tgctcgttcc ccattactcg gagaagattc tgctcagtct gcgcgagatt    2340
attcgcgagg aggaccagaa cacccgcgtc accttgctgg agtacctcaa gcagctccac    2400
cctgtcgaat gggacaactt cgtcaaggac accaagatct tggcggaaga gtcgggcgac    2460
gtccaggaca gaagcgcgc gcgcacggac gacttgccgt tctactgcat cgggttcaag    2520
acctcgtcac cagagtacac cctgcgtacg cgtatctggg cttcactgcg cgcacagacg    2580
ctgtaccgca cggtctccgg tatgatgaac tactccaagg cgatcaagct cctctatcgc    2640
gtcgagaacc cggatgtcgt tcatgccttc ggtgggaaca cggaacgtct tgaacgcgag    2700
cttgagcgca tgtctcgccg caagttcaag ttcgtcatct cgatgcagcg gtactctaag    2760
ttcaacaagg aggagcaaga aacgccgaa ttccttctgc gcgcgtaccc ggatttgcag    2820
atcgcgtacc tcgatgaaga gcccggtccc agcaagagcg acgaggttcg gttgttttcg    2880
acactcatcg atggacactc cgaggtggat gagaagaccg gccgccgcaa gcccaagttc    2940
cgcattgagc tgcccggtaa ccccatcctc ggtgacggga agtcggataa ccagaaccac    3000
gccattgtct tctaccgcgg cgagtacatc caggtcatcg acgctaacca ggacaattac    3060
ctggaagagt gtctcaagat ccgtaacgtc ctgggcgagt ttgaggaata ctccgtgtcg    3120
agccagagcc cgtacgcaca gtggggccac aaggagttca acaagtgccc cgtcgctatc    3180
ctgggttctc gcgagtacat cttctcggag aacatcggta tcctcggtga catcgccgcc    3240
ggcaaggaac agacgttcgg taccattacg gcgcgtgcgc ttgcgtggat cggcggcaag    3300
ctgcattacg gtcacccgga tttcctcaat gcgacgttca tgacgacgcg tggtggcgtg    3360
tcaaaagcgc agaagggctt gcatctcaac gaggatatct tcgctggtat gaccgccgtg    3420
tcccgcggag ggcgcatcaa gcacatggag tactaccagt gcggcaaagg tcgtgatctc    3480
ggtttcggca cgatcttgaa cttccagacg aagatcggta ctggtatggg cgagcagctc    3540
ctctcgcgcg agtactacta cctgggcacg caattgccta tcgaccggtt cttgacgttc    3600
tactacgcgc acgctggttt ccacgtcaac aacatcctgg tcatctactc catccaggtc    3660
ttcatggtca ccttgctgta cctgggcaca ttgaacaagc agctgttcat ctgcaaggtc    3720
aactccaatg ccaggttct tagtggacaa gctgggtgct acaacctcat cccggtcttc    3780
gagtggattc gccggagtat catctccatc ttcttggtgt tcttcatcgc cttcttgcct    3840
ctattcttgc aagagctgtg cgagcgcgga acgggaaagg cgttgctgcg tctcgggaag    3900
cacttcttgt cactgtcgcc cattttcgaa gtgttctcca cccagattta ctcgcaggcg    3960
ctcttgaaca acatgagctt cggtggtgcg cgctacatcg ccacaggtcg tggtttcgcg    4020
actagtcgca taccctcaa catcctctac tcgcgtttcg cgccgccaag catctacatg    4080
ggcatgcgta acctgctgct cctgctgtac gcgacgatgg ccatttggat cccgcacctg    4140
atctacttct ggttctccgt cctctccctc tgcatcgcgc cattcatgtt caatccgcat    4200
caattctcgt acgccgactt catcatcgac taccggagt tcttgcgctg gatgtcgcgc    4260
ggtaactcgc gaacgaaggc gagcagctgg tacggatact gccgtctgtc gcgtaccgcg    4320
attactgggt acaagaagaa gaagctggga cacccgtcgg agaagctgtc gggcgacgta    4380
ccgcgtgcgc cgtggaggaa cgttatcttc tcggagatcc tgtggcccat cggcgcgtgc    4440
atcatcttca tcgtcgcgta catgttcgtc aagtcgttcc ccgacgagca gggcaacgcg    4500
ccgccgagcc cgctggtccg gattctgctc atcgcggttg gccctactgt gtggaacgcg    4560
gcggtgctca taacgctgtt cttcctgtcg ctccttcctgg gcccgatgat ggatggctgg    4620
gtcaagttcg gctcggtcat ggcggcccct tgcgcatggcc tggcgcttat aggcatgctc    4680
```

-continued

```
acgttctttg agttcttctg gttccttgag ctctgggatg cctcgcacgc cgtgctcggc    4740
gtcatcgcta tcattgccgt tcagcgcggg atccagaaga tcctcattgc cgtcttcctg    4800
acgcgtgagt acaagcacga cgagacgaac cgcgcgtggt ggacaggtaa atggtatgga    4860
cgcgggctgg gtacctcggc catgtcccag ccggcgcgcg agttcatcgt gaagatcgtg    4920
gagatgtcgt tgtggacgtc ggacttcctg cttgcgcacc tgttgctcat catcttgacg    4980
gtgccgctac tgctgccgtt cttcaactca attcattcga cgatgctttt ctggttgcgc    5040
ccttcgaagc agattaggca acctctgttc tccaccaagc agaagcggca acggcgatgg    5100
attgtcatga agtataccgt ggtatatctc gtggtggtgg cttttcctcgt cgcgctcatc    5160 gctctgcccg ccctcttccg cgagagcatc cacttcaact gcgagatctg ccagagtata    5220
tag                                                                  5223
```

<210> SEQ ID NO 14
<211> LENGTH: 1740
<212> TYPE: PRT
<213> ORGANISM: Schizophyllum commune

<400> SEQUENCE: 14

```
Met Ser Gly Pro Gly Tyr Gly Arg Asn Pro Phe Asp Asn Pro Pro Pro
1               5                   10                  15

Asn Arg Gly Pro Tyr Gly Gln Gln Pro Gly Phe Pro Gly Pro Gly Pro
            20                  25                  30

Arg Pro Tyr Asp Ser Asp Ala Asp Met Ser Gln Thr Tyr Gly Ser Thr
        35                  40                  45

Thr Arg Leu Ala Gly Ser Ala Gly Tyr Ser Arg Asn Gly Ser Phe
    50                  55                  60

Asp Gly Asp Arg Ser Tyr Ala Pro Ser Ile Asp Ser Arg Ala Ser Val
65                  70                  75                  80

Pro Ser Ile Ser Pro Phe Ala Asp Pro Gly Ile Gly Ser Asn Glu Pro
                85                  90                  95

Tyr Pro Ala Trp Ser Val Glu Arg Gln Ile Pro Met Ser Thr Glu Glu
            100                 105                 110

Ile Glu Asp Ile Phe Leu Asp Leu Thr Gln Lys Phe Gly Phe Gln Arg
        115                 120                 125

Asp Ser Met Arg Asn Thr Phe Asp Phe Met Met His Leu Leu Asp Ser
    130                 135                 140

Arg Ala Ser Arg Met Thr Pro Asn Gln Ala Leu Leu Thr Leu His Ala
145                 150                 155                 160

Asp Tyr Ile Gly Gly Gln His Ala Asn Tyr Arg Lys Trp Tyr Phe Ala
                165                 170                 175

Ala Gln Leu Asn Leu Asp Asp Ala Val Gly Gln Thr Asn Asn Pro Gly
            180                 185                 190

Ile Gln Arg Leu Lys Thr Ile Lys Gly Ala Thr Lys Thr Lys Ser Leu
        195                 200                 205

Asp Ser Ala Leu Asn Arg Trp Arg Asn Ala Met Asn Asn Met Ser Gln
    210                 215                 220

Tyr Asp Arg Leu Arg Gln Ile Ala Leu Tyr Leu Leu Cys Trp Gly Glu
225                 230                 235                 240

Ala Gly Asn Ile Arg Leu Ala Pro Glu Cys Leu Cys Phe Ile Phe Lys
                245                 250                 255

Cys Ala Asp Tyr Tyr Arg Ser Pro Glu Cys Gln Asn Arg Met Asp
            260                 265                 270
```

```
Pro Val Pro Glu Gly Leu Tyr Leu Gln Thr Val Ile Lys Pro Leu Tyr
            275                 280                 285

Arg Phe Leu Arg Asp Gln Ala Tyr Glu Val Val Asp Gly Lys Gln Val
290                 295                 300

Lys Arg Glu Lys Asp His Asp Gln Ile Ile Gly Tyr Asp Asp Val Asn
305                 310                 315                 320

Gln Leu Phe Trp Tyr Pro Glu Gly Leu Ala Lys Ile Val Met Ser Asp
                325                 330                 335

Asn Thr Arg Leu Val Asp Val Pro Ala Gln Arg Phe Met Lys Phe
                340                 345                 350

Ala Lys Ile Glu Trp Asn Arg Val Phe Phe Lys Thr Tyr Phe Glu Lys
            355                 360                 365

Arg Ser Thr Ala His Leu Leu Val Asn Phe Asn Arg Ile Trp Ile Leu
            370                 375                 380

His Val Ser Met Tyr Phe Phe Tyr Thr Ala Phe Asn Ser Pro Arg Val
385                 390                 395                 400

Tyr Ala Pro His Gly Lys Leu Asp Pro Ser Pro Glu Met Thr Trp Ser
                405                 410                 415

Ala Thr Ala Leu Gly Gly Ala Val Ser Thr Met Ile Met Ile Leu Ala
            420                 425                 430

Thr Ile Ala Glu Tyr Thr Tyr Ile Pro Thr Thr Trp Asn Asn Ala Ser
            435                 440                 445

His Leu Thr Thr Arg Leu Ile Phe Leu Leu Val Ile Leu Ala Leu Thr
            450                 455                 460

Ala Gly Pro Thr Phe Tyr Ile Ala Met Ile Asp Gly Arg Thr Asp Ile
465                 470                 475                 480

Gly Gln Val Pro Leu Ile Val Ala Ile Val Gln Phe Phe Ile Ser Val
                485                 490                 495

Val Ala Thr Leu Ala Phe Ala Thr Ile Pro Ser Gly Arg Met Phe Gly
            500                 505                 510

Asp Arg Val Ala Gly Lys Ser Arg Lys His Met Ala Ser Gln Thr Phe
            515                 520                 525

Thr Ala Ser Tyr Pro Ser Met Lys Arg Ser Ser Arg Val Ala Ser Ile
            530                 535                 540

Met Leu Trp Leu Leu Val Phe Gly Cys Lys Tyr Val Glu Ser Tyr Phe
545                 550                 555                 560

Phe Leu Thr Ser Ser Phe Ser Ser Pro Ile Ala Val Met Ala Arg Thr
                565                 570                 575

Lys Val Gln Gly Cys Asn Asp Arg Ile Phe Gly Ser Gln Leu Cys Thr
            580                 585                 590

Asn Gln Val Pro Phe Ala Leu Ala Ile Met Tyr Val Met Asp Leu Val
            595                 600                 605

Leu Phe Phe Leu Asp Thr Tyr Leu Trp Tyr Ile Ile Trp Leu Val Ile
610                 615                 620

Phe Ser Met Val Arg Ala Phe Lys Leu Gly Ile Ser Ile Trp Thr Pro
625                 630                 635                 640

Trp Ser Glu Ile Phe Thr Arg Met Pro Lys Arg Ile Tyr Ala Lys Leu
                645                 650                 655

Leu Ala Thr Ala Glu Met Glu Val Lys Tyr Lys Pro Lys Val Leu Val
            660                 665                 670

Ser Gln Ile Trp Asn Ala Val Ile Ile Ser Met Tyr Arg Glu His Leu
            675                 680                 685
```

-continued

```
Leu Ser Ile Glu His Val Gln Arg Leu Leu Tyr His Gln Val Asp Gly
    690                 695                 700

Pro Asp Gly Arg Arg Thr Leu Arg Ala Pro Pro Phe Phe Thr Ser Gln
705                 710                 715                 720

Arg Thr Ala Lys Pro Gly Leu Phe Phe Pro Gly Gly Ala Glu
                725                 730                 735

Arg Arg Ile Ser Phe Phe Ala Ser Ser Leu Thr Thr Ala Leu Pro Glu
                740                 745                 750

Pro Leu Pro Ile Asp Ala Met Pro Thr Phe Thr Val Leu Val Pro His
        755                 760                 765

Tyr Ser Glu Lys Ile Leu Leu Ser Leu Arg Glu Ile Ile Arg Glu Glu
770                 775                 780

Asp Gln Asn Thr Arg Val Thr Leu Leu Glu Tyr Leu Lys Gln Leu His
785                 790                 795                 800

Pro Val Glu Trp Asp Asn Phe Val Lys Asp Thr Lys Ile Leu Ala Glu
                805                 810                 815

Glu Ser Gly Asp Val Gln Asp Glu Lys Arg Ala Arg Thr Asp Asp Leu
                820                 825                 830

Pro Phe Tyr Cys Ile Gly Phe Lys Thr Ser Ser Pro Glu Tyr Thr Leu
                835                 840                 845

Arg Thr Arg Ile Trp Ala Ser Leu Arg Ala Gln Thr Leu Tyr Arg Thr
850                 855                 860

Val Ser Gly Met Met Asn Tyr Ser Lys Ala Ile Lys Leu Leu Tyr Arg
865                 870                 875                 880

Val Glu Asn Pro Asp Val Val His Ala Phe Gly Gly Asn Thr Glu Arg
                885                 890                 895

Leu Glu Arg Glu Leu Glu Arg Met Ser Arg Arg Lys Phe Lys Phe Val
                900                 905                 910

Ile Ser Met Gln Arg Tyr Ser Lys Phe Asn Lys Glu Glu Gln Glu Asn
            915                 920                 925

Ala Glu Phe Leu Leu Arg Ala Tyr Pro Asp Leu Gln Ile Ala Tyr Leu
        930                 935                 940

Asp Glu Glu Pro Gly Pro Ser Lys Ser Asp Glu Val Arg Leu Phe Ser
945                 950                 955                 960

Thr Leu Ile Asp Gly His Ser Glu Val Asp Lys Thr Gly Arg Arg
                965                 970                 975

Lys Pro Lys Phe Arg Ile Glu Leu Pro Gly Asn Pro Ile Leu Gly Asp
                980                 985                 990

Gly Lys Ser Asp Asn Gln Asn His Ala Ile Val Phe Tyr Arg Gly Glu
            995                 1000                1005

Tyr Ile Gln Val Ile Asp Ala Asn Gln Asp Asn Tyr Leu Glu Glu
        1010                1015                1020

Cys Leu Lys Ile Arg Asn Val Leu Gly Glu Phe Glu Glu Tyr Ser
        1025                1030                1035

Val Ser Ser Gln Ser Pro Tyr Ala Gln Trp Gly His Lys Glu Phe
        1040                1045                1050

Asn Lys Cys Pro Val Ala Ile Leu Gly Ser Arg Glu Tyr Ile Phe
        1055                1060                1065

Ser Glu Asn Ile Gly Ile Leu Gly Asp Ile Ala Ala Gly Lys Glu
        1070                1075                1080

Gln Thr Phe Gly Thr Ile Thr Ala Arg Ala Leu Ala Trp Ile Gly
        1085                1090                1095

Gly Lys Leu His Tyr Gly His Pro Asp Phe Leu Asn Ala Thr Phe
```

-continued

```
                1100                1105                1110
Met Thr Thr Arg Gly Gly Val Ser Lys Ala Gln Lys Gly Leu His
    1115                1120                1125

Leu Asn Glu Asp Ile Phe Ala Gly Met Thr Ala Val Ser Arg Gly
    1130                1135                1140

Gly Arg Ile Lys His Met Glu Tyr Tyr Gln Cys Gly Lys Gly Arg
    1145                1150                1155

Asp Leu Gly Phe Gly Thr Ile Leu Asn Phe Gln Thr Lys Ile Gly
    1160                1165                1170

Thr Gly Met Gly Glu Gln Leu Leu Ser Arg Glu Tyr Tyr Tyr Leu
    1175                1180                1185

Gly Thr Gln Leu Pro Ile Asp Arg Phe Leu Thr Phe Tyr Tyr Ala
    1190                1195                1200

His Ala Gly Phe His Val Asn Asn Ile Leu Val Ile Tyr Ser Ile
    1205                1210                1215

Gln Val Phe Met Val Thr Leu Leu Tyr Leu Gly Thr Leu Asn Lys
    1220                1225                1230

Gln Leu Phe Ile Cys Lys Val Asn Ser Asn Gly Gln Val Leu Ser
    1235                1240                1245

Gly Gln Ala Gly Cys Tyr Asn Leu Ile Pro Val Phe Glu Trp Ile
    1250                1255                1260

Arg Arg Ser Ile Ile Ser Ile Phe Leu Val Phe Phe Ile Ala Phe
    1265                1270                1275

Leu Pro Leu Phe Leu Gln Glu Leu Cys Glu Arg Gly Thr Gly Lys
    1280                1285                1290

Ala Leu Leu Arg Leu Gly Lys His Phe Leu Ser Leu Ser Pro Ile
    1295                1300                1305

Phe Glu Val Phe Ser Thr Gln Ile Tyr Ser Gln Ala Leu Leu Asn
    1310                1315                1320

Asn Met Ser Phe Gly Gly Ala Arg Tyr Ile Ala Thr Gly Arg Gly
    1325                1330                1335

Phe Ala Thr Ser Arg Ile Pro Phe Asn Ile Leu Tyr Ser Arg Phe
    1340                1345                1350

Ala Pro Pro Ser Ile Tyr Met Gly Met Arg Asn Leu Leu Leu Leu
    1355                1360                1365

Leu Tyr Ala Thr Met Ala Ile Trp Ile Pro His Leu Ile Tyr Phe
    1370                1375                1380

Trp Phe Ser Val Leu Ser Leu Cys Ile Ala Pro Phe Met Phe Asn
    1385                1390                1395

Pro His Gln Phe Ser Tyr Ala Asp Phe Ile Ile Asp Tyr Arg Glu
    1400                1405                1410

Phe Leu Arg Trp Met Ser Arg Gly Asn Ser Arg Thr Lys Ala Ser
    1415                1420                1425

Ser Trp Tyr Gly Tyr Cys Arg Leu Ser Arg Thr Ala Ile Thr Gly
    1430                1435                1440

Tyr Lys Lys Lys Lys Leu Gly His Pro Ser Glu Lys Leu Ser Gly
    1445                1450                1455

Asp Val Pro Arg Ala Pro Trp Arg Asn Val Ile Phe Ser Glu Ile
    1460                1465                1470

Leu Trp Pro Ile Gly Ala Cys Ile Ile Phe Ile Val Ala Tyr Met
    1475                1480                1485

Phe Val Lys Ser Phe Pro Asp Glu Gln Gly Asn Ala Pro Pro Ser
    1490                1495                1500
```

```
Pro Leu Val Arg Ile Leu Leu Ile Ala Val Gly Pro Thr Val Trp
    1505                1510                1515

Asn Ala Ala Val Leu Ile Thr Leu Phe Phe Leu Ser Leu Phe Leu
    1520                1525                1530

Gly Pro Met Met Asp Gly Trp Val Lys Phe Gly Ser Val Met Ala
    1535                1540                1545

Ala Leu Ala His Gly Leu Ala Leu Ile Gly Met Leu Thr Phe Phe
    1550                1555                1560

Glu Phe Phe Trp Phe Leu Glu Leu Trp Asp Ala Ser His Ala Val
    1565                1570                1575

Leu Gly Val Ile Ala Ile Ile Ala Val Gln Arg Gly Ile Gln Lys
    1580                1585                1590

Ile Leu Ile Ala Val Phe Leu Thr Arg Glu Tyr Lys His Asp Glu
    1595                1600                1605

Thr Asn Arg Ala Trp Trp Thr Gly Lys Trp Tyr Gly Arg Gly Leu
    1610                1615                1620

Gly Thr Ser Ala Met Ser Gln Pro Ala Arg Glu Phe Ile Val Lys
    1625                1630                1635

Ile Val Glu Met Ser Leu Trp Thr Ser Asp Phe Leu Leu Ala His
    1640                1645                1650

Leu Leu Leu Ile Ile Leu Thr Val Pro Leu Leu Pro Phe Phe
    1655                1660                1665

Asn Ser Ile His Ser Thr Met Leu Phe Trp Leu Arg Pro Ser Lys
    1670                1675                1680

Gln Ile Arg Gln Pro Leu Phe Ser Thr Lys Gln Lys Arg Gln Arg
    1685                1690                1695

Arg Trp Ile Val Met Lys Tyr Thr Val Val Tyr Leu Val Val Val
    1700                1705                1710

Ala Phe Leu Val Ala Leu Ile Ala Leu Pro Ala Leu Phe Arg Glu
    1715                1720                1725

Ser Ile His Phe Asn Cys Glu Ile Cys Gln Ser Ile
    1730                1735                1740
```

<210> SEQ ID NO 15
<211> LENGTH: 5352
<212> TYPE: DNA
<213> ORGANISM: Schizophyllum commune

<400> SEQUENCE: 15

```
atgccgaggc cgggcggcac cagcgcagaa ggcggctacg catcatcgcc gtcgatggag      60
acgaccccca gcgatccctt cggaaccgcg aacggcgcgc cccgccgcta ctacgacaat     120
gattctgagg agtacggacc tggccgtaga gacacctacg cgtccgacag cagtaatcag     180
ggcctcacgg acccgggcta ctacgaccag aatggcgcct atgatcccta tccgaccggg     240
gacaccgatt ccgacggcga cgtctacggc cagcgatatg accctcagc agagtcgctt      300 ggcacccaca gttcggcca ttccgattca tccacgccga cttttgtcga ctacagcgca     360
tcctccggcg ggagggattc gtaccctgca tggactgccg aacgcaacat cccgctgtcc     420
aaggaggaga tcgaggacat cttcctcgat ttgacgcaga agtttggctt tcagcgggat     480
tccatgcgga atatgttcga cttcaccatg cagctgcttg acagccgagc gtctcgtatg     540
acccccaacc aggcgctcct caccctccac gccgactaca ttggtggcca gcatgcgaac     600
taccggaagt ggtacttcgc ggcgcagctc gaccttgacg acgccgtggg acaaactcag     660
```

```
aatccgggtc tcaaccgcct caagtccact cgcggatcgg gcaagcgacc acgccatgaa    720
aagtcgctga acacggcatt ggagcgctgg cggcaagcca tgaacaacat gtcgcagtat    780
gaccgcttac gccagatcgc gctctacctg ctctgctggg gcgaagcggc gcaagtgcga    840
ttcatgcccg agtgcttgtg cttcatcttc aagtgcgccg acgactacta tcgttcgccg    900
gagtgccaga acaggatgga gccggtaccg gagggtctct acctgaggac ggtcgtaaag    960
ccgctctaca gatttgtccg ggatcaaggc tatgaggtgg tggagggaaa attcgtacgg   1020
cgggaacggg atcacgacca aatcattggt tacgatgacg tgaatcagct gttctggtac   1080
ccggagggaa ttgcccgtat cgtcctgtcg acaagagtc gtctagtcga cctcccccca   1140
gcacagcgct tcatgaagtt cgaccgtatc gagtggaatc gcgtcttctt caagacgttt   1200
tacgagactc gatccttcac gcatctttg gtcgacttca accgtatctg gtcgtgcac    1260
atcgctctct acttcttcta cactgcatac aactccccca cgatctacgc catcaacggc   1320
aacacaccga cgtctctggc ttggagcgcg actgcgctcg gcggtgcggt agcgacaggt   1380
atcatgatcc tcgccacgat cgccgagttc tcgcacatcc ccacgacatg gaacaacacc   1440
tcgcatctga ctcgccgcct cgccttcctc ctcgtcacgc tcggcctcac atgtggtccg   1500
acgttctacg tcgcgattgc agagagcaac gggagcggcg gctcttttggc cttgattctc   1560
ggtatcgtcc agttcttcat ctccgtcgtg gcaactgcgc tcttcactat catgccttct   1620
ggtcgtatgt tcggcgaccg tgtcgcaggc aagagtcgca agtatctcgc cagccagacg   1680
ttcacggcca gctacccgtc gttgcccaag caccagcggt tcgcctcact cctgatgtgg   1740
ttcctcatct tcgggtgcaa gttgacggag agttacttct ttctgacgct gtccttccgc   1800
gaccctatcc gcgtcatggt cggcatgaag atccagaact gcgaggacaa gattttcggc   1860
agcggccttt gcaggaatca cgcagcattc accctcacga tcatgtacat catggacctc   1920
gtcttgttct cctcgacac cttcctttgg tatgtcatct ggaactcggt tttcagtatc   1980
gcacgctctt tcgtactcgg ccttcgatc tggacaccgt ggagagacat cttccagcgt   2040
ctgccgaagc ggatctacgc gaagcttctg gcgactggcg acatggaggt caagtacaag   2100
cccaaggtct tggtctcgca aatctggaac gccatcatca tctccatgta ccgcgagcac   2160
ttgctctcta ttgagcacgt ccagaagctc ctgtaccacc aagtggacac tggcgaagcc   2220
ggcaagcgga gtcttcgcgc gcctccgttc ttcgtcgcgc agggcagcag cggtggctcg   2280
ggcgagttct tcccgcctgg cagcgaggcc gagcgtcgta tctcttttctt cgcgcagtcg   2340
ctttctacgg agattcctca gcccatcccg gtcgacgcca tgccgacgtt cacggtgctt   2400
acgcctcact acagcgagaa gatccttctc tctctccgtg aaattatccg cgaggaggac   2460
cagaacactc gcgttacgtt gctcgagtac ctgaagcagc tgcatccggt cgagtgggag   2520
aatttcgtca aggacactaa aattttggcc gaggagtccg ctatgtttaa cggtccgagt   2580
cctttcggca acgacgagaa gggtcagtcc aagatggacg atctaccgtt ctactgcatc   2640
ggtttcaaga gcgccgcgcc cgagtacacc ctccgcaccc gtatctgggc gtccctgcgc   2700
gcgcagacgc tgtaccgcac ggtctccggc atgatgaact atgcgaaggc gatcaagctg   2760
ctctaccgcg ttgagaaccc ggaggtcgta caacagttcg gcggcaacac ggacaagctc   2820
gagcgcgagt tggagcggat ggcgcgacgg aagttcaagt tcctcgtgtc catgcagcgc   2880
tactcgaagt tcaacaagga ggagcacgag aacgccgagt tcttgctccg cgcgtacccg   2940
gacttgcaga tcgcgtacct cgaggaagag cccctcgca aggagggcgg cgatccacgc   3000
atcttctctg ccctcgtcga cggccacagc gacatcatcc cggagaccgg caagcggcgc   3060
```

-continued

```
cccaagttcc gtatcgagct gcccggtaac cccattctcg gtgacggtaa atccgacaat    3120
cagaaccacg ctatcgtctt ctaccgcggc gagtacctcc agcttatcga cgccaaccag    3180
gacaactacc tcgaggagtg cttgaagatc cgtaacgtgc tcgccgagtt tgaggagtac    3240
gacgtctcca gccagagccc gtacgcgcag tggagtgtca aggagttcaa gcgctctccg    3300
gtcgccatcg tcggtgcacg cgagtacatc ttctcagagc acatcggtat cctcggtgat    3360
ctggcggctg gcaaggaaca gacgttcggt acgctcacgg cacgcaacaa cgccttcctt    3420
ggcggcaagc tgcactacgg tcaccccgat ttcctcaacg ccctctacat gaacacgcgc    3480
ggtggtgtct ccaaggcgca gaagggtctc catctcaacg aggatatcta cgccggtatg    3540
aacgcggtcg gtcgcggtgg acgcattaag cacagcgagt actatcagtg cggcaagggt    3600
cgtgacctcg gtttcggcac catcttgaac ttccagacca agatcggtac gggtatgggc    3660
gagcagatcc tctcgcgcga gtactactat ctcggaacac aactgcccat cgatcgcttc    3720
ctcacgttct actacgcgca cccgggtttc cagatcaaca acatgctggt catcctctcc    3780
gtgcaggtct tcatcgttac catggtcttc ctcggtacct gaagtcttc ggtcacgatc    3840
tgcaagtaca cgtccagcgg tcagtacatc ggtggtcaat ccggttgcta caacctcgtc    3900
ccggtcttcc agtggatcga gcgctgcatc atcagcatct tcttggtgtt catgatcgct    3960
ttcatgccgc tcttcctgca agaactcgtc gagcgcggta cctggagtgc catctggcgt    4020
ctgctcaagc agtttatgtc gctgtcgcct gtcttcgagg tgttctccac ccagattcag    4080
acgcactccg tgttgagcaa cttgacgttc ggtggtgcgc gttacatcgc taccggtcgt    4140
gggttcgcca ccagtcgtat cagcttcagc atcttgttct cgcgtttcgc aggcccgagt    4200
atctacctcg gcatgcgcac gctcattatg ctgctctacg tgacgttgac gatctggacg    4260
ccatgggtca tttacttctg ggtttccatt ctctcgctct gcatcgcgcc gttcttgttc    4320
aacccgcatc aattcgtatt ctcggacttc ctcatcgact acagggaata cctgcggtgg    4380
atgtcgcgtg gcaactcgcg ctcgcacaac aactcctgga ttgggtactg ccggttgtcc    4440
cgcacgatga tcactgggta caagaagaag aagctgggcc acccgtcgga gaagctttcc    4500
ggcgacgttc ctcgtgcagg ctggcgcgcc gtcttgttct cggagatcat cttcccggcg    4560
tgcatggcca tcctcttcat catcgcgtac atgttcgtca agtcgttccc tctcgacggc    4620
aagcagcctc cctccggcct cgttcgcatc gccgtcgtgt ctatcggccc catcgtgtgg    4680
aacgccgcca tcctgttgac gctcttcctt gtgtcgttgt tcctcggccc catgctcgac    4740
ccggtcttcc cctcttcgg ttccgttatg gccttcatcg cgcatttcct tggcacaatc    4800
ggaatgattg ggttcttcga gttcctgtgg ttcctcgagt cctgggaggc gtcgcatgcc    4860
gtgctgggtc tcatcgccgt catctccatc cagcgcgcca ttcacaagat ccttatcgcc    4920
gttttcctca gtcgcgagtt caagcacgac gagacgaaca gggcctggtg gactggtcgc    4980
tggtatggcc gtggcctcgg cacgcacgcc atgtcgcagc cggcgcgtga gttcgtcgtc    5040
aagatcatcg agttgtcgct ttggagctcg gatctcatac tcggccacat cctgctgttc    5100
atgcttactc cggccgtcct catcccgtac ttcgaccgtt tgcacgccat gatgctcttc    5160
tggctgcgtc cctcgaagca aatccgcgcg cctctgtact cgatcaagca gaagaggcaa    5220
agacgctgga ttatcatgaa gtacggtact gtatacgtta ccgtcatcgc gatcttcgtc    5280
gcgctcatcg cgcttcccct cgtattccga cacactctaa aggtcgagtg ctcccttttgc    5340
gacagcttgt aa                                                        5352
```

<210> SEQ ID NO 16
<211> LENGTH: 1783
<212> TYPE: PRT
<213> ORGANISM: Schizophyllum commune

<400> SEQUENCE: 16

```
Met Pro Arg Pro Gly Gly Thr Ser Ala Glu Gly Gly Tyr Ala Ser Ser
1               5                   10                  15

Pro Ser Met Glu Thr Thr Pro Ser Asp Pro Phe Gly Thr Ala Asn Gly
            20                  25                  30

Ala Pro Arg Arg Tyr Tyr Asp Asn Asp Ser Glu Glu Tyr Gly Pro Gly
        35                  40                  45

Arg Arg Asp Thr Tyr Ala Ser Asp Ser Ser Asn Gln Gly Leu Thr Asp
    50                  55                  60

Pro Gly Tyr Tyr Asp Gln Asn Gly Ala Tyr Asp Pro Tyr Pro Thr Gly
65                  70                  75                  80

Asp Thr Asp Ser Asp Gly Asp Val Tyr Gly Gln Arg Tyr Gly Pro Ser
                85                  90                  95

Ala Glu Ser Leu Gly Thr His Lys Phe Gly His Ser Asp Ser Ser Thr
            100                 105                 110

Pro Thr Phe Val Asp Tyr Ser Ala Ser Ser Gly Gly Arg Asp Ser Tyr
        115                 120                 125

Pro Ala Trp Thr Ala Glu Arg Asn Ile Pro Leu Ser Lys Glu Glu Ile
    130                 135                 140

Glu Asp Ile Phe Leu Asp Leu Thr Gln Lys Phe Gly Phe Gln Arg Asp
145                 150                 155                 160

Ser Met Arg Asn Met Phe Asp Phe Thr Met Gln Leu Leu Asp Ser Arg
                165                 170                 175

Ala Ser Arg Met Thr Pro Asn Gln Ala Leu Leu Thr Leu His Ala Asp
            180                 185                 190

Tyr Ile Gly Gly Gln His Ala Asn Tyr Arg Lys Trp Tyr Phe Ala Ala
        195                 200                 205

Gln Leu Asp Leu Asp Asp Ala Val Gly Gln Thr Gln Asn Pro Gly Leu
    210                 215                 220

Asn Arg Leu Lys Ser Thr Arg Gly Ser Gly Lys Arg Pro Arg His Glu
225                 230                 235                 240

Lys Ser Leu Asn Thr Ala Leu Glu Arg Trp Arg Gln Ala Met Asn Asn
                245                 250                 255

Met Ser Gln Tyr Asp Arg Leu Arg Gln Ile Ala Leu Tyr Leu Leu Cys
            260                 265                 270

Trp Gly Glu Ala Ala Gln Val Arg Phe Met Pro Glu Cys Leu Cys Phe
        275                 280                 285

Ile Phe Lys Cys Ala Asp Asp Tyr Tyr Arg Ser Pro Glu Cys Gln Asn
    290                 295                 300

Arg Met Glu Pro Val Pro Glu Gly Leu Tyr Leu Arg Thr Val Val Lys
305                 310                 315                 320

Pro Leu Tyr Arg Phe Val Arg Asp Gln Gly Tyr Glu Val Val Glu Gly
                325                 330                 335

Lys Phe Val Arg Arg Glu Arg Asp His Asp Gln Ile Ile Gly Tyr Asp
            340                 345                 350

Asp Val Asn Gln Leu Phe Trp Tyr Pro Glu Gly Ile Ala Arg Ile Val
        355                 360                 365

Leu Ser Asp Lys Ser Arg Leu Val Asp Leu Pro Pro Ala Gln Arg Phe
    370                 375                 380
```

```
Met Lys Phe Asp Arg Ile Glu Trp Asn Arg Val Phe Phe Lys Thr Phe
385                 390                 395                 400

Tyr Glu Thr Arg Ser Phe Thr His Leu Leu Val Asp Phe Asn Arg Ile
            405                 410                 415

Trp Val Val His Ile Ala Leu Tyr Phe Phe Tyr Thr Ala Tyr Asn Ser
                420                 425                 430

Pro Thr Ile Tyr Ala Ile Asn Gly Asn Thr Pro Thr Ser Leu Ala Trp
        435                 440                 445

Ser Ala Thr Ala Leu Gly Gly Ala Val Ala Thr Gly Ile Met Ile Leu
    450                 455                 460

Ala Thr Ile Ala Glu Phe Ser His Ile Pro Thr Thr Trp Asn Asn Thr
465                 470                 475                 480

Ser His Leu Thr Arg Arg Leu Ala Phe Leu Leu Val Thr Leu Gly Leu
                485                 490                 495

Thr Cys Gly Pro Thr Phe Tyr Val Ala Ile Ala Glu Ser Asn Gly Ser
            500                 505                 510

Gly Gly Ser Leu Ala Leu Ile Leu Gly Ile Val Gln Phe Phe Ile Ser
        515                 520                 525

Val Val Ala Thr Ala Leu Phe Thr Ile Met Pro Ser Gly Arg Met Phe
    530                 535                 540

Gly Asp Arg Val Ala Gly Lys Ser Arg Lys Tyr Leu Ala Ser Gln Thr
545                 550                 555                 560

Phe Thr Ala Ser Tyr Pro Ser Leu Pro Lys His Gln Arg Phe Ala Ser
                565                 570                 575

Leu Leu Met Trp Phe Leu Ile Phe Gly Cys Lys Leu Thr Glu Ser Tyr
            580                 585                 590

Phe Phe Leu Thr Leu Ser Phe Arg Asp Pro Ile Arg Val Met Val Gly
        595                 600                 605

Met Lys Ile Gln Asn Cys Glu Asp Lys Ile Phe Gly Ser Gly Leu Cys
    610                 615                 620

Arg Asn His Ala Ala Phe Thr Leu Thr Ile Met Tyr Ile Met Asp Leu
625                 630                 635                 640

Val Leu Phe Phe Leu Asp Thr Phe Leu Trp Tyr Val Ile Trp Asn Ser
                645                 650                 655

Val Phe Ser Ile Ala Arg Ser Phe Val Leu Gly Leu Ser Ile Trp Thr
            660                 665                 670

Pro Trp Arg Asp Ile Phe Gln Arg Leu Pro Lys Arg Ile Tyr Ala Lys
        675                 680                 685

Leu Leu Ala Thr Gly Asp Met Glu Val Lys Tyr Lys Pro Lys Val Leu
    690                 695                 700

Val Ser Gln Ile Trp Asn Ala Ile Ile Ser Met Tyr Arg Glu His
705                 710                 715                 720

Leu Leu Ser Ile Glu His Val Gln Lys Leu Leu Tyr His Gln Val Asp
                725                 730                 735

Thr Gly Glu Ala Gly Lys Arg Ser Leu Arg Ala Pro Pro Phe Phe Val
            740                 745                 750

Ala Gln Gly Ser Ser Gly Gly Ser Gly Glu Phe Phe Pro Pro Gly Ser
        755                 760                 765

Glu Ala Glu Arg Arg Ile Ser Phe Ala Gln Ser Leu Ser Thr Glu
770                 775                 780

Ile Pro Gln Pro Ile Pro Val Asp Ala Met Pro Thr Phe Thr Val Leu
785                 790                 795                 800
```

```
Thr Pro His Tyr Ser Glu Lys Ile Leu Leu Ser Leu Arg Glu Ile Ile
            805                 810                 815

Arg Glu Glu Asp Gln Asn Thr Arg Val Thr Leu Leu Glu Tyr Leu Lys
            820                 825                 830

Gln Leu His Pro Val Glu Trp Glu Asn Phe Val Lys Asp Thr Lys Ile
            835                 840                 845

Leu Ala Glu Glu Ser Ala Met Phe Asn Gly Pro Ser Pro Phe Gly Asn
850                 855                 860

Asp Glu Lys Gly Gln Ser Lys Met Asp Asp Leu Pro Phe Tyr Cys Ile
865                 870                 875                 880

Gly Phe Lys Ser Ala Ala Pro Glu Tyr Thr Leu Arg Thr Arg Ile Trp
            885                 890                 895

Ala Ser Leu Arg Ala Gln Thr Leu Tyr Arg Thr Val Ser Gly Met Met
            900                 905                 910

Asn Tyr Ala Lys Ala Ile Lys Leu Leu Tyr Arg Val Glu Asn Pro Glu
            915                 920                 925

Val Val Gln Gln Phe Gly Gly Asn Thr Asp Lys Leu Glu Arg Glu Leu
            930                 935                 940

Glu Arg Met Ala Arg Arg Lys Phe Lys Phe Leu Val Ser Met Gln Arg
945                 950                 955                 960

Tyr Ser Lys Phe Asn Lys Glu Glu His Glu Asn Ala Glu Phe Leu Leu
            965                 970                 975

Arg Ala Tyr Pro Asp Leu Gln Ile Ala Tyr Leu Glu Glu Pro Pro
            980                 985                 990

Arg Lys Glu Gly Gly Asp Pro Arg  Ile Phe Ser Ala Leu  Val Asp Gly
            995                 1000                1005

His Ser  Asp Ile Ile Pro Glu  Thr Gly Lys Arg Arg  Pro Lys Phe
   1010                 1015                1020

Arg Ile  Glu Leu Pro Gly Asn  Pro Ile Leu Gly Asp  Gly Lys Ser
   1025                 1030                1035

Asp Asn  Gln Asn His Ala Ile  Val Phe Tyr Arg Gly  Glu Tyr Leu
   1040                 1045                1050

Gln Leu  Ile Asp Ala Asn Gln  Asp Asn Tyr Leu Glu  Glu Cys Leu
   1055                 1060                1065

Lys Ile  Arg Asn Val Leu Ala  Glu Phe Glu Glu Tyr  Asp Val Ser
   1070                 1075                1080

Ser Gln  Ser Pro Tyr Ala Gln  Trp Ser Val Lys Glu  Phe Lys Arg
   1085                 1090                1095

Ser Pro  Val Ala Ile Val Gly  Ala Arg Glu Tyr Ile  Phe Ser Glu
   1100                 1105                1110

His Ile  Gly Ile Leu Gly Asp  Leu Ala Ala Gly Lys  Glu Gln Thr
   1115                 1120                1125

Phe Gly  Thr Leu Thr Ala Arg  Asn Asn Ala Phe Leu  Gly Gly Lys
   1130                 1135                1140

Leu His  Tyr Gly His Pro Asp  Phe Leu Asn Ala Leu  Tyr Met Asn
   1145                 1150                1155

Thr Arg  Gly Gly Val Ser Lys  Ala Gln Lys Gly Leu  His Leu Asn
   1160                 1165                1170

Glu Asp  Ile Tyr Ala Gly Met  Asn Ala Val Gly Arg  Gly Gly Arg
   1175                 1180                1185

Ile Lys  His Ser Glu Tyr Tyr  Gln Cys Gly Lys Gly  Arg Asp Leu
   1190                 1195                1200

Gly Phe  Gly Thr Ile Leu Asn  Phe Gln Thr Lys Ile  Gly Thr Gly
```

```
            1205                1210                1215
Met Gly Glu Gln Ile Leu Ser Arg Glu Tyr Tyr Tyr Leu Gly Thr
            1220                1225                1230
Gln Leu Pro Ile Asp Arg Phe Leu Thr Phe Tyr Tyr Ala His Pro
            1235                1240                1245
Gly Phe Gln Ile Asn Asn Met Leu Val Ile Leu Ser Val Gln Val
            1250                1255                1260
Phe Ile Val Thr Met Val Phe Leu Gly Thr Leu Lys Ser Ser Val
            1265                1270                1275
Thr Ile Cys Lys Tyr Thr Ser Ser Gly Gln Tyr Ile Gly Gly Gln
            1280                1285                1290
Ser Gly Cys Tyr Asn Leu Val Pro Val Phe Gln Trp Ile Glu Arg
            1295                1300                1305
Cys Ile Ile Ser Ile Phe Leu Val Phe Met Ile Ala Phe Met Pro
            1310                1315                1320
Leu Phe Leu Gln Glu Leu Val Glu Arg Gly Thr Trp Ser Ala Ile
            1325                1330                1335
Trp Arg Leu Leu Lys Gln Phe Met Ser Leu Ser Pro Val Phe Glu
            1340                1345                1350
Val Phe Ser Thr Gln Ile Gln Thr His Ser Val Leu Ser Asn Leu
            1355                1360                1365
Thr Phe Gly Gly Ala Arg Tyr Ile Ala Thr Gly Arg Gly Phe Ala
            1370                1375                1380
Thr Ser Arg Ile Ser Phe Ser Ile Leu Phe Ser Arg Phe Ala Gly
            1385                1390                1395
Pro Ser Ile Tyr Leu Gly Met Arg Thr Leu Ile Met Leu Leu Tyr
            1400                1405                1410
Val Thr Leu Thr Ile Trp Thr Pro Trp Val Ile Tyr Phe Trp Val
            1415                1420                1425
Ser Ile Leu Ser Leu Cys Ile Ala Pro Phe Leu Phe Asn Pro His
            1430                1435                1440
Gln Phe Val Phe Ser Asp Phe Leu Ile Asp Tyr Arg Glu Tyr Leu
            1445                1450                1455
Arg Trp Met Ser Arg Gly Asn Ser Arg Ser His Asn Asn Ser Trp
            1460                1465                1470
Ile Gly Tyr Cys Arg Leu Ser Arg Thr Met Ile Thr Gly Tyr Lys
            1475                1480                1485
Lys Lys Lys Leu Gly His Pro Ser Glu Lys Leu Ser Gly Asp Val
            1490                1495                1500
Pro Arg Ala Gly Trp Arg Ala Val Leu Phe Ser Glu Ile Ile Phe
            1505                1510                1515
Pro Ala Cys Met Ala Ile Leu Phe Ile Ile Ala Tyr Met Phe Val
            1520                1525                1530
Lys Ser Phe Pro Leu Asp Gly Lys Gln Pro Pro Ser Gly Leu Val
            1535                1540                1545
Arg Ile Ala Val Val Ser Ile Gly Pro Ile Val Trp Asn Ala Ala
            1550                1555                1560
Ile Leu Leu Thr Leu Phe Leu Val Ser Leu Phe Leu Gly Pro Met
            1565                1570                1575
Leu Asp Pro Val Phe Pro Leu Phe Gly Ser Val Met Ala Phe Ile
            1580                1585                1590
Ala His Phe Leu Gly Thr Ile Gly Met Ile Gly Phe Phe Glu Phe
            1595                1600                1605
```

Leu Trp Phe Leu Glu Ser Trp Glu Ala Ser His Ala Val Leu Gly
    1610                1615                1620

Leu Ile Ala Val Ile Ser Ile Gln Arg Ala Ile His Lys Ile Leu
    1625                1630                1635

Ile Ala Val Phe Leu Ser Arg Glu Phe Lys His Asp Glu Thr Asn
    1640                1645                1650

Arg Ala Trp Trp Thr Gly Arg Trp Tyr Gly Arg Gly Leu Gly Thr
    1655                1660                1665

His Ala Met Ser Gln Pro Ala Arg Glu Phe Val Val Lys Ile Ile
    1670                1675                1680

Glu Leu Ser Leu Trp Ser Ser Asp Leu Ile Leu Gly His Ile Leu
    1685                1690                1695

Leu Phe Met Leu Thr Pro Ala Val Leu Ile Pro Tyr Phe Asp Arg
    1700                1705                1710

Leu His Ala Met Met Leu Phe Trp Leu Arg Pro Ser Lys Gln Ile
    1715                1720                1725

Arg Ala Pro Leu Tyr Ser Ile Lys Gln Lys Arg Gln Arg Arg Trp
    1730                1735                1740

Ile Ile Met Lys Tyr Gly Thr Val Tyr Val Thr Val Ile Ala Ile
    1745                1750                1755

Phe Val Ala Leu Ile Ala Leu Pro Leu Val Phe Arg His Thr Leu
    1760                1765                1770

Lys Val Glu Cys Ser Leu Cys Asp Ser Leu
    1775                1780

<210> SEQ ID NO 17
<211> LENGTH: 620
<212> TYPE: DNA
<213> ORGANISM: Schizophyllum commune

<400> SEQUENCE: 17
atcgccattg taagccgcag acgggcacgc ttccaacccc catcgatggg cgctcgatgt      60
ccatctcatc ggcgactcat cattgtatct cgcgcagtcc catccctcgc cgctcgcctg     120
tagtttatgc tatttatctt tgcaccagtc gttgtattac tccctcgtcg tgtagaaagt     180
accagataaa atgcatgtaa tcctaatgaa atttgcacga cacgaagatc cggcagggtt     240
gtgggcaagg ggcagcggga acgaatggat ggcggggtac agcgagtacc cggcagtgcc     300
acagtcagtg tcacacacgt gactgattgt ccattagcgt gaccgataac atcgatcaaa     360
aattttattt cagaggacga taaataaggg ccgacggtgc cgtccgtct  ttctctcaac     420 cctcatcttc ctctcgtctc tcactcttcc ccctccacc actaccaagt aagttcaaac      480
ttcctctcat cgcctttgca cacatcgcct acgcccatc tctctccatc tgcctcgcga      540
acggcgcccc catcgtcgct ttcccgcgcg agatcttgtg cgatctagtt tactgacaat     600
ctcacctaga aacatcaaa                                                   620

<210> SEQ ID NO 18
<211> LENGTH: 440
<212> TYPE: DNA
<213> ORGANISM: Schizophyllum commune

<400> SEQUENCE: 18
atccaagtcc ggtggcaagg tcaccaagtc cgccgagaag gccgccaaga agaagtaaat      60
gtagatgtac atatgtattt tctcattccg tttccttcct cttgttgttg tttcactggt     120

-continued

| | |
|---|---|
| cctctcgtgc tcgctcgcat cgcatacagc cattgttgtc accactataa cttcacgcat | 180 |
| tctgtatttc atgccaggcg acggggtgtt cctgccaggc ctgtcgcttg ttgtaacgct | 240 |
| aatgaaaagt cacgagtagt ggacgaacga cgatgtattt ctatgtgctg tagcgattat | 300 |
| ccatttcgag ttcgccatcg agctctcttc aaacctaggt gcgacgttgt gaatgcagta | 360 |
| gcaagtgcag agtattgcag actcgtccat tgatgataac ttcaagctac gtcagagcca | 420 |
| gatgctactg aacccgggcc | 440 |

<210> SEQ ID NO 19
<211> LENGTH: 36
<212> TYPE: DNA
<213> ORGANISM: Artificial sequence
<220> FEATURE:
<223> OTHER INFORMATION: Ura_forw (NotI) primer

<400> SEQUENCE: 19
ataagaatgc ggccgctcca gctcgacctt gcgccg    36

<210> SEQ ID NO 20
<211> LENGTH: 30
<212> TYPE: DNA
<213> ORGANISM: Artificial sequence
<220> FEATURE:
<223> OTHER INFORMATION: Ura_rev (XbaI) primer

<400> SEQUENCE: 20
ctagtctaga ggatccgacg tggaggagcc    30

<210> SEQ ID NO 21
<211> LENGTH: 30
<212> TYPE: DNA
<213> ORGANISM: Artificial sequence
<220> FEATURE:
<223> OTHER INFORMATION: TefP_forw (XbaI) primer

<400> SEQUENCE: 21
ctagtctaga atcgccattg taagccgcag    30

<210> SEQ ID NO 22
<211> LENGTH: 30
<212> TYPE: DNA
<213> ORGANISM: Artificial sequence
<220> FEATURE:
<223> OTHER INFORMATION: TefP_rev (SpeI) primer

<400> SEQUENCE: 22
ctagactagt tttgatgttt tctaggtgag    30

<210> SEQ ID NO 23
<211> LENGTH: 30
<212> TYPE: DNA
<213> ORGANISM: Artificial sequence
<220> FEATURE:
<223> OTHER INFORMATION: TefT_forw (SalI) primer

<400> SEQUENCE: 23
acgcgtcgac caagtccggt ggcaaggtca    30

<210> SEQ ID NO 24
<211> LENGTH: 31
<212> TYPE: DNA
<213> ORGANISM: Artificial sequence
<220> FEATURE:
<223> OTHER INFORMATION: TefT_rev (SalI) primer -continued

```
<400> SEQUENCE: 24
ccgacgtcga cgggttcagt agcatctggc t                                    31

<210> SEQ ID NO 25
<211> LENGTH: 32
<212> TYPE: DNA
<213> ORGANISM: Artificial sequence
<220> FEATURE:
<223> OTHER INFORMATION: TefT_forw (EcoRV) primer

<400> SEQUENCE: 25
catggtgata tccaagtccg gtggcaaggt ca                                   32

<210> SEQ ID NO 26
<211> LENGTH: 32
<212> TYPE: DNA
<213> ORGANISM: Artificial sequence
<220> FEATURE:
<223> OTHER INFORMATION: TefT_rev (ApaI) primer

<400> SEQUENCE: 26
ccgtatgggc ccgggttcag tagcatctgg ct                                   32

<210> SEQ ID NO 27
<211> LENGTH: 30
<212> TYPE: DNA
<213> ORGANISM: Artificial sequence
<220> FEATURE:
<223> OTHER INFORMATION: GS1_forw (SpeI) primer

<400> SEQUENCE: 27
ctagactagt cccgtccctc aaggccgttc                                      30

<210> SEQ ID NO 28
<211> LENGTH: 36
<212> TYPE: DNA
<213> ORGANISM: Artificial sequence
<220> FEATURE:
<223> OTHER INFORMATION: GS1_rev (SalI) primer

<400> SEQUENCE: 28
aatggccgac gtcgacatgg tatatgcaat gctatg                               36

<210> SEQ ID NO 29
<211> LENGTH: 30
<212> TYPE: DNA
<213> ORGANISM: Artificial sequence
<220> FEATURE:
<223> OTHER INFORMATION: Fusion TefP_GS1_forw (XbaI) primer

<400> SEQUENCE: 29
ctagtctaga atcgccattg taagccgcag                                      30

<210> SEQ ID NO 30
<211> LENGTH: 36
<212> TYPE: DNA
<213> ORGANISM: Artificial sequence
<220> FEATURE:
<223> OTHER INFORMATION: Fusion TefP_GS1_rev (SalI) primer

<400> SEQUENCE: 30
aatggccgac gtcgacatgg tatatgcaat gctatg                               36

<210> SEQ ID NO 31
```

```
<211> LENGTH: 30
<212> TYPE: DNA
<213> ORGANISM: Artificial sequence
<220> FEATURE:
<223> OTHER INFORMATION: GS2_forw (SpeI) primer

<400> SEQUENCE: 31
ctagactagt ctgtccaaag aagagatcga                                      30

<210> SEQ ID NO 32
<211> LENGTH: 33
<212> TYPE: DNA
<213> ORGANISM: Artificial sequence
<220> FEATURE:
<223> OTHER INFORMATION: GS2_rev (EcoRV) primer

<400> SEQUENCE: 32
tacatgcgat atcttttatg cagactctcc ctg                                  33

<210> SEQ ID NO 33
<211> LENGTH: 1614
<212> TYPE: DNA
<213> ORGANISM: Schizophyllum commune

<400> SEQUENCE: 33
tccagctcga ccttgcgccg cttggagtaa cgttcagcgt cttcgtcgtc ctcgtcgcgc     60
tcgtgtacga tgatgggctc agccatggca ggtatacaag ctcagagtca atggggacg    120
aggtctcaag ccgtgaaagt cgtcgtcgaa caacgtcaag ttcgagacgg accagagttg   180
gatttcgtga ttagatctac gctcgatcac agaatgatca agaacaaag cttgccaaaa    240
ggggatctcc catcaacttc aacttgcccc aaaccatcat gaccgccgct cataagctca   300
catacggtca gcgcgctgca aggttcacca atcccgcggc gaaagccctg ctggaaacca   360
tggagcgcaa gaagagcaat ctatccgtca gcgtcgacgt cgtaaaatcc gccgatctgc   420
tcgctattgt cgataccgtc gggccctata tctgtctgat aaaggcattg cactgtcgct   480
tgcggtcttg ggatgctgct tatactctat gaagacccat gtggatgttg tcgaagactt   540
cgactcgtcg ctcgtcacca agcttcaggc tctggccgag aagcatgatt tcctcatctt   600
tgaggacaga aaattcgccg acataggtct gtccgtcgaa tctctatcga tgtcaactct   660
gatgacttgc acaggcaaca ccgtcgctct gcagtactct agtggcgtgc acaaaattgc   720
cagctggtcg cacatcacga acgcacaccc tgttccagga ccgtcaatca tcagtggcct   780
cgcatcggta ggacaacccc tcggtcgcgg actcctcctg ctcgcagaga tgagcacgaa   840
gggctcactt gcgacaggcg cgtacactga agccgccgtc cagatggcaa gggagaaccg   900
cggcttcgtc atcgggttca tcgcccaacg gcggatggag gtattggcg cgcctccagg    960
ggtgaatgtc gaggacgagg attttcttgt cttgacacca ggtgtcggac tcgatgtgaa  1020
gggcgatggg atggggcagc aatacaggac gccgaagcaa gtggtacagg aagatgggtg  1080
cgatgtaatc atcgtgggtc gcgggattta tgcaaggac ccatcgaagg tggaagagat   1140
acggaggcag gcagagcgtt accaggctgc aggatgggcg gcgtacattg agagggtcaa  1200
cgccttggta tagctaatct gatcggtgtt gtcttgttaa cgtcaggct caatggaacg    1260
cttttggacga gcggagagta acttgaatta gcagtgtata cttcgggcaa atcaatcgtg  1320
ataaatacaa gagcacgctc acgcacgtcc aatctccctc aaaatctcca tcttctcgc    1380
ctcattcacc ttcctgaacc cagccggcga catctcgaac agaccatgcc cacccgacag  1440
cgcacgcagc ctattcgagt agtccagcat ccggctgagc ggcgccaccg cctgcaccgc  1500
```

```
gcgcttcatc ttcacgcccg ccgcctccct cgccgcagtg ccgccagagg gcgacaccca    1560
ctccgggggc acgtacacgc cgtccgcagg gtacggctcc tccacgtcgg atcc          1614
```

<210> SEQ ID NO 34
<211> LENGTH: 278
<212> TYPE: PRT
<213> ORGANISM: Schizophyllum commune

<400> SEQUENCE: 34

```
Met Thr Ala Ala His Lys Leu Thr Tyr Gly Gln Arg Ala Ala Arg Phe
1               5                   10                  15

Thr Asn Pro Ala Ala Lys Ala Leu Leu Glu Thr Met Glu Arg Lys Lys
            20                  25                  30

Ser Asn Leu Ser Val Ser Val Asp Val Val Lys Ser Ala Asp Leu Leu
        35                  40                  45

Ala Ile Val Asp Thr Val Gly Pro Tyr Ile Cys Leu Ile Lys Thr His
    50                  55                  60

Val Asp Val Val Glu Asp Phe Asp Ser Ser Leu Val Thr Lys Leu Gln
65                  70                  75                  80

Ala Leu Ala Glu Lys His Asp Phe Leu Ile Phe Glu Asp Arg Lys Phe
                85                  90                  95

Ala Asp Ile Gly Asn Thr Val Ala Leu Gln Tyr Ser Ser Gly Val His
            100                 105                 110

Lys Ile Ala Ser Trp Ser His Ile Thr Asn Ala His Pro Val Pro Gly
        115                 120                 125

Pro Ser Ile Ile Ser Gly Leu Ala Ser Val Gly Gln Pro Leu Gly Arg
    130                 135                 140

Gly Leu Leu Leu Leu Ala Glu Met Ser Thr Lys Gly Ser Leu Ala Thr
145                 150                 155                 160

Gly Ala Tyr Thr Glu Ala Ala Val Gln Met Ala Arg Glu Asn Arg Gly
                165                 170                 175

Phe Val Ile Gly Phe Ile Ala Gln Arg Arg Met Asp Gly Ile Gly Ala
            180                 185                 190

Pro Pro Gly Val Asn Val Glu Asp Glu Asp Phe Leu Val Leu Thr Pro
        195                 200                 205

Gly Val Gly Leu Asp Val Lys Gly Asp Gly Met Gly Gln Gln Tyr Arg
    210                 215                 220

Thr Pro Lys Gln Val Val Gln Glu Asp Gly Cys Asp Val Ile Ile Val
225                 230                 235                 240

Gly Arg Gly Ile Tyr Gly Lys Asp Pro Ser Lys Val Glu Glu Ile Arg
                245                 250                 255

Arg Gln Ala Glu Arg Tyr Gln Ala Ala Gly Trp Ala Ala Tyr Ile Glu
            260                 265                 270

Arg Val Asn Ala Leu Val
            275
```